US012089490B2

(12) United States Patent
Kawakami et al.

(10) Patent No.: US 12,089,490 B2
(45) Date of Patent: Sep. 10, 2024

(54) ORGANIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Sachiko Kawakami, Kanagawa (JP); Rina Shimazaki, Kanagawa (JP); Takumu Okuyama, Kanagawa (JP); Tsunenori Suzuki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 770 days.

(21) Appl. No.: 17/263,248

(22) PCT Filed: Jul. 24, 2019

(86) PCT No.: PCT/IB2019/056303
§ 371 (c)(1),
(2) Date: Jan. 26, 2021

(87) PCT Pub. No.: WO2020/026077
PCT Pub. Date: Feb. 6, 2020

(65) Prior Publication Data
US 2021/0159422 A1 May 27, 2021

(30) Foreign Application Priority Data
Jul. 31, 2018 (JP) ................................ 2018-144189

(51) Int. Cl.
*C07D 405/12* (2006.01)
*H10K 85/60* (2023.01)
*H10K 50/15* (2023.01)

(52) U.S. Cl.
CPC ......... *H10K 85/636* (2023.02); *C07D 405/12* (2013.01); *H10K 50/15* (2023.02); *H10K 85/6572* (2023.02); *H10K 85/6574* (2023.02)

(58) Field of Classification Search
CPC ............. H10K 85/636; H10K 85/6574; H10K 85/6572; H10K 50/15; C07D 405/12
See application file for complete search history.

(56) References Cited

U.S. PATENT DOCUMENTS

| | | | | |
|---|---|---|---|---|
| 8,822,434 | B2 | 9/2014 | Liang et al. | |
| 10,411,193 | B2 | 9/2019 | Kawakami et al. | |
| 10,439,146 | B2 | 10/2019 | Ogita et al. | |
| 11,063,226 | B1 * | 7/2021 | Lee | H10K 85/653 |
| 2004/0021136 | A1 | 2/2004 | Matsuo et al. | |
| 2004/0265630 | A1 | 12/2004 | Suh et al. | |
| 2007/0037011 | A1 | 2/2007 | Nakashima et al. | |
| 2007/0096639 | A1 | 5/2007 | Nakashima et al. | |
| 2007/0149784 | A1 | 6/2007 | Murata et al. | |
| 2007/0215867 | A1 | 9/2007 | Kawakami et al. | |
| 2007/0215889 | A1 | 9/2007 | Kawakami et al. | |
| 2008/0206598 | A1 | 8/2008 | Ohsawa et al. | |
| 2009/0284140 | A1 | 11/2009 | Osaka et al. | |
| 2010/0245217 | A1 | 9/2010 | Nomura et al. | |
| 2010/0301744 | A1 | 12/2010 | Osaka et al. | |
| 2011/0168992 | A1 | 7/2011 | Bae et al. | |
| 2011/0240969 | A1 | 10/2011 | Kim et al. | |
| 2012/0305898 | A1 | 12/2012 | Okamoto | |
| 2014/0183500 | A1 | 7/2014 | Ikeda et al. | |
| 2015/0031900 | A1 | 1/2015 | Kawakami et al. | |
| 2015/0060813 | A1 | 3/2015 | Kawakami et al. | |
| 2015/0318495 | A1 | 11/2015 | Kawakami et al. | |
| 2016/0079314 | A1 | 3/2016 | Seo et al. | |
| 2017/0040535 | A1 | 2/2017 | Ogita et al. | |
| 2017/0125689 | A1 | 5/2017 | Lee et al. | |
| 2017/0222156 | A1 | 8/2017 | Kawakami et al. | |
| 2019/0229271 | A1 | 7/2019 | Lee et al. | |
| 2019/0296244 | A1 | 9/2019 | Mun et al. | |
| 2019/0296248 | A1 | 9/2019 | Mun et al. | |
| 2019/0300535 | A1 | 10/2019 | Mun et al. | |
| 2019/0341551 | A1 | 11/2019 | Ogita et al. | |
| 2019/0363259 | A1 | 11/2019 | Kawakami et al. | |
| 2021/0384440 | A1 | 12/2021 | Kawakami et al. | |
| 2022/0093870 | A1 | 3/2022 | Mun et al. | |

FOREIGN PATENT DOCUMENTS

| | | | |
|---|---|---|---|
| CN | 106432157 | A | 2/2017 |
| CN | 108336246 | A | 7/2018 |
| CN | 108604641 | A | 9/2018 |
| CN | 109195950 | A | 1/2019 |
| CN | 109476596 | A | 3/2019 |
| DE | 10 2016 214 546 | A1 | 2/2017 |
| EP | 3 466 926 | A1 | 4/2019 |
| JP | 2009-298767 | A | 12/2009 |
| JP | 2017-036267 | A | 2/2017 |
| JP | 2017-139457 | A | 8/2017 |

(Continued)

OTHER PUBLICATIONS

International Search Report (Application No. PCT/IB2019/056303) Dated Oct. 21, 2019.

(Continued)

*Primary Examiner* — D Margaret M Seaman
(74) *Attorney, Agent, or Firm* — Husch Blackwell LLP

(57) ABSTRACT

A novel organic compound is provided. A novel organic compound having a hole-transport property is provided. A novel hole-transport material is provided. A novel light-emitting element is provided. Alight-emitting element with a favorable lifetime is provided. A light-emitting element with favorable emission efficiency is provided. An organic compound having a substituted or unsubstituted benzonaphthofuran skeleton, a substituted or unsubstituted carbazole skeleton, and a substituted or unsubstituted amine skeleton is provided. Alternatively, a light-emitting element that uses the hole-transport material is provided.

14 Claims, 37 Drawing Sheets

(56) References Cited

FOREIGN PATENT DOCUMENTS

| | | | |
|---|---|---|---|
| JP | 2017-222714 | A | 12/2017 |
| JP | 2019-522676 | | 8/2019 |
| JP | 2021-044595 | A | 3/2021 |
| JP | 2022-140558 | A | 9/2022 |
| KR | 2015-0004099 | A | 1/2015 |
| KR | 2017-0017761 | A | 2/2017 |
| KR | 10-1789998 | B1 | 10/2017 |
| KR | 2017-0134215 | A | 12/2017 |
| KR | 2018-0008286 | A | 1/2018 |
| KR | 2018-0008291 | A | 1/2018 |
| KR | 2018-0042943 | A | 4/2018 |
| KR | 2018-0096458 | A | 8/2018 |
| KR | 2018-0107159 | A | 10/2018 |
| TW | 201736357 | | 10/2017 |
| WO | WO 2010/036027 | A2 | 4/2010 |
| WO | WO 2017/130079 | A1 | 8/2017 |
| WO | WO 2017/204556 | A1 | 11/2017 |
| WO | WO 2017/204557 | A1 | 11/2017 |
| WO | WO 2018/012780 | A1 | 1/2018 |
| WO | WO 2018/012781 | A1 | 1/2018 |

OTHER PUBLICATIONS

Written Opinion (Application No. PCT/IB2019/056303) Dated Oct. 21, 2019.

* cited by examiner

ORGANIC COMPOUND, LIGHT-EMITTING ELEMENT, LIGHT-EMITTING DEVICE, ELECTRONIC DEVICE, AND LIGHTING DEVICE

This application is a 371 of international application PCT/IB2019/056303 filed on Jul. 24, 2019 which is incorporated herein by reference.

TECHNICAL FIELD

One embodiment of the present invention relates to a light-emitting element, a display module, a lighting module, a display device, a light-emitting device, an electronic device, and a lighting device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Thus, more specifically, a semiconductor device, a display device, a liquid crystal display device, a light-emitting device, a lighting device, a power storage device, a memory device, an imaging device, a driving method thereof, or a manufacturing method thereof can be given as an example of the technical field of one embodiment of the present invention disclosed in this specification.

BACKGROUND ART

Light-emitting elements (organic EL elements) that use organic compounds and utilize electroluminescence (EL) have been put into practical use. In the basic structure of such light-emitting elements, an organic compound layer (EL layer) containing a light-emitting material is sandwiched between a pair of electrodes. Carriers are injected by application of voltage to this element, and recombination energy of the carriers is used, whereby light emission can be obtained from the light-emitting material.

Since such a light-emitting element is of a self-luminous type, the light-emitting element is suitably used in a pixel of a display because such a display can have higher visibility than a liquid crystal display. The display using such a light-emitting element is also highly advantageous in that it requires no backlight and can be fabricated thin and lightweight. Moreover, an extremely fast response speed is also a feature.

Since light-emitting layers of such light-emitting elements can be successively formed two-dimensionally, planar light emission can be obtained. This feature is difficult to obtain with point light sources typified by incandescent lamps and LEDs or linear light sources typified by fluorescent lamps. Thus, light-emitting elements are also of great utility value as planar light sources, which can be applied to lighting and the like.

Displays or lighting devices using light-emitting elements can be suitably used in a variety of electronic devices as described above, and research and development of light-emitting elements have progressed for more favorable efficiency or lifetimes.

The characteristics of light-emitting elements have been improved remarkably, but are still insufficient to satisfy advanced requirements for various characteristics including efficiency and durability.

REFERENCE

Patent Document

[Patent Document 1] PCT International Publication No. 2010/036027

SUMMARY OF THE INVENTION

Problems to be Solved by the Invention

An object of one embodiment of the present invention is to provide a novel organic compound. Another object of one embodiment of the present invention is to provide a novel organic compound having a hole-transport property. Another object of one embodiment of the present invention is to provide a novel hole-transport material. Another object is to provide a novel light-emitting element. Another object is to provide a light-emitting element with a favorable lifetime. Another object is to provide a light-emitting element with favorable emission efficiency. Another object is to provide an element with a small voltage change over driving time.

Another object of one embodiment of the present invention is to provide a light-emitting device, an electronic device, and a display device each having high reliability. An object of another embodiment of the present invention is to provide a light-emitting device, an electronic device, and a display device each having low power consumption.

It is only necessary that at least one of the above-described objects be achieved in the present invention.

Means for Solving the Problems

An embodiment of the present invention is an organic compound represented by General Formula (G1) below.

[Chemical Formula 1]

(G1)

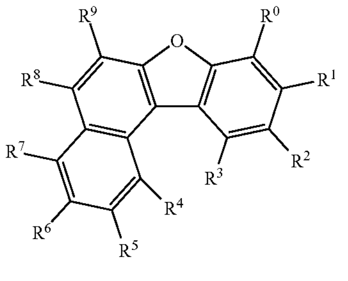

Note that in General Formula (G1), one of $R^0$ to $R^9$ is a group represented by General Formula (g1) below, and the others each independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms.

[Chemical Formula 2]

(g1)

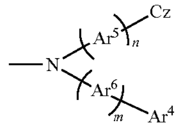

In General Formula (g1), Cz represents a substituted or unsubstituted carbazolyl group. Furthermore, $Ar^4$ represents any one of a substituted or unsubstituted aromatic hydrocarbon group having 6 to 60 carbon atoms and a substituted or unsubstituted carbazolyl group. In addition, $Ar^5$ and $Ar^6$ each independently represent any one of substituted or unsubstituted divalent aromatic hydrocarbon groups having 6 to 54 carbon atoms. Moreover, n is any one integer of 1 to 3 and m is any one integer of 0 to 3; however, when $Ar^4$ is a carbazolyl group, m is any one integer of 1 to 3. Furthermore, a plurality of $Ar^5$ or $Ar^6$ may exist depending on the value of n or m; the plurality of $Ar^5$ or $Ar^6$ each independently represent any one of substituted or unsubstituted divalent aromatic hydrocarbon groups having 6 to 54 carbon atoms. Furthermore, the sum of the numbers of carbon atoms of Cz and $Ar^5$ and the sum of the numbers of carbon atoms of $Ar^4$ and $Ar^6$ are each smaller than or equal to 60.

Alternatively, another embodiment of the present invention is an organic compound represented by General Formula (G1) below.

[Chemical Formula 3]

Note that in General Formula (G1), one of $R^0$ to $R^9$ is a group represented by General Formula (g1) below, and the others each independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms.

[Chemical Formula 4]

(G1)

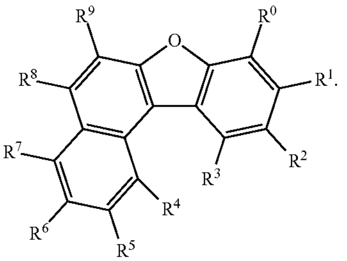

In General Formula (g1), Cz represents a group represented by General Formula (g2) below. Furthermore, $Ar^4$ represents any one of a substituted or unsubstituted aromatic hydrocarbon group having 6 to 60 carbon atoms and a group represented by General Formula (g3) below. In addition, $Ar^5$ and $Ar^6$ each independently represent any one of substituted or unsubstituted divalent aromatic hydrocarbon groups having 6 to 54 carbon atoms. Moreover, n is any one integer of 1 to 3 and m is any one integer of 0 to 3; however, when $Ar^4$ is a carbazolyl group, m is any one integer of 1 to 3. Furthermore, a plurality of $Ar^5$ or $Ar^6$ may exist depending on the value of n or m; the plurality of $Ar^5$ or $Ar^6$ each independently represent any one of substituted or unsubstituted divalent aromatic hydrocarbons group having 6 to 54 carbon atoms. Furthermore, the sum of the numbers of carbon atoms of Cz and $Ar^5$ and the sum of the numbers of carbon atoms of $Ar^4$ and $Ar^6$ are each smaller than or equal to 60.

[Chemical Formula 5]

(g2)

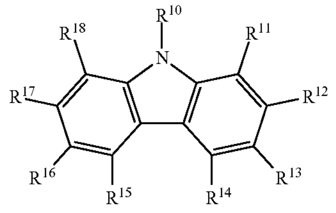

In General Formula (g2), one of $R^{10}$ to $R^{18}$ represents a dangling bond bonded to $Ar^5$, and the others each independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms.

[Chemical Formula 6]

(g3)

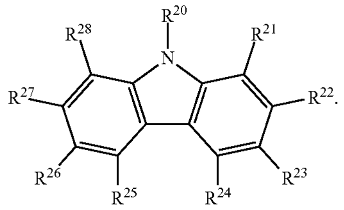

In General Formula (g3), one of $R^{20}$ to $R^{28}$ represents a dangling bond bonded to $Ar^6$, and the others each independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms.

Alternatively, another embodiment of the present invention is the organic compound in the above-described structures, in which $R^0$ or $R^9$ is the above-described group represented by General Formula (g1).

Alternatively, another embodiment of the present invention is the organic compound in the above-described structures, in which the n is any one integer of 1 to 3.

Alternatively, another embodiment of the present invention is the organic compound in the above-described structures, in which $Ar^4$ is any one of substituted or unsubstituted aromatic hydrocarbon groups having 6 to 60 carbon atoms.

Alternatively, another embodiment of the present invention is the organic compound in the above-described structure, in which $Ar^4$ is a substituted or unsubstituted phenyl group.

Alternatively, another embodiment of the present invention is the organic compound in the above-described structures, in which $Ar^5$ and $Ar^6$ are substituted or unsubstituted phenylene groups.

Alternatively, another embodiment of the present invention is the organic compound in the above-described structures, in which $R^0$ in General Formula (G1) is the group represented by General Formula (g1).

Alternatively, another embodiment of the present invention is the organic compound in the above-described structures, in which $R^9$ in General Formula (G1) is the group represented by General Formula (g1).

Alternatively, another embodiment of the present invention is the organic compound in the above-described structures, in which $R^9$ in General Formula (G1) is a substituted or unsubstituted phenyl group.

Alternatively, another embodiment of the present invention is the organic compound in the above-described structures, in which $R^{10}$ in General Formula (g2) is a dangling bond.

Alternatively, another embodiment of the present invention is the organic compound in the above-described structures, in which $R^{16}$ in General Formula (g2) is a dangling bond.

Alternatively, another embodiment of the present invention is the organic compound in the above-described structures, in which the $R^{10}$ is a substituted or unsubstituted phenyl group.

Alternatively, another embodiment of the present invention is a light-emitting element including an anode, a cathode, and an EL layer, in which the EL layer is positioned between the anode and the cathode and the EL layer includes the organic compound described above.

Alternatively, another embodiment of the present invention is a light-emitting device including the light-emitting element having the above-described structure, and a transistor or a substrate.

Alternatively, another embodiment of the present invention is an electronic device including the above-described light-emitting device; and at least one of a sensor, an operation button, a speaker, and a microphone.

Alternatively, another embodiment of the present invention is a lighting device including the light-emitting device having the above-described structure and a housing.

Note that the light-emitting device in this specification includes an image display device using a light-emitting element. Moreover, the light-emitting device may also include a module in which a connector such as an anisotropic conductive film or a TCP (Tape Carrier Package) is connected to a light-emitting element, a module in which a printed wiring board is provided on the tip of a TCP, or a module in which an IC (integrated circuit) is directly mounted on a light-emitting element by a COG (Chip On Glass) method. Furthermore, in some cases, lighting equipment or the like includes the light-emitting device.

Effect of the Invention

One embodiment of the present invention can provide a novel organic compound. Alternatively, a novel organic compound having a hole-transport property can be provided. Alternatively, a novel hole-transport material can be provided. Alternatively, a novel light-emitting element can be provided. Alternatively, a light-emitting element with a favorable lifetime can be provided. Alternatively, a light-emitting element with favorable emission efficiency can be provided. Alternatively, a light-emitting element with a low driving voltage can be provided. Alternatively, an element with a small voltage change over driving time can be provided.

Another embodiment of the present invention can provide a light-emitting device, an electronic device, and a display device each having high reliability. Another embodiment of the present invention can provide a light-emitting device, an electronic device, and a display device each having low power consumption.

Note that the descriptions of these effects do not disturb the existence of other effects. Note that one embodiment of the present invention does not have to have all of these effects. Effects other than these are apparent from and can be derived from the descriptions of the specification, the drawings, the claims, and the like.

BRIEF DESCRIPTION OF THE DRAWINGS

FIGS. 7(A) to 7(C) are diagrams illustrating electronic devices.

MODE FOR CARRYING OUT THE INVENTION

Figure 1A:
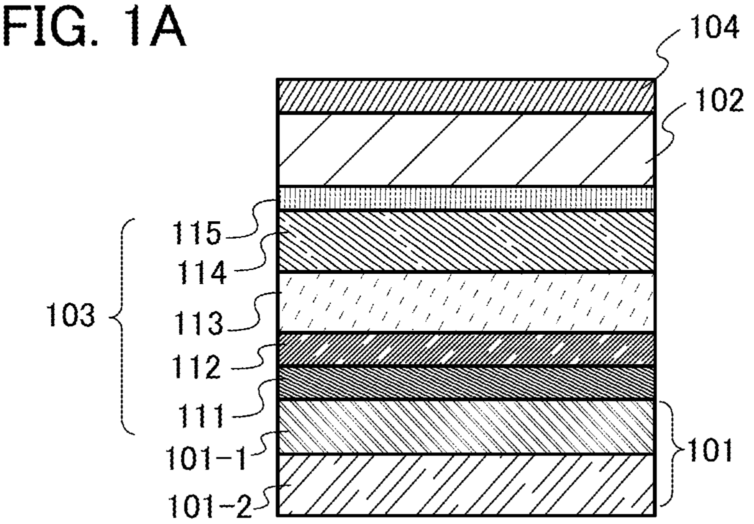
FIGS. 1(A) to 1(C) are schematic diagrams of light-emitting elements.

Embodiments of the present invention are described in detail below with reference to drawings. Note that the present invention is not limited to the following description, and it will be readily appreciated by those skilled in the art that modes and details of the present invention can be modified in various ways without departing from the spirit and scope of the present invention. Thus, the present invention should not be construed as being limited to the descriptions in the following embodiments.

Embodiment 1

An organic compound of one embodiment of the present invention is an organic compound represented by General Formula (G1) below.

[Chemical Formula 7]

(G1)

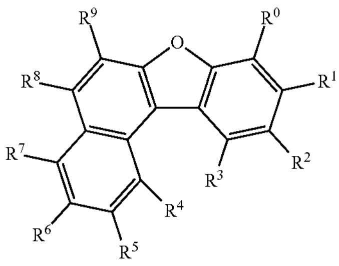

Note that in the organic compound represented by General Formula (G1), one of $R^0$ to $R^9$ is a group represented by General Formula (g1) below, and the others each independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms.

Among the organic compounds represented by General Formula (G1) above, the organic compounds in which $R^0$ or $R^9$ is the group represented by General Formula (g1) below have comparatively deep HOMO levels and thus are preferable for higher properties of hole injection to a host material having a deep HOMO level contained in a light-emitting layer. In the case where $R^0$ is the group represented by General Formula (g1) below in particular, a hole-transport material having a high T1 level can be provided. In this case, $R^9$ is preferably any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, and a haloalkyl group having 1 to 6 carbon atoms for a high T1 level, and is preferably a substituted or unsubstituted phenyl group in order to provide a highly reliable element. A hole-transport material having a high T1 level can be suitably used as a host material of a phosphorescent light-emitting layer or a material included in a hole-transport layer adjacent to a phosphorescent light-emitting layer.

[Chemical Formula 8]

(g1)

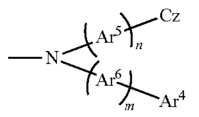

In General Formula (g1), Cz represents a substituted or unsubstituted carbazolyl group. A light-emitting element that uses the organic compound of one embodiment of the present invention having the carbazolyl group in this position can have favorable emission efficiency. Note that Cz may be a group represented by General Formula (g2) below.

[Chemical Formula 9]

(g2)

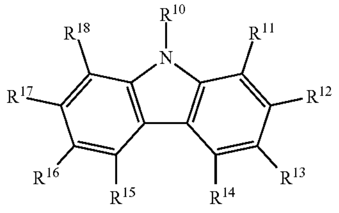

In General Formula (g2), one of $R^{10}$ to $R^{18}$ represents a dangling bond bonded to $Ar^5$ of the group represented by General Formula (g1) above. Note that the dangling bond is preferably $R^{10}$ or $R^{16}$ in order to provide an organic compound having a high hole-transport property. In the case where the dangling bond is $R^{16}$, $R^{10}$ is preferably a substituted or unsubstituted phenyl group in order to provide an organic compound having a high hole-transport property. $R^{10}$ to $R^{18}$ except the dangling bond each independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms.

Furthermore, in General Formula (g1), $Ar^4$ represents any one of a substituted or unsubstituted aromatic hydrocarbon group having 6 to 60 carbon atoms and a substituted or unsubstituted carbazolyl group. The carbazolyl group may be a group represented by General Formula (g3) below. Note that $Ar^4$ is preferably a substituted or unsubstituted aromatic hydrocarbon group having 6 to 60 carbon atoms in order to provide an organic compound having a high hole-transport property and a relatively deep HOMO level. When the organic compound having a high hole-transport property and a relatively deep HOMO level is used in a hole-transport layer adjacent to a light-emitting layer, an element having an enhanced property of hole injection to the light-emitting layer and thus having high emission efficiency can be provided. Furthermore, $Ar^4$ is further preferably a substituted or unsubstituted phenyl group, especially an unsubstituted phenyl group, in order to provide an organic compound having a high hole-transport property.

[Chemical Formula 10]

(g3)

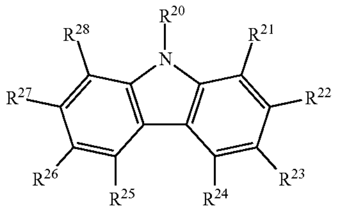

In General Formula (g3), one of $R^{20}$ to $R^{28}$ represents a dangling bond bonded to $Ar^6$ of the group represented by General Formula (g1) above. Note that the dangling bond is preferably $R^{20}$ or $R^{26}$ in order to provide an organic compound having a high hole-transport property. In the case where the dangling bond is $R^{26}$, $R^{20}$ is preferably a substituted or unsubstituted phenyl group in order to provide an organic compound having a high hole-transport property. $R^{20}$ to $R^{28}$ except the dangling bond each independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms.

In the group represented by General Formula (g1) above, $Ar^5$ and $Ar^6$ each independently represent a substituted or unsubstituted divalent aromatic hydrocarbon group having 6 to 54 carbon atoms. Note that $Ar^5$ and $Ar^6$ are preferably substituted or unsubstituted phenylene groups in order to provide an organic compound having a high hole-transport property and a relatively deep HOMO level. When the organic compound having a high hole-transport property and a relatively deep HOMO level is used in a hole-transport layer adjacent to a light-emitting layer, an element having an enhanced property of hole injection to the light-emitting layer and thus having high emission efficiency can be provided. Furthermore, $Ar^5$ and $Ar^6$ are further preferably unsubstituted phenylene groups in order to provide an organic compound having a high hole-transport property.

Here, in the group represented by General Formula (g1) above, n is any one integer of 1 to 3 and m is any one integer of 0 to 3. It should be noted that when $Ar^4$ is a carbazolyl group, m is any one integer of 1 to 3. Furthermore, a plurality of $Ar^5$ or $Ar^6$ may exist depending on the value of n or m; the plurality of $Ar^5$ or $Ar^6$ each independently represent any one of substituted or unsubstituted divalent aromatic hydrocarbon groups having 6 to 54 carbon atoms.

In order to provide an organic compound having a high hole-transport property, the sum of the numbers of carbon atoms of Cz and $Ar^5$ and the sum of the numbers of carbon atoms of $Ar^4$ and $Ar^6$ are each smaller than or equal to 60.

As specific substituents that can be used as General Formulae above $R^0$ to $R^9$, $R^{10}$ to $R^{18}$, and $R^{20}$ to $R^{28}$, substituents represented by Structural Formulae (1-1) to (1-40) below or substituents represented by Structural Formulae (2-1) to (2-13) below and the like can be given. Note that the substitution position of Structural Formulae (2-1) to (2-13) below is not limited, and Structural Formulae (2-1) to (2-13) below may further have a substituent.
[Chemical Formula 11]
(1-1)
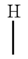
(1-2)
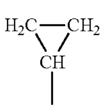
(1-3)
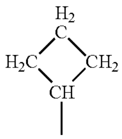
(1-4)
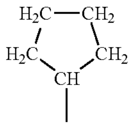
(1-5)
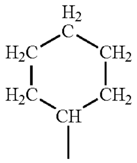
(1-6)
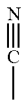
(1-7)
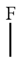
(1-8)
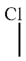
(1-9)
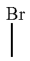
(1-10)
(1-11)
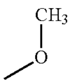
(1-12)
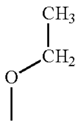
(1-13)
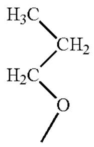
-continued
(1-14)
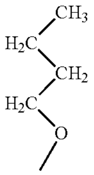
(1-15)
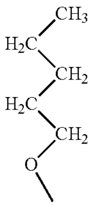
(1-16)
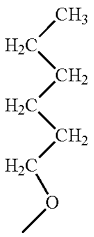
(1-17)
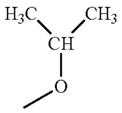
(1-18)
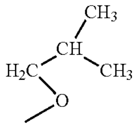
(1-19)
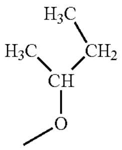
(1-20)
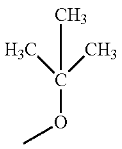
(1-21)
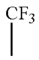
(1-22)
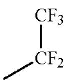
(1-23)
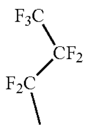

-continued
(1-24)
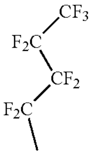
(1-25)
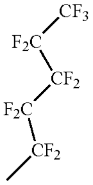
(1-26)
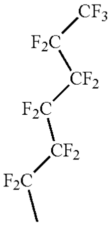
(1-27)
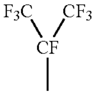
(1-28)
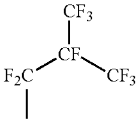
(1-29)
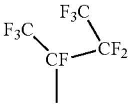
(1-30)
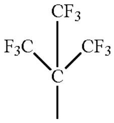
(1-31)
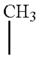
(1-32)
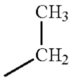
(1-33)
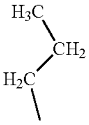
(1-34)
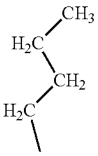
-continued
(1-35)
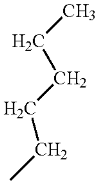
(1-36)
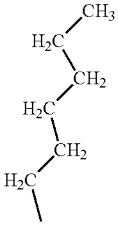
(1-37)
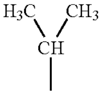
(1-38)
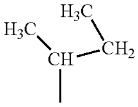
(1-39)
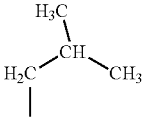
(1-40)
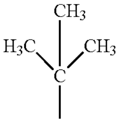
[Chemical Formula 12]
(2-1)
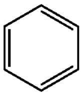
(2-2)
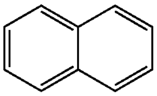
(2-3)
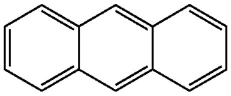
(2-4)
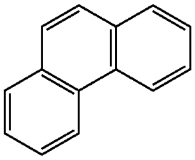

-continued (2-5)

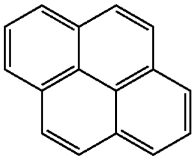

(2-6)

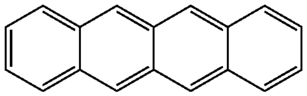

(2-7)

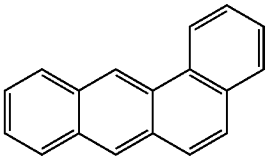

(2-8)

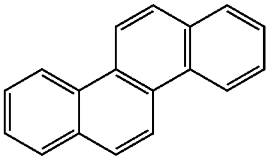

(2-9)

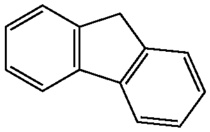

(2-10)

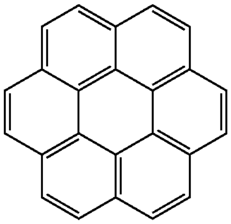

(2-11)

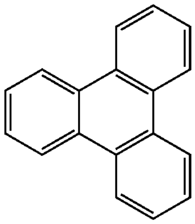

(2-12)

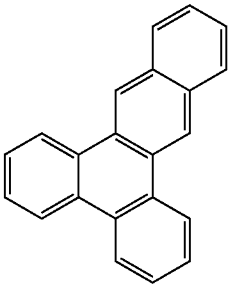

-continued (2-13)

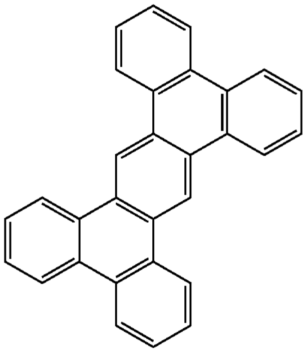

$Ar^4$ represents any one of a substituted or unsubstituted aromatic hydrocarbon group having 6 to 60 carbon atoms and a substituted or unsubstituted carbazolyl group. As specific examples of the substituted or unsubstituted aromatic hydrocarbon group having 6 to 60 carbon atoms, substituents represented by Structural Formulae (2-1) to (2-13) below and the like can be given. Note that the substitution position of Structural Formulae (2-1) to (2-13) below is not limited. Furthermore, they may further have a substituent.

[Chemical Formula 13]

(2-1)

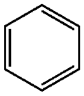

(2-2)

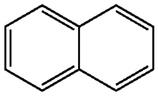

(2-3)

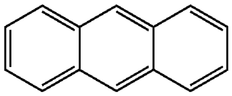

(2-4)

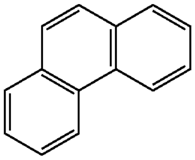

(2-5)

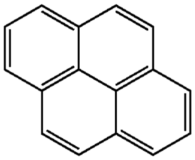

(2-6)

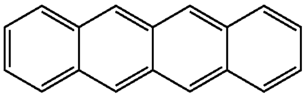

-continued (2-7)

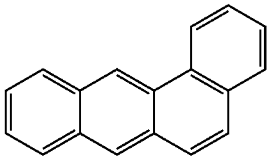

(2-8)

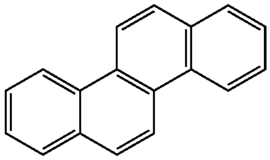

(2-9)

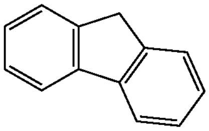

(2-10)

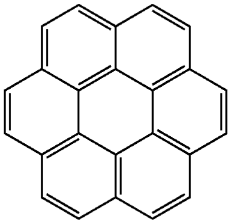

(2-11)

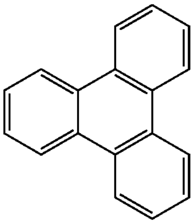

(2-12)

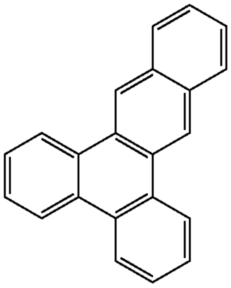

(2-13)

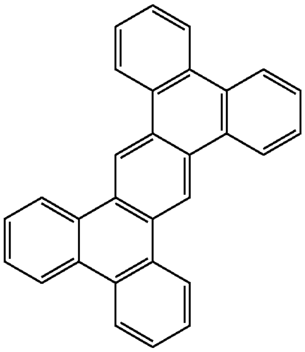

Moreover, the above-mentioned Cz represents a substituted or unsubstituted carbazolyl group, and the above-mentioned $Ar^4$ is a substituted or unsubstituted carbazolyl group in some cases. As specific examples of Cz and $Ar^4$, substituents represented by Structural Formulae (3-1) to (3-24) below and the like can be given. Note that they may further have a substituent.

[Chemical Formula 14]

(3-1)

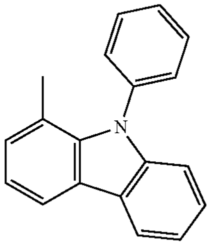

(3-2)

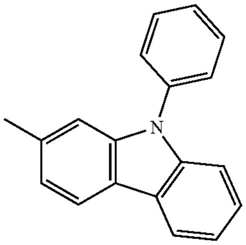

(3-3)

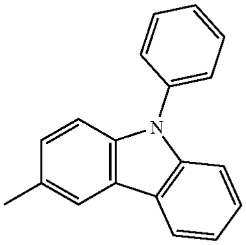

(3-4)

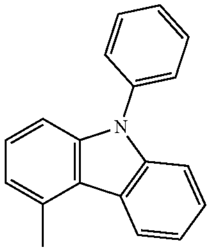

(3-5)

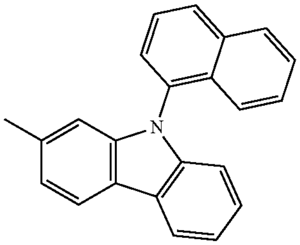

-continued
(3-6)
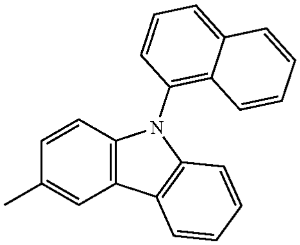
(3-7)
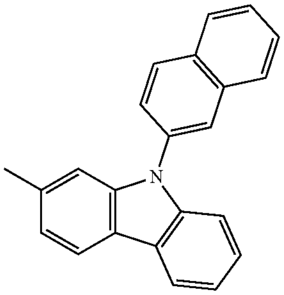
(3-8)
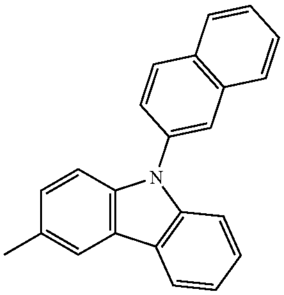
(3-9)
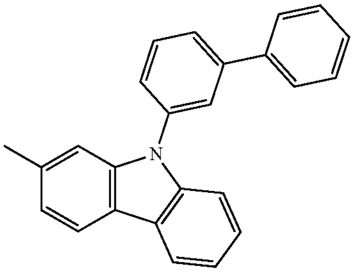
(3-10)
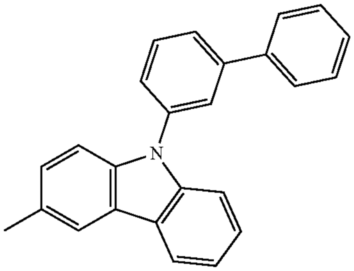
-continued
(3-11)
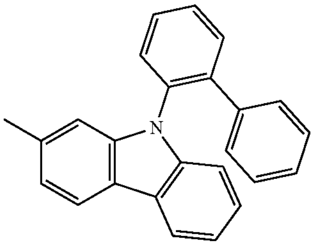
(3-12)
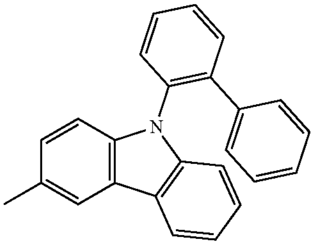
(3-13)
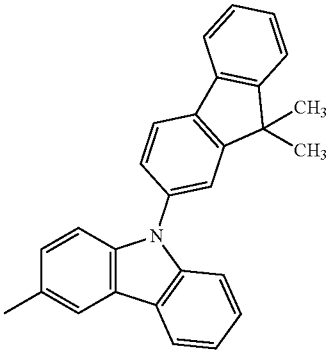
(3-14)
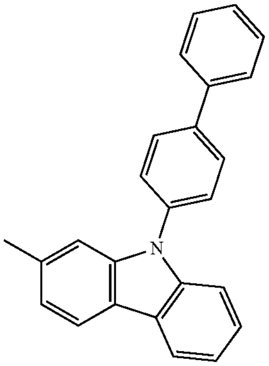
(3-15)
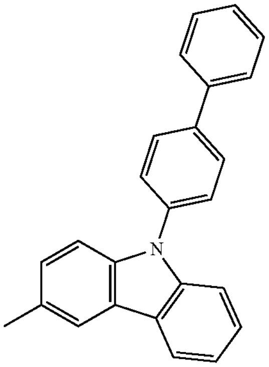

-continued (3-16)

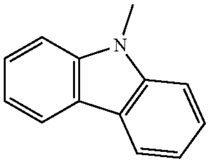

(3-17)

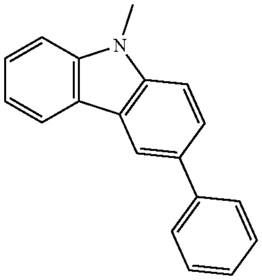

(3-18)

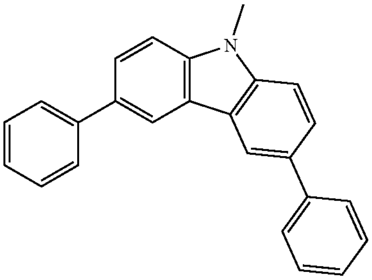

(3-19)

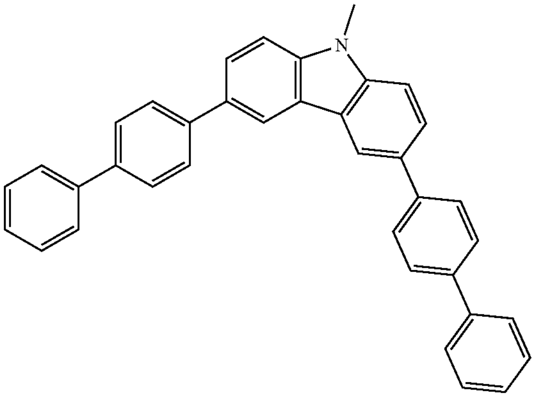

(3-20)

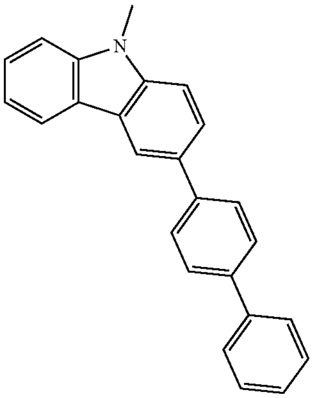

-continued (3-21)

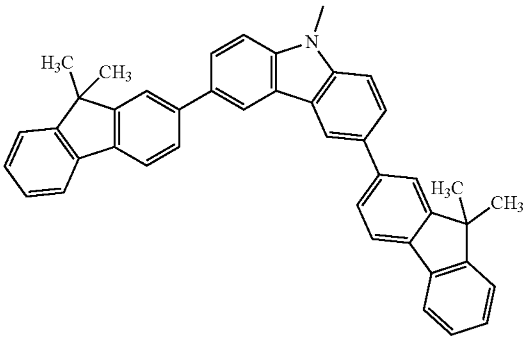

(3-22)

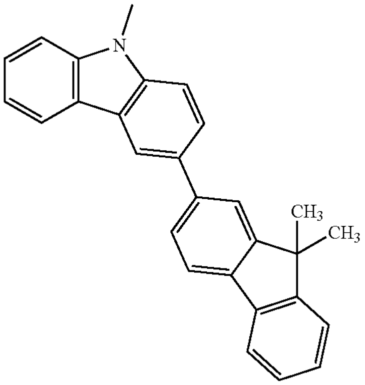

(3-23)

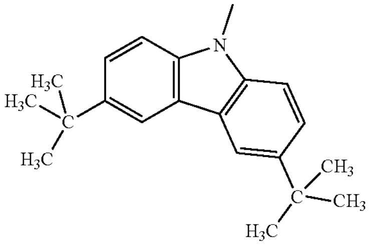

(3-24)

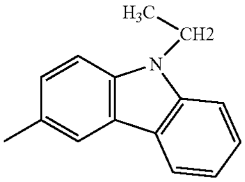

Furthermore, $Ar^5$ and $Ar^6$ each independently represent a substituted or unsubstituted divalent aromatic hydrocarbon group having 6 to 54 carbon atoms. As the substituted or unsubstituted divalent aromatic hydrocarbon group having 6 to 54 carbon atoms, the groups represented by Structural Formulae (2-1) to (2-13) below can be specifically used, for example. Note that the substitution position of Structural Formulae (2-1) to (2-13) below is not limited. Furthermore, they may further have a substituent.

[Chemical Formula 15]

(2-1)

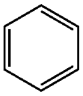

-continued (2-2)

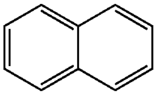

(2-3)

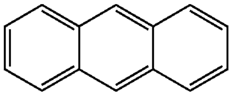

(2-4)

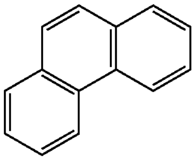

(2-5)

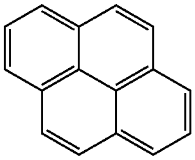

(2-6)

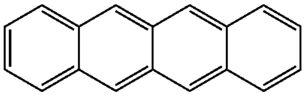

(2-7)

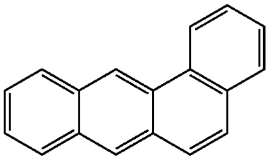

(2-8)

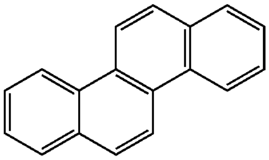

(2-9)

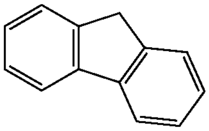

(2-10)

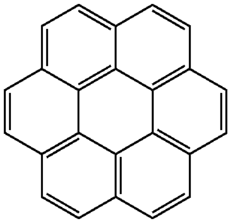

(2-11)

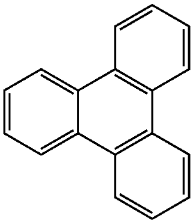

-continued (2-12)

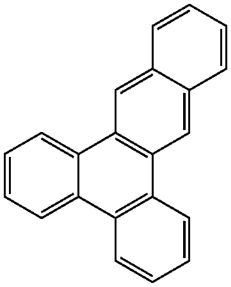

(2-13)

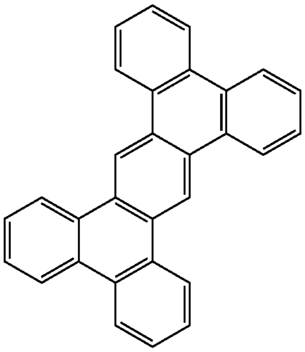

In the case where $R^0$ to $R^9$, $R^{10}$ to $R^{18}$, and $R^{20}$ to $R^{28}$ are aromatic hydrocarbon groups and have a substituent or where $Ar^4$, Cz, $Ar^5$, and $Ar^6$ further have a substituent, the substituent can be any one or more of an aromatic hydrocarbon group having 6 to 10 carbon atoms, a hydrocarbon group having 1 to 6 carbon atoms, a cyclic hydrocarbon group having 3 to 6 carbon atoms, an alkoxy group having 1 to 6 carbon atoms, a cyano group, halogen, and a haloalkyl group having 1 to 6 carbon atoms. As specific examples of the hydrocarbon group having 1 to 6 carbon atoms, the cyclic hydrocarbon group having 3 to 6 carbon atoms, the alkoxy group having 1 to 6 carbon atoms, the cyano group, halogen, and the haloalkyl group having 1 to 6 carbon atoms, the ones represented by Structural Formulae (1-1) to (1-40) below can be given. Furthermore, a phenyl group, a naphthyl group, or the like can be given as the aromatic hydrocarbon group having 6 to 10 carbon atoms, for example.

[Chemical Formula 16]

(1-1)

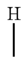

(1-2)

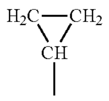

(1-3)

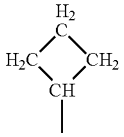

-continued
(1-4)
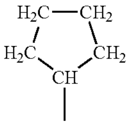
(1-5)
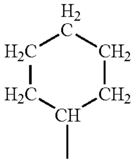
(1-6)
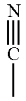
(1-7)
(1-8)
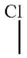
(1-9)
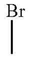
(1-10)
(1-11)
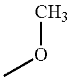
(1-12)
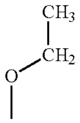
(1-13)
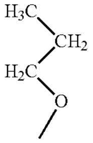
(1-14)
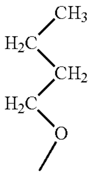
(1-15)
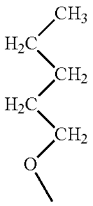
-continued
(1-16)
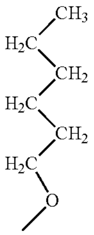
(1-17)
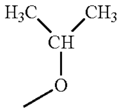
(1-18)
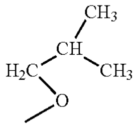
(1-19)
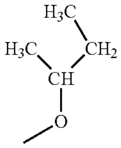
(1-20)
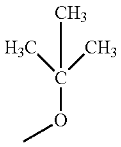
(1-21)
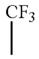
(1-22)
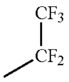
(1-23)
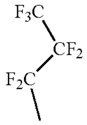
(1-24)
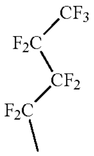
(1-25)
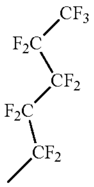

-continued
(1-26)
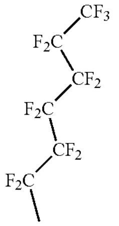
(1-27)
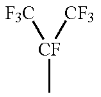
(1-28)
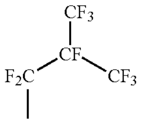
(1-29)
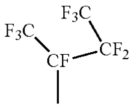
(1-30)
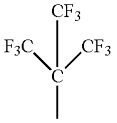
(1-31)
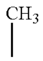
(1-32)
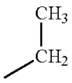
(1-33)
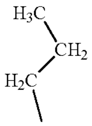
-continued
(1-34)
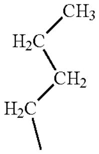
(1-35)
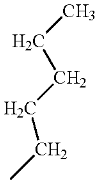
(1-36)
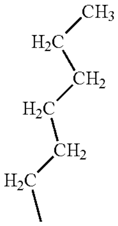
(1-37)
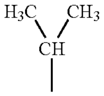
(1-38)
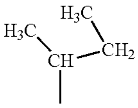
(1-39)
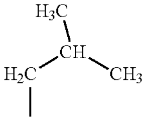
(1-40)
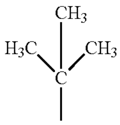

Specific examples of the organic compound having the above-described structure are shown below.
[Chemical Formula 17]
(300)
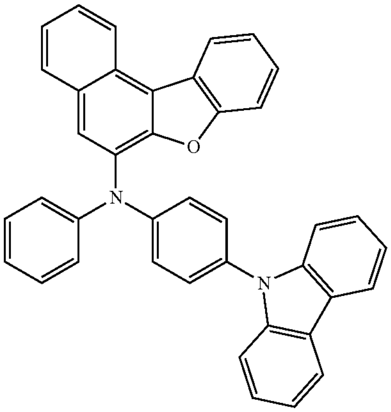
(301)
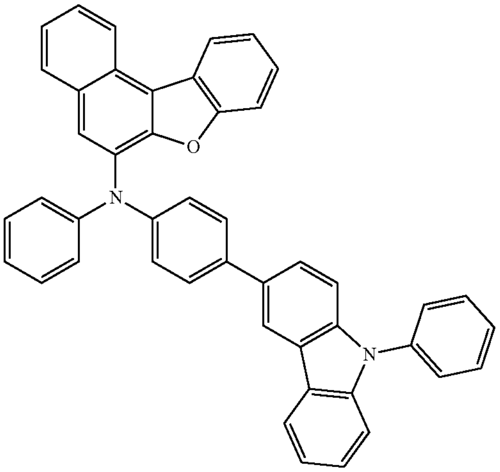
(302)
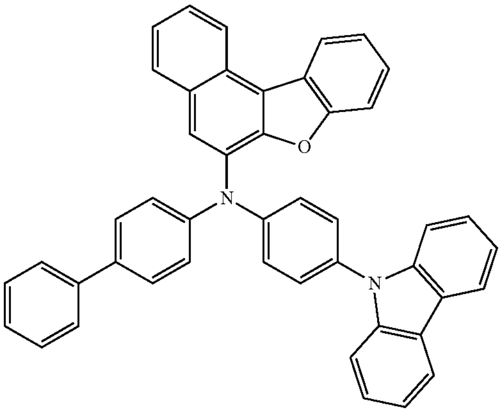
(303)
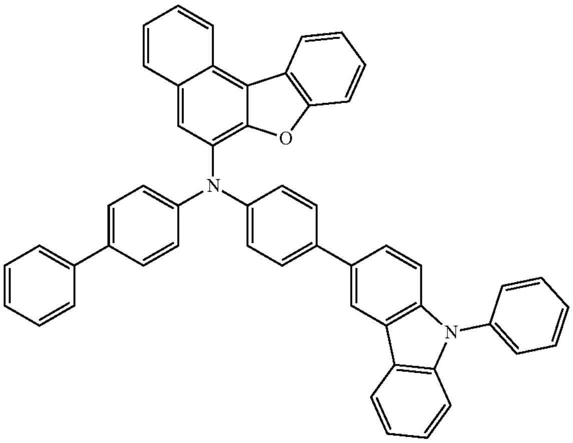
(304)
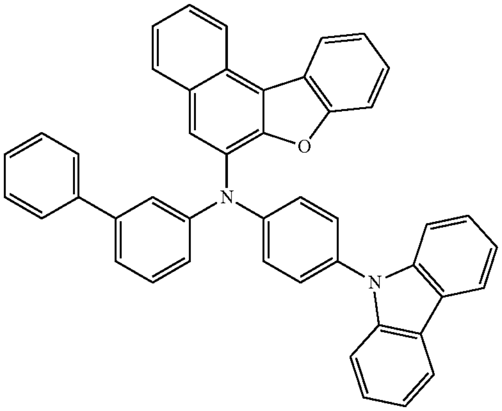
(305)
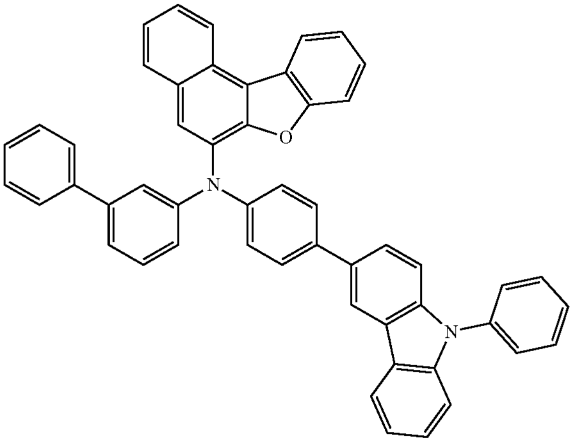

-continued
(306)
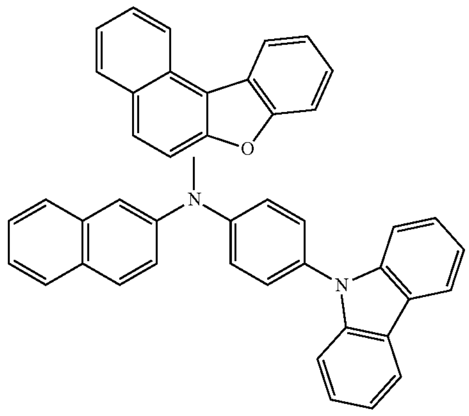
(307)
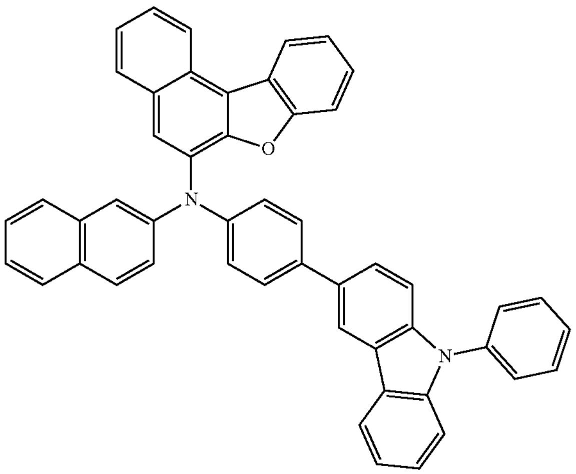
(308)
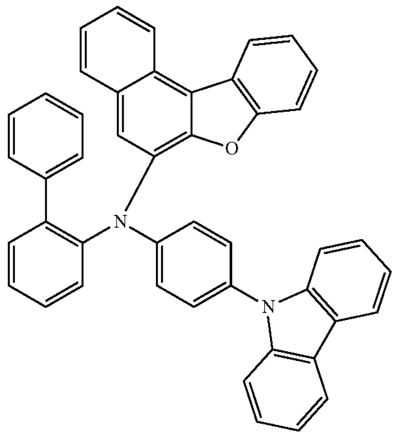
(309)
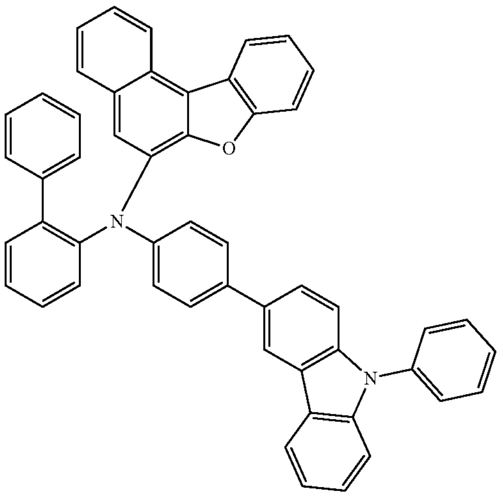
(310)
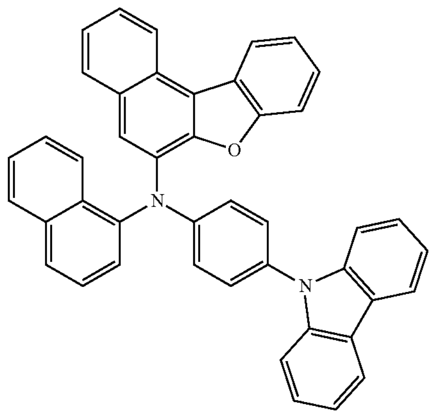
(311)
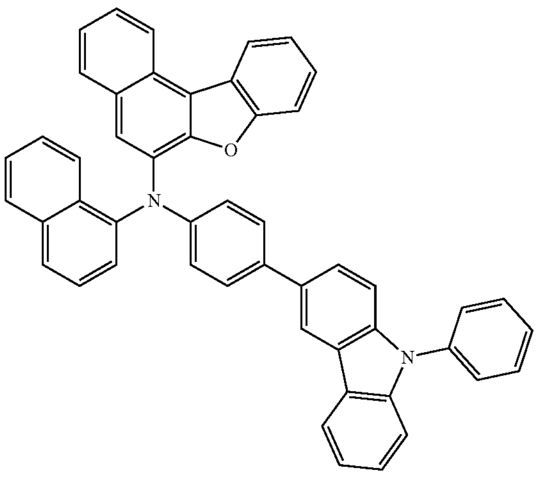

-continued
(312)
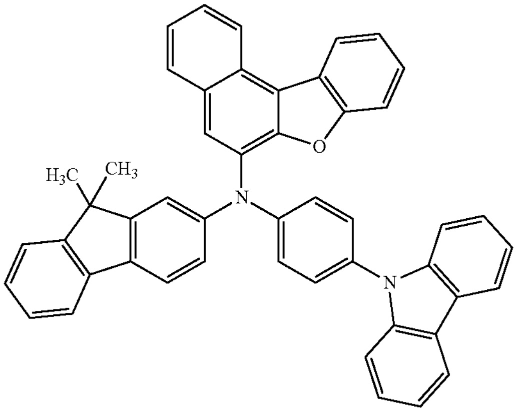
(313)
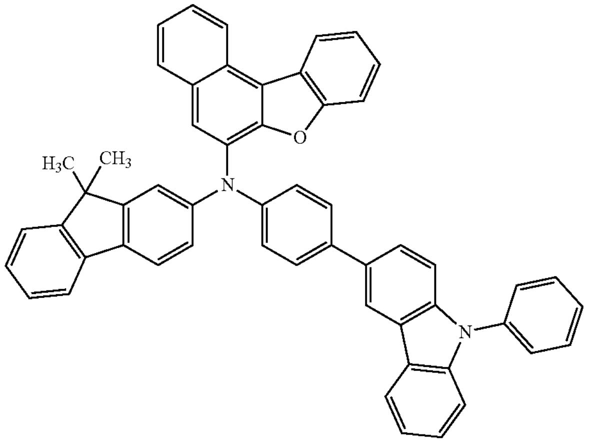
[Chemical Formula 18]
(314)
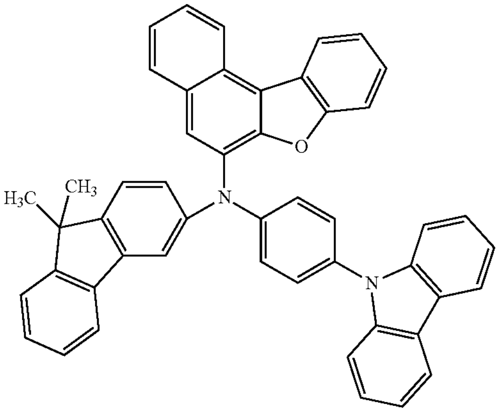
(315)
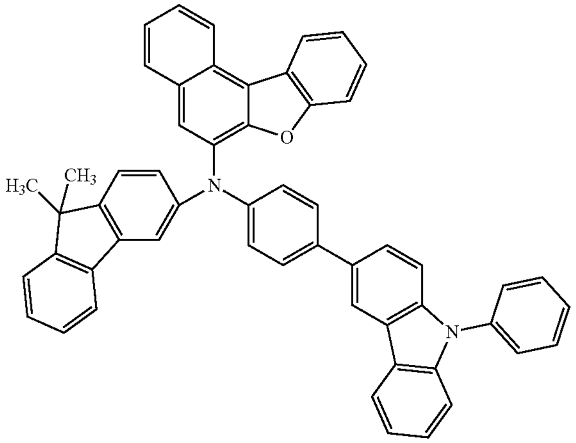
(316)
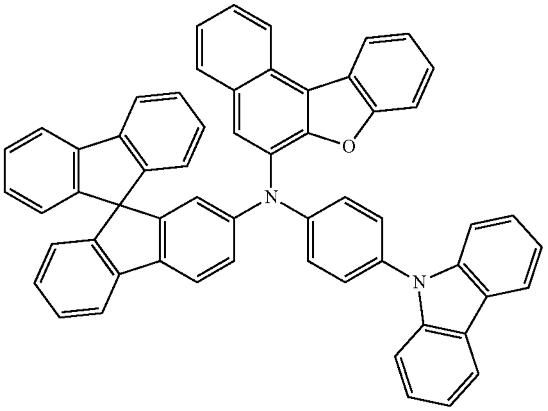
(317)
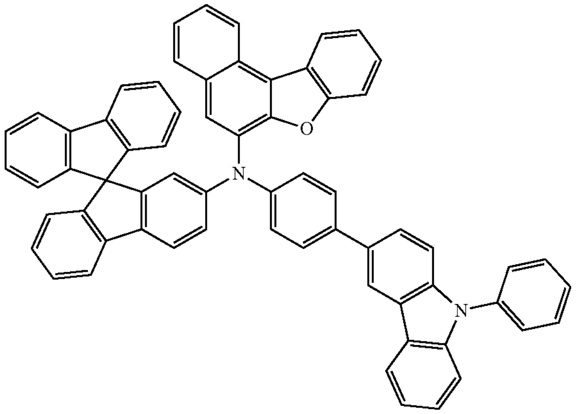

-continued
(318)
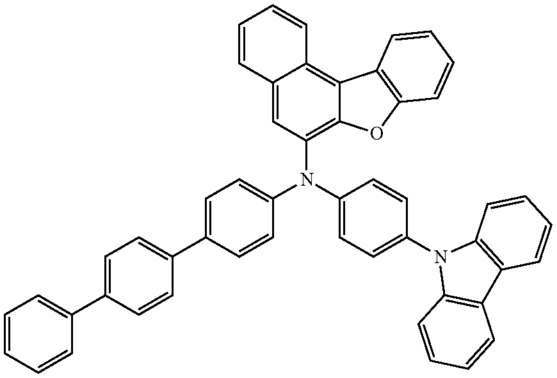
(319)
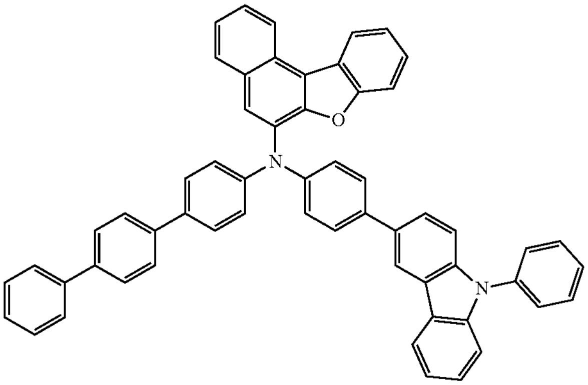
(320)
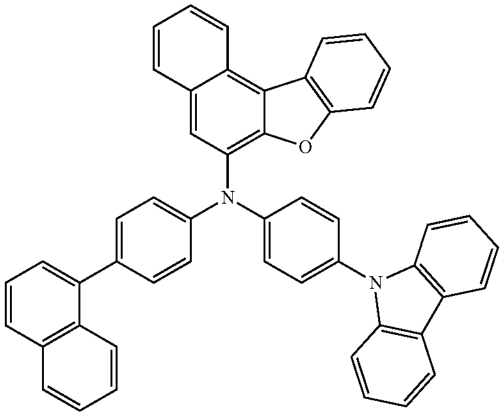
(321)
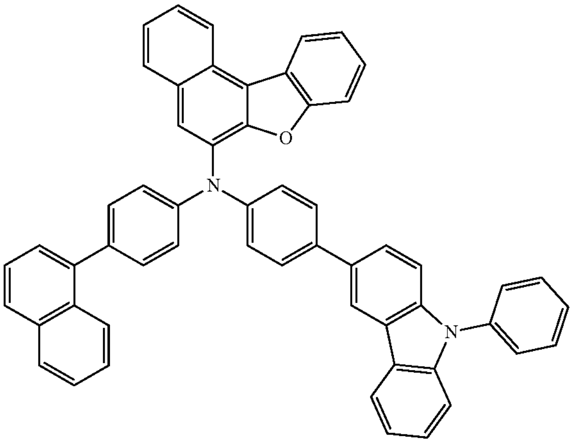
(322)
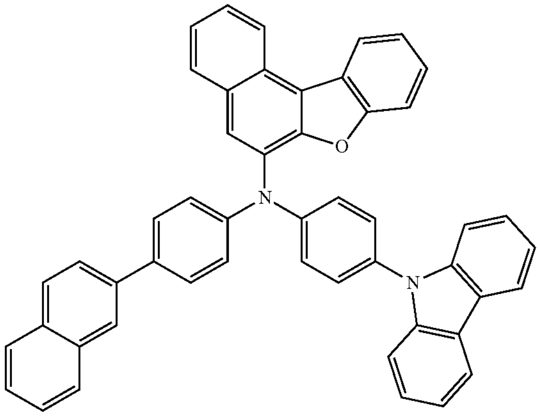
(323)
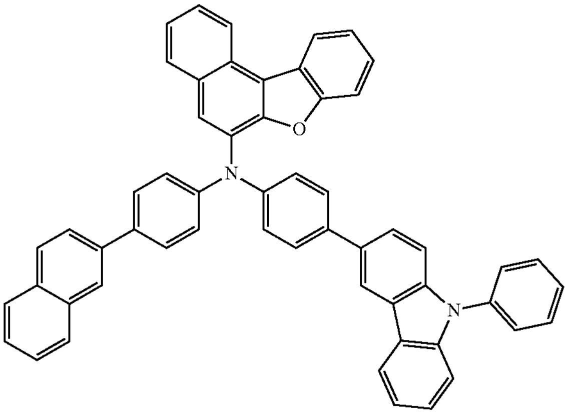

-continued
(324)
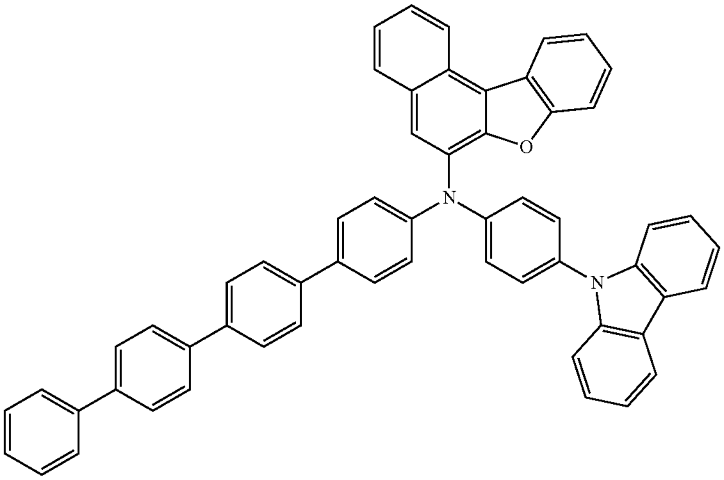
(325)
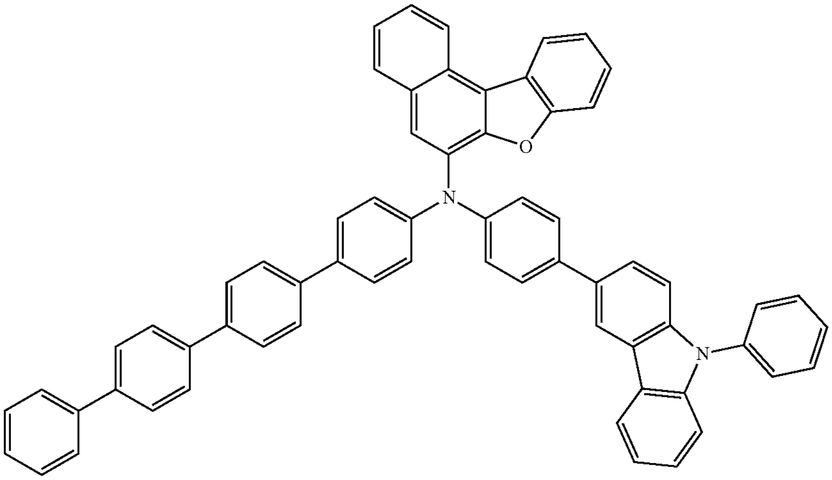
[Chemical Formula 19]
(326)
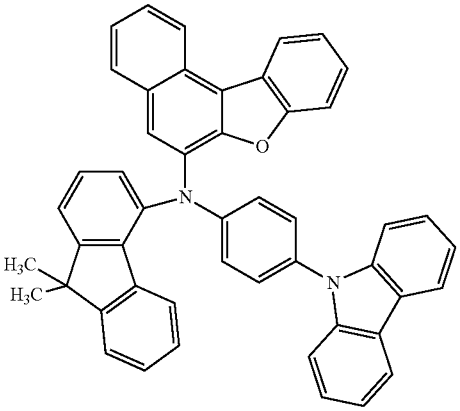
(327)
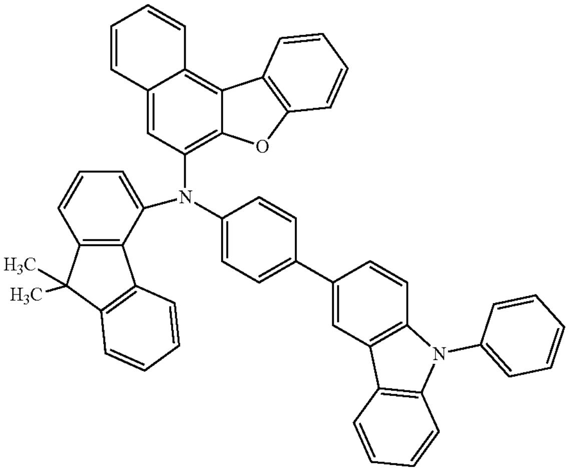

-continued
(328)
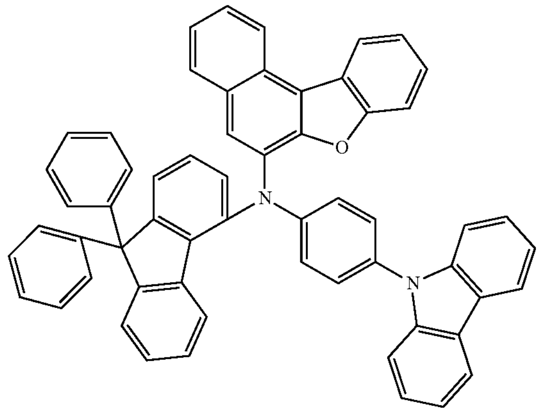
(329)
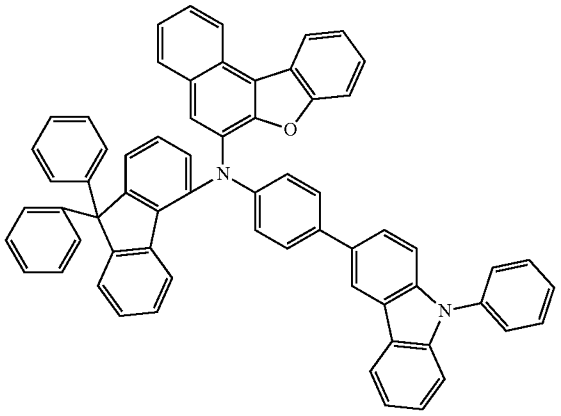
(330)
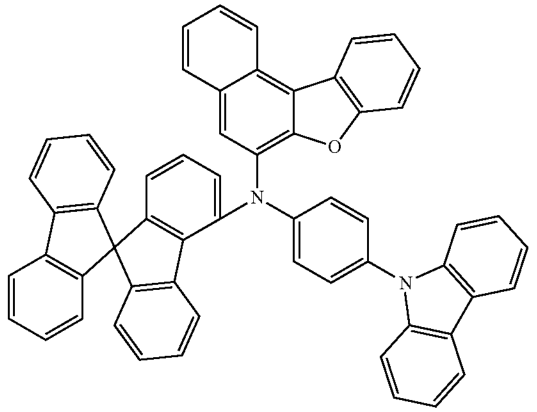
(331)
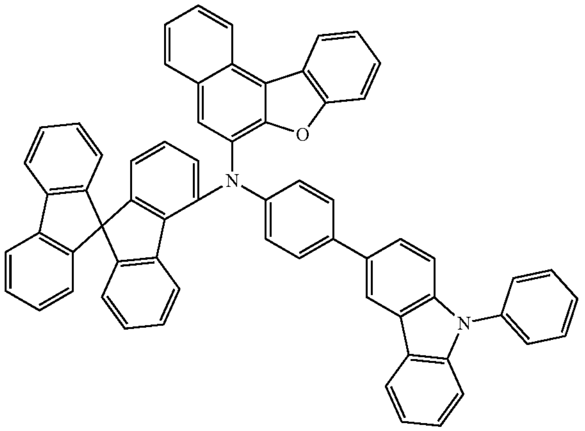
(332)
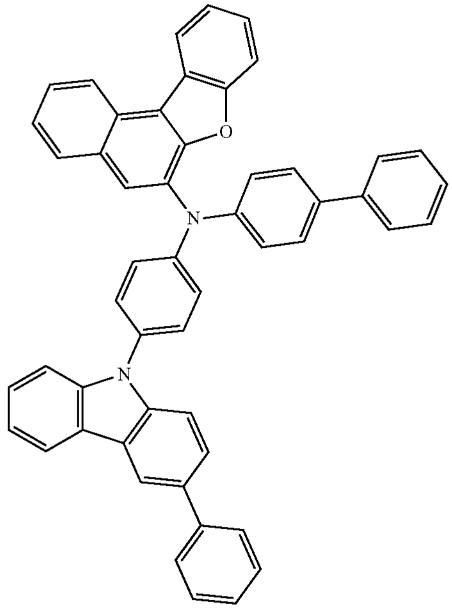
(333)
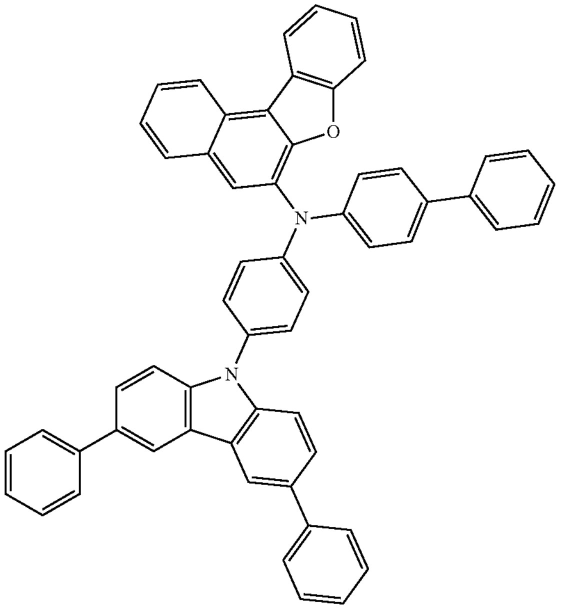

-continued
(334)
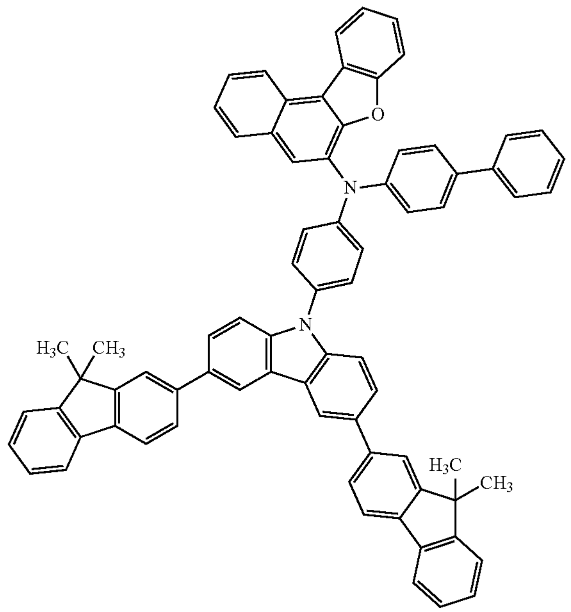
(335)
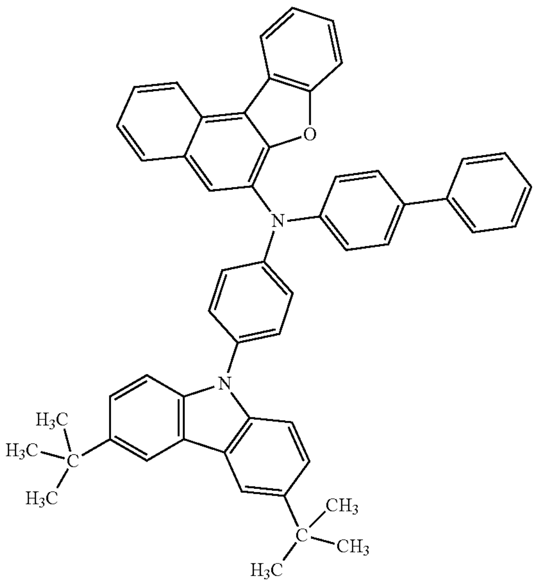
(336)
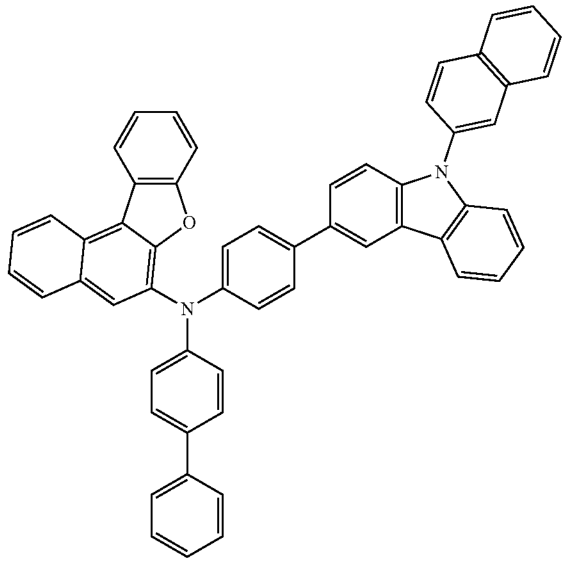
(337)
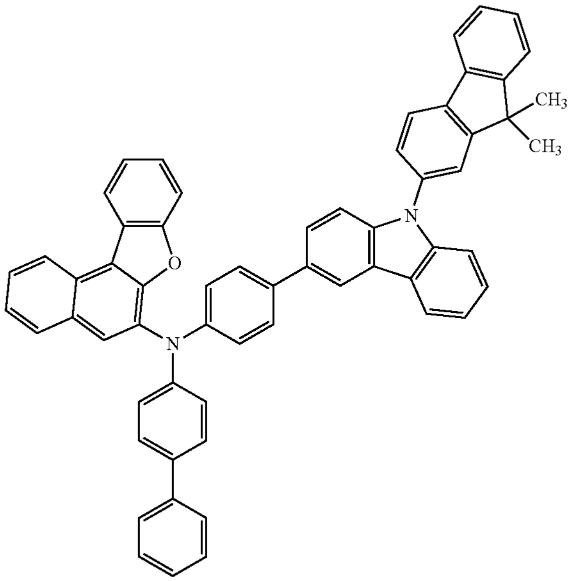

-continued
[Chemical Formula 20]
(338)
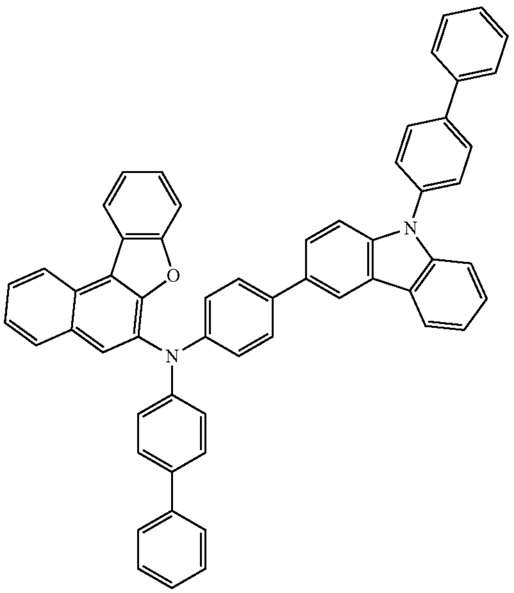
(339)
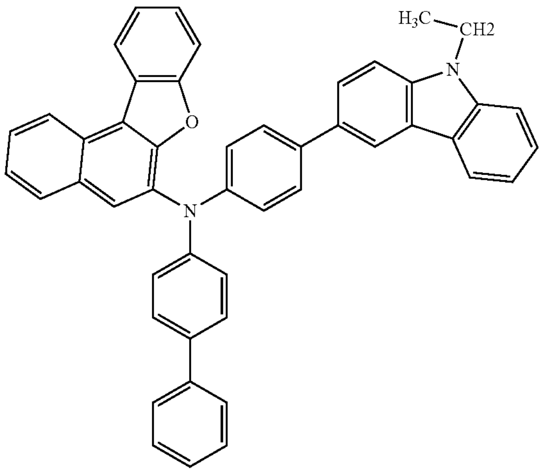
(340)
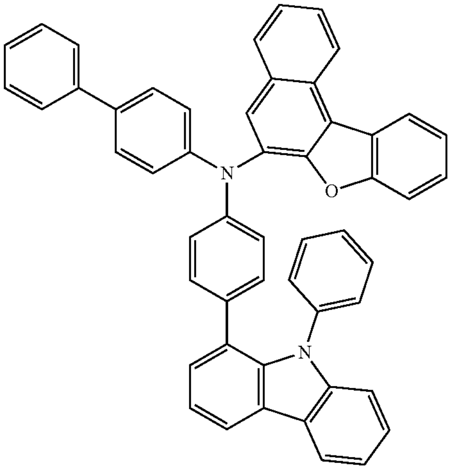
(341)
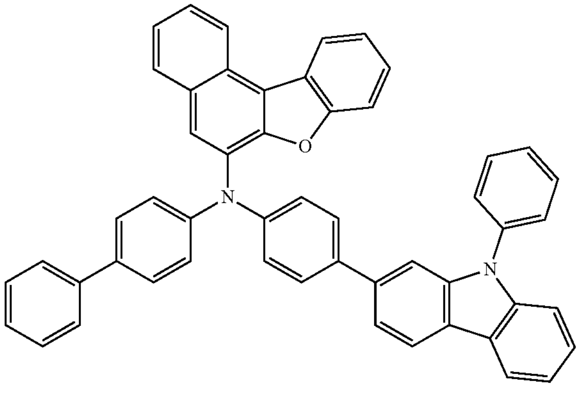

-continued
(342)
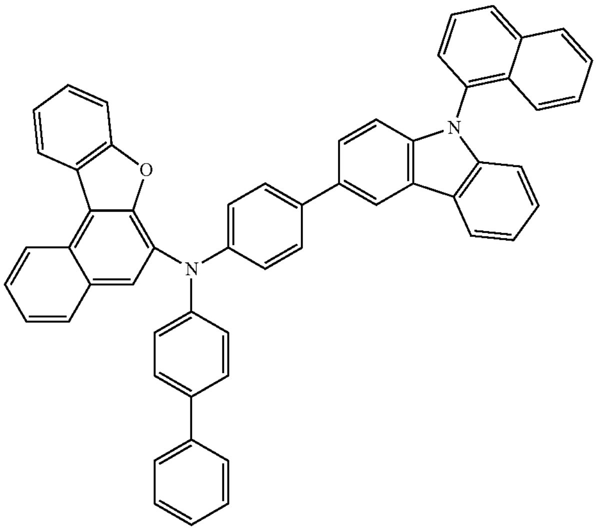
(343)
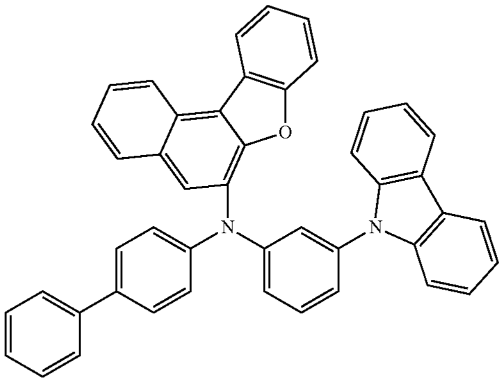
(344)
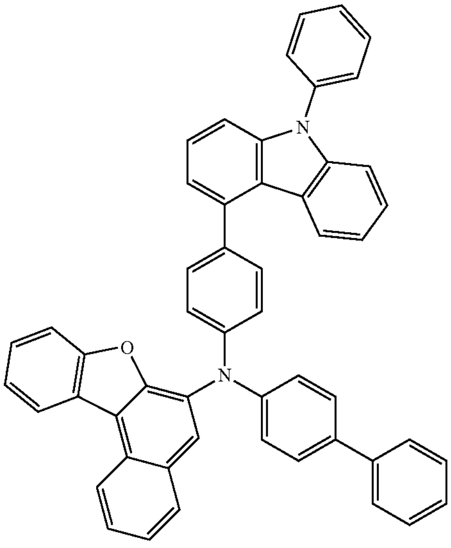
(345)
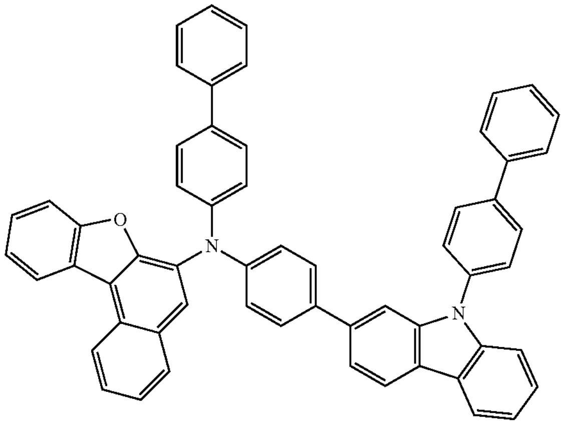
(346)
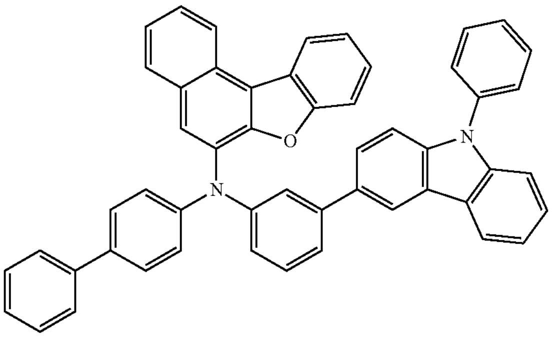
(347)
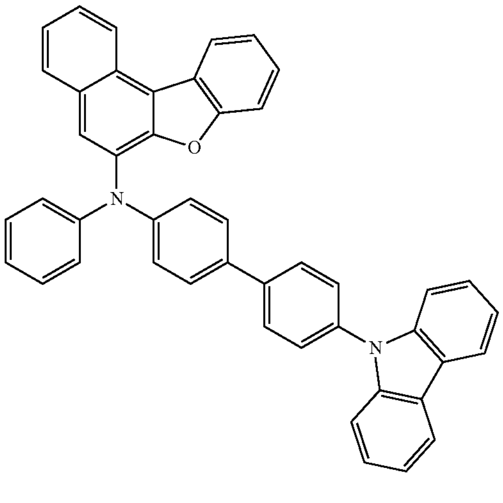

-continued
(348)
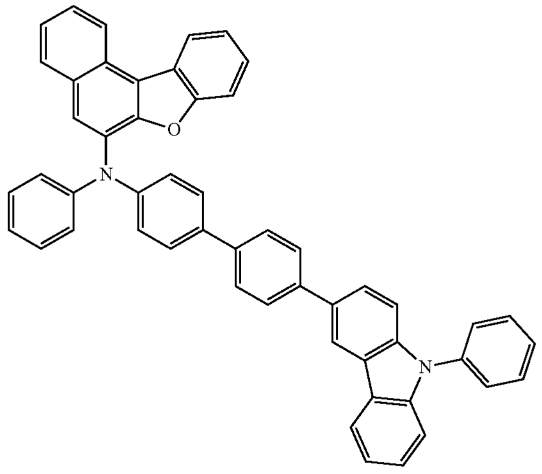
(349)
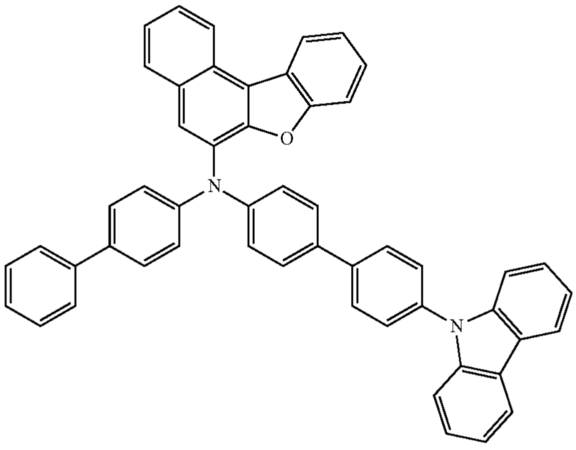
(350)
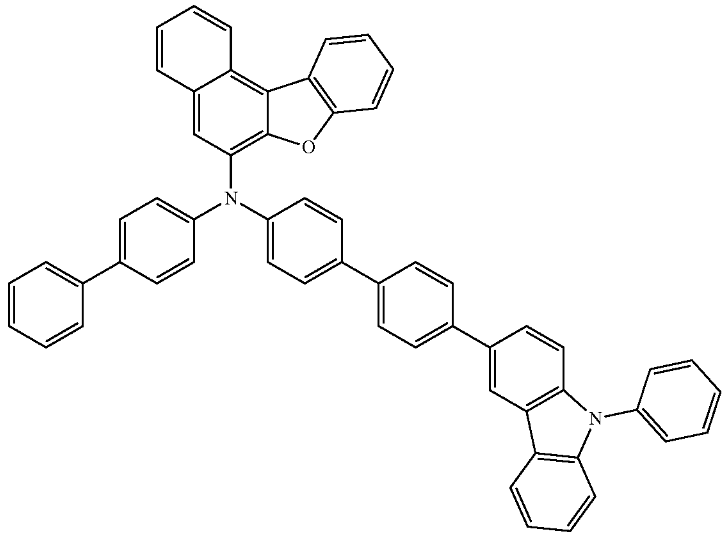
[Chemical Formula 21]
(351)
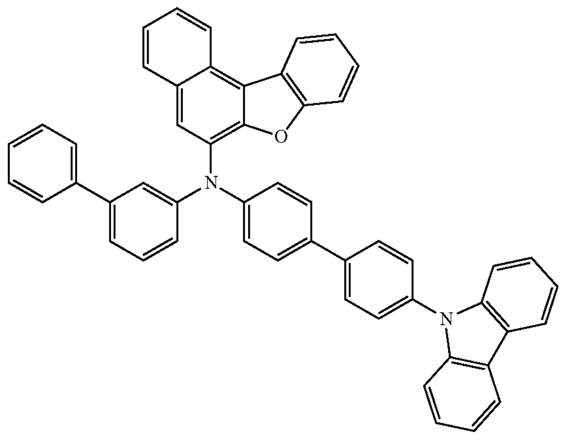
(352)
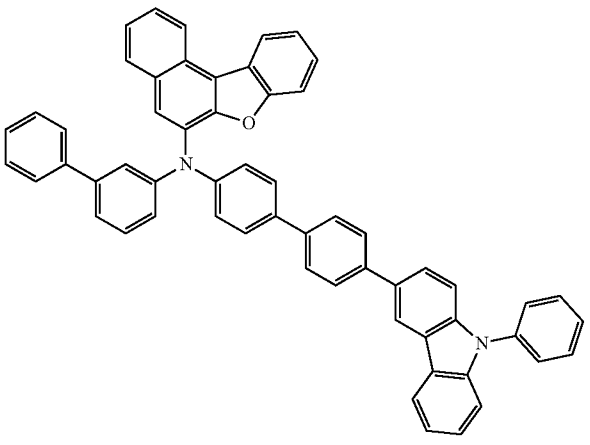

-continued
(353)
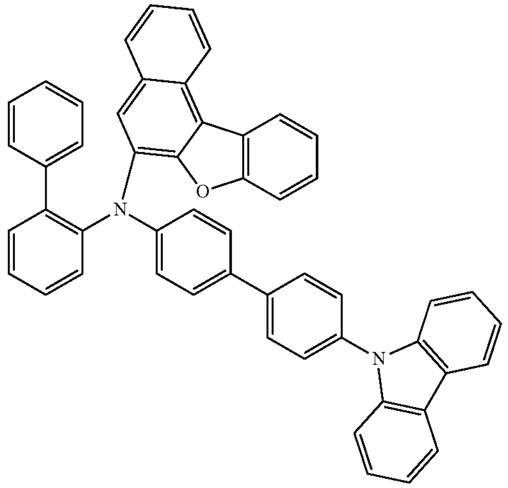
(354)
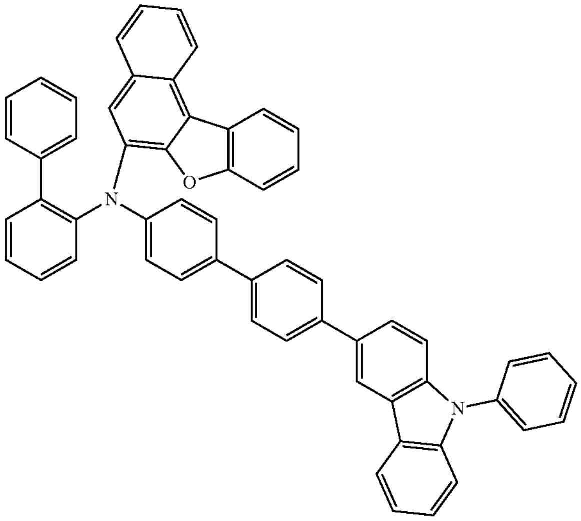
(355)
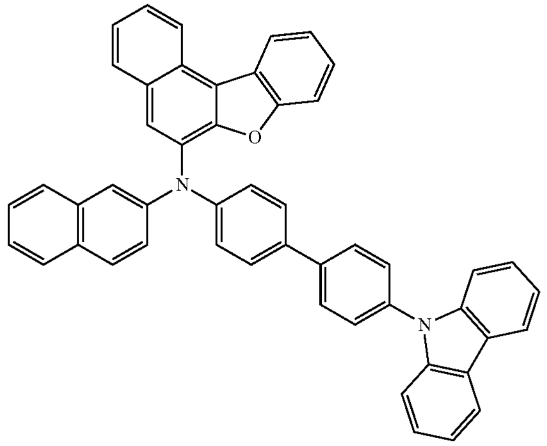
(356)
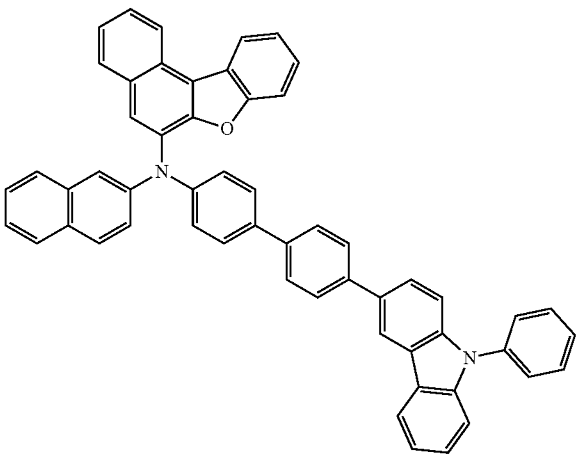
(357)
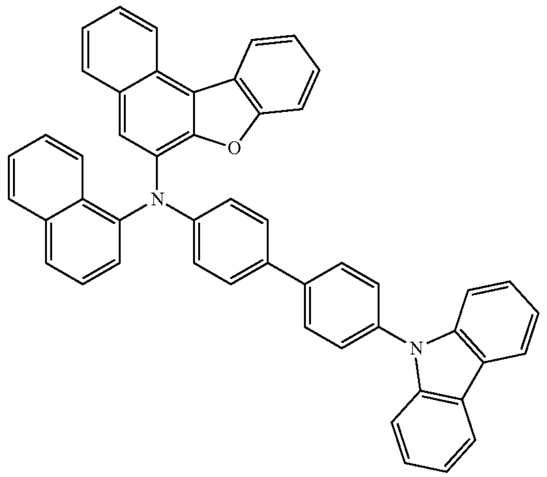
(358)
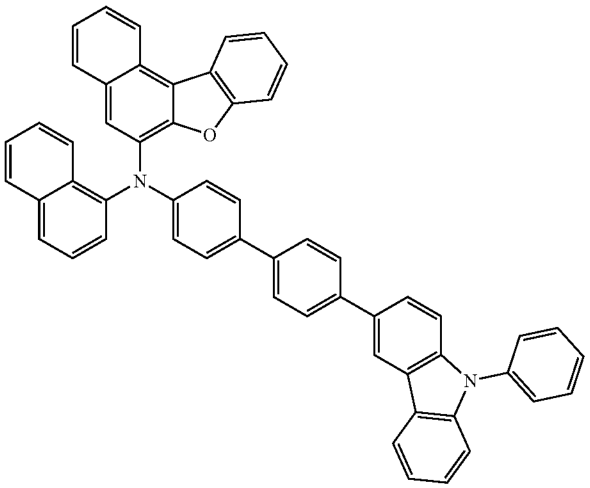

-continued
(359)
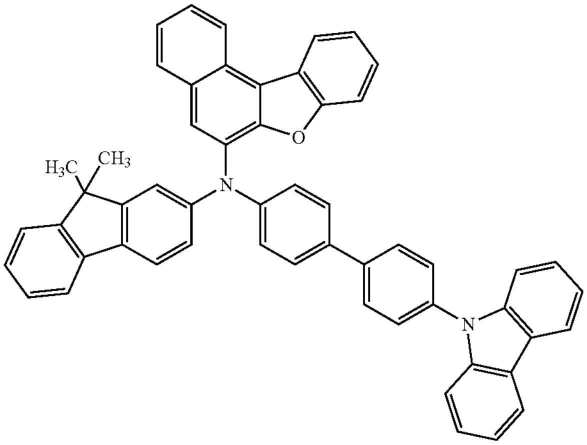
(360)
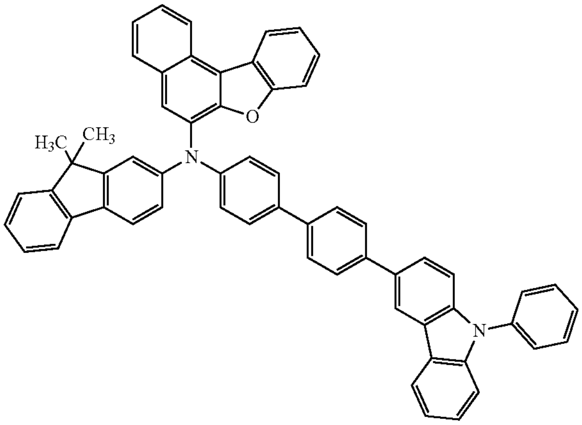
(361)
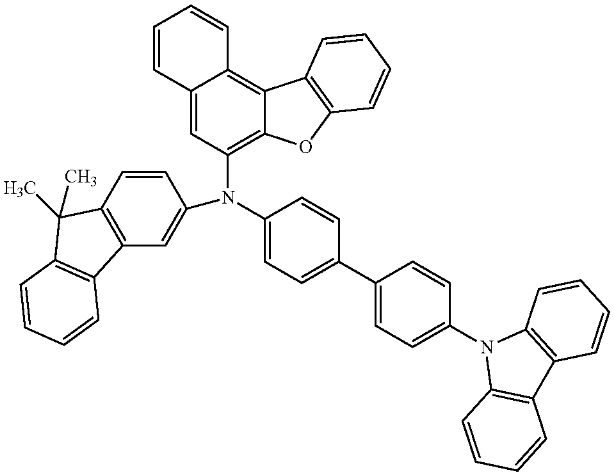
[Chemical Formula 22]
(362)
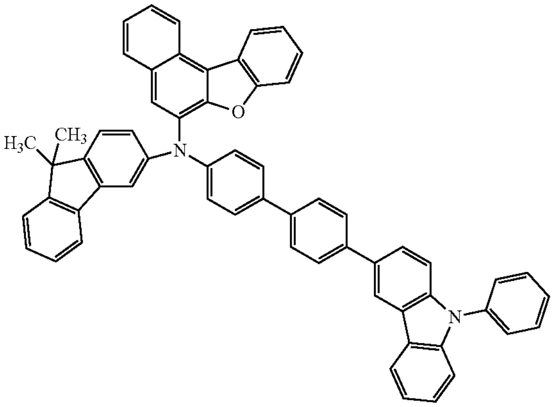
(363)
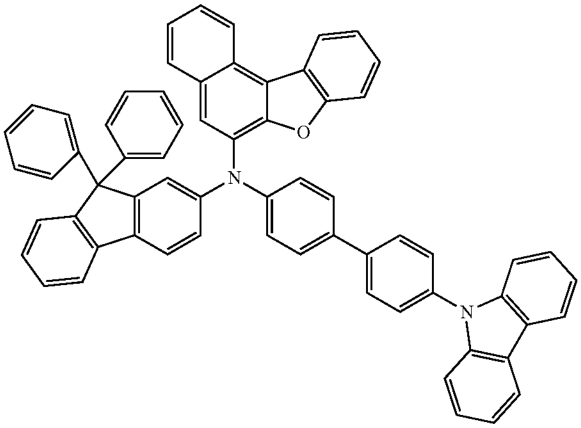

-continued
(364)
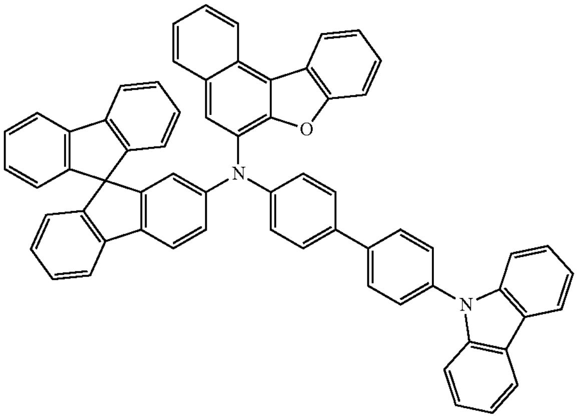
(365)
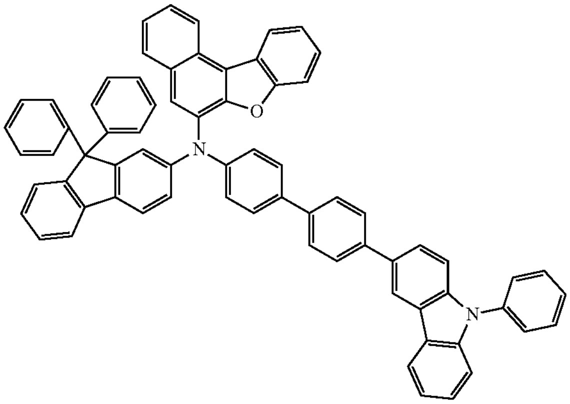
(366)
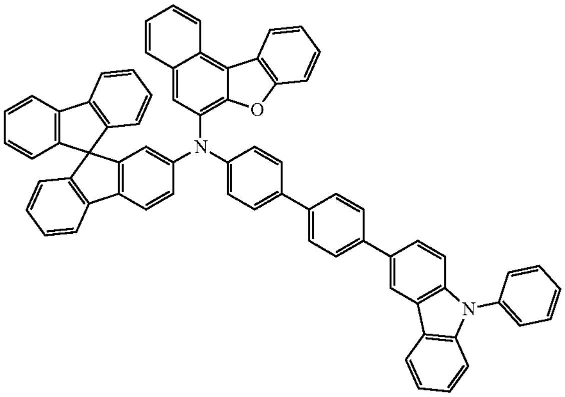
(367)
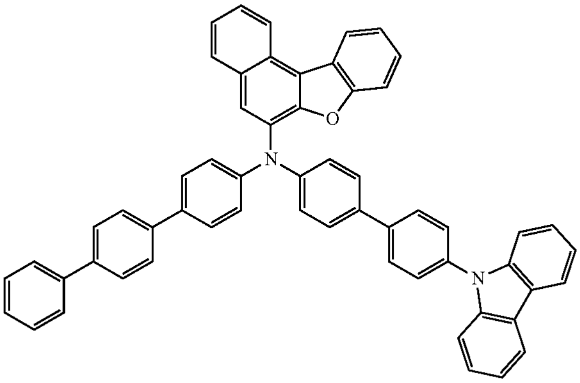
(368)
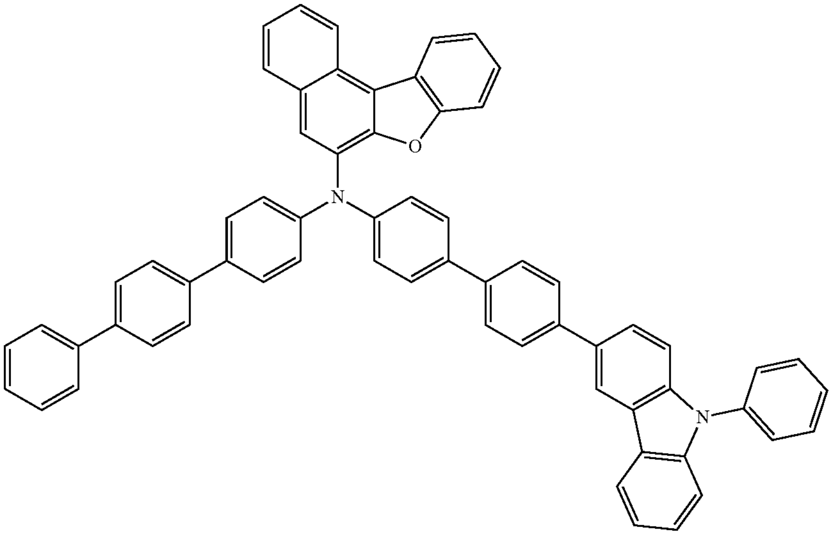

-continued
(369)
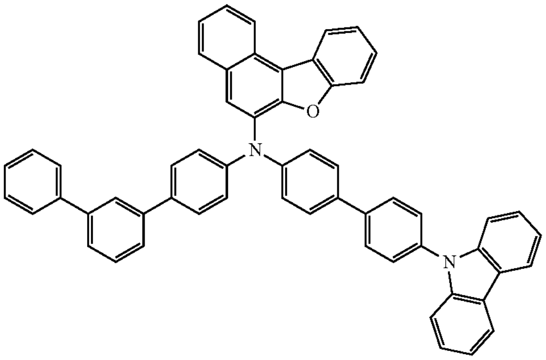
(370)
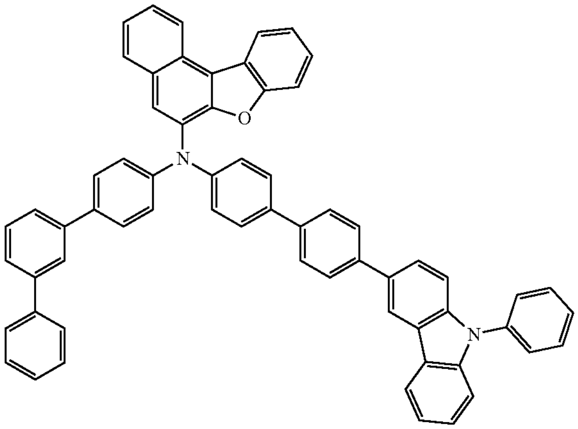
(371)
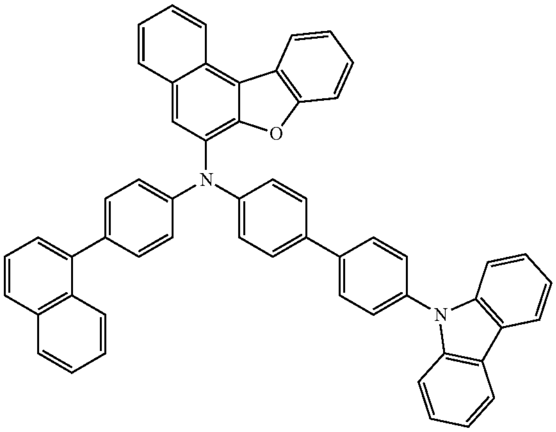
(372)
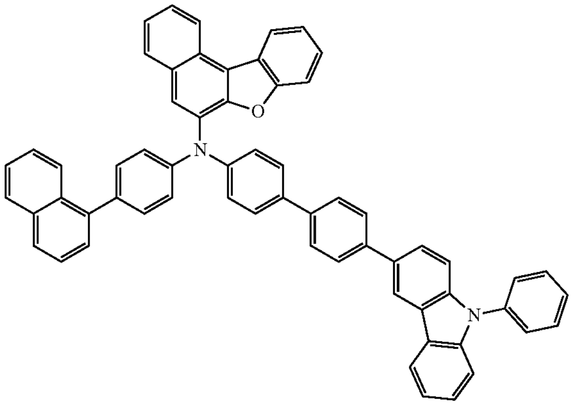
[Chemical Formula 23]
(373)
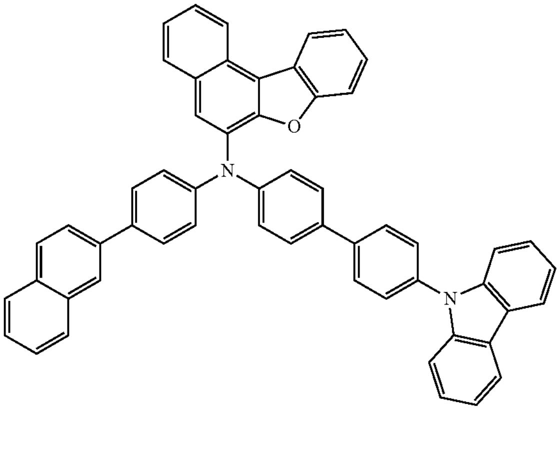
(374)
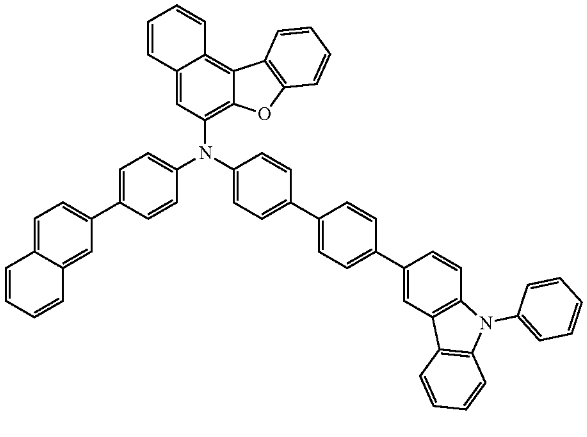

-continued
(375)
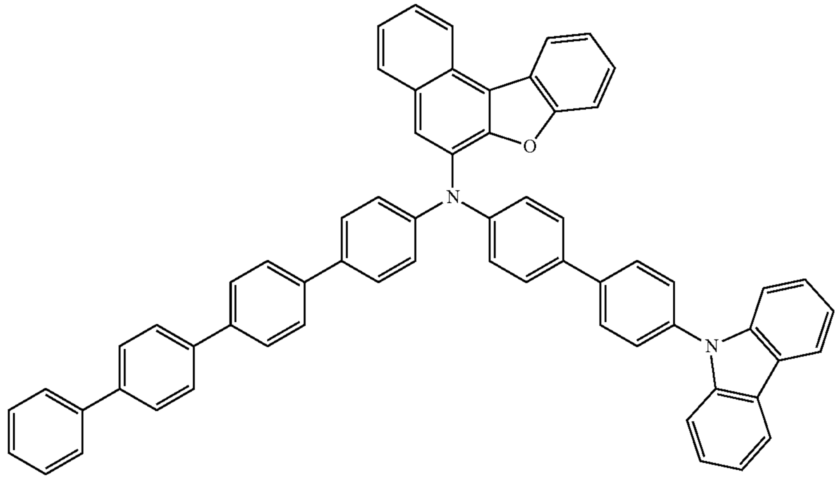
(376)
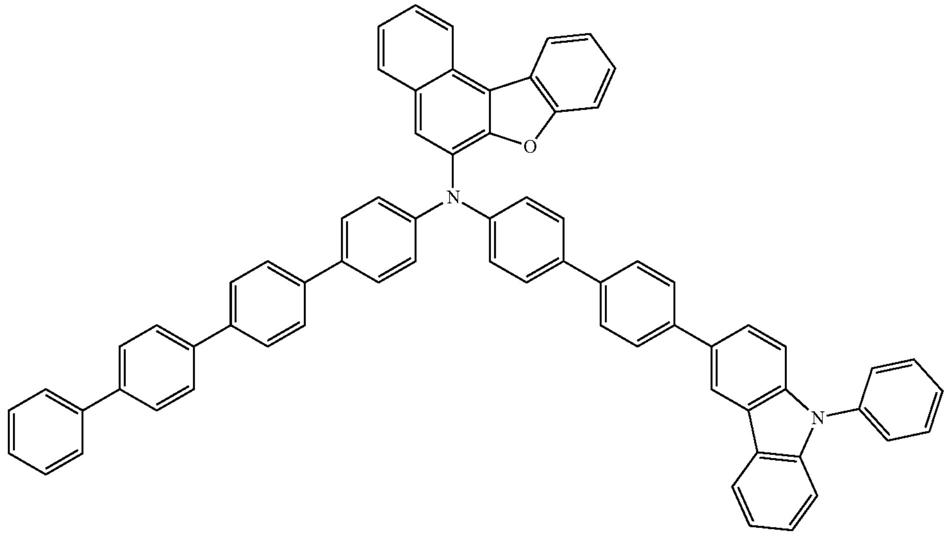
(377)
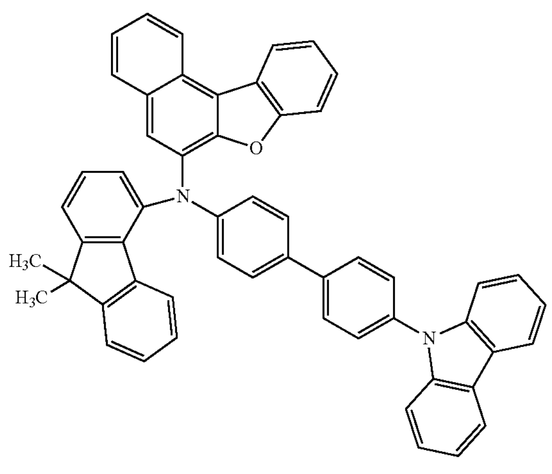
(378)
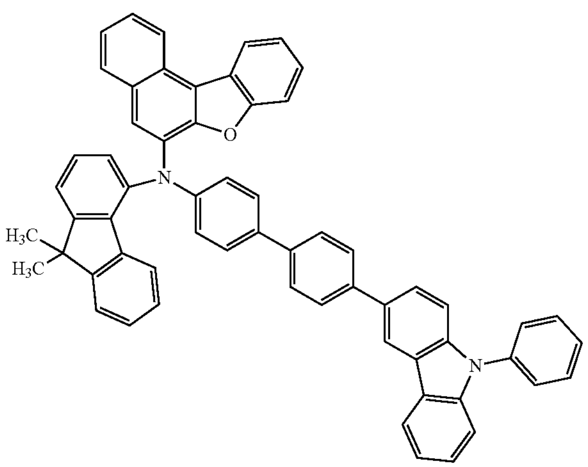

-continued
(379)
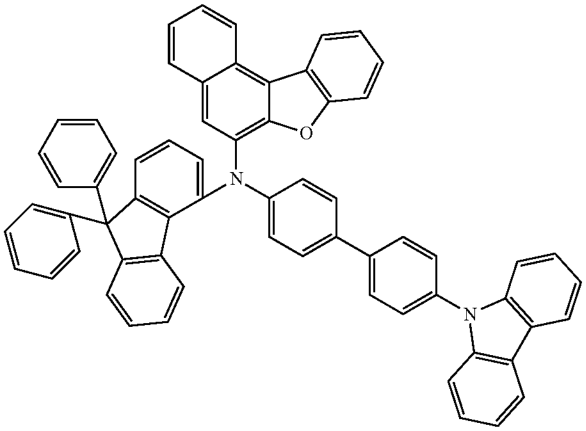
(380)
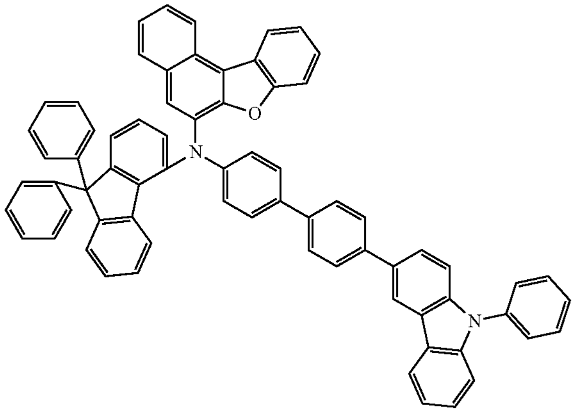
(381)
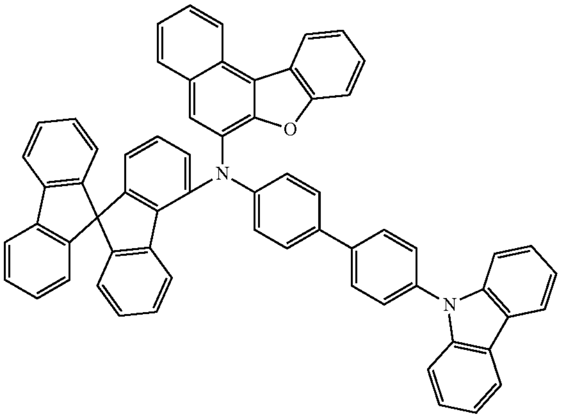
(382)
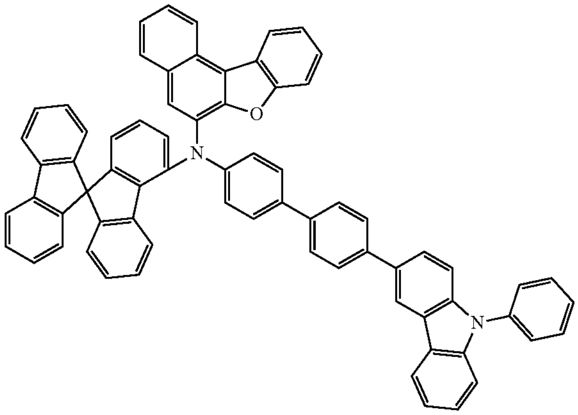
[Chemical Formula 24]
(383)
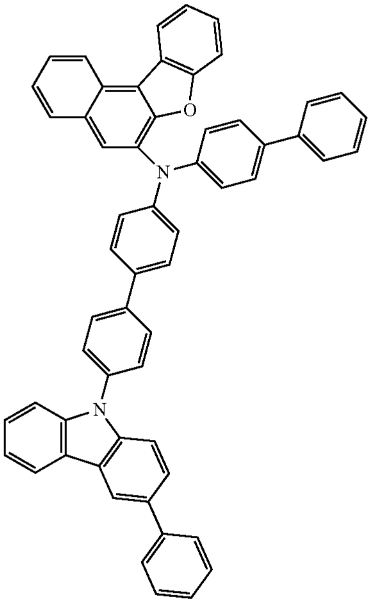
(384)
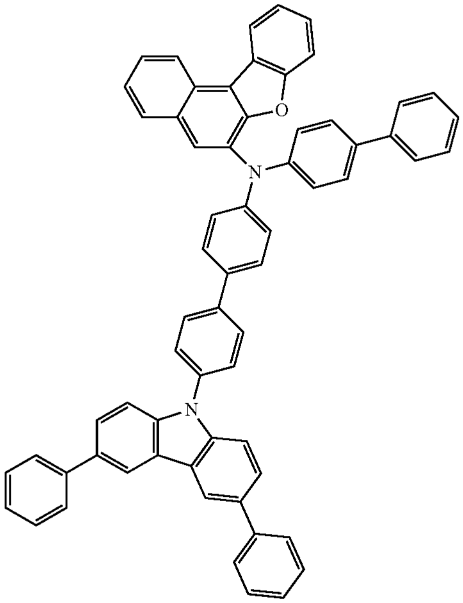

-continued
(385)
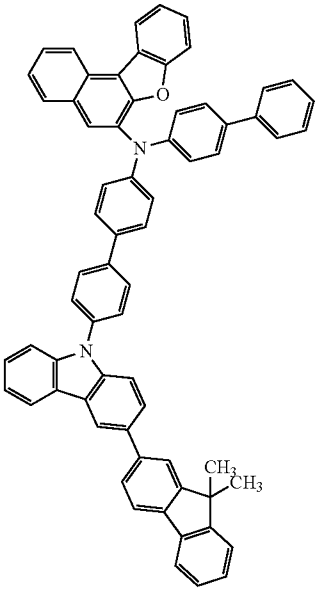
(386)
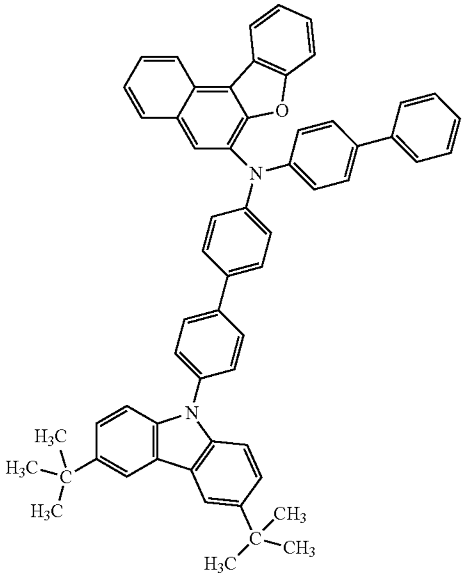
(387)
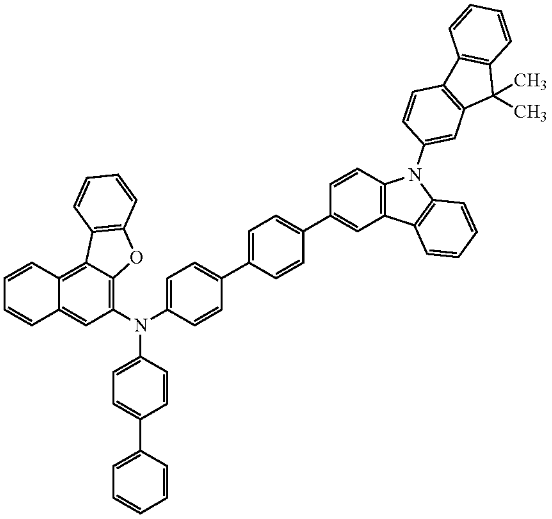
(388)
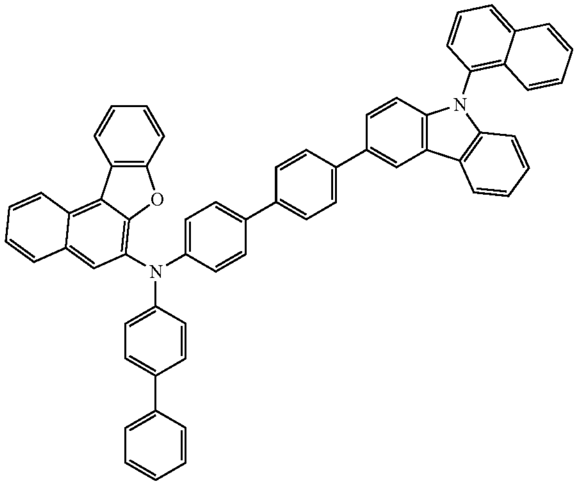
(389)
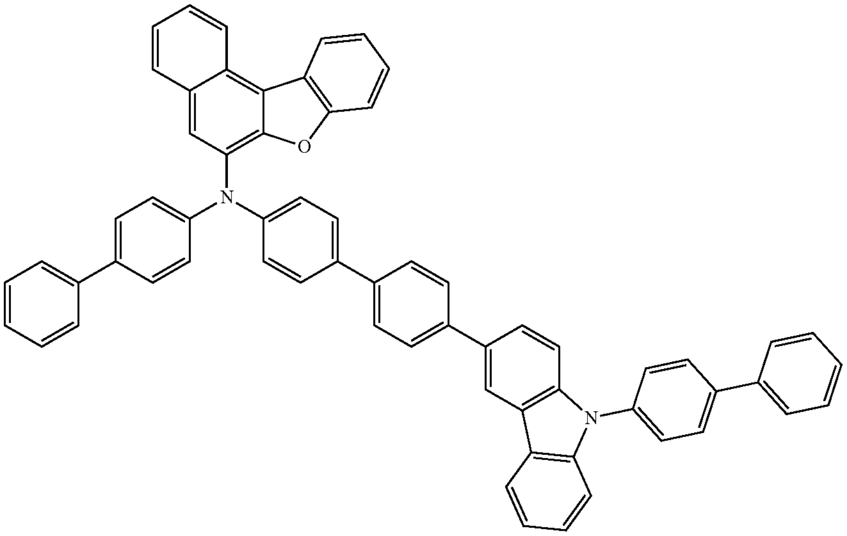

-continued
(390)
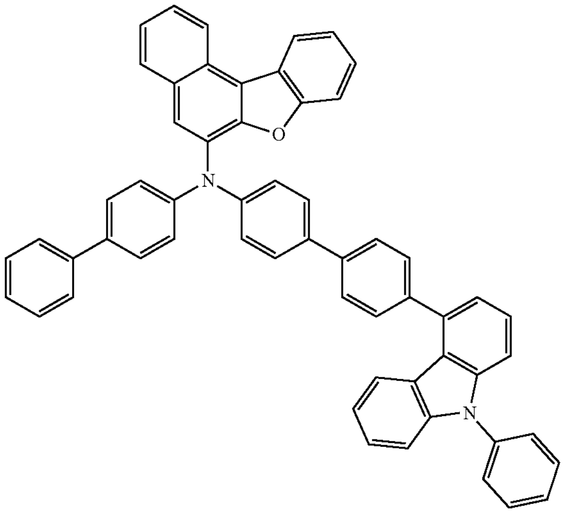
(391)
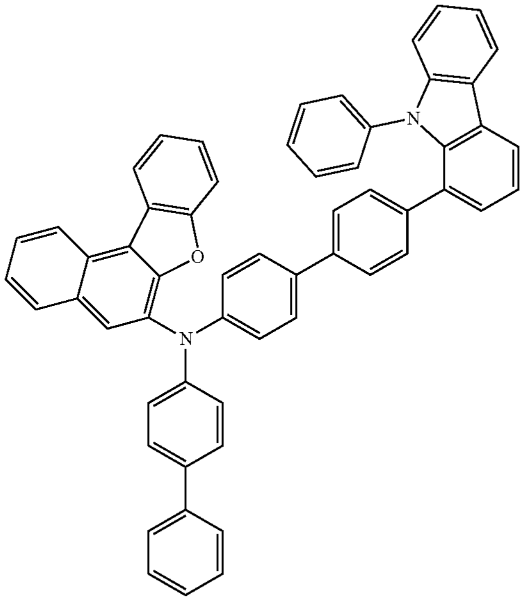
(392)
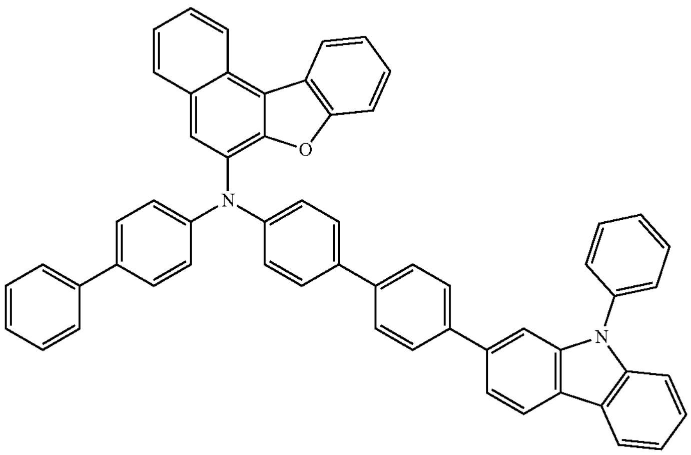

-continued
[Chemical Formula 25]
(393)
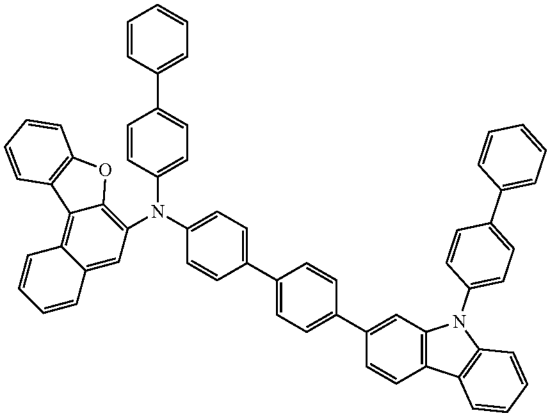
(394)
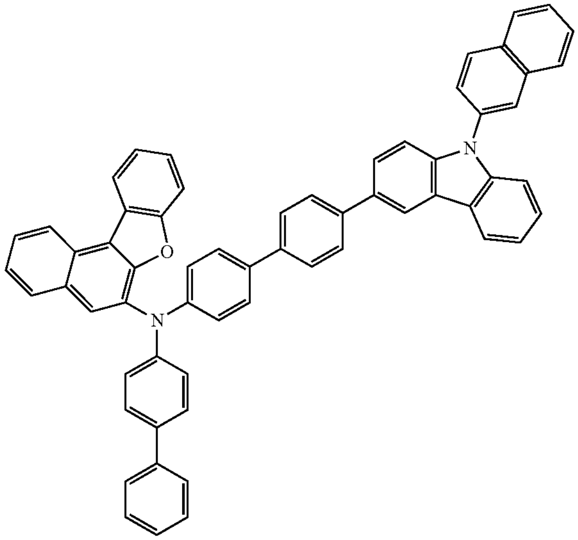
(395)
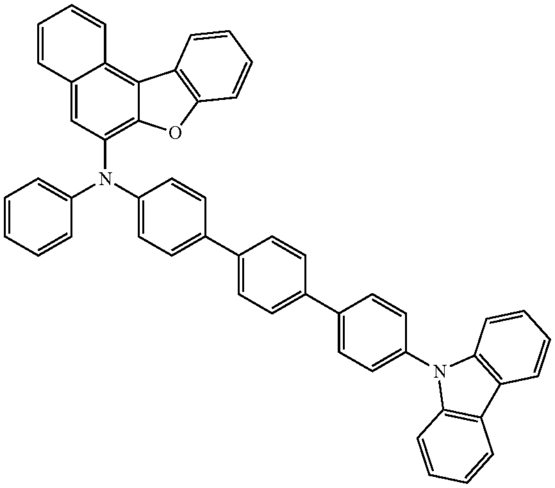
(396)
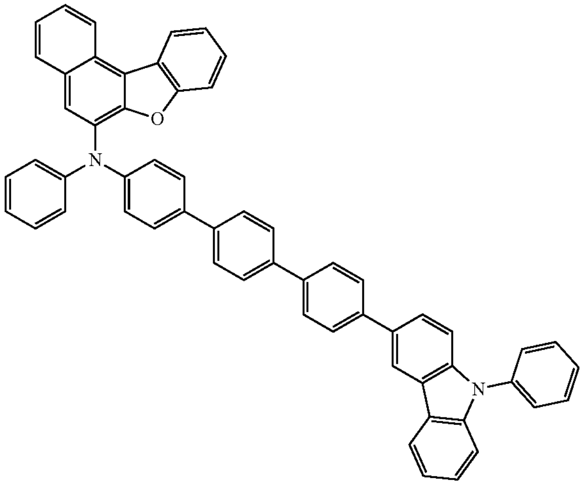
(397)
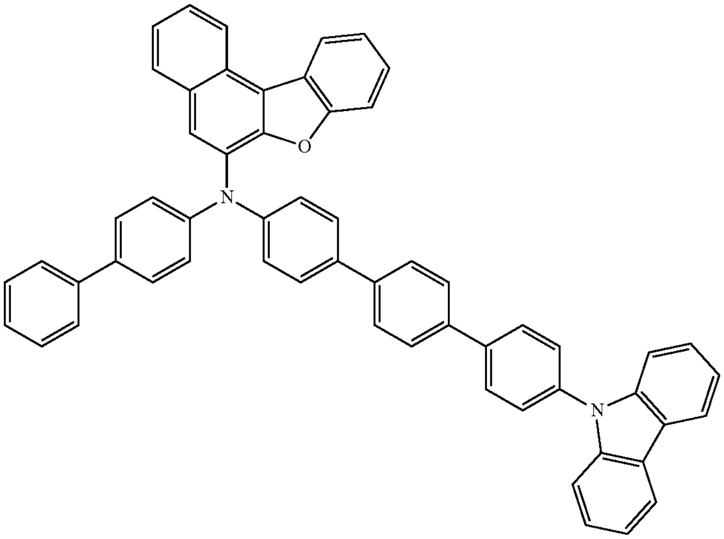

-continued
(398)
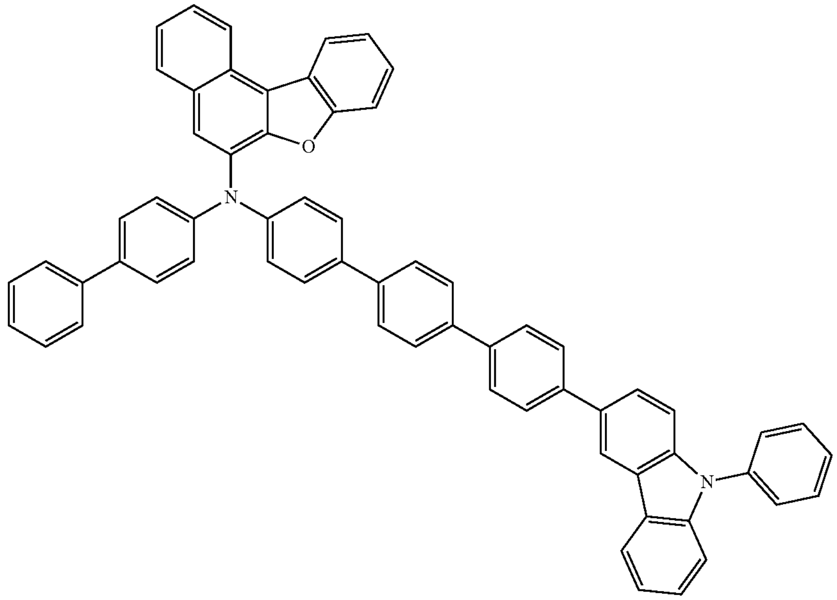
(399)
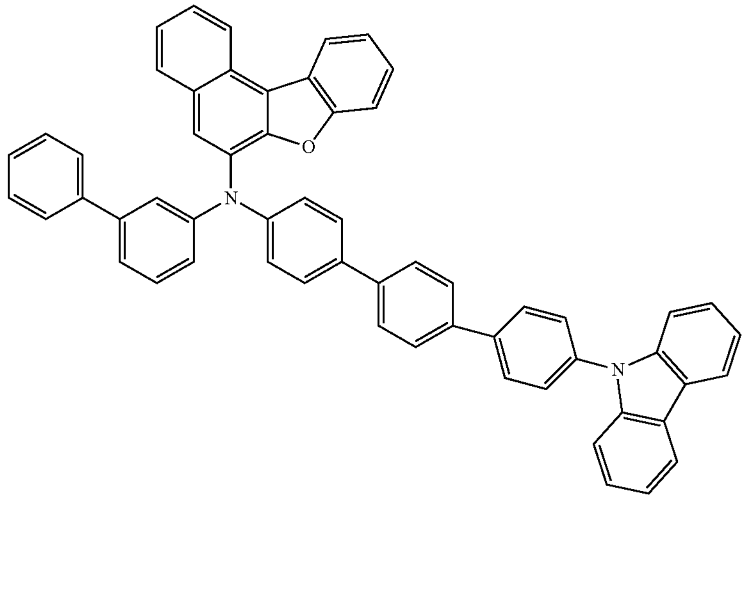

-continued
(400)
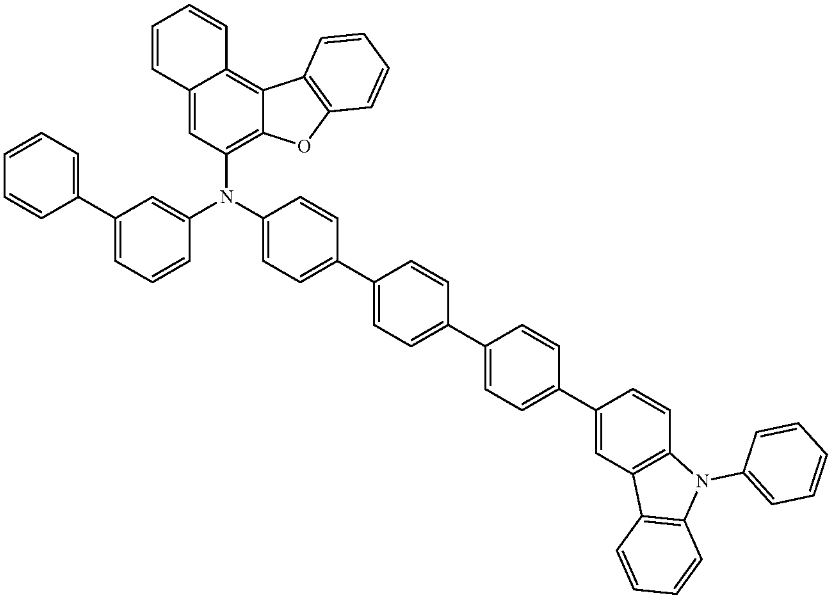
(401)
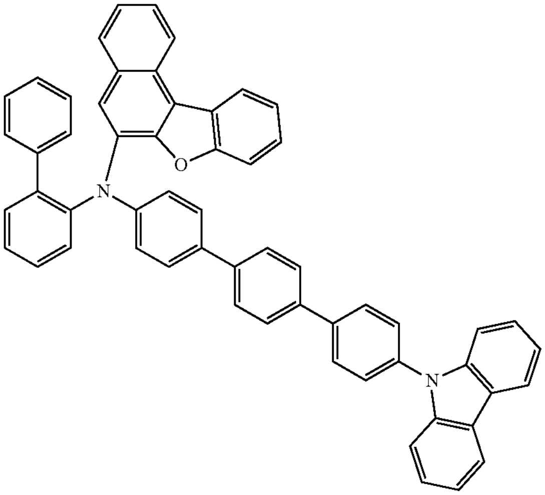
(402)
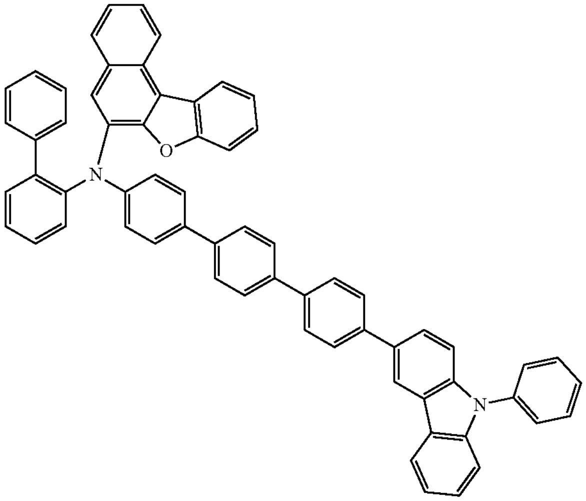
(403)
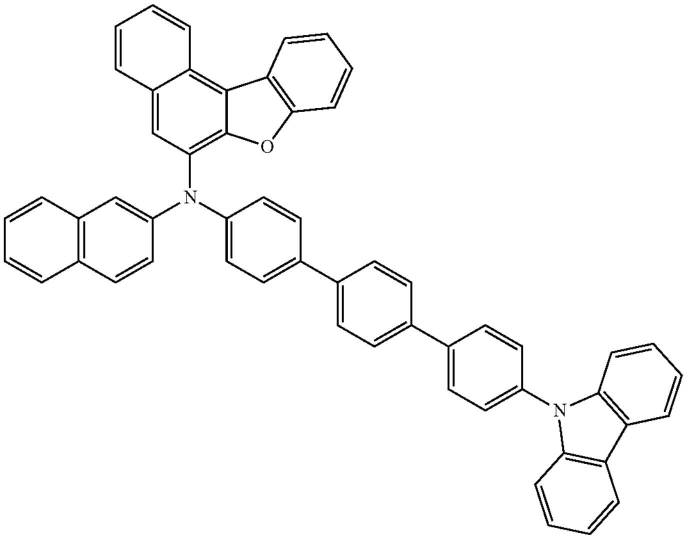

-continued
[Chemical Formula 26]
(404)
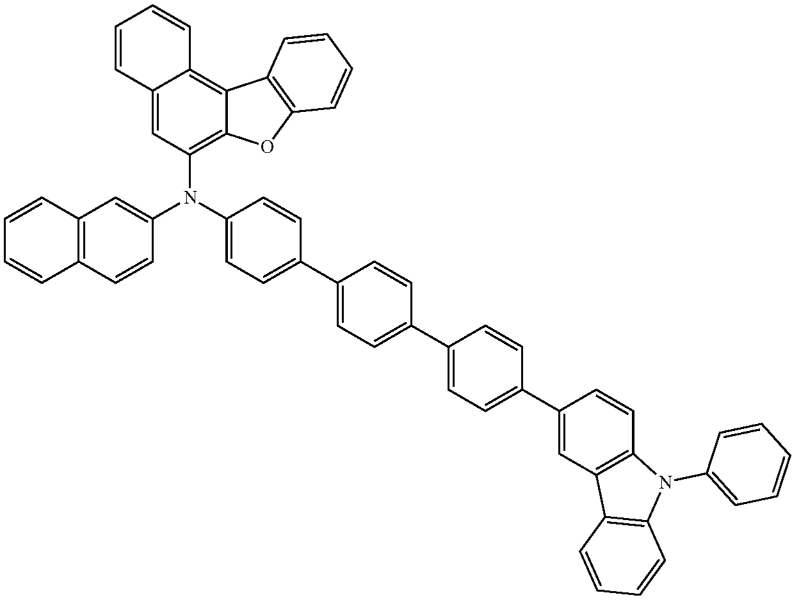
(405)
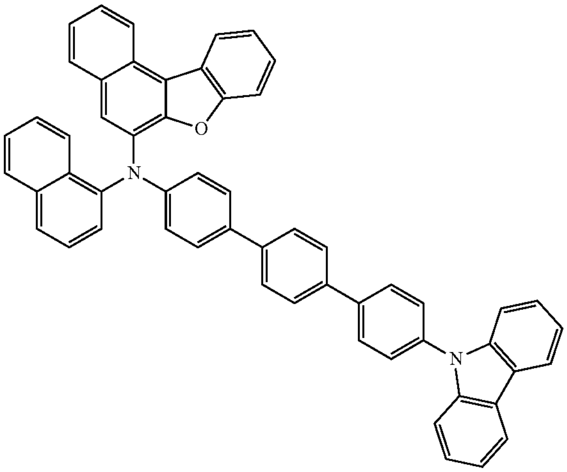
(406)
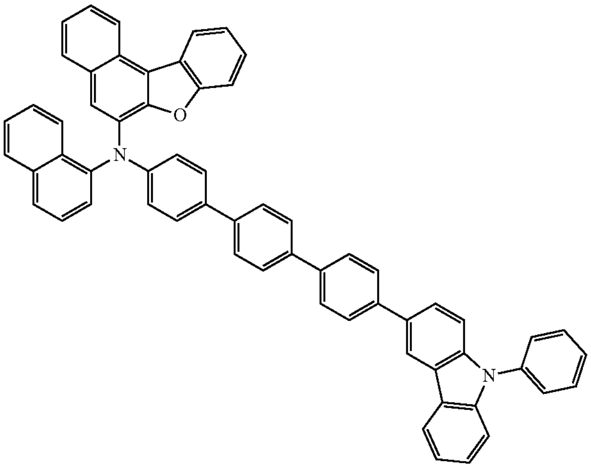

-continued
(407)
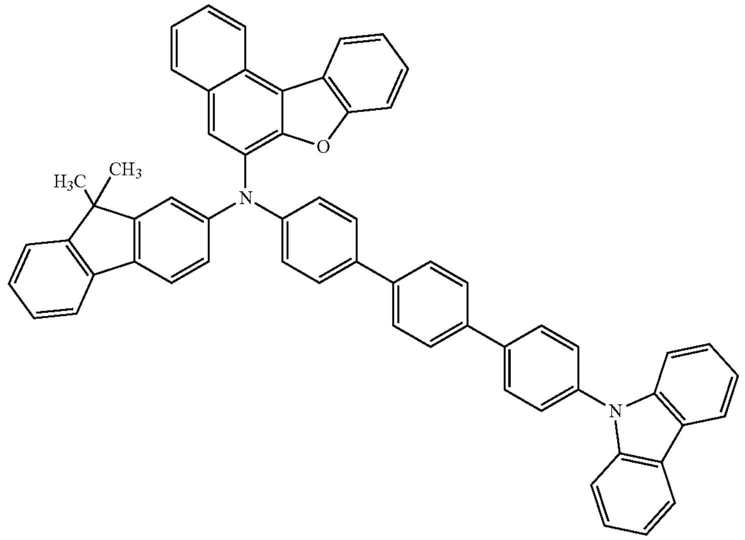
(408)
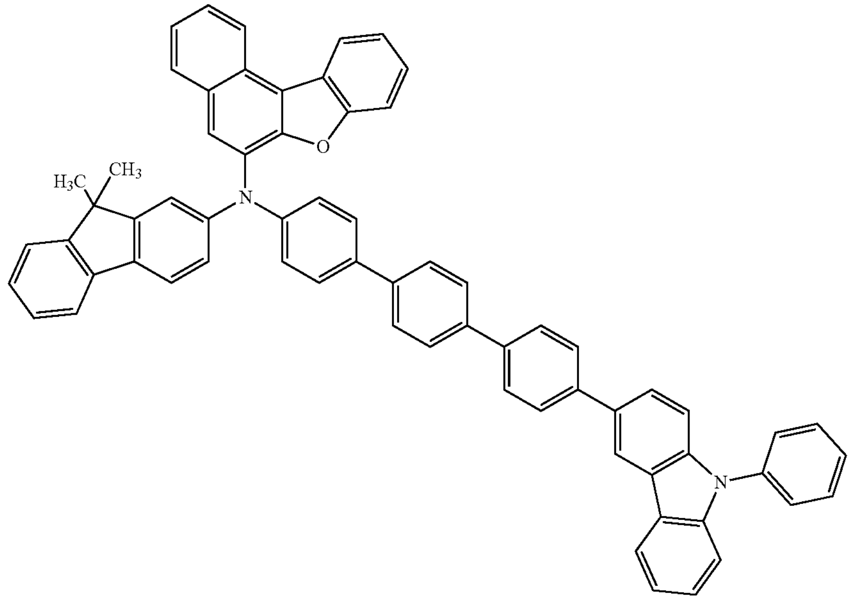

-continued
(409)
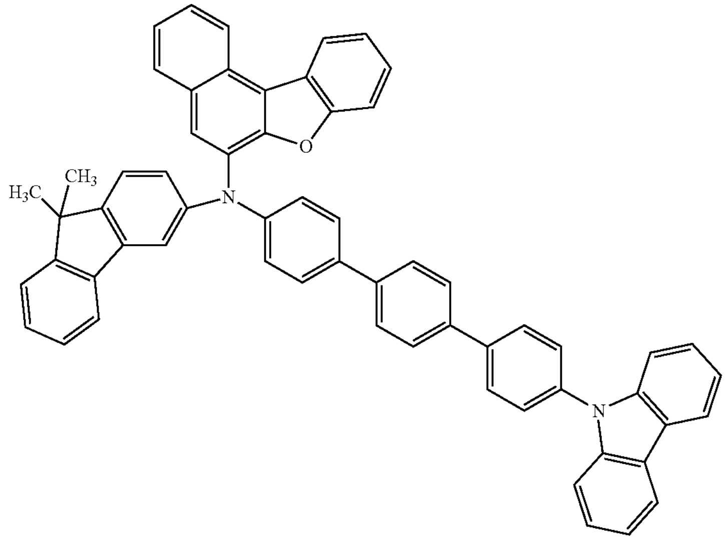
(410)
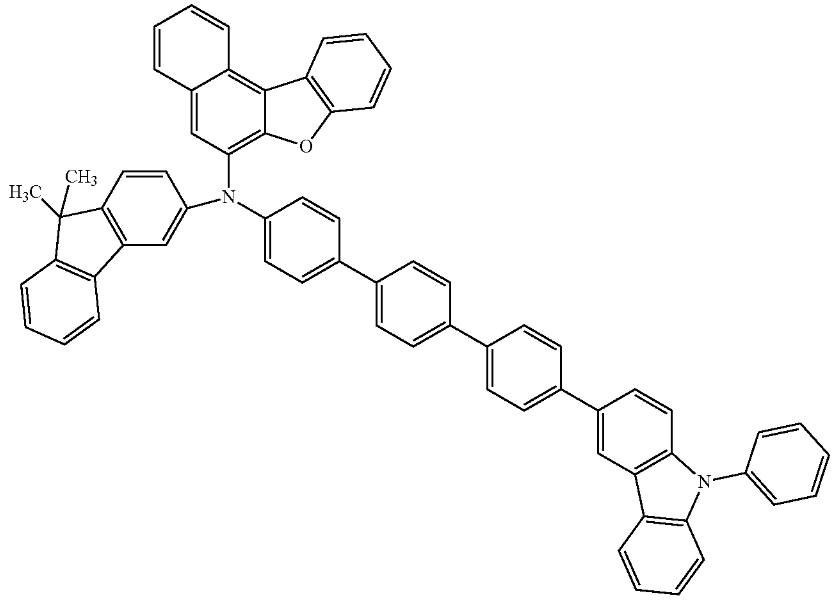

-continued
(411)
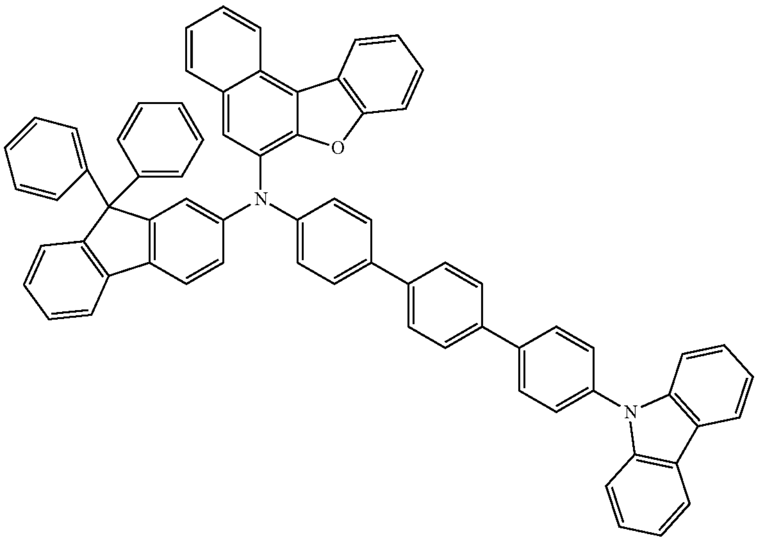
(412)
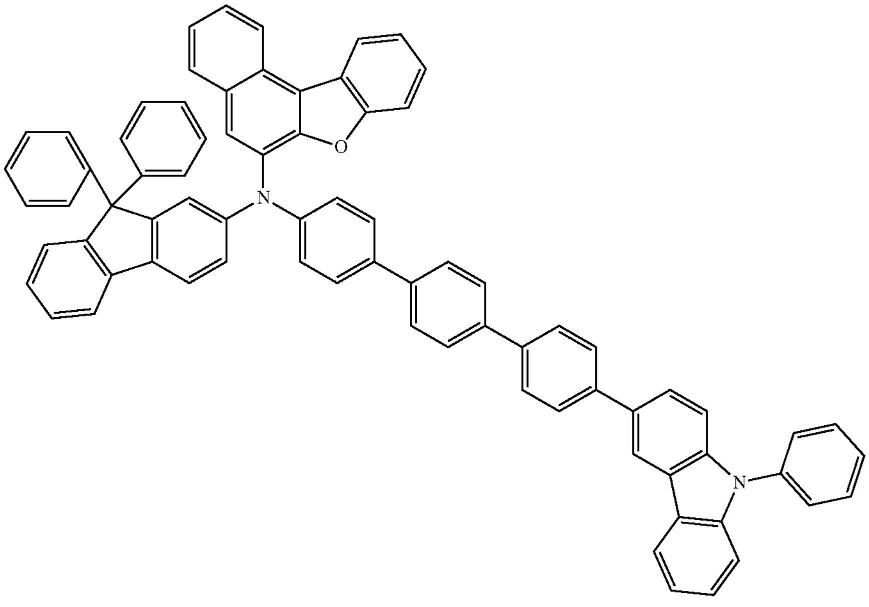

-continued
(413)
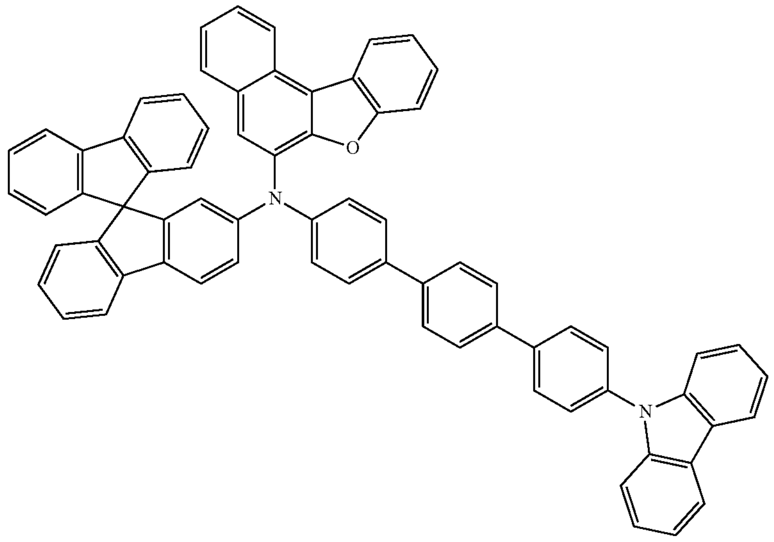
(414)
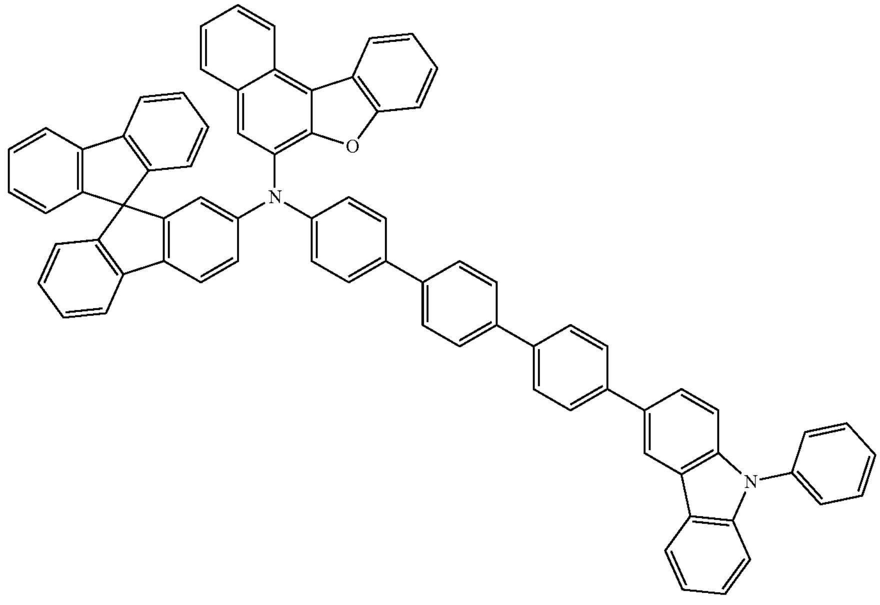

-continued
[Chemical Formula 27]
(415)
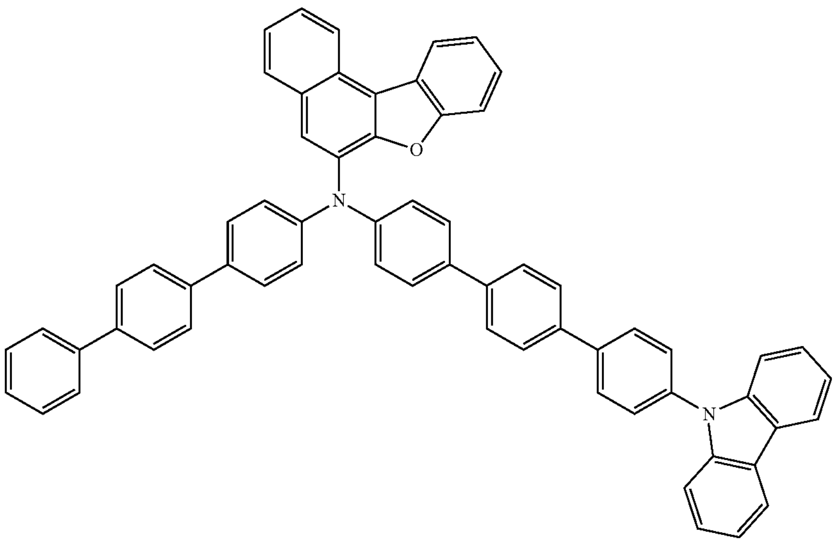
(416)
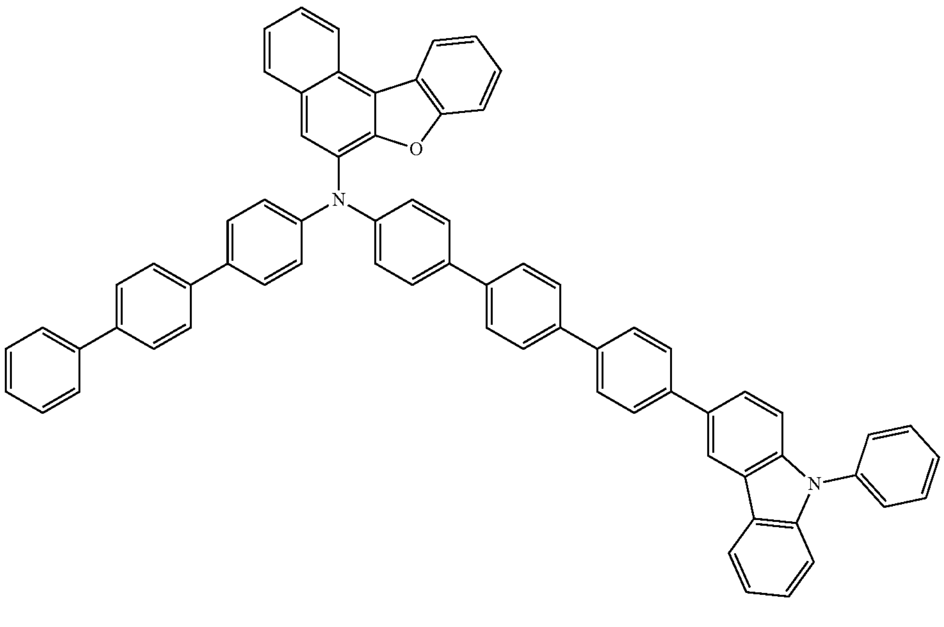

-continued
(417)
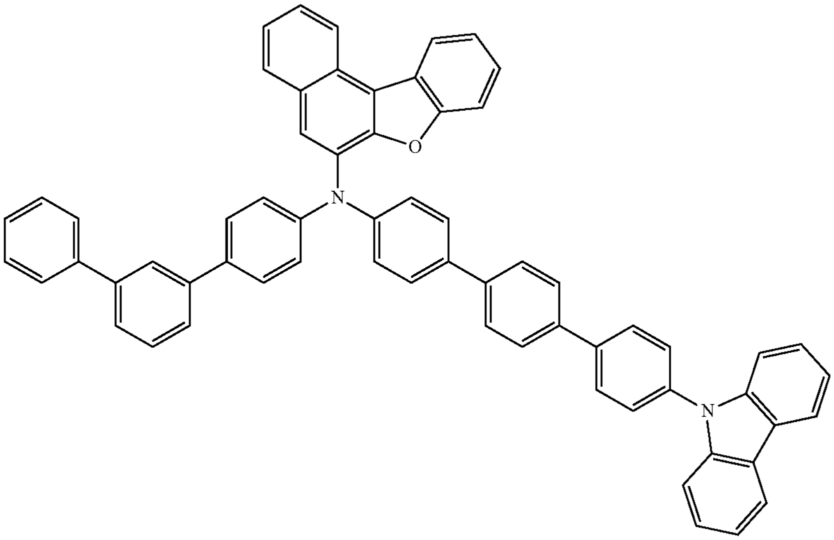
(418)
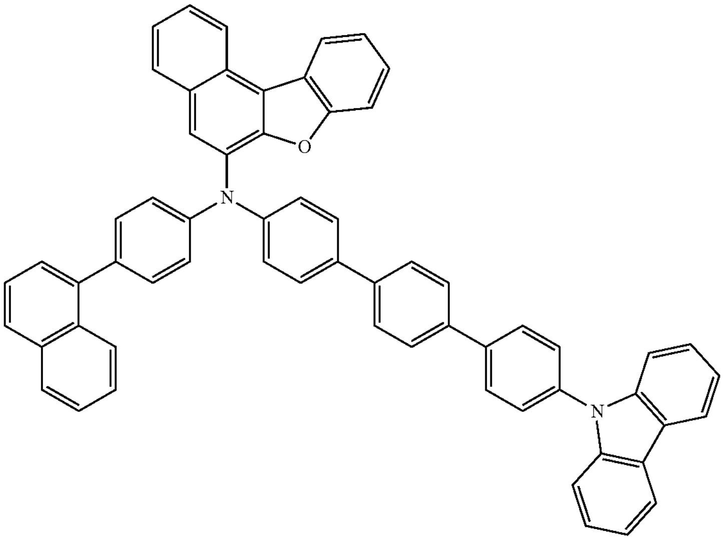

-continued
(419)
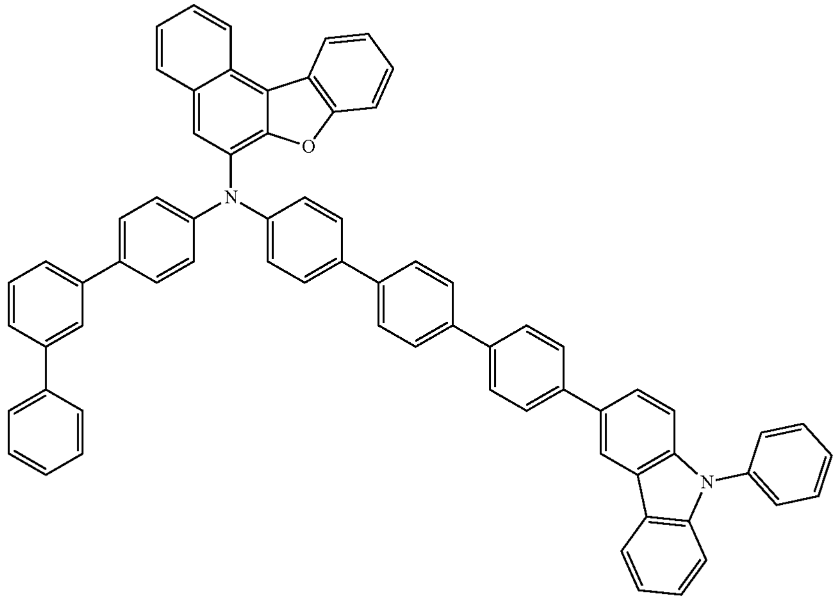
(420)
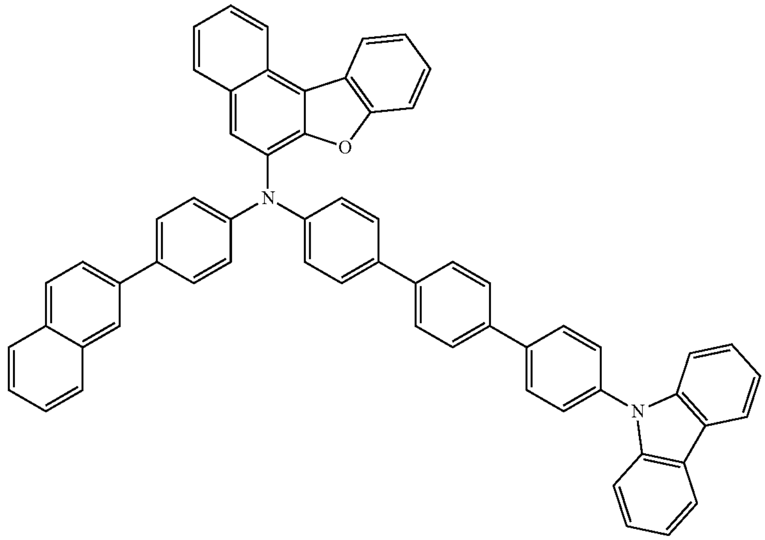

-continued
(421)
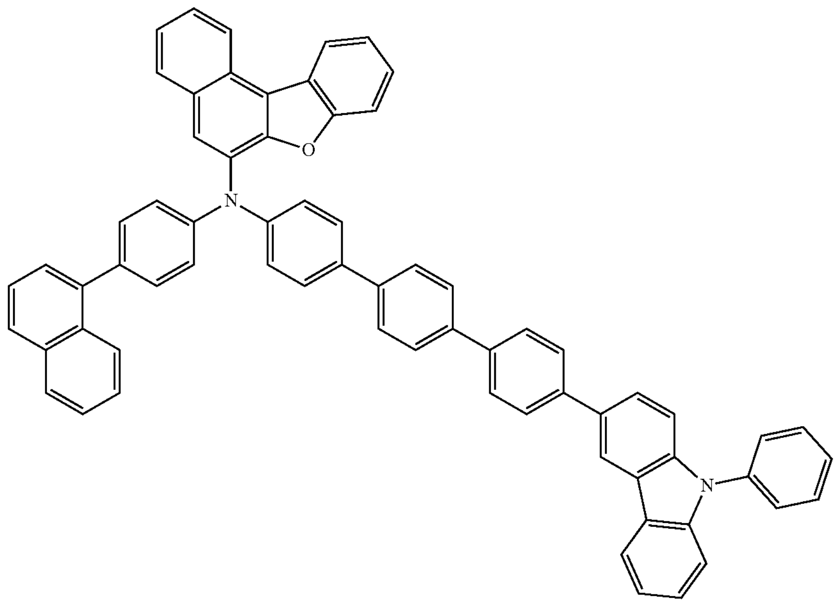
(422)
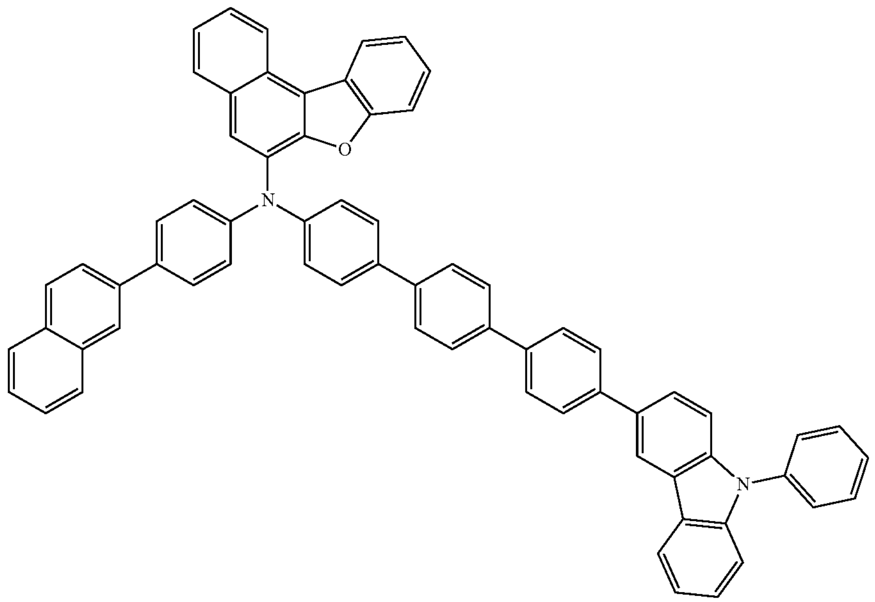

-continued
(423)
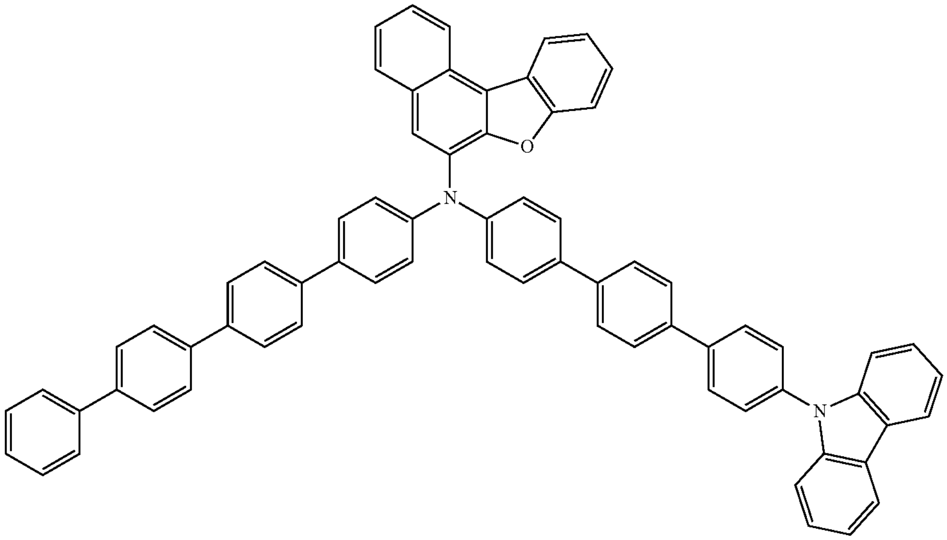
[Chemical Formula 28]
(424)
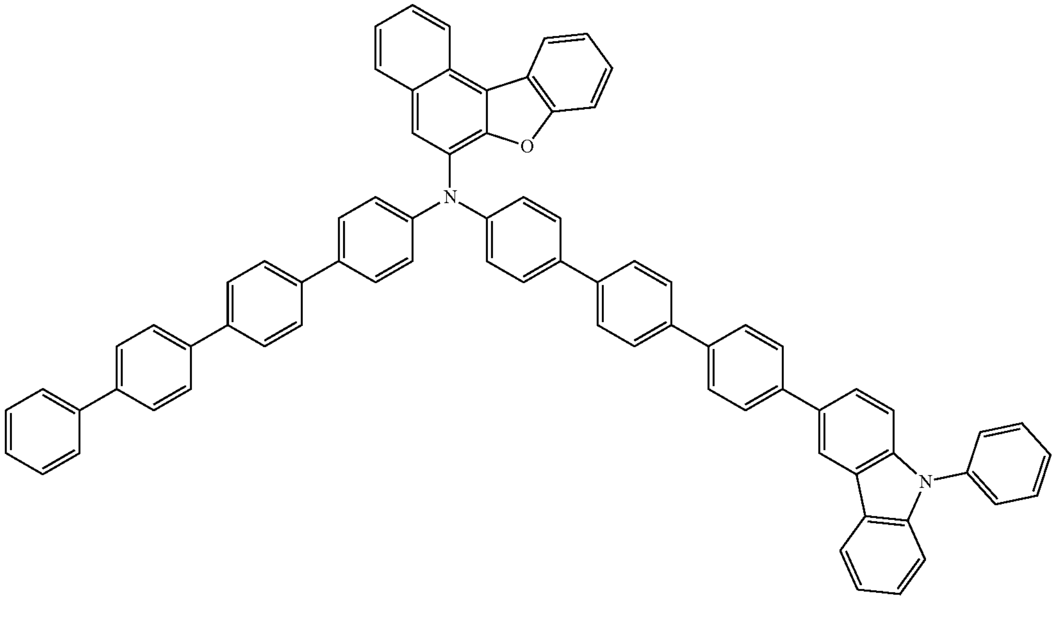

-continued
(425)
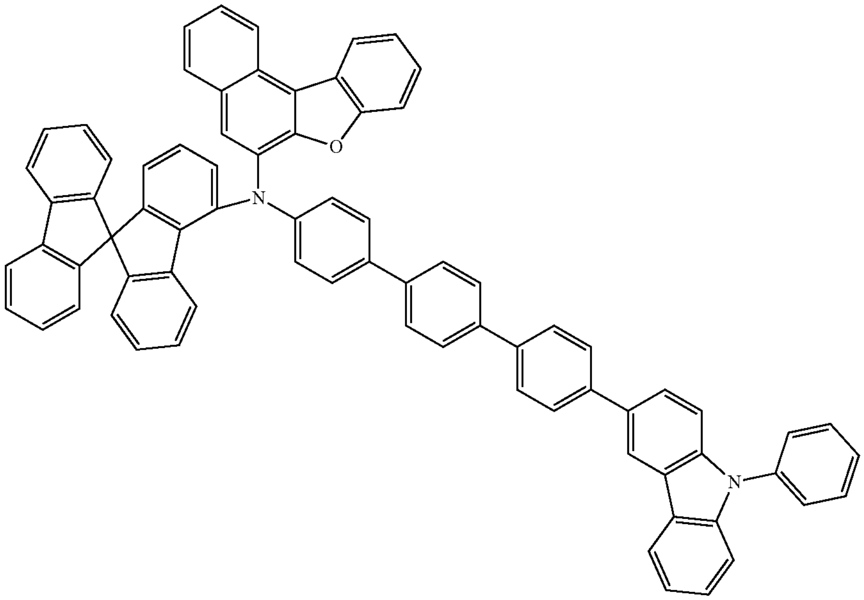
(426)
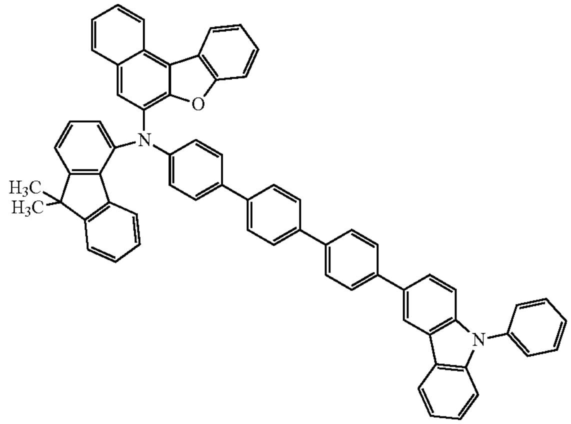
(427)
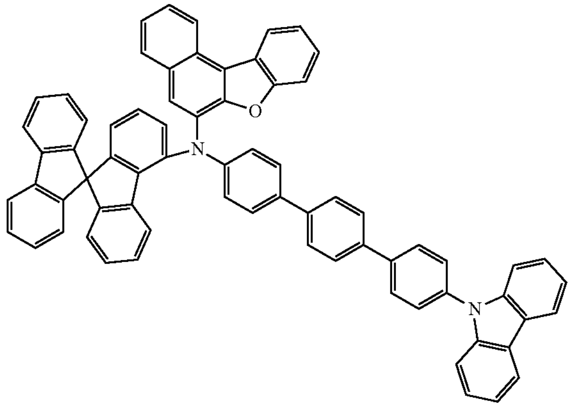
(428)
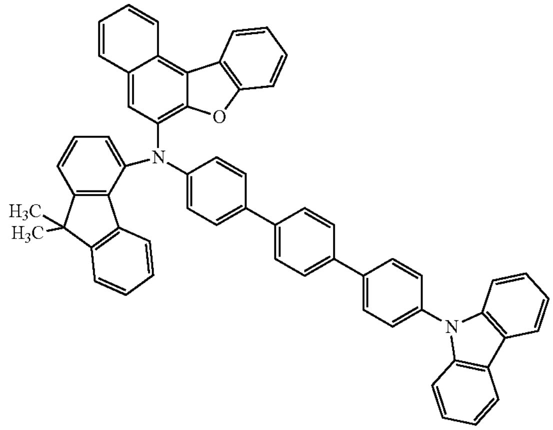
(429)
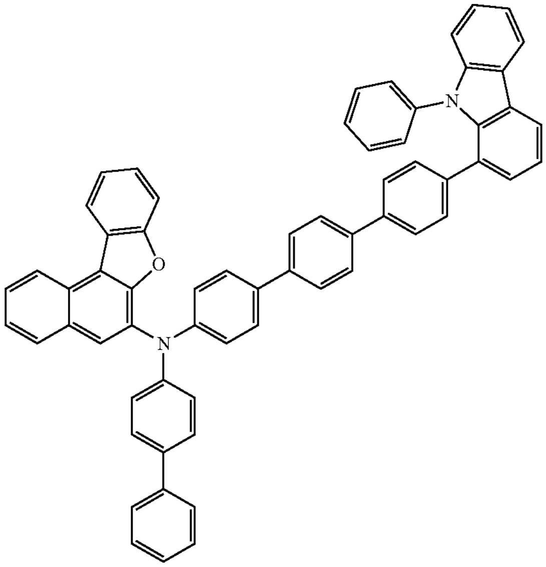

-continued
(430)
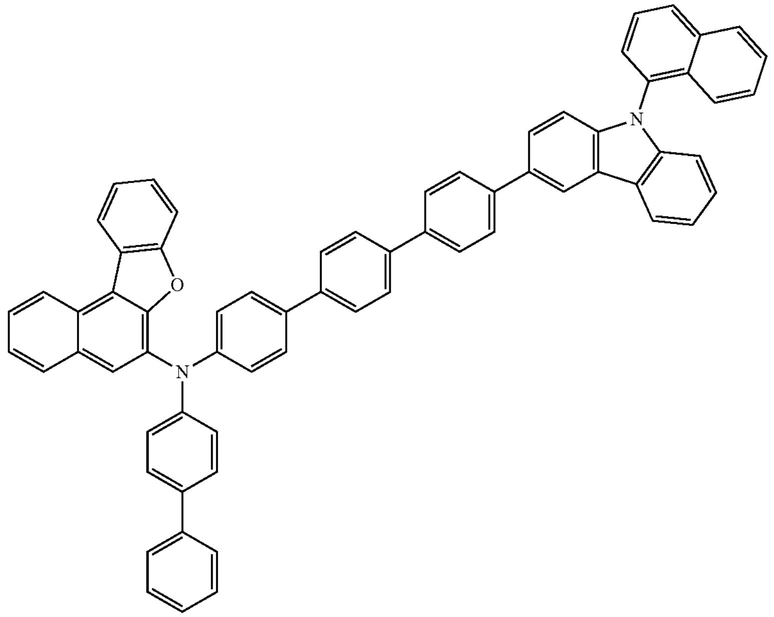
(431)
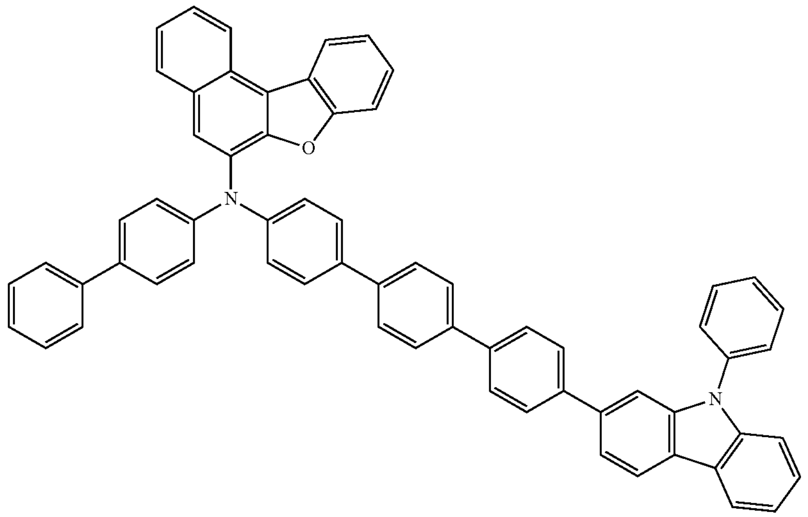

-continued
[Chemical Formula 29]
(432)
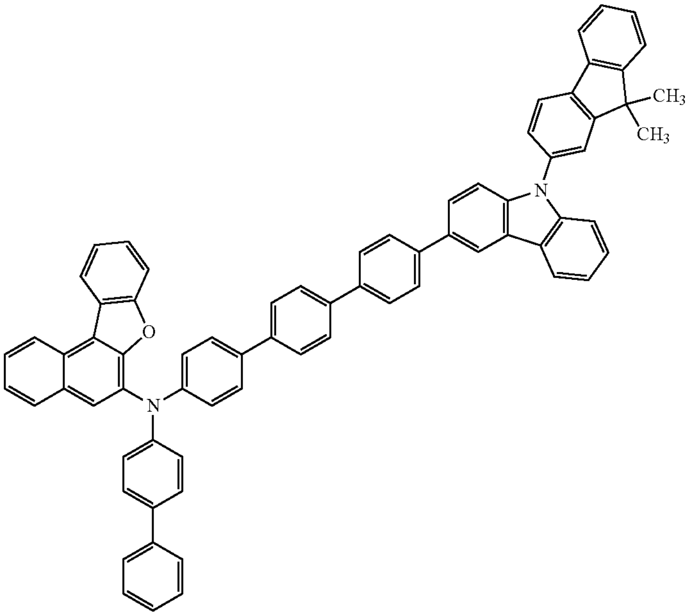
(433)
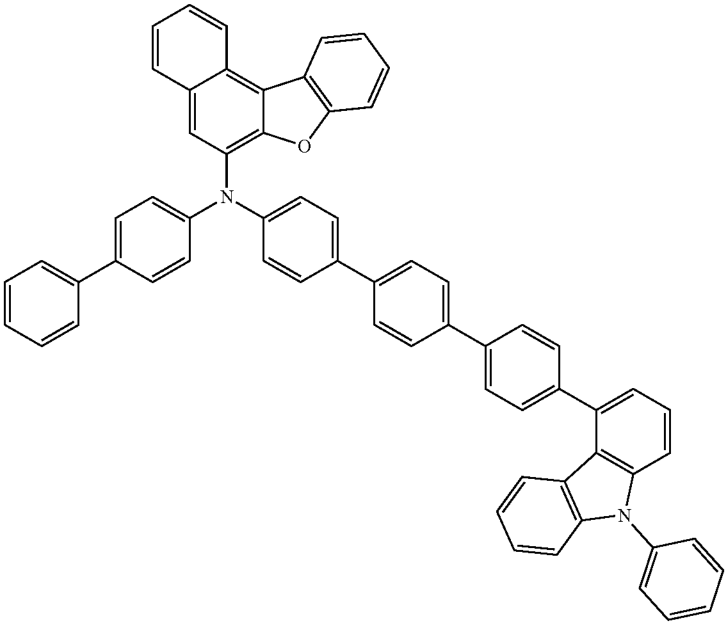

-continued
(434)
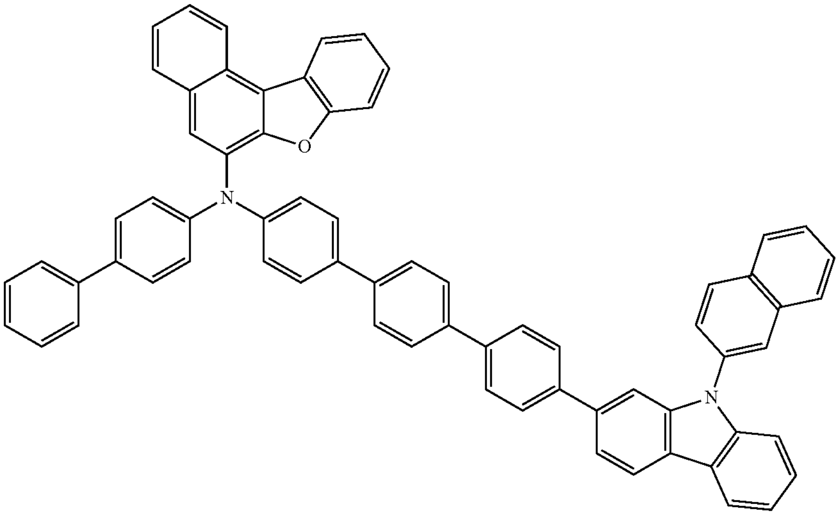
(435)
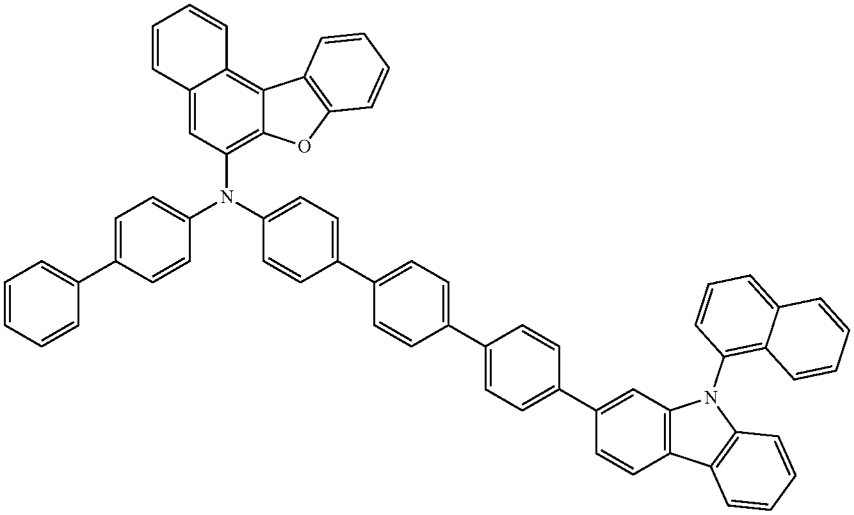
(436)
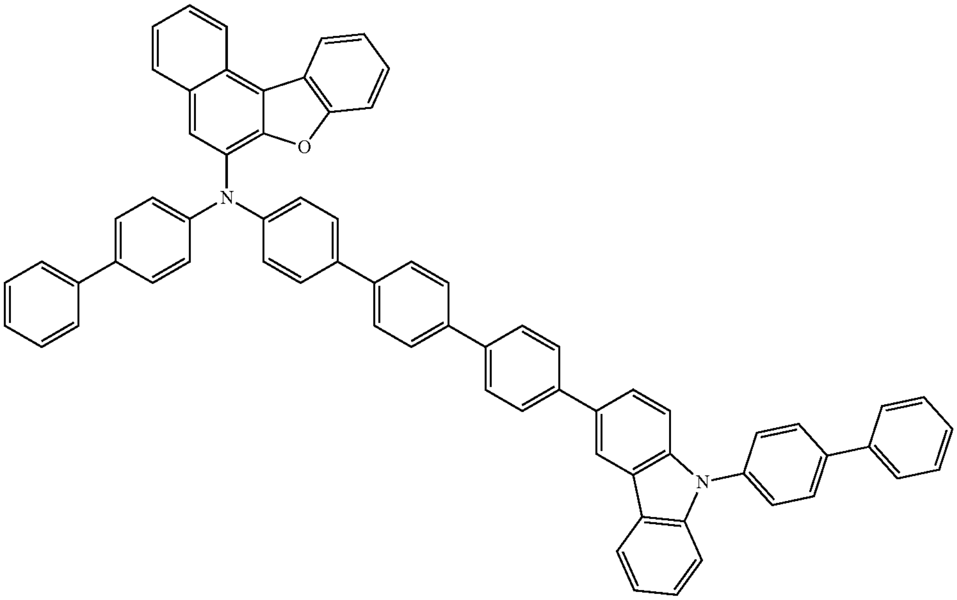

-continued
(437)
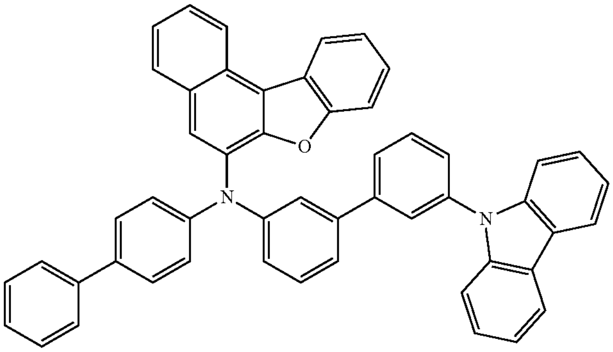
(438)
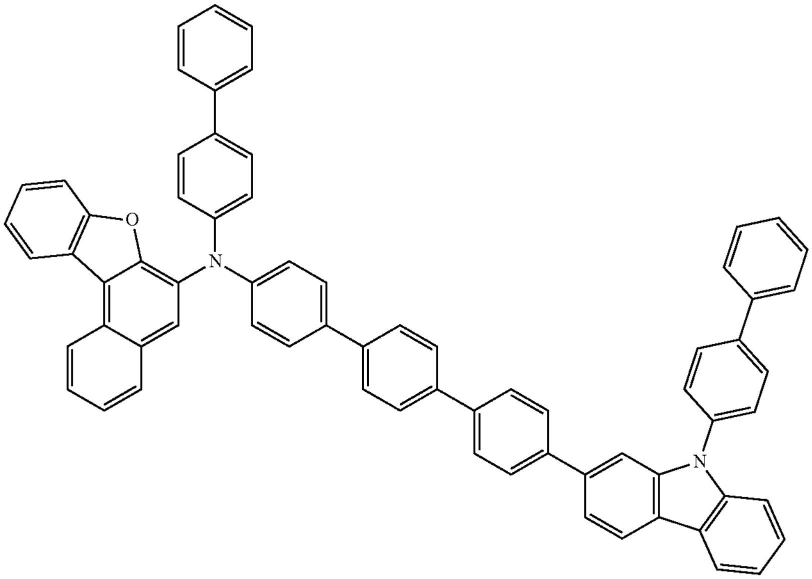
(439)
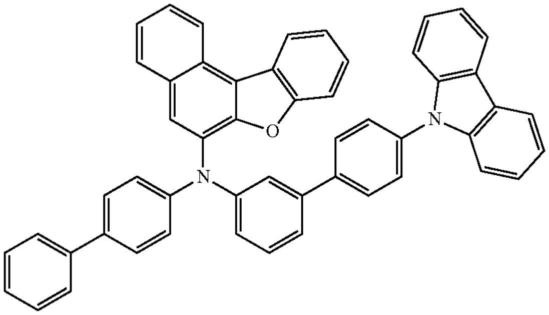
(440)
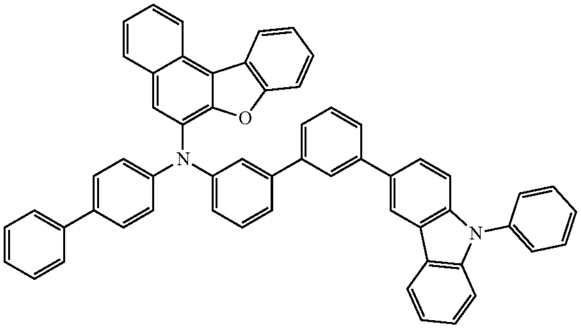

[Chemical Formula 30]
(441)
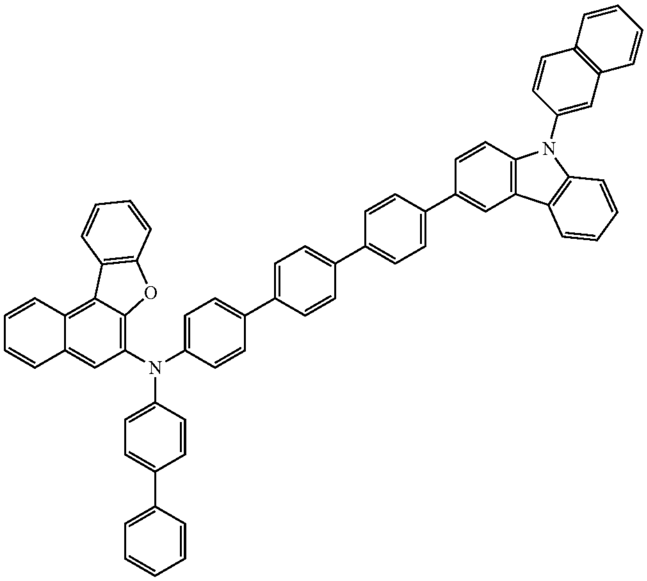
(442)
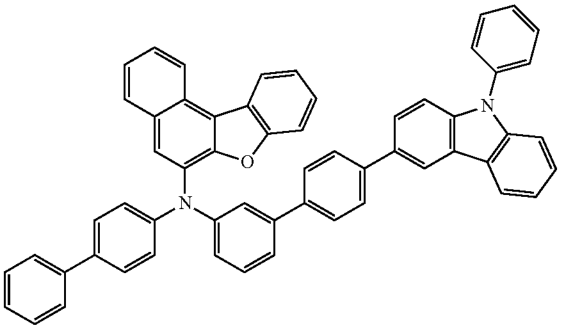
(443)
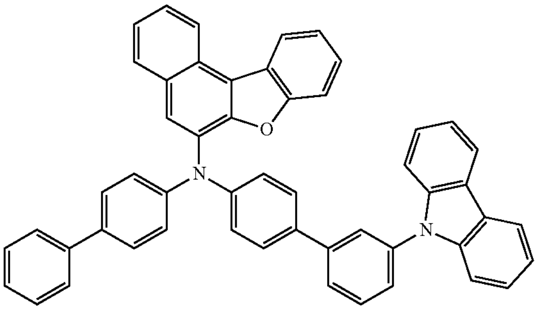
(444)
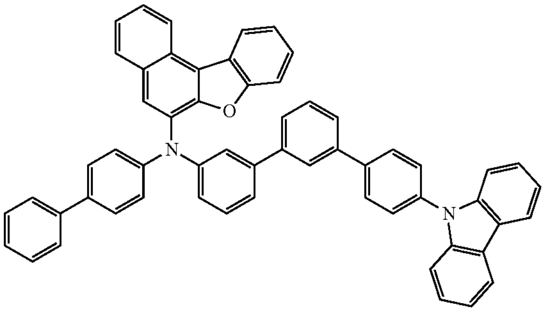
(445)
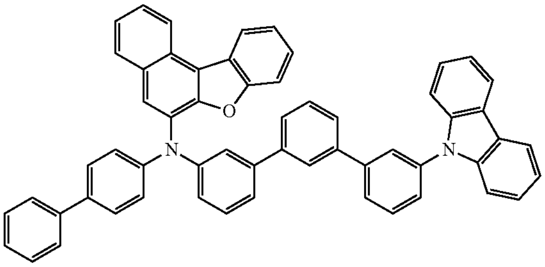

-continued
(446)
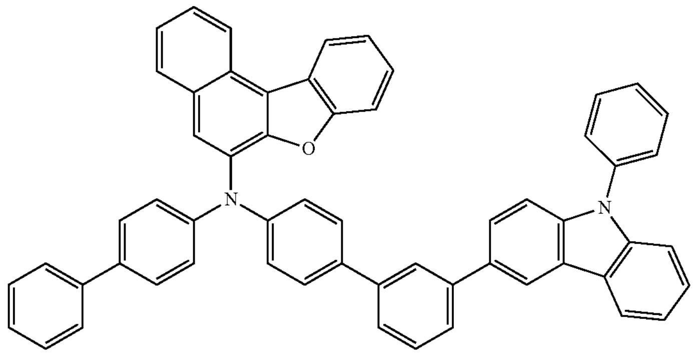
(447)
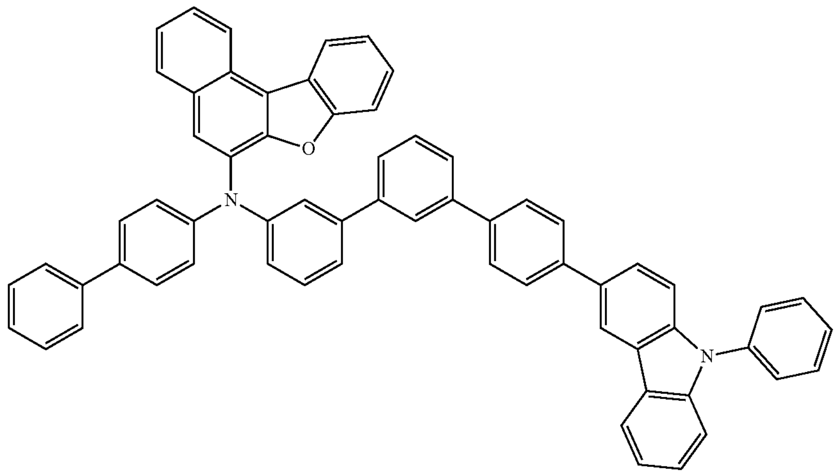
(448)
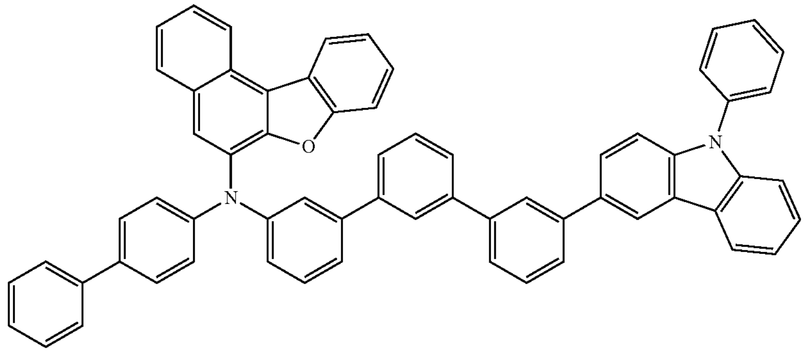
(449)
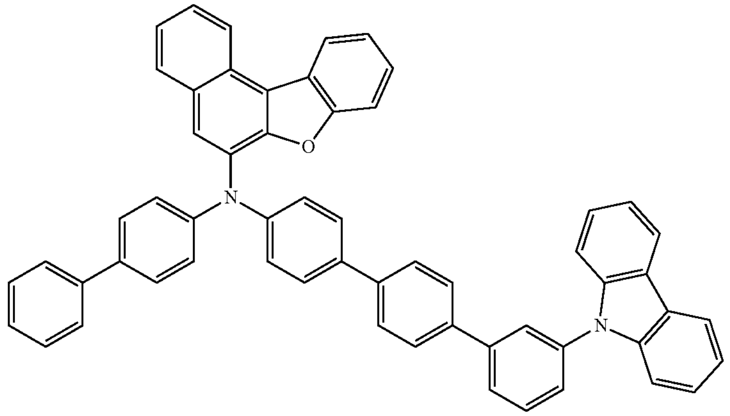

-continued
(450)
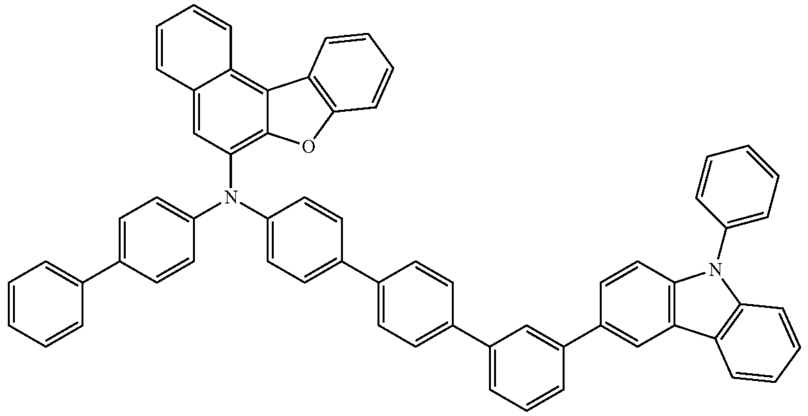
(451)
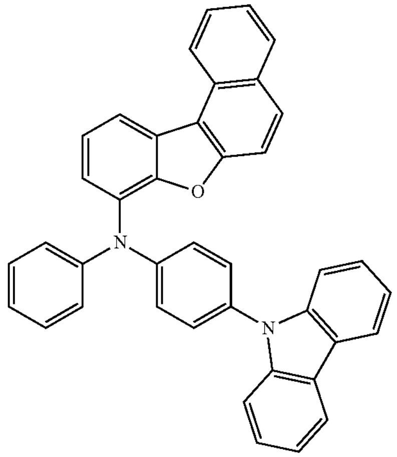
(452)
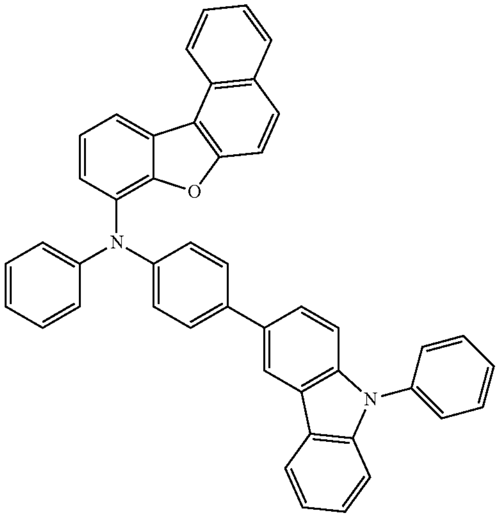
[Chemical Formula 31]
(453)
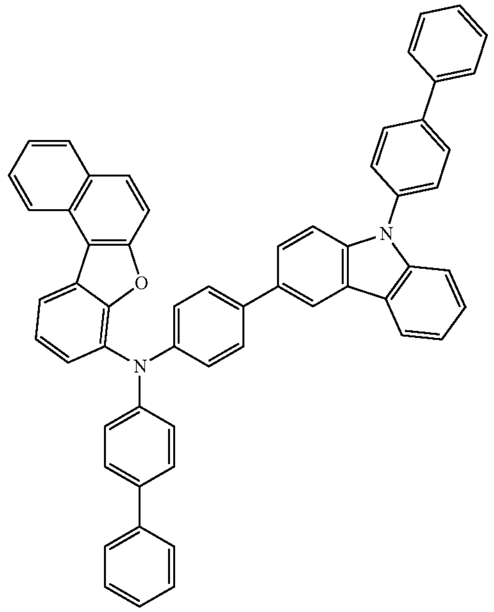
(454)
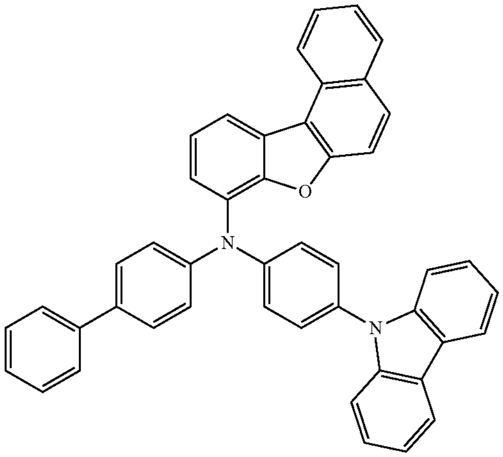

-continued
(455)
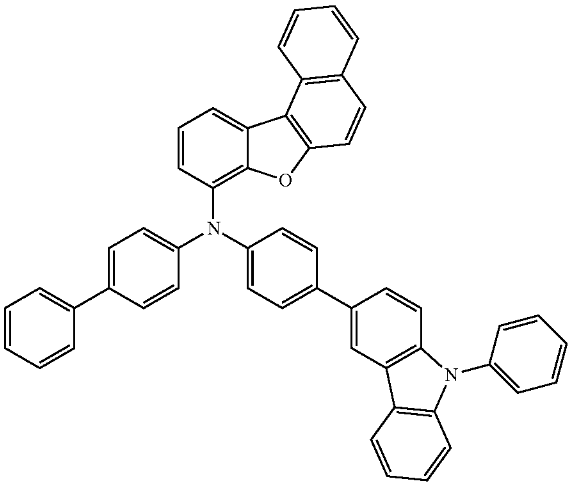
(456)
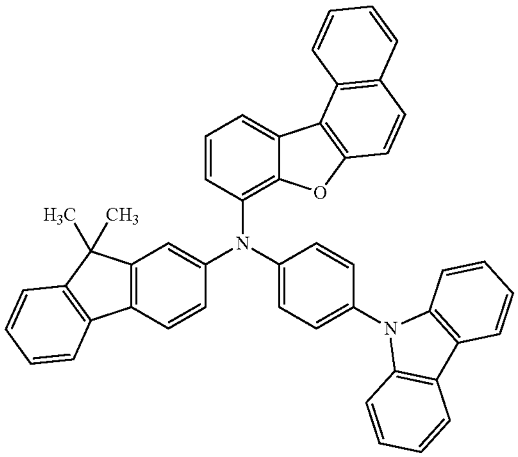
(457)
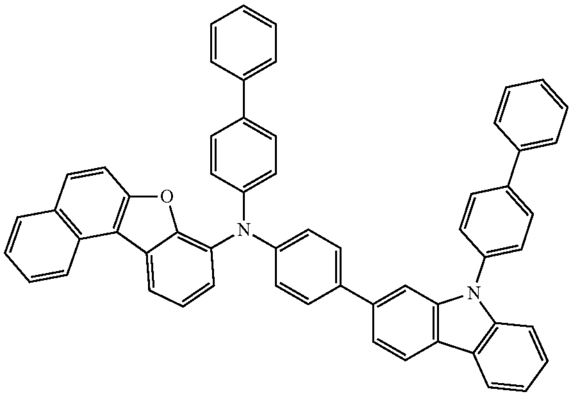
(458)
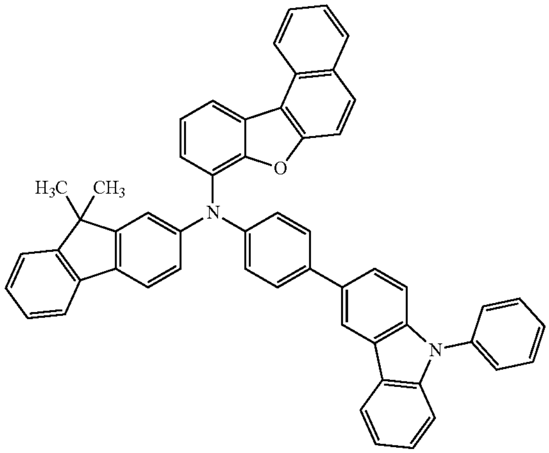
(459)
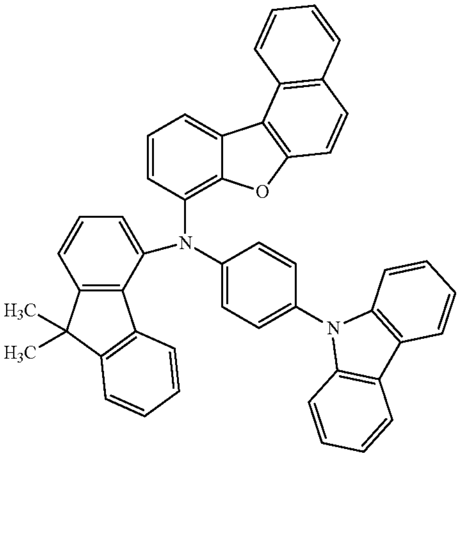
(460)
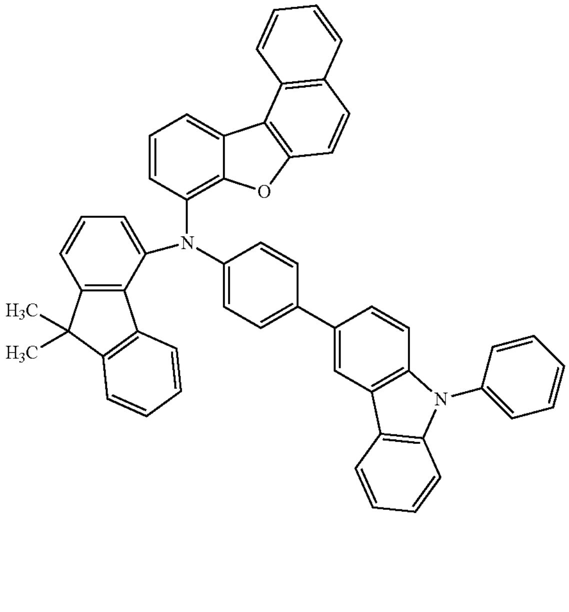

-continued
(461)
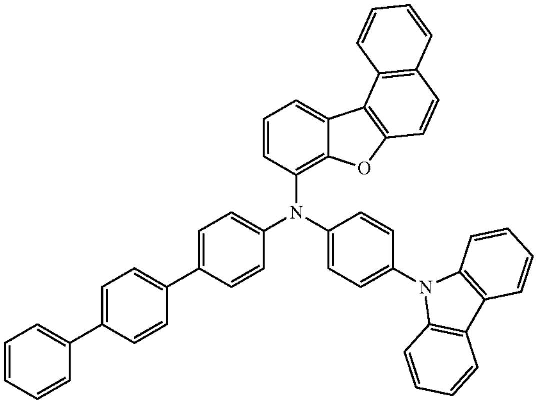
(462)
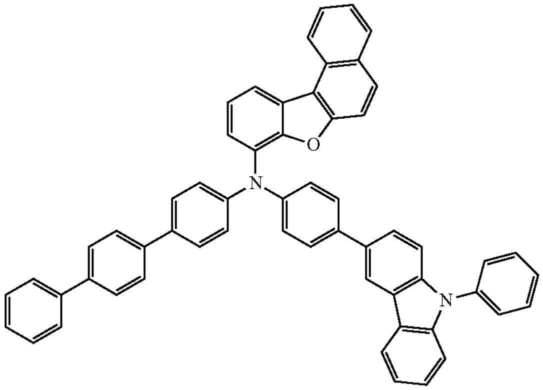
(463)
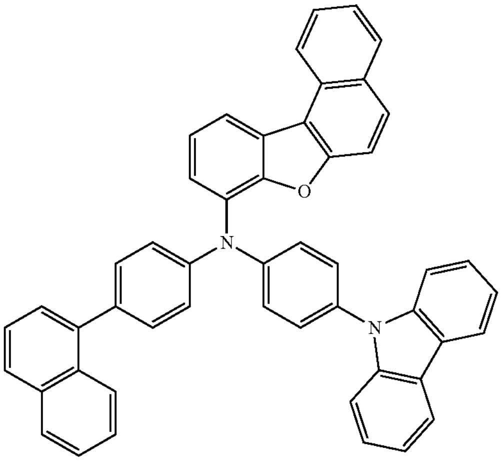
(464)
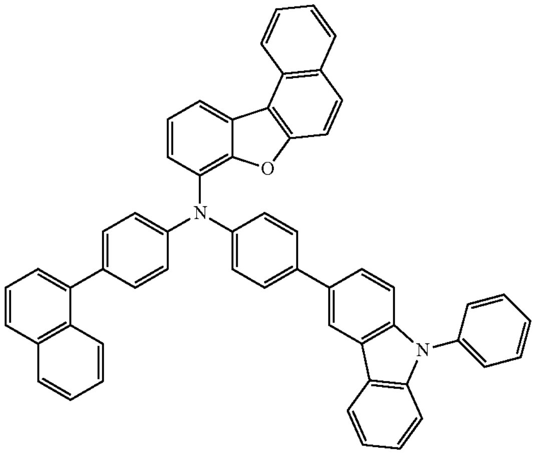
[Chemical Formula 32]
(465)
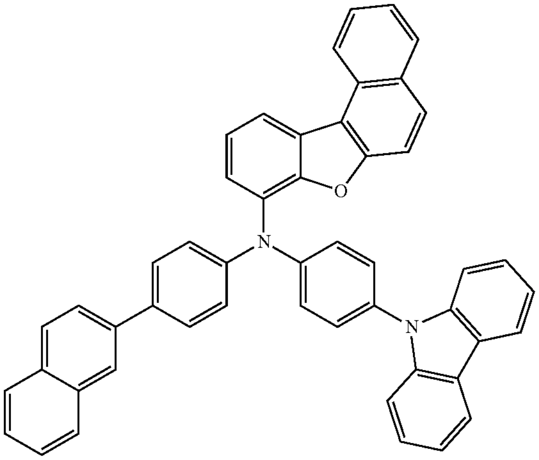
(466)
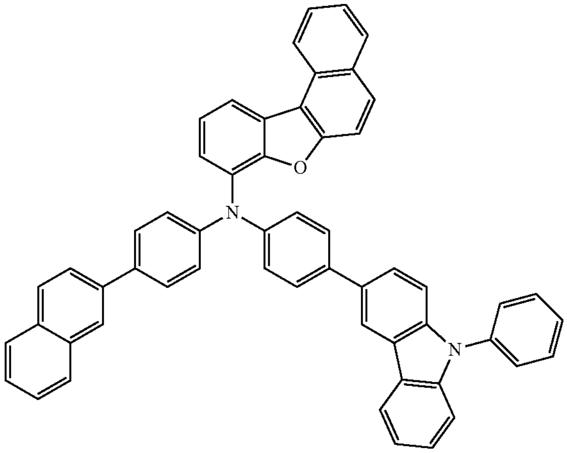

-continued
(467)
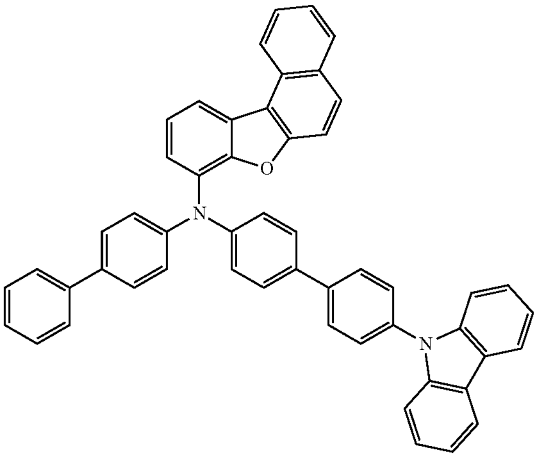
(468)
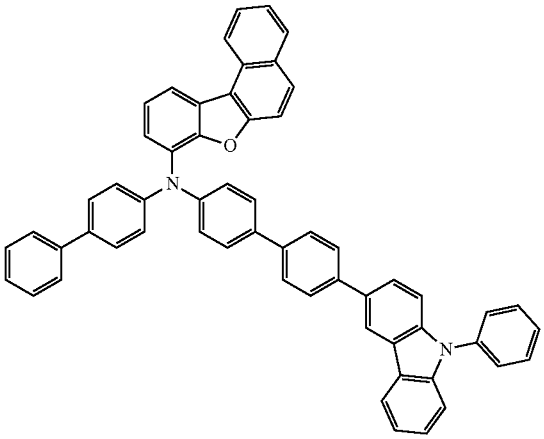
(469)
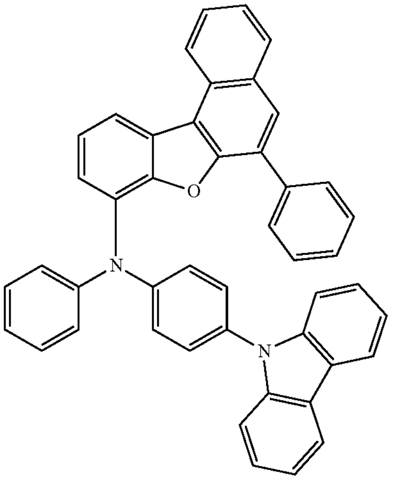
(470)
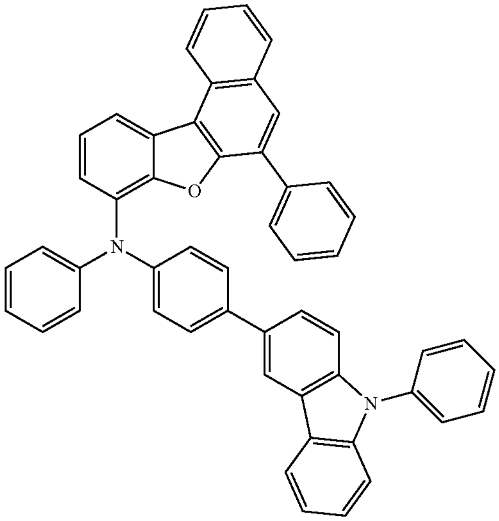
(471)
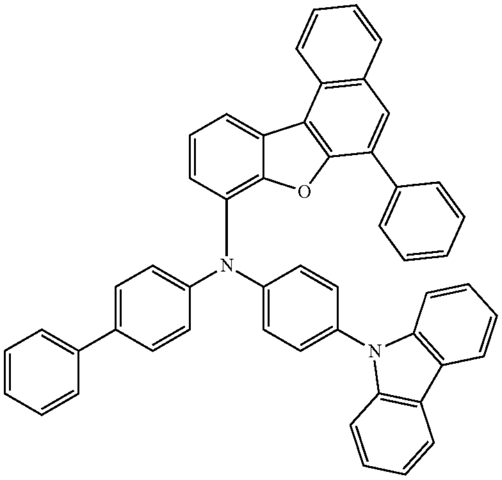
(472)
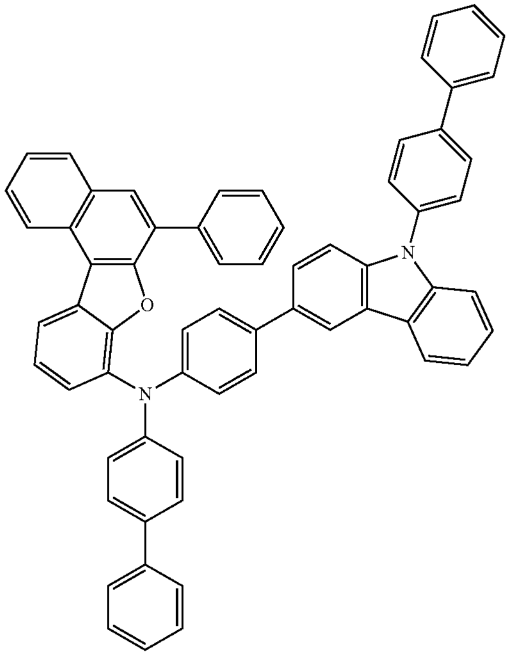

-continued
(473)
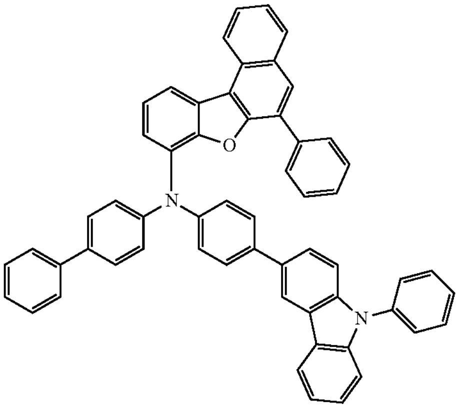
(474)
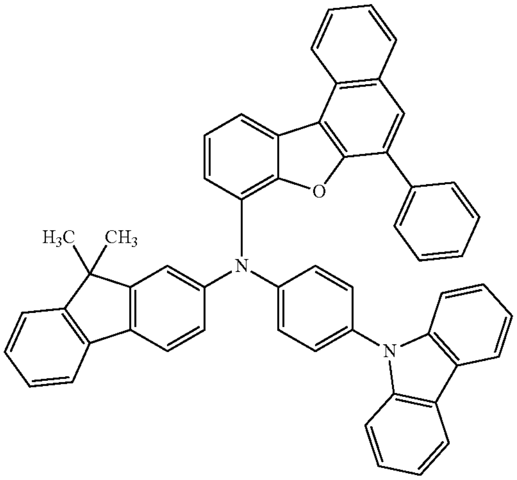
(475)
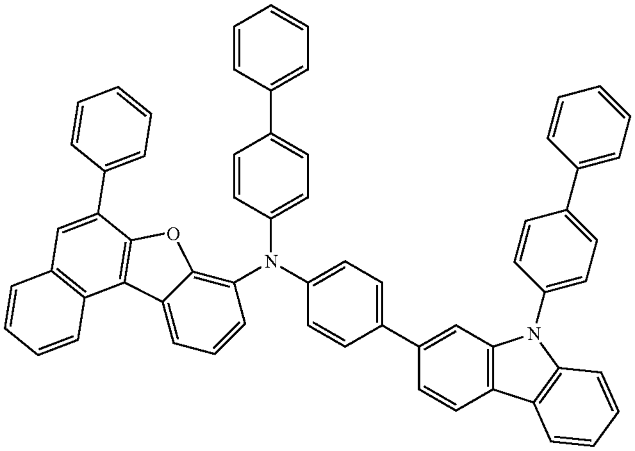
[Chemical Formula 33]
(476)
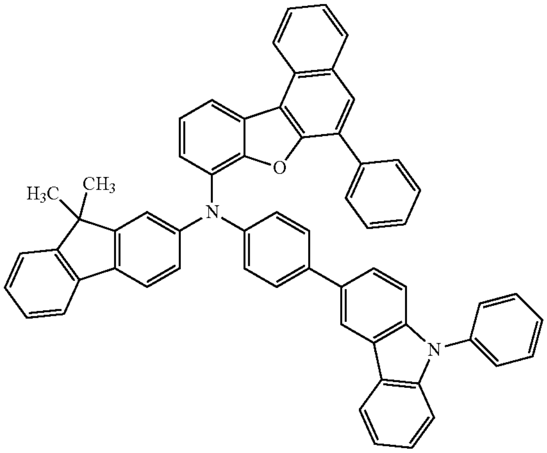
(477)
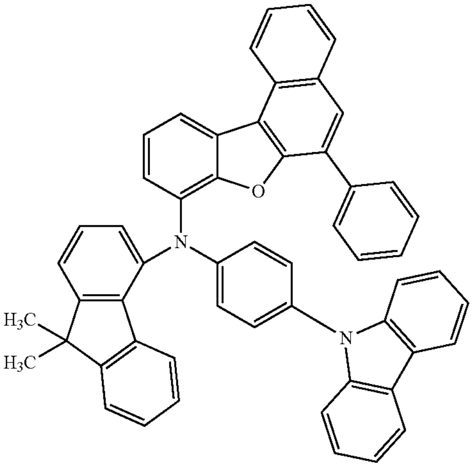

-continued
(478)
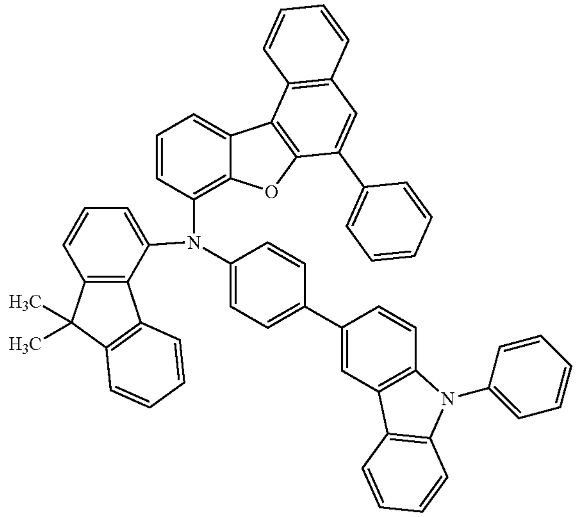
(479)
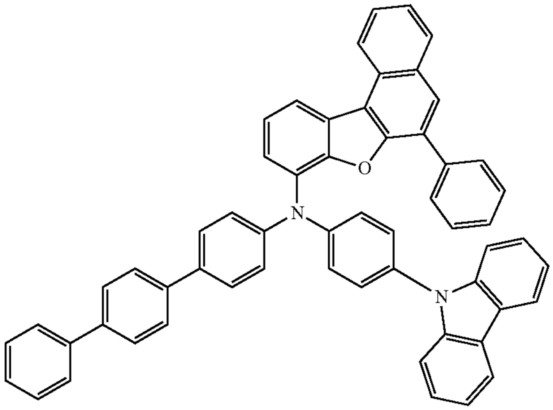
(480)
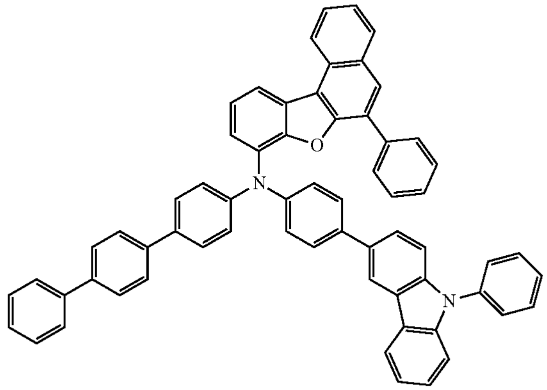
(481)
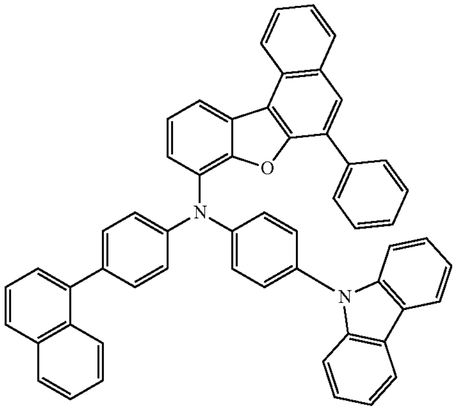
(482)
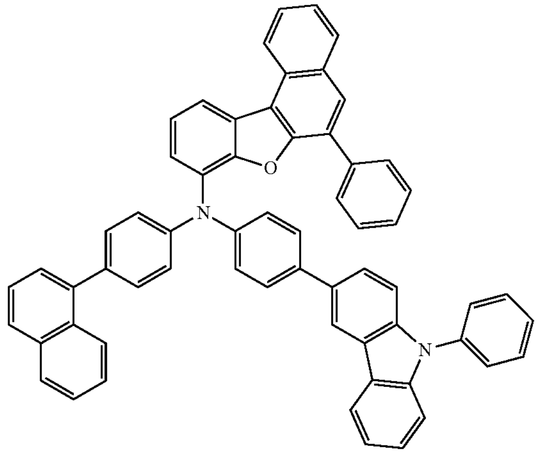
(483)
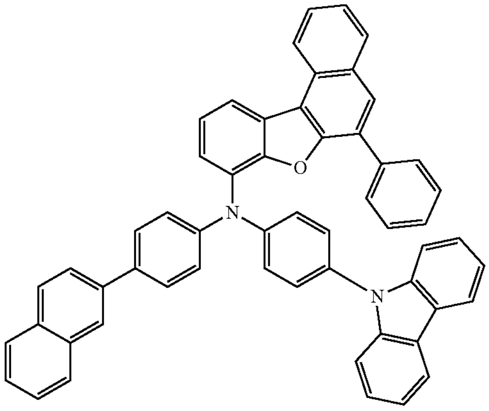

-continued
(484)
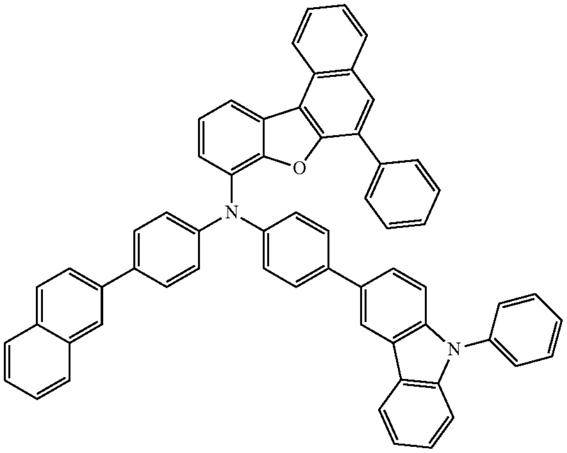
(485)
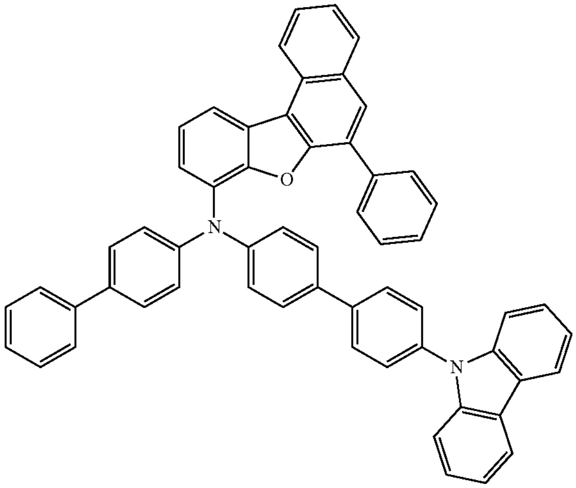
(486)
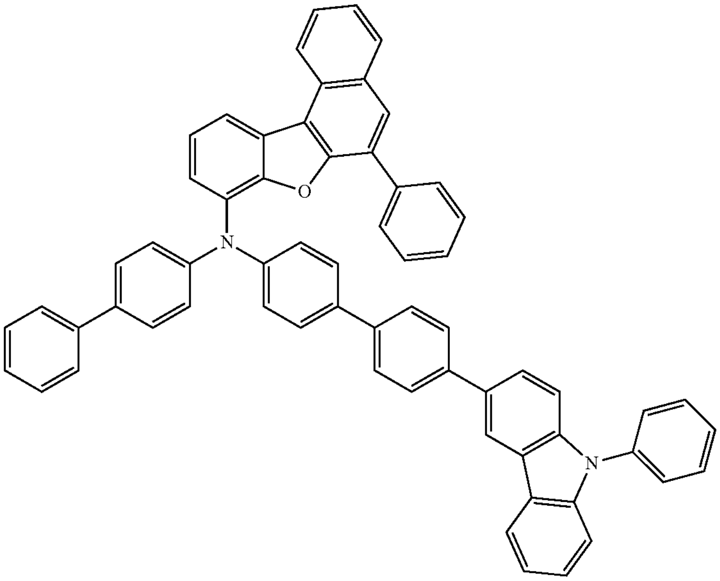
[Chemical Formula 34]
(487)
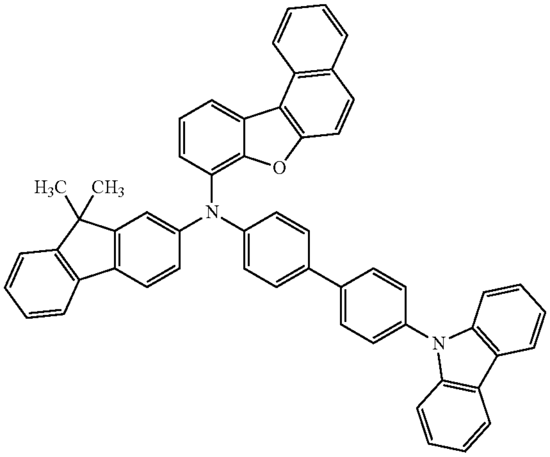
(488)
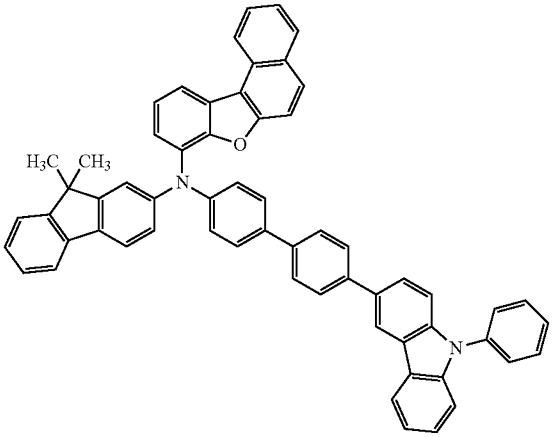

-continued
(489)
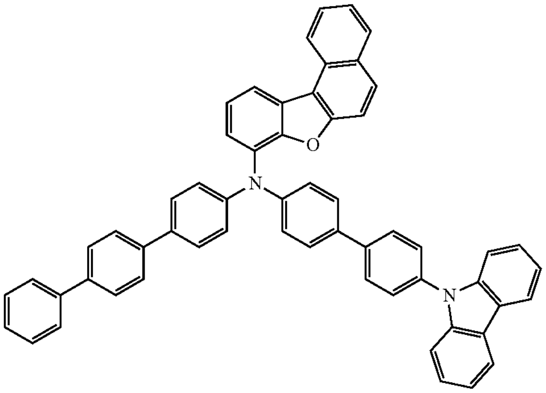
(490)
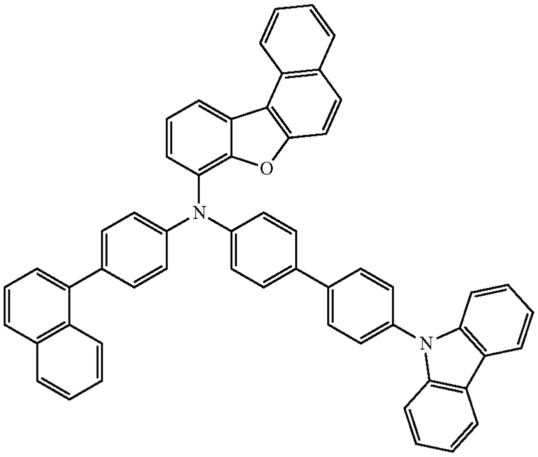
(491)
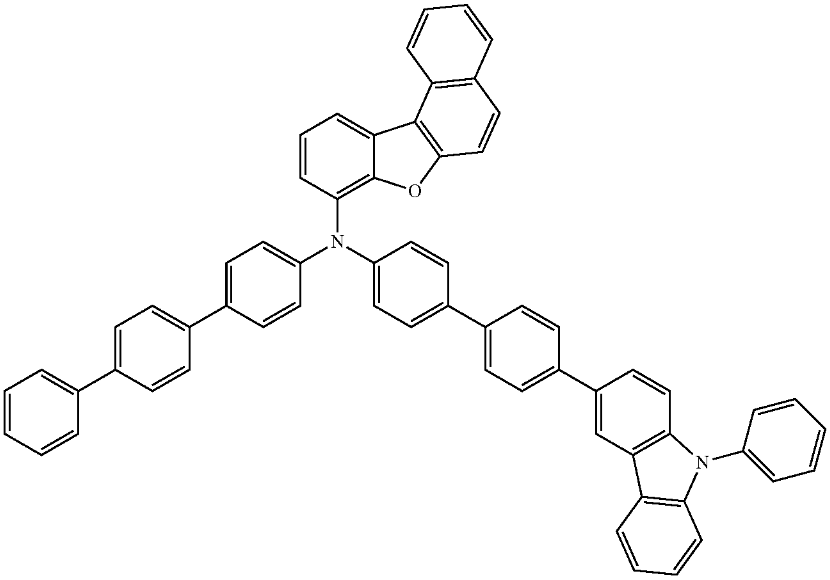
(492)
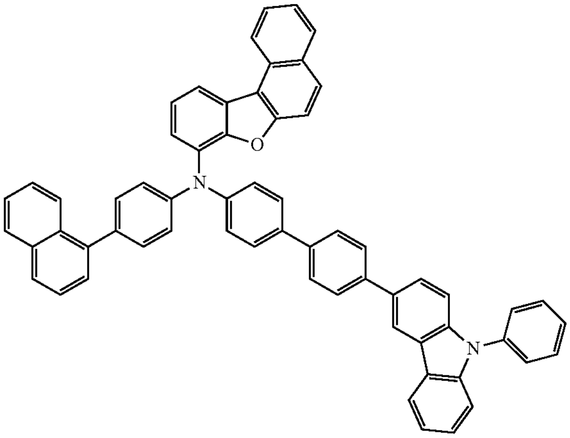
(493)
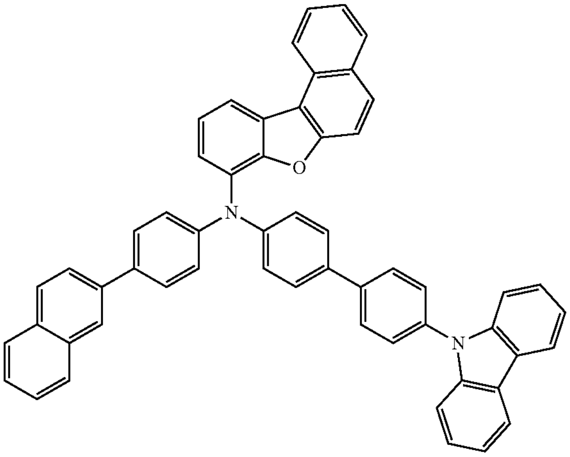

-continued
(494)
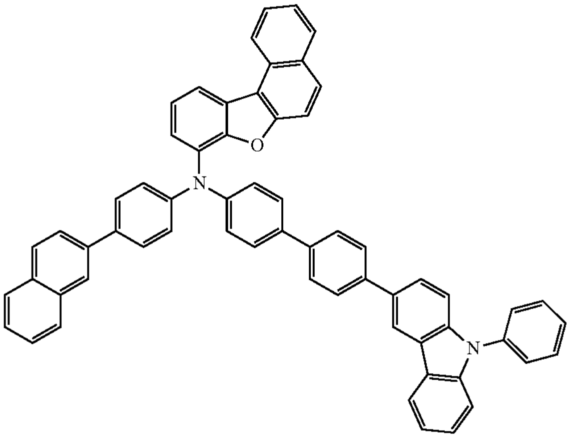
(495)
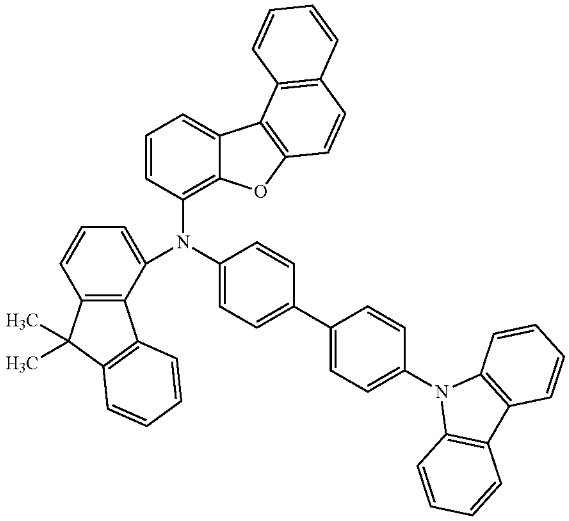
(496)
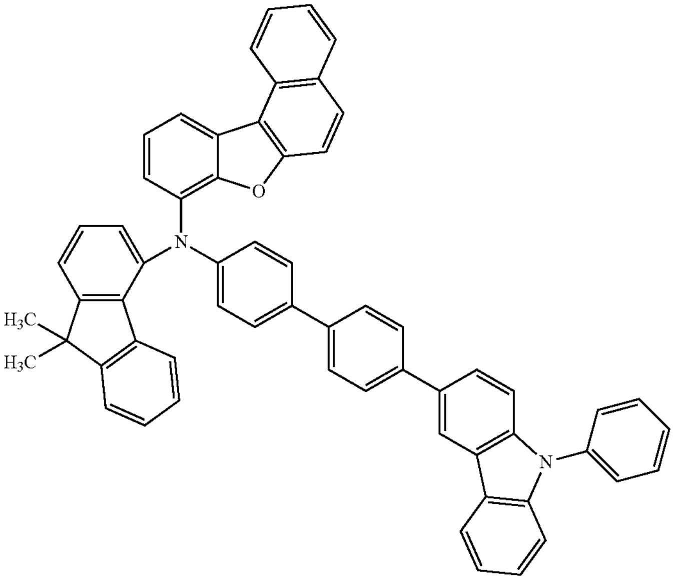

-continued
[Chemical Formula 35]
(497)
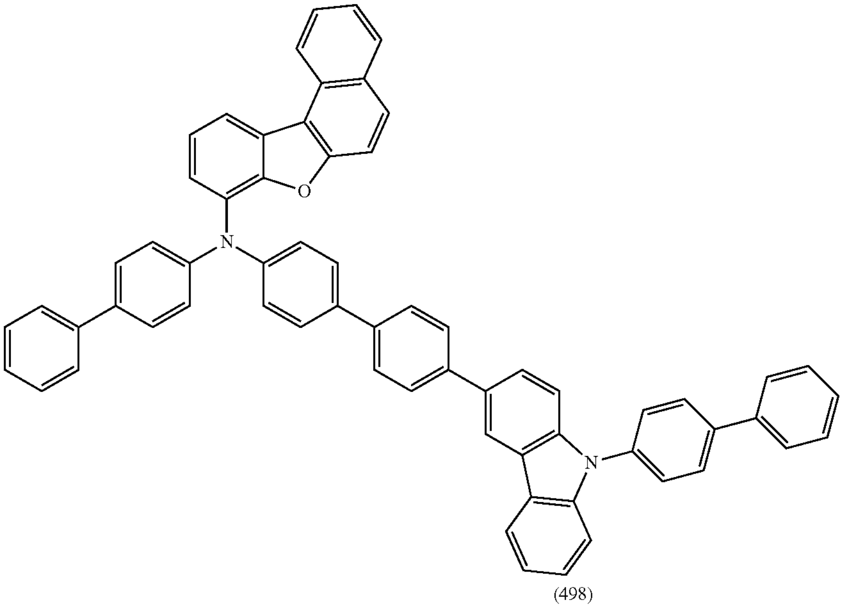
(498)
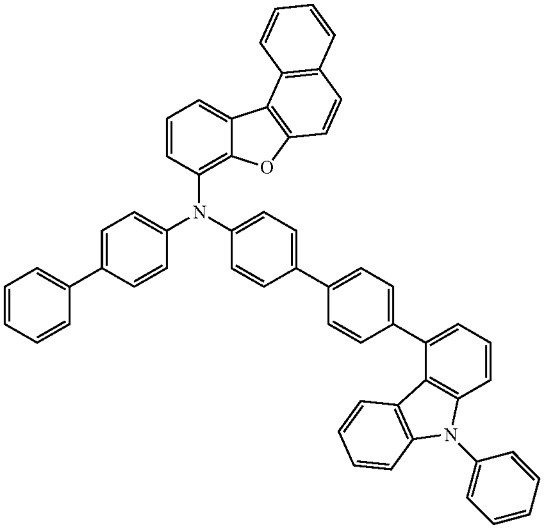
(499)
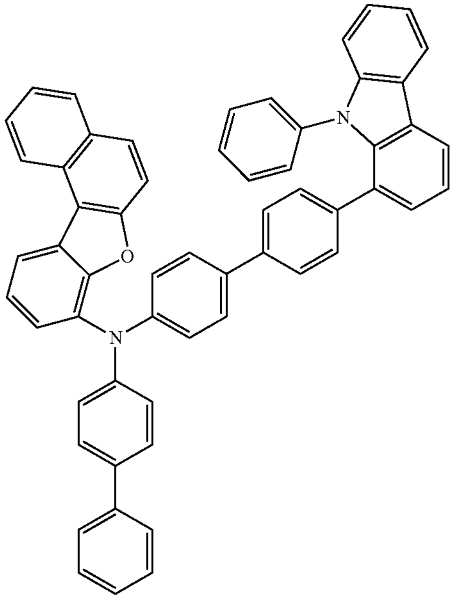
(500)
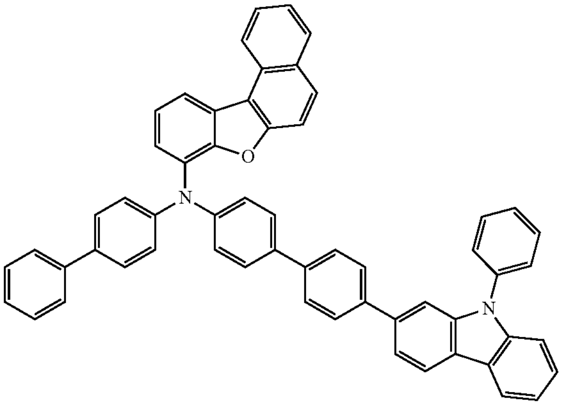
(501)
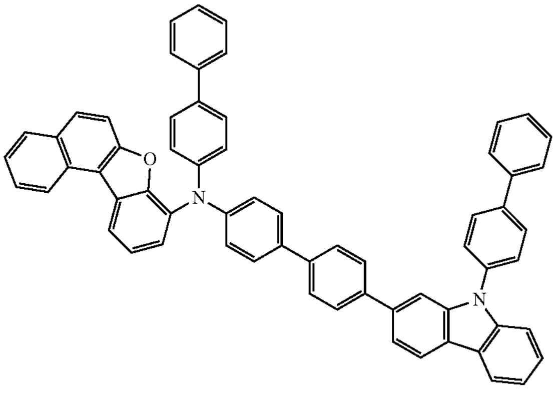

-continued
(502)
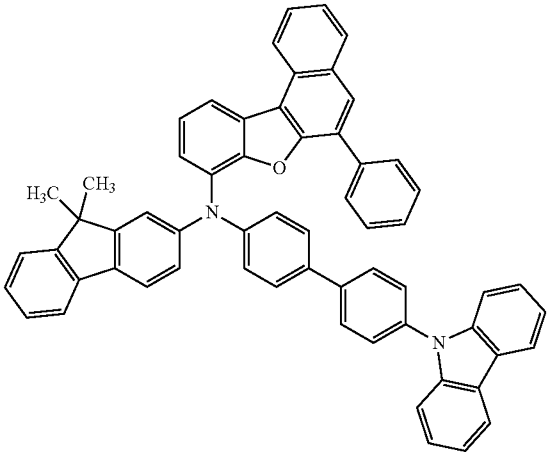
(503)
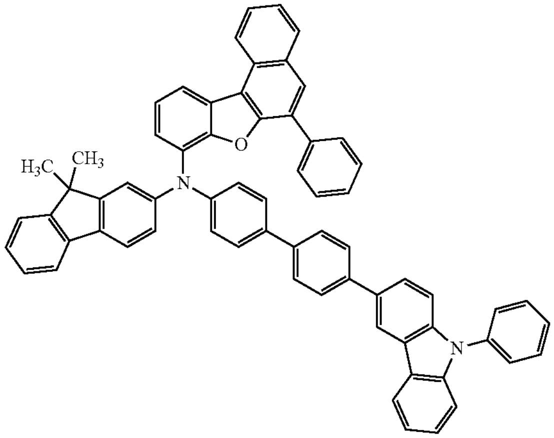
(504)
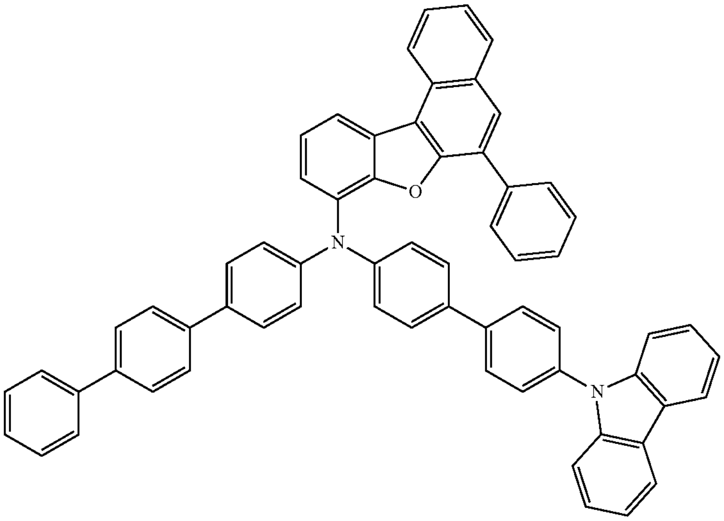
(505)
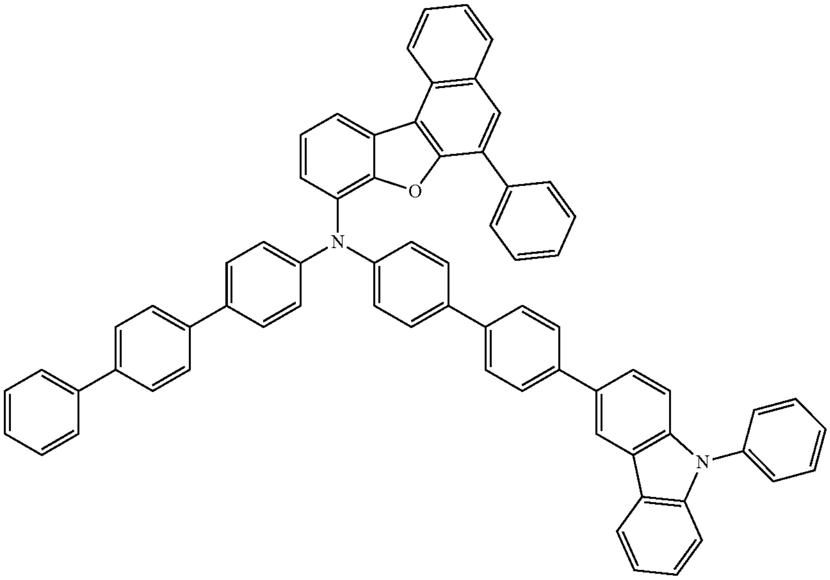

-continued
(506)
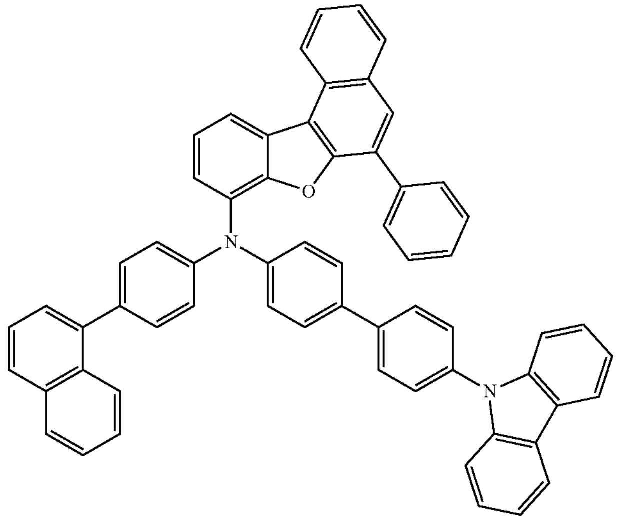
[Chemical Formula 36]
(507)
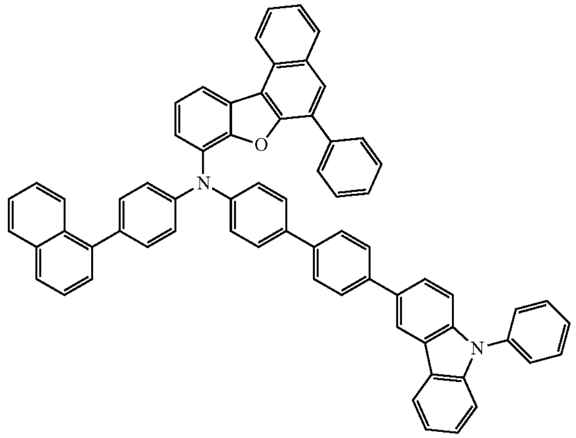
(508)
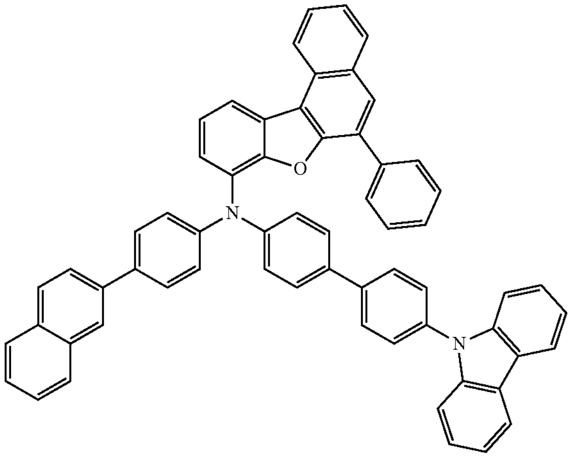
(509)
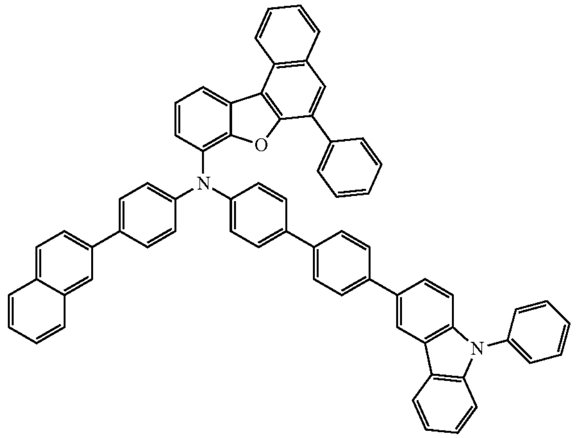
(510)
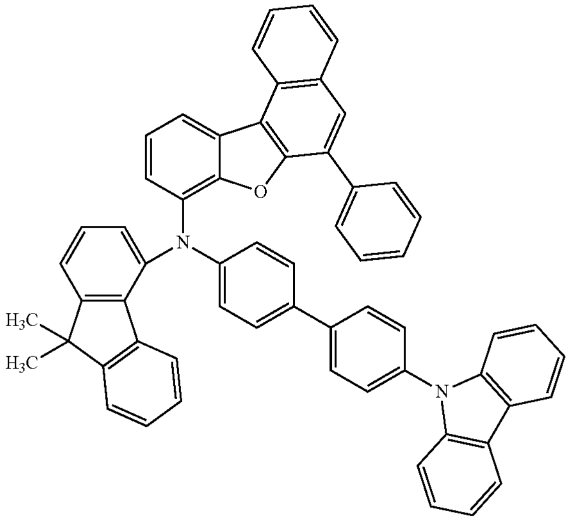

-continued
(511)
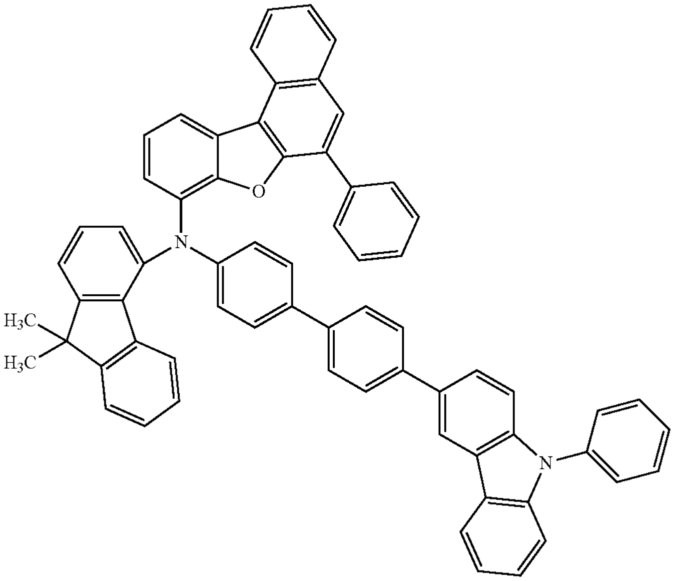
(512)
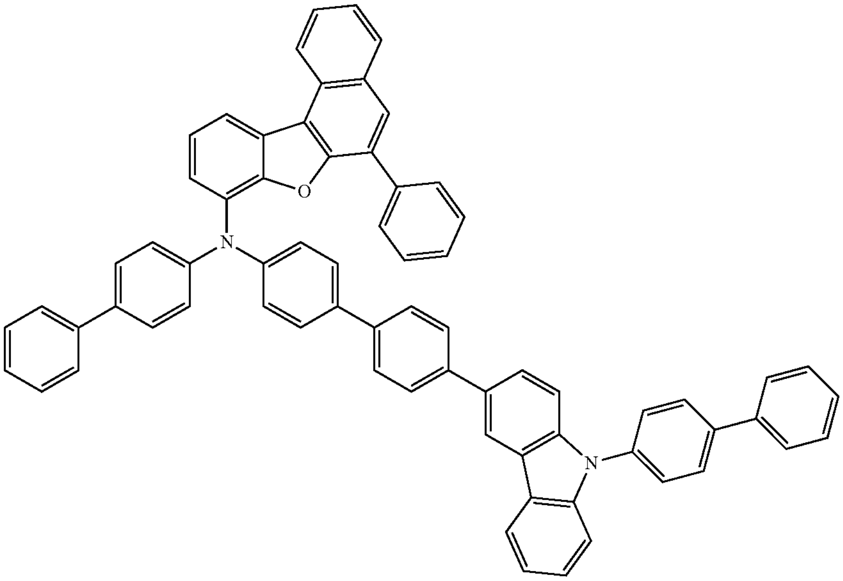

-continued
(513)
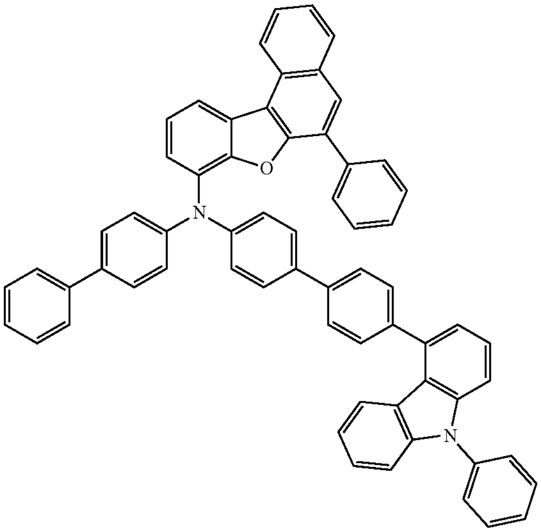
(514)
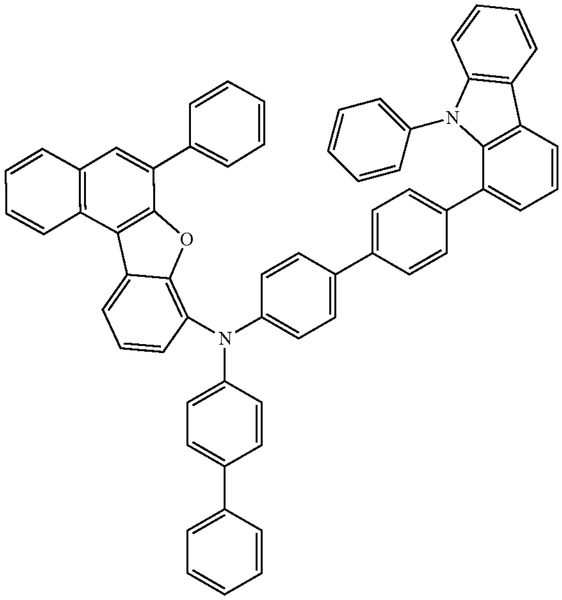
(515)
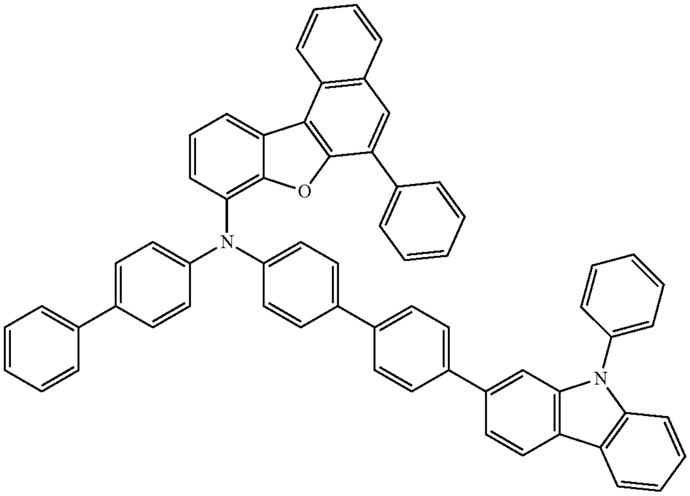
(517)
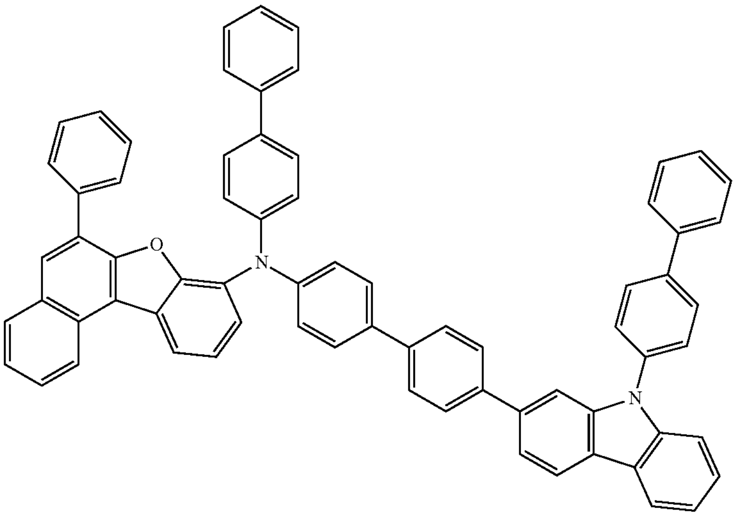

-continued
[Chemical Formula 37]
(518)
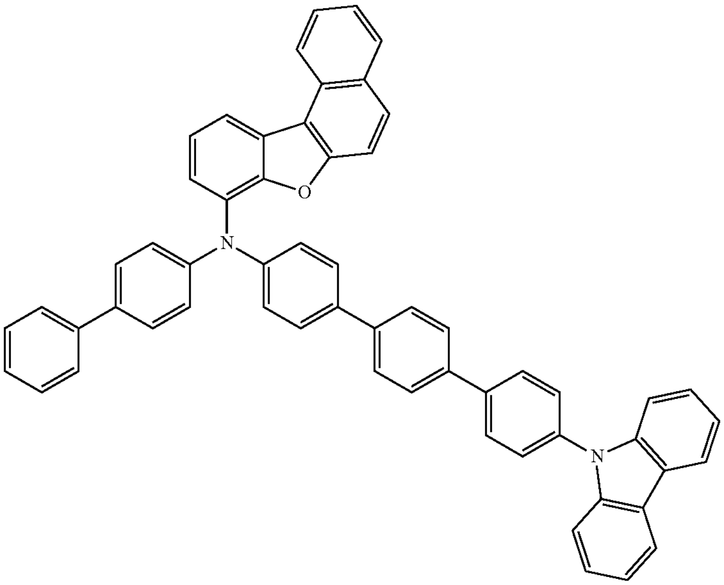
(519)
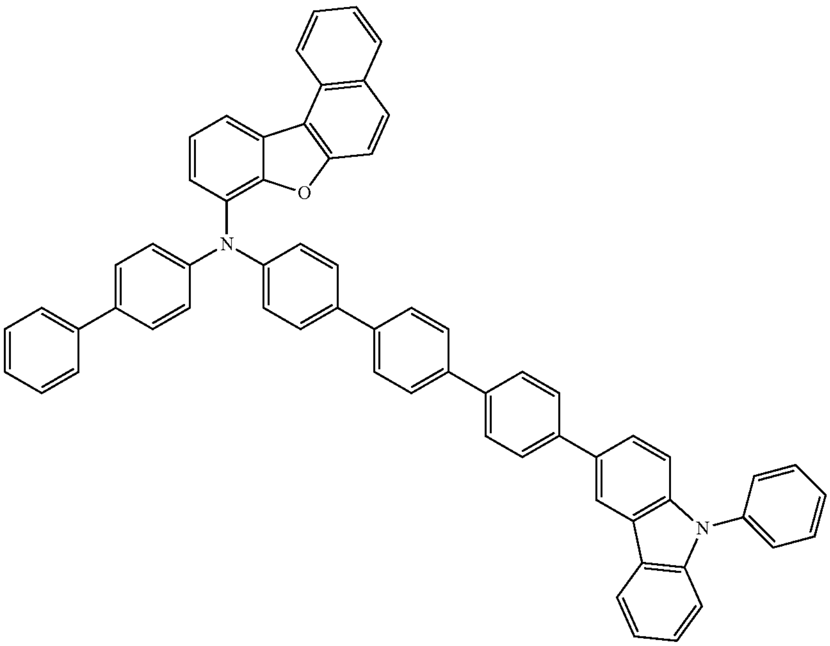

-continued
(520)
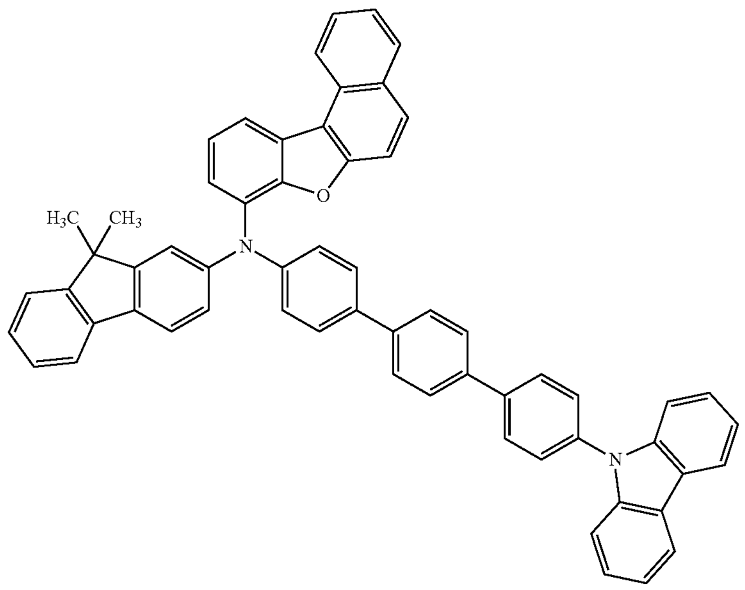
(521)
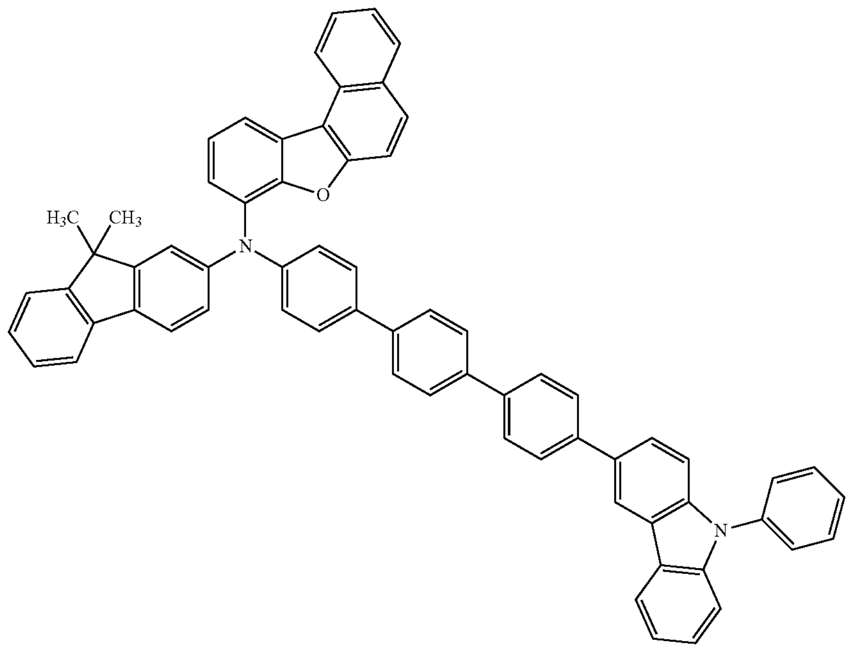

-continued
(522)
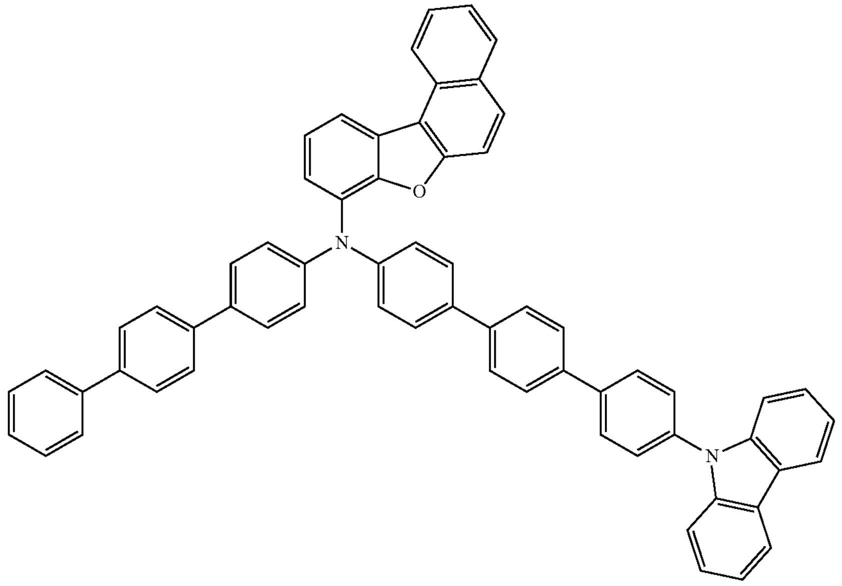
(523)
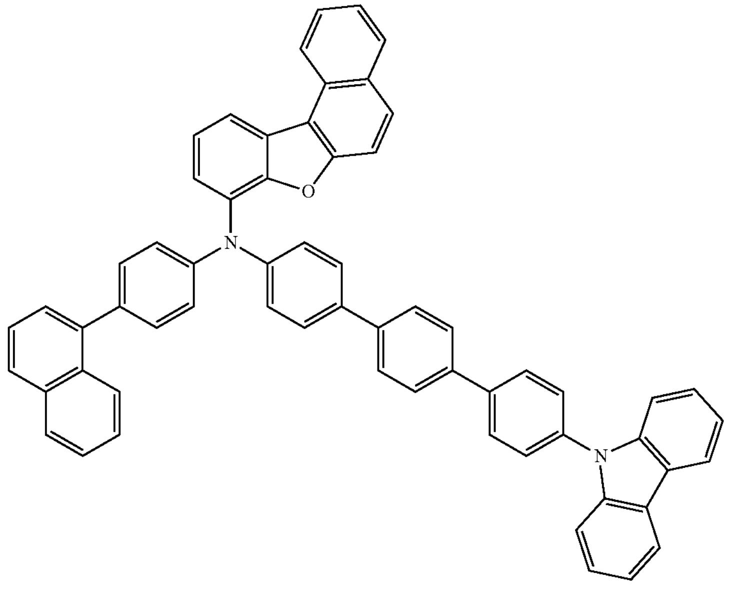

-continued
(524)
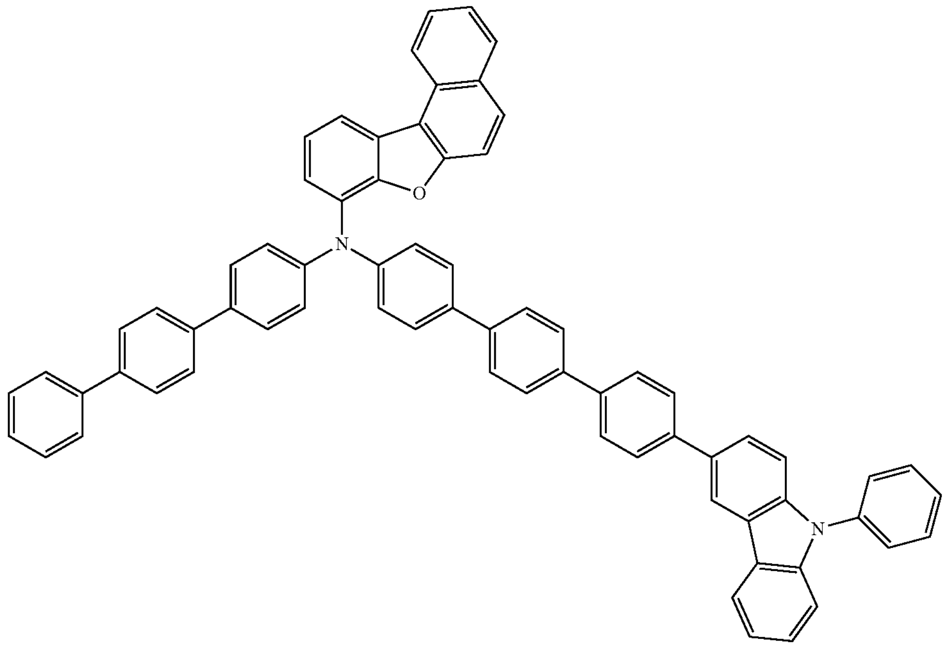
(525)
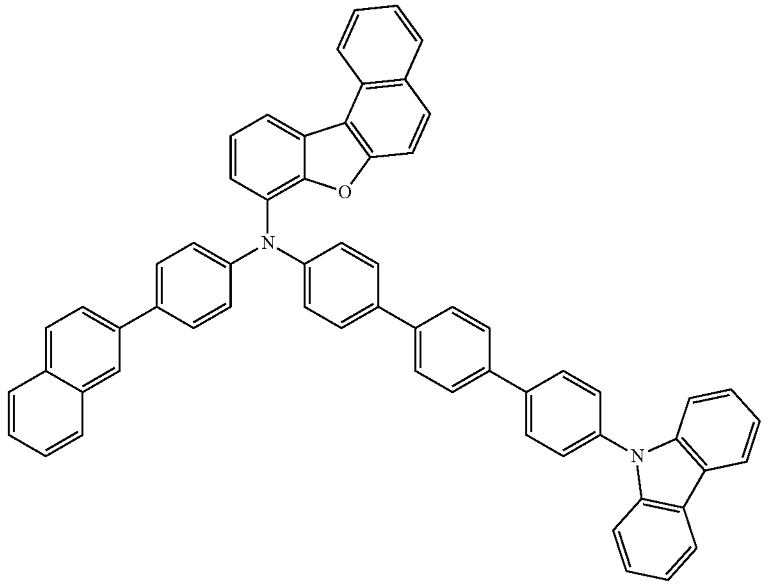

-continued
(526)
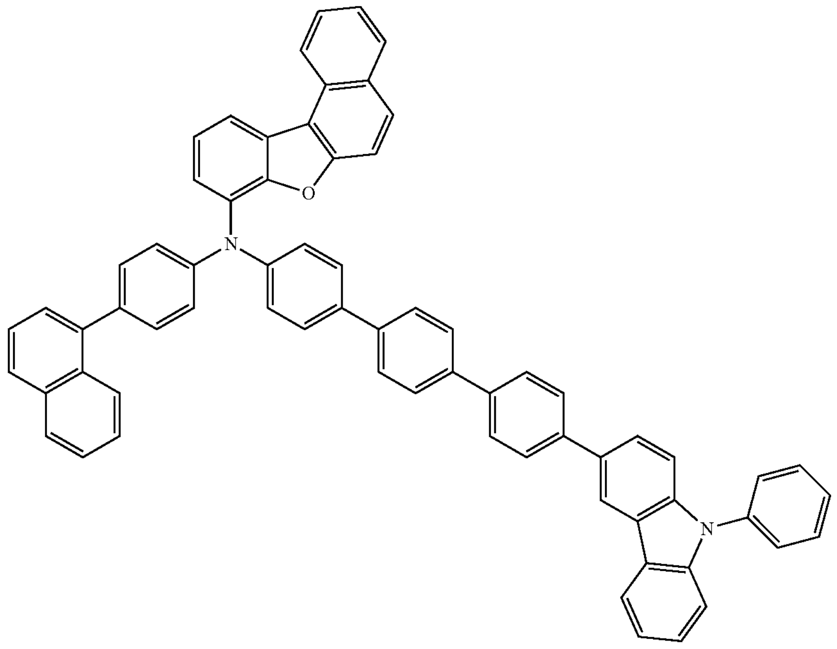
(527)
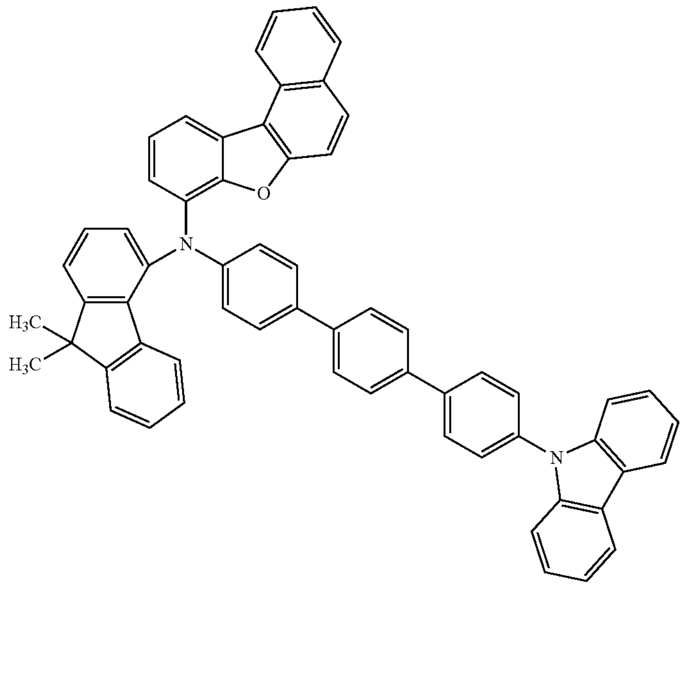

-continued
[Chemical Formula 38]
(528)
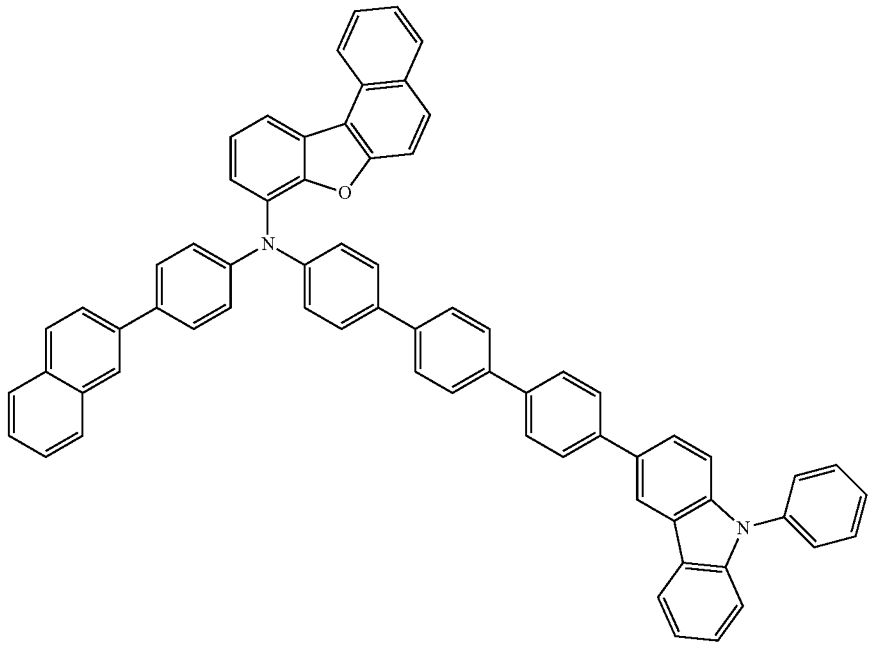
(529)
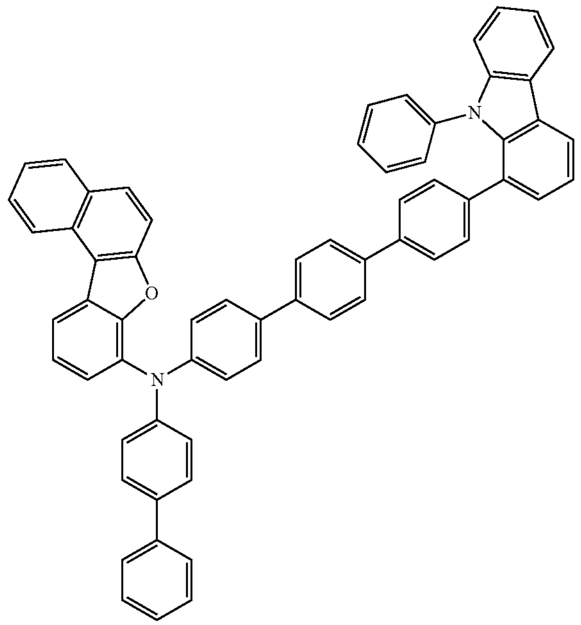

-continued
(530)
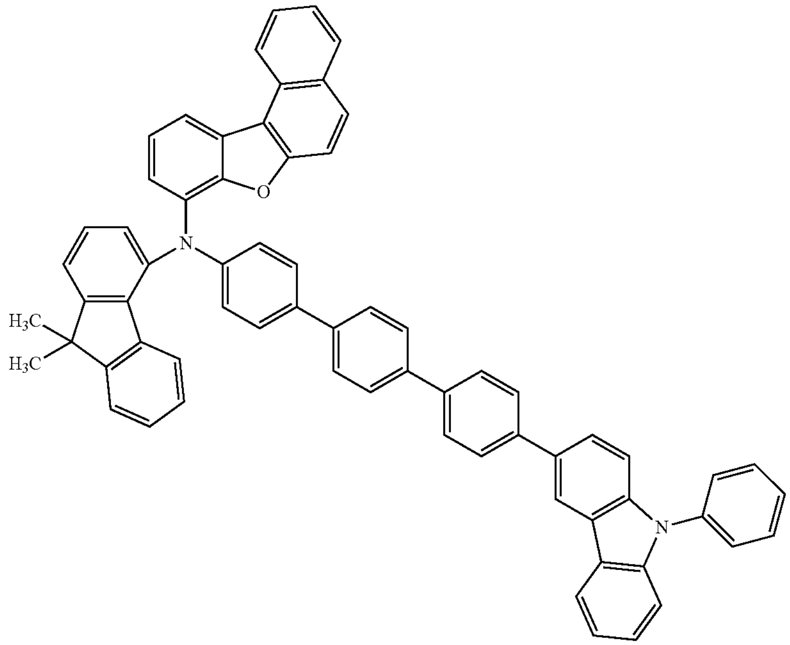
(531)
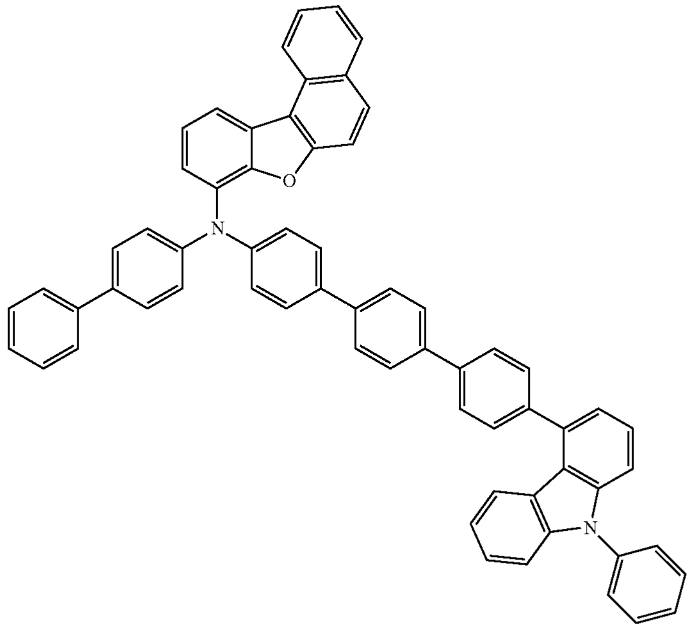

-continued
(532)
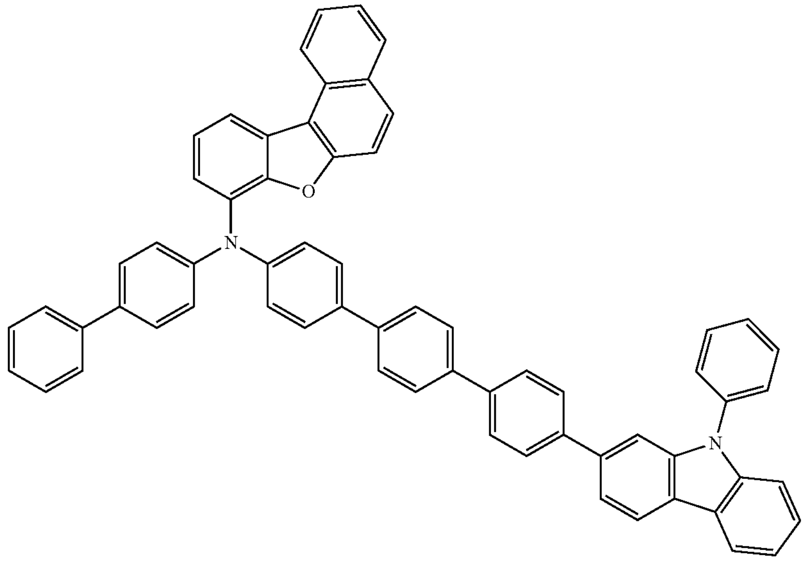
(533)
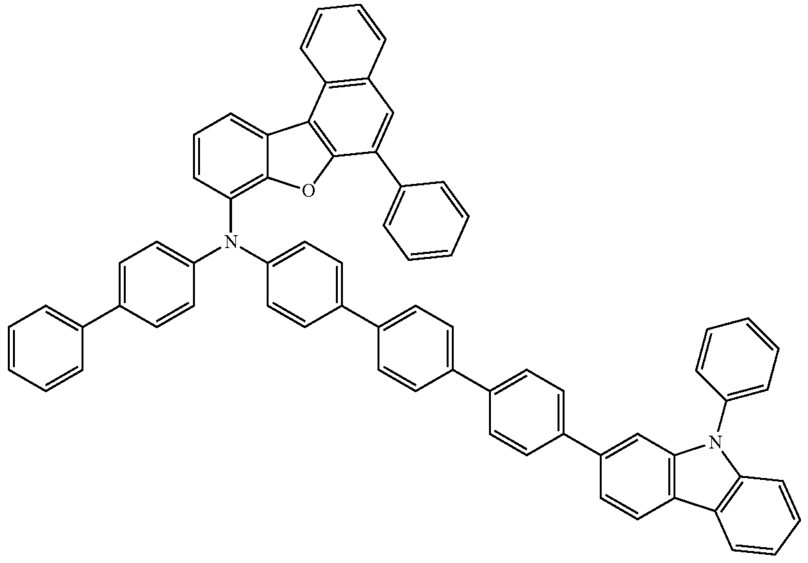

-continued
(534)
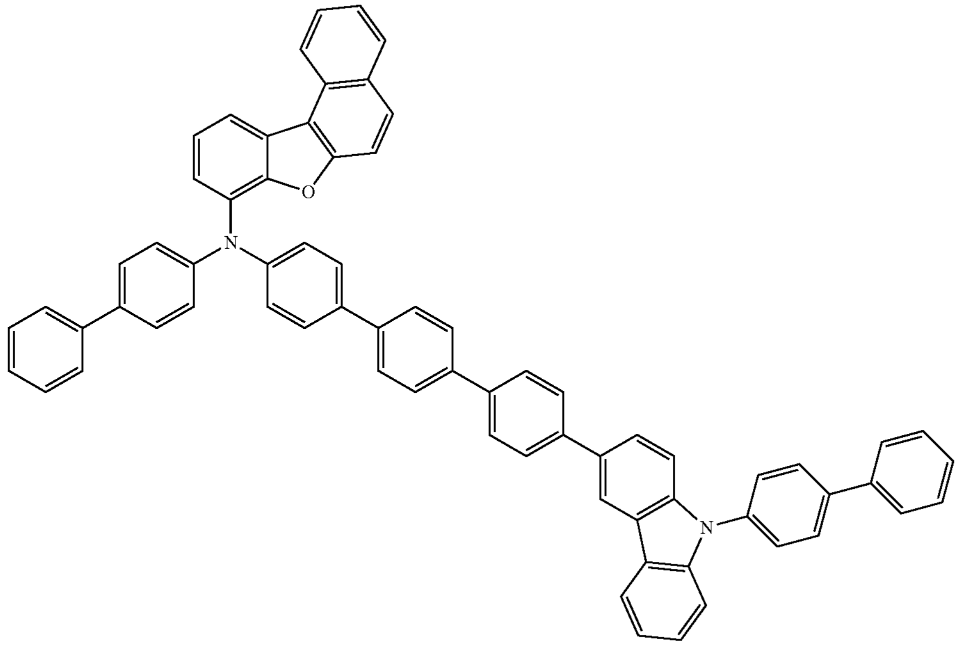
(535)
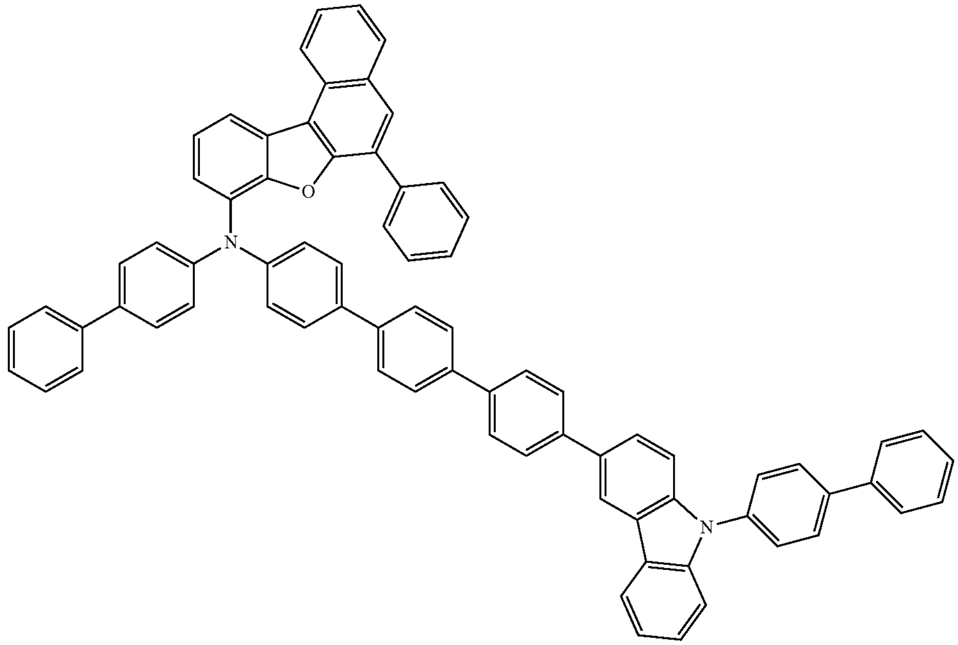

-continued
(536)
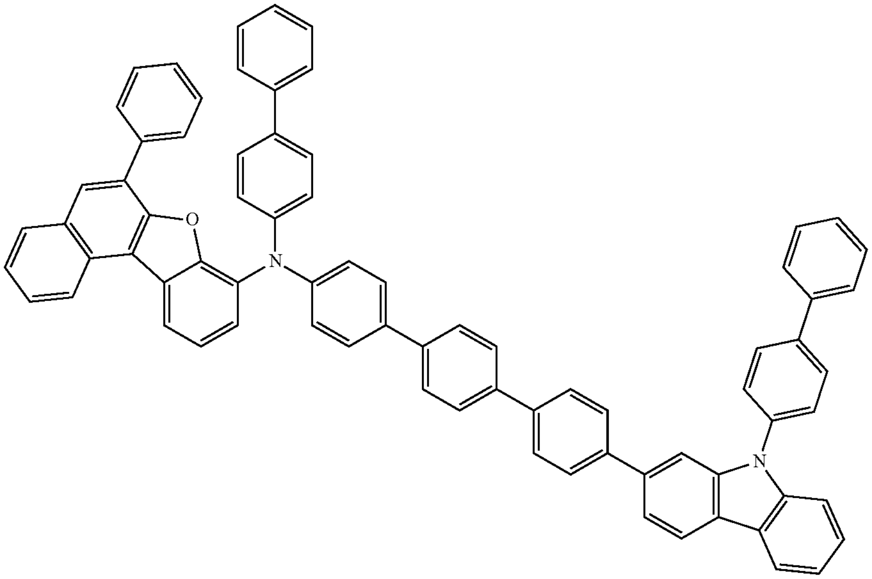
[Chemical Formula 39]
(537)
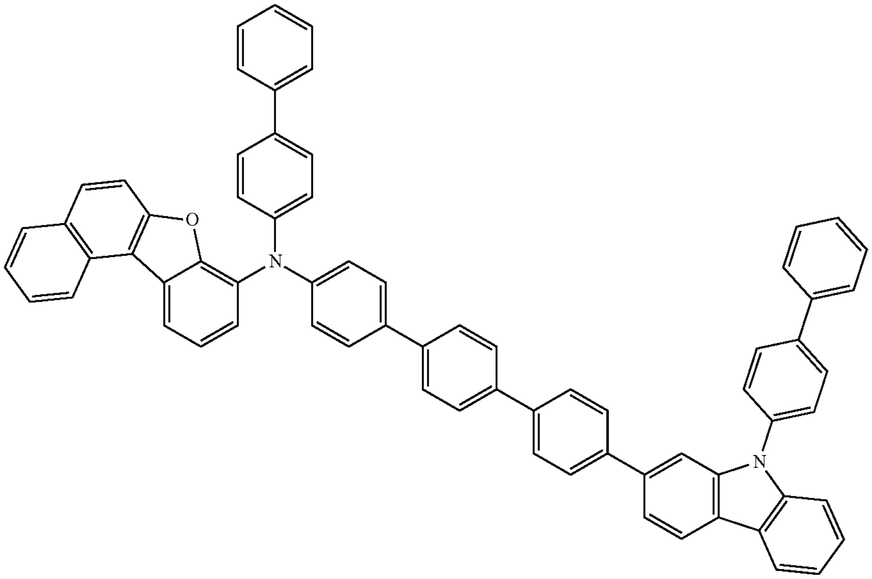

-continued
(538)
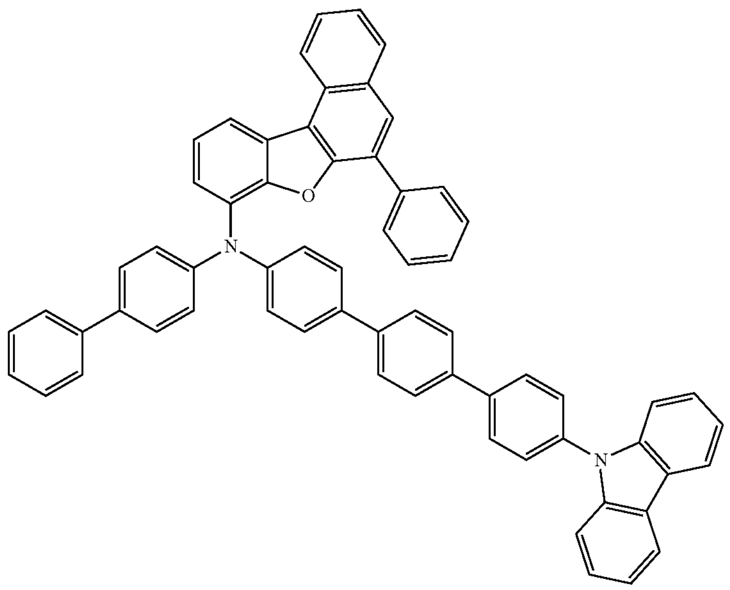
(539)
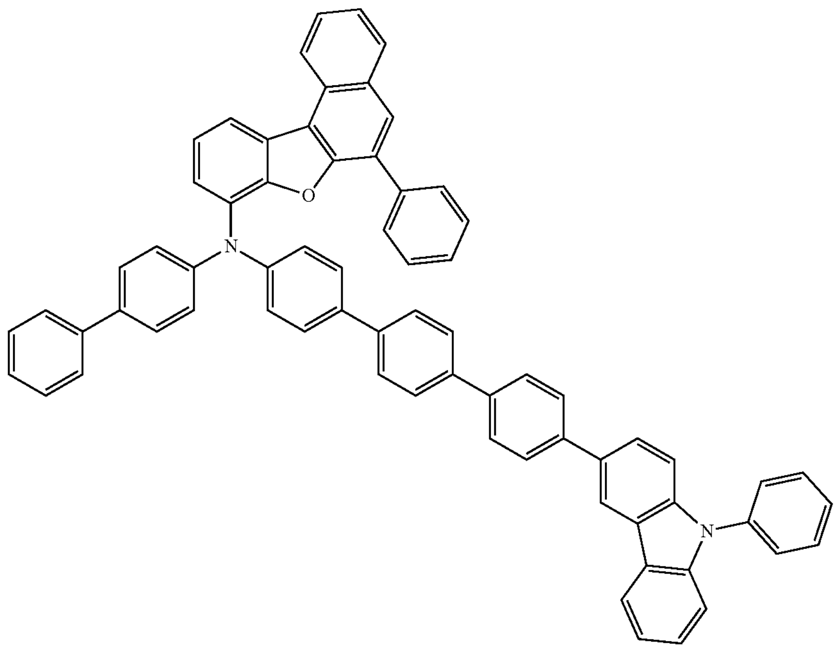

-continued
(540)
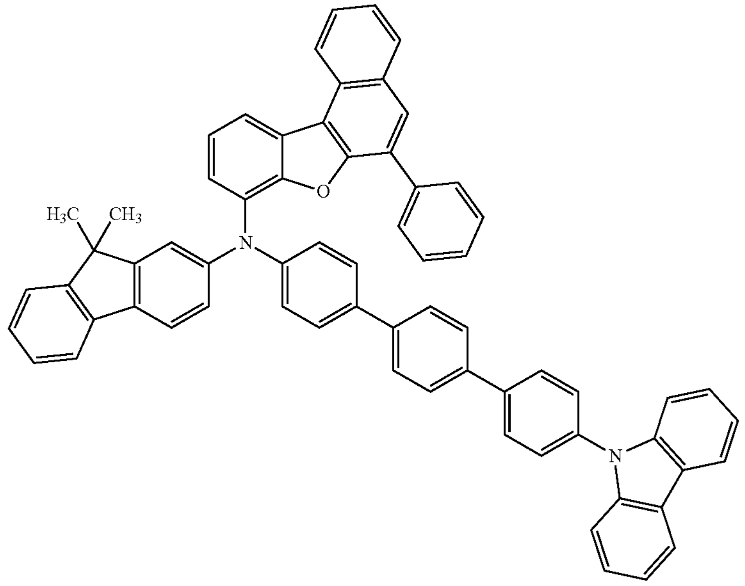
(541)
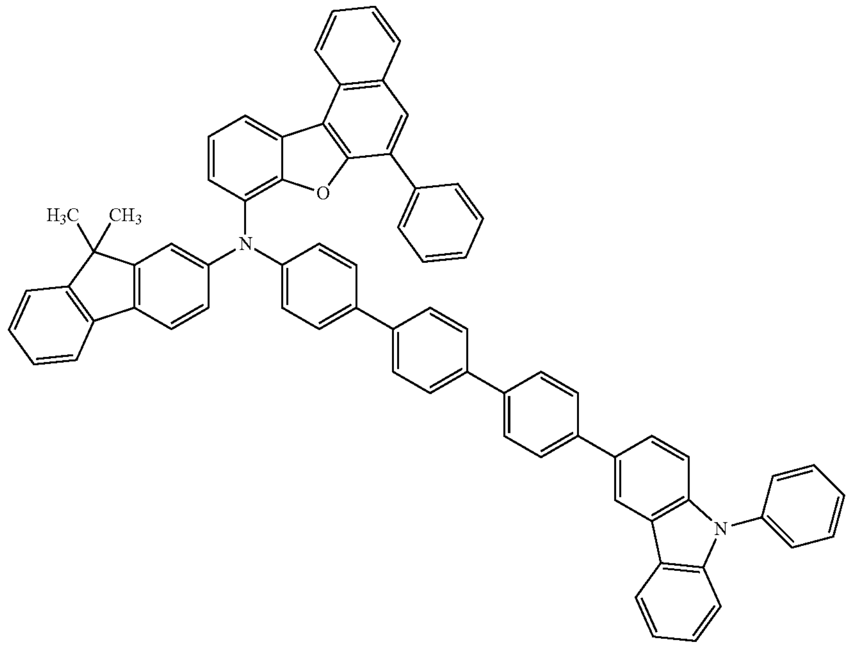

-continued
(542)
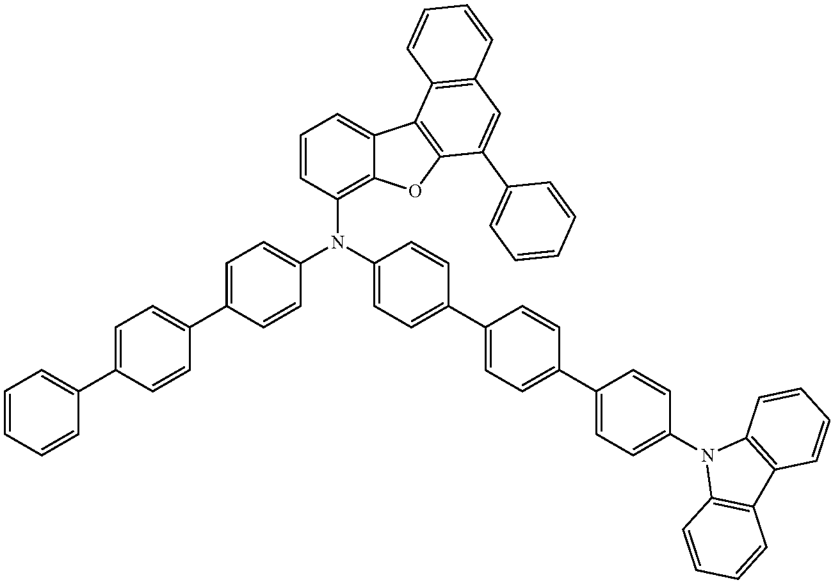
(543)
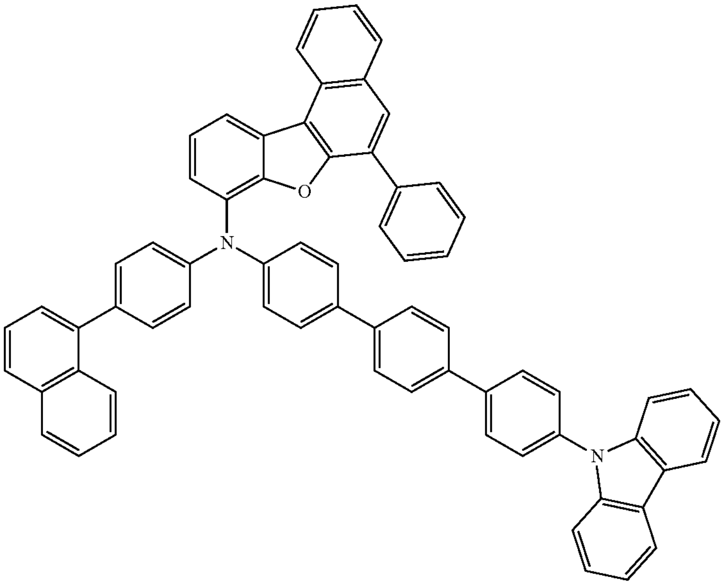

-continued
(544)
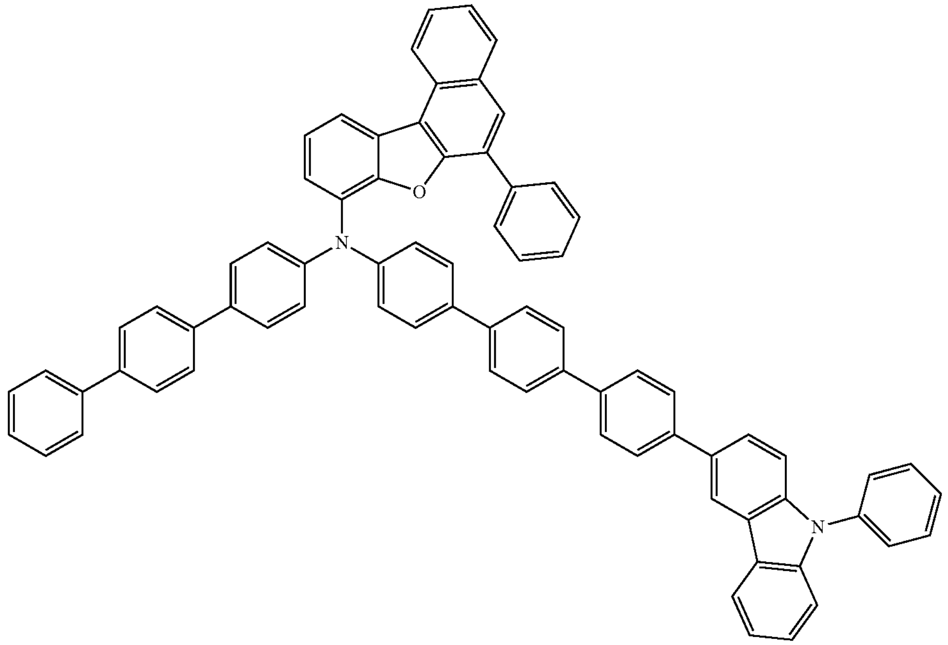
(545)
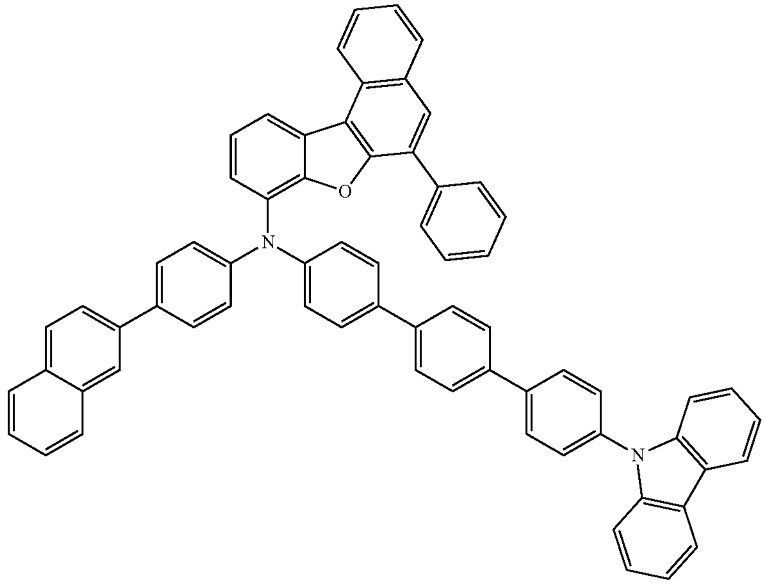

-continued
(546)
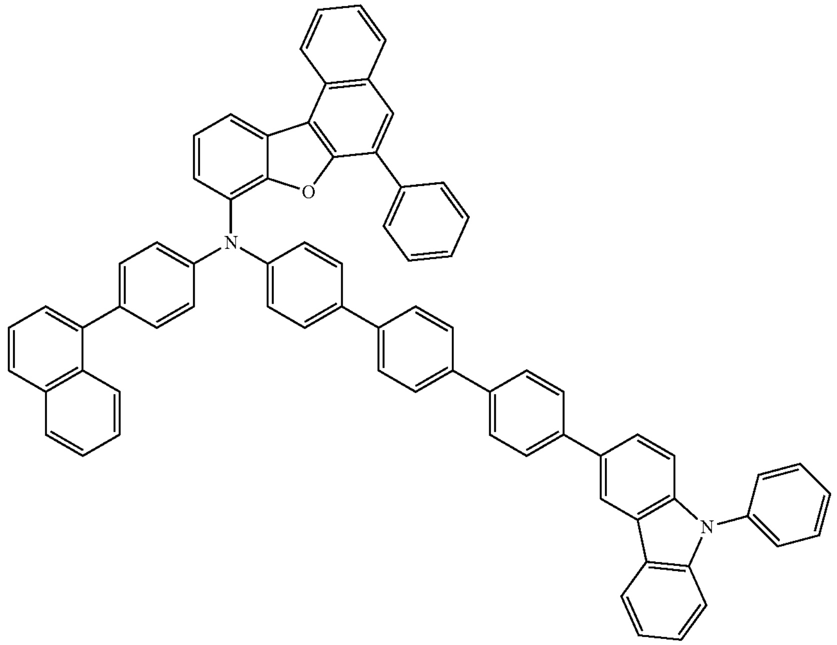
[Chemical Formula 40]
(547)
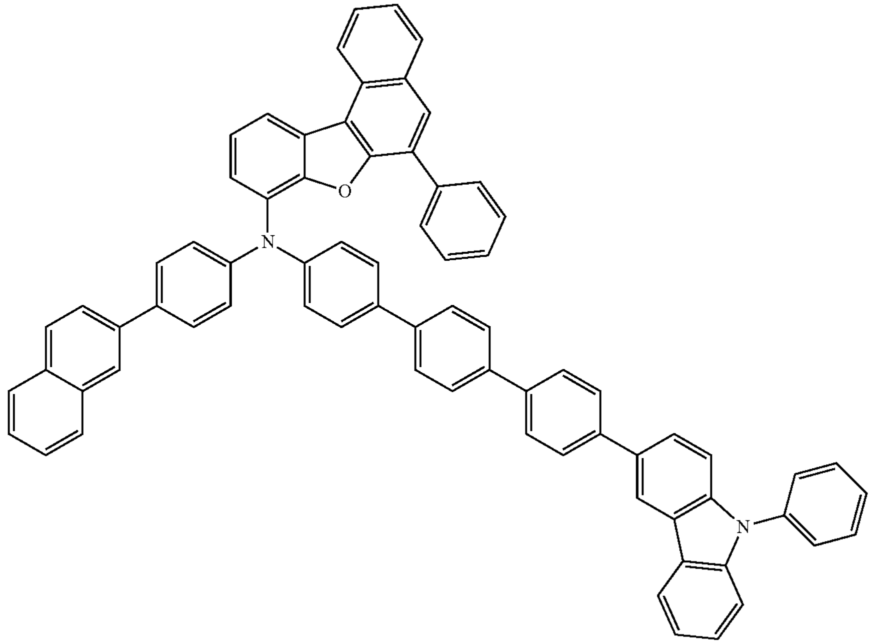

-continued
(548)
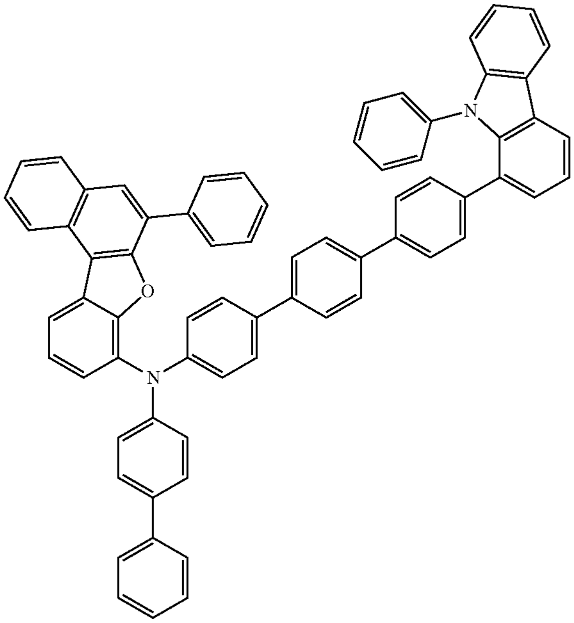
(549)
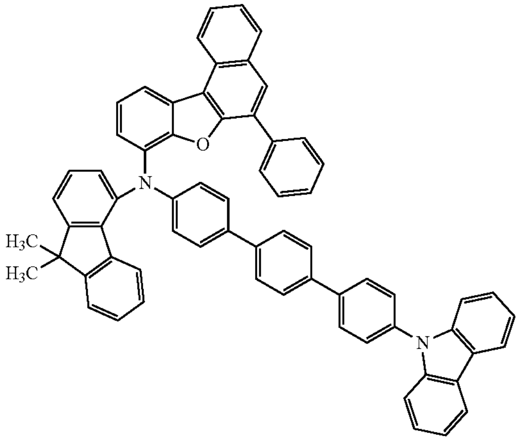
(550)
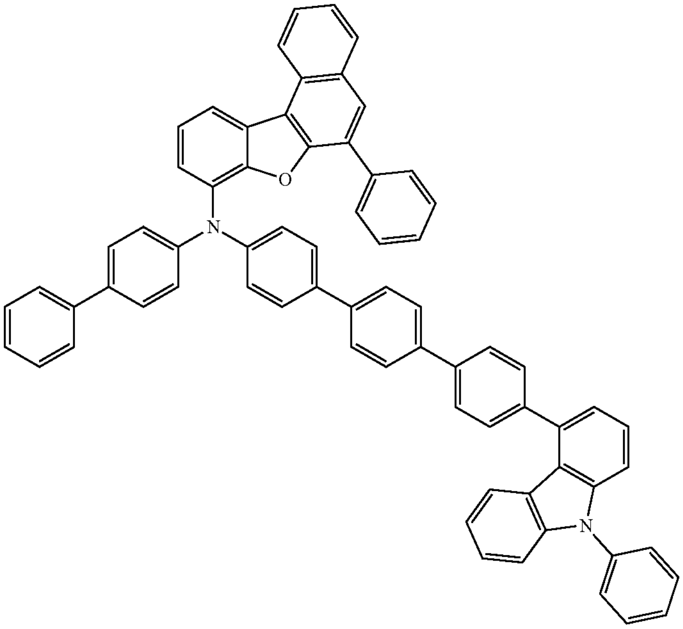

-continued
(551)
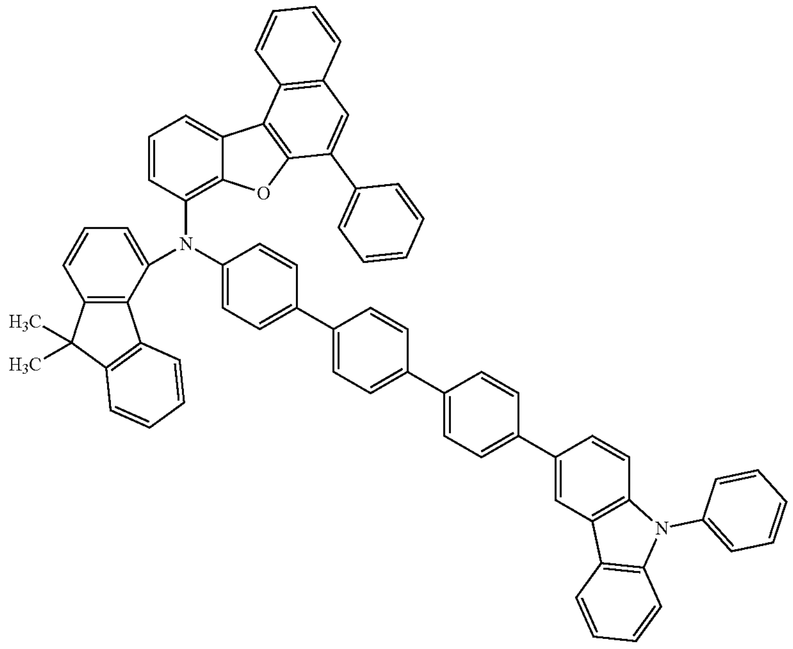
(552)
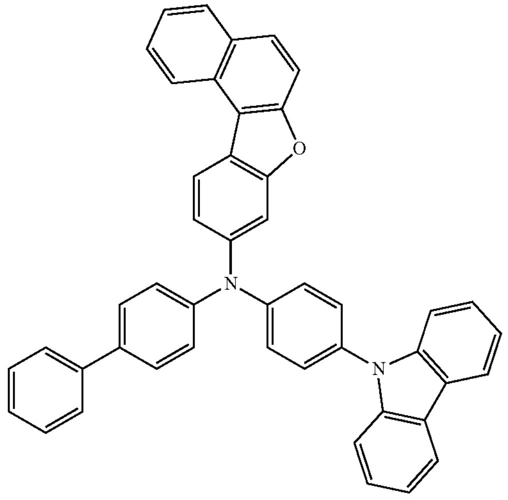
(553)
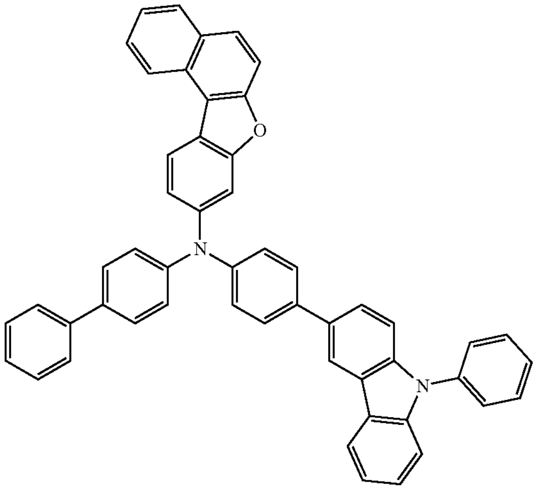
(554)
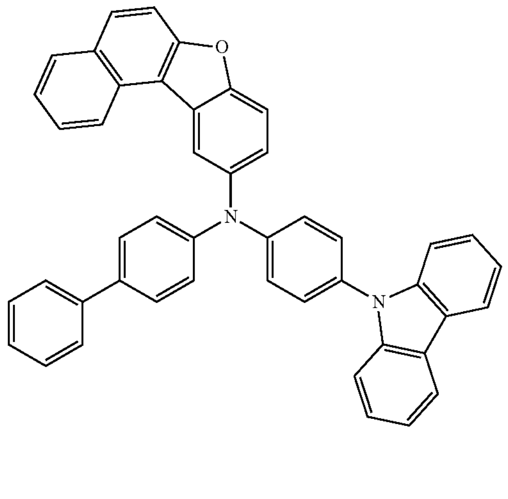
(555)
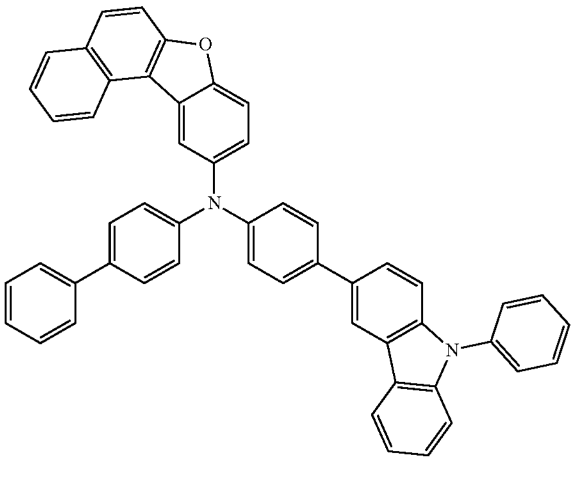

-continued
(556)
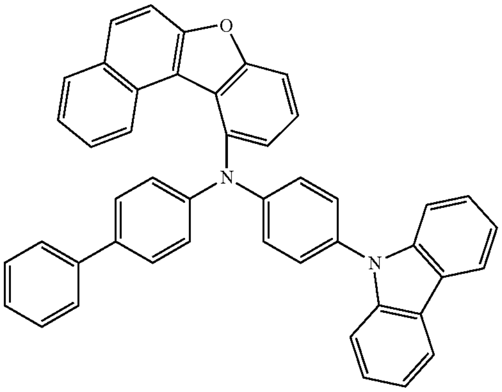
(557)
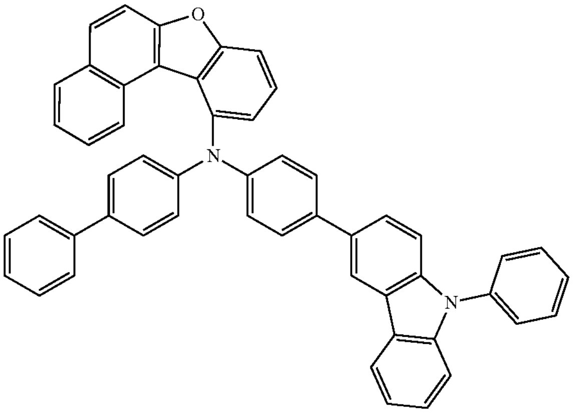
[Chemical Formula 41]
(558)
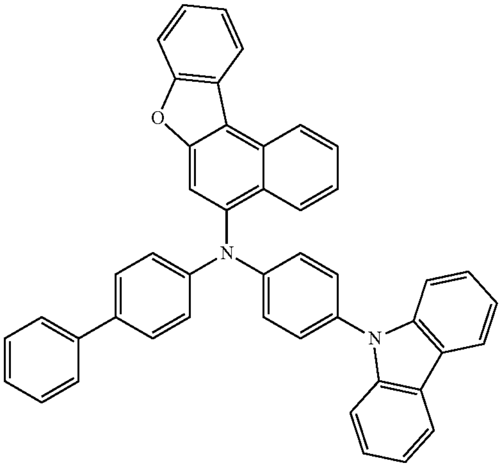
(559)
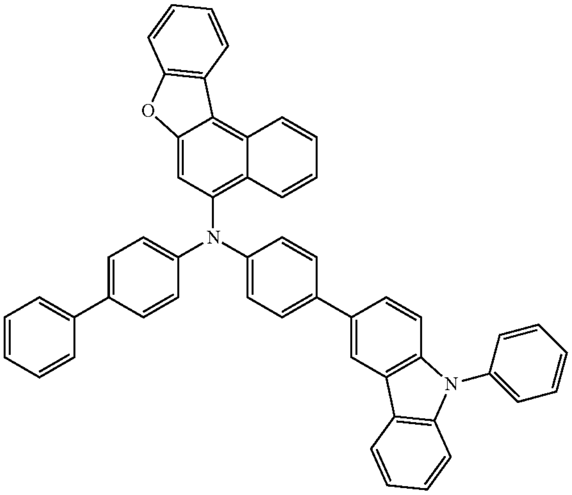
(560)
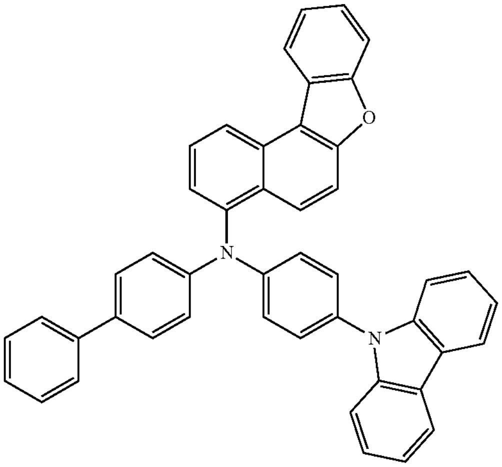
(561)
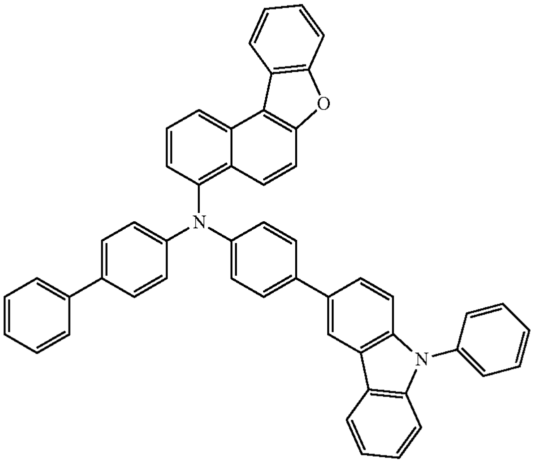

-continued
(562)
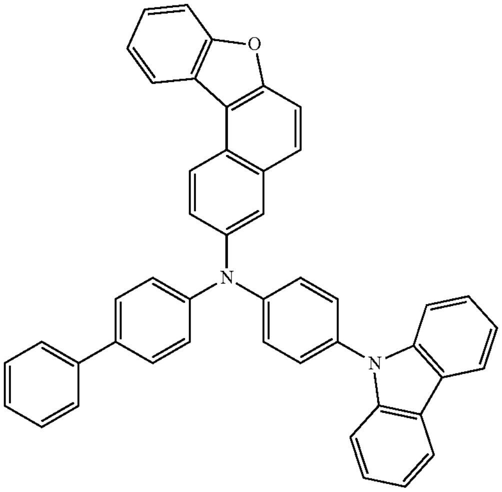
(563)
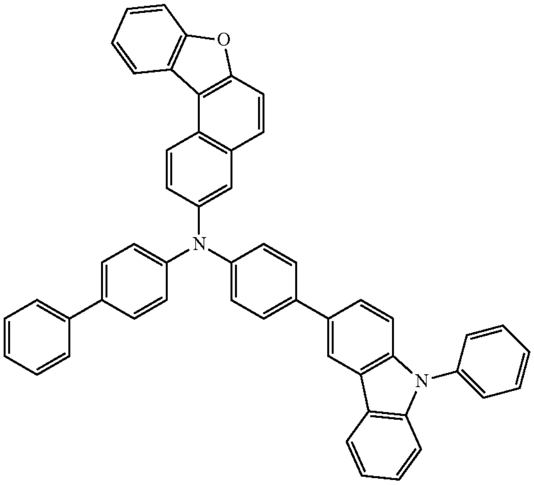
(564)
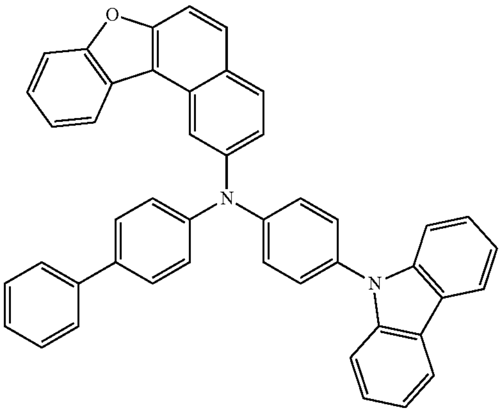
(565)
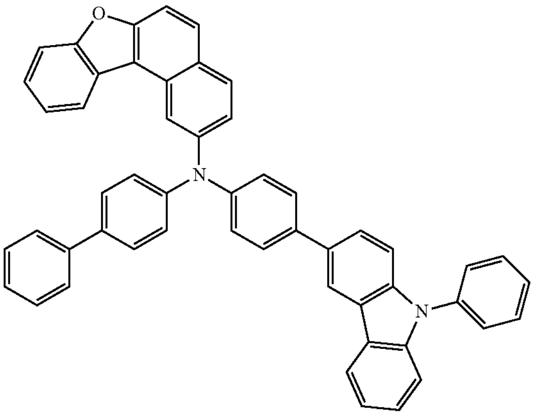
(566)
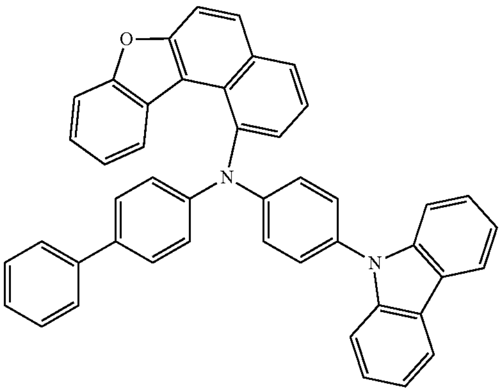
(567)
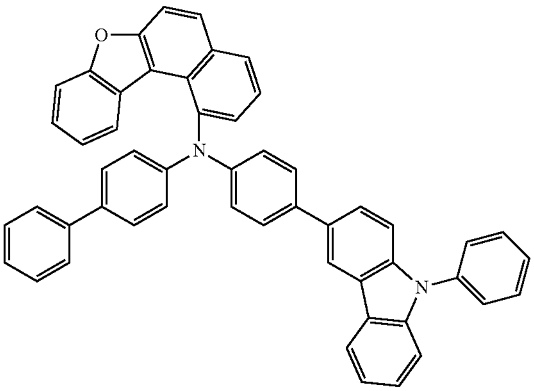

-continued
(568)
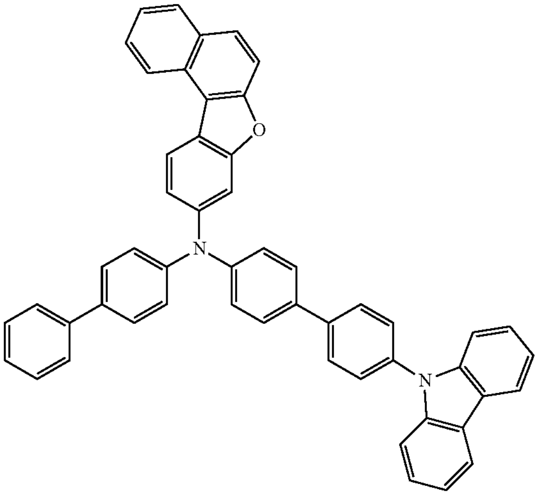
(569)
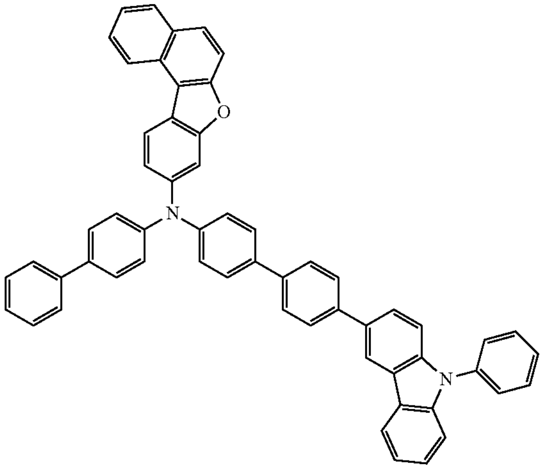
[Chemical Formula 42]
(570)
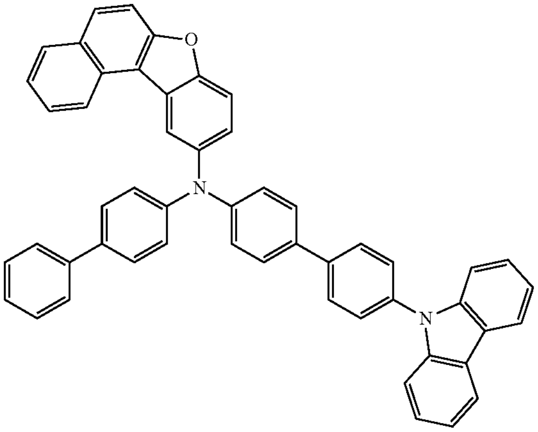
(571)
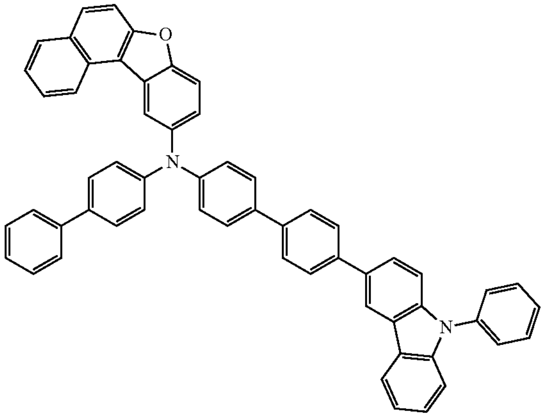
(572)
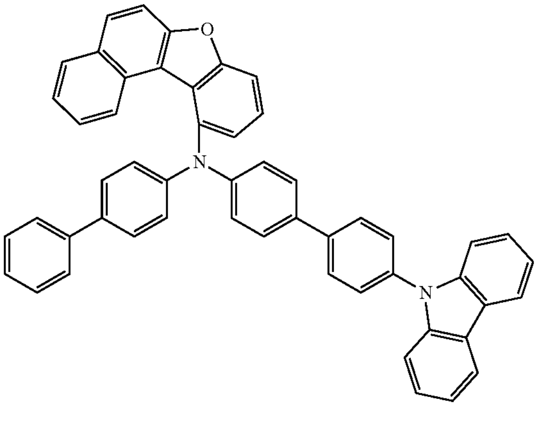
(573)
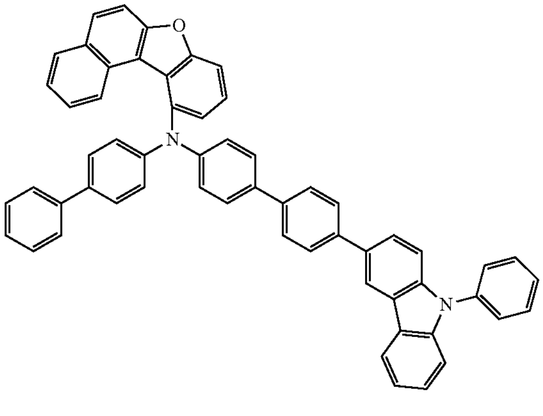

-continued
(574)
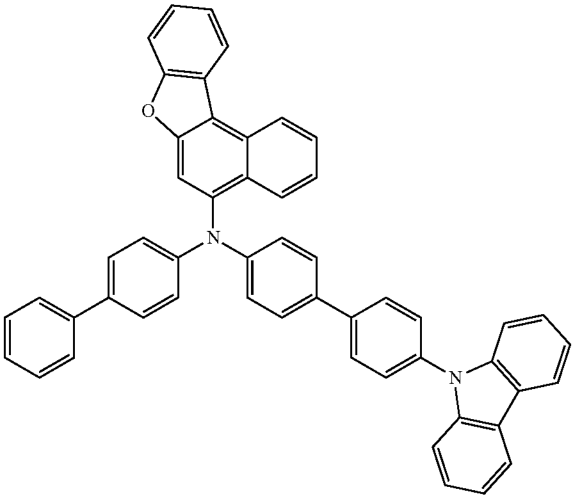
(575)
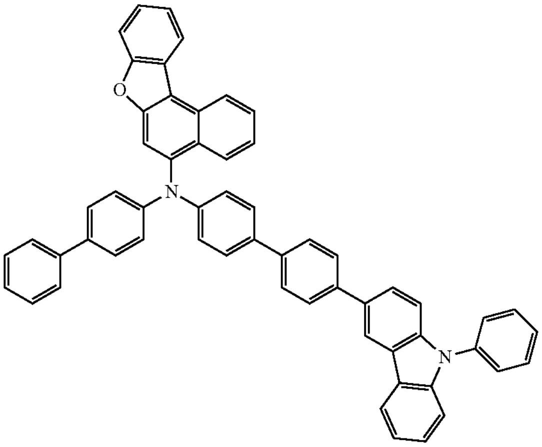
(576)
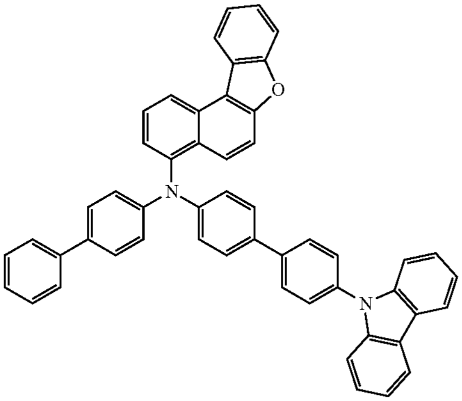
(577)
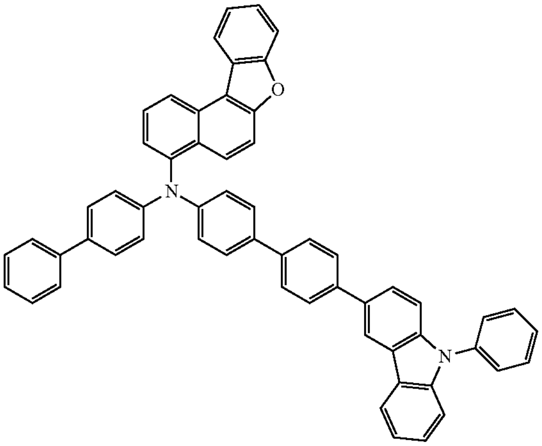
(578)
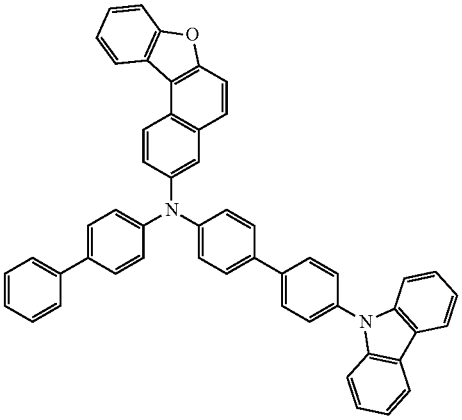
(579)
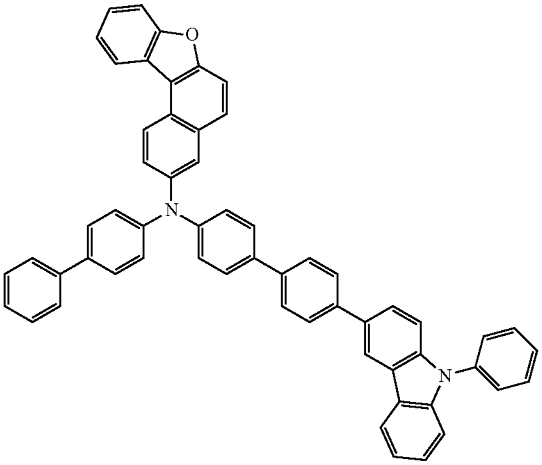

-continued
(580)
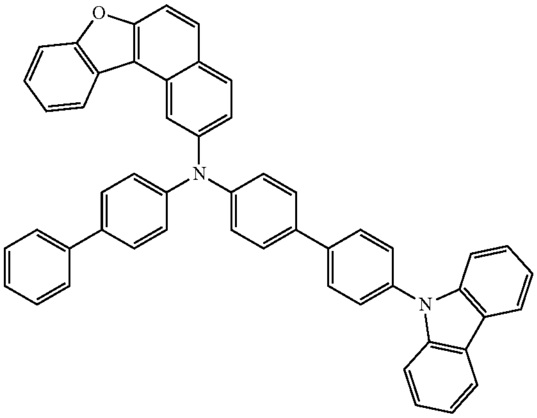
(581)
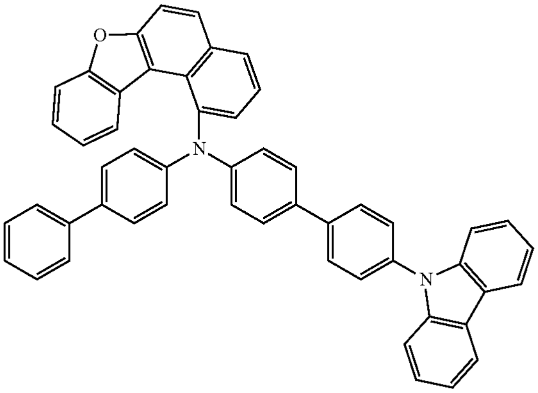
(582)
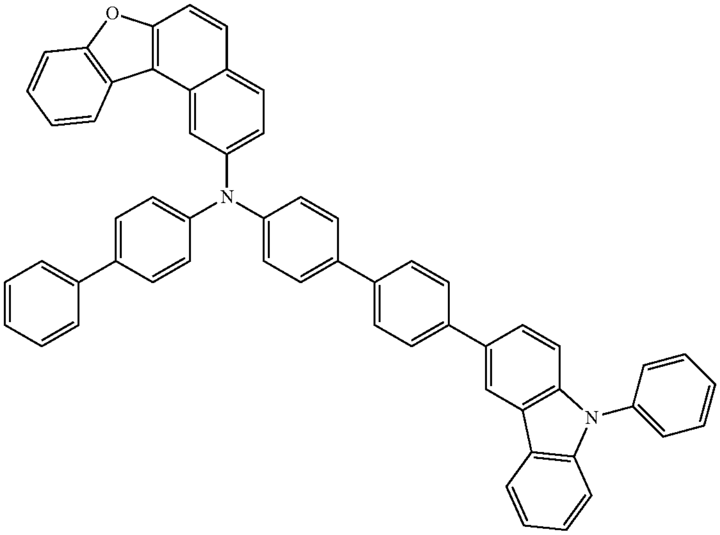
[Chemical Formula 43]
(583)
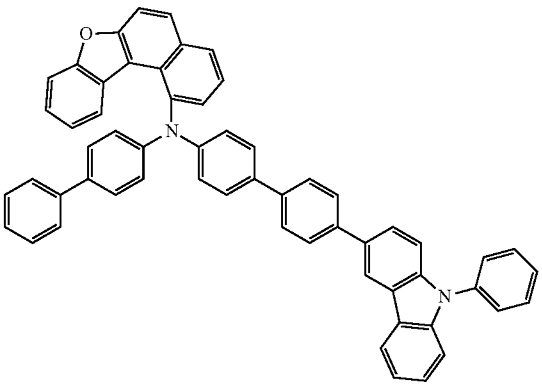
(584)
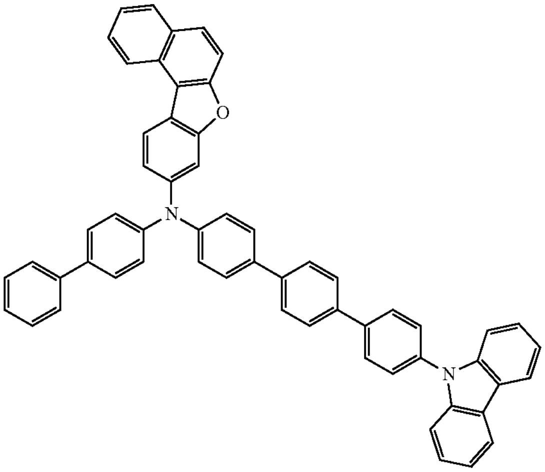

-continued
(585)
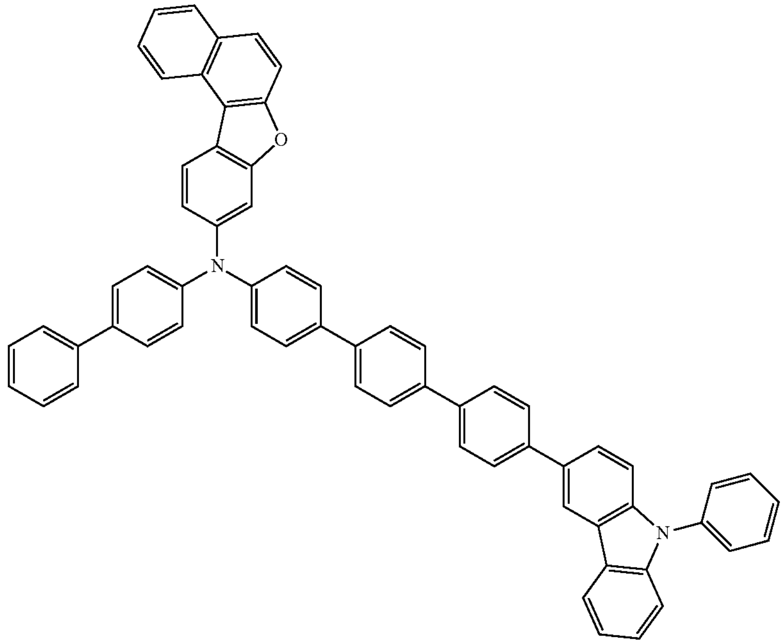
(586)
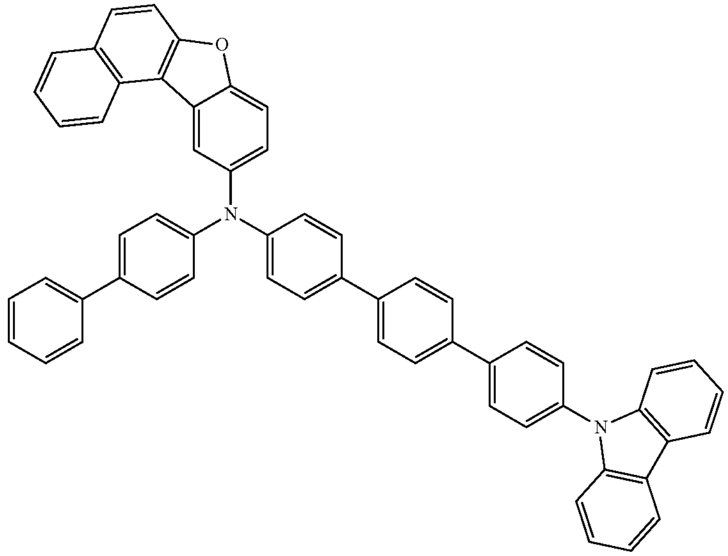

-continued
(587)
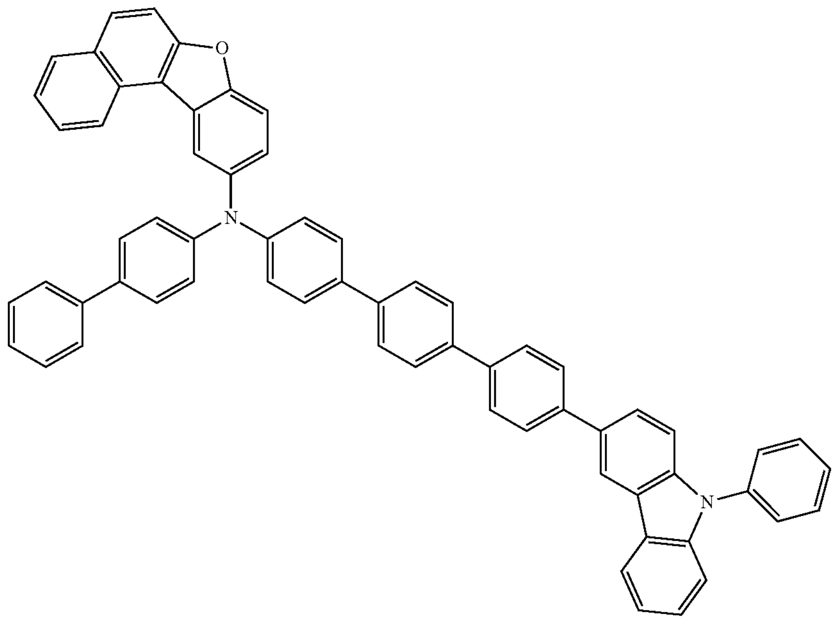
(588)
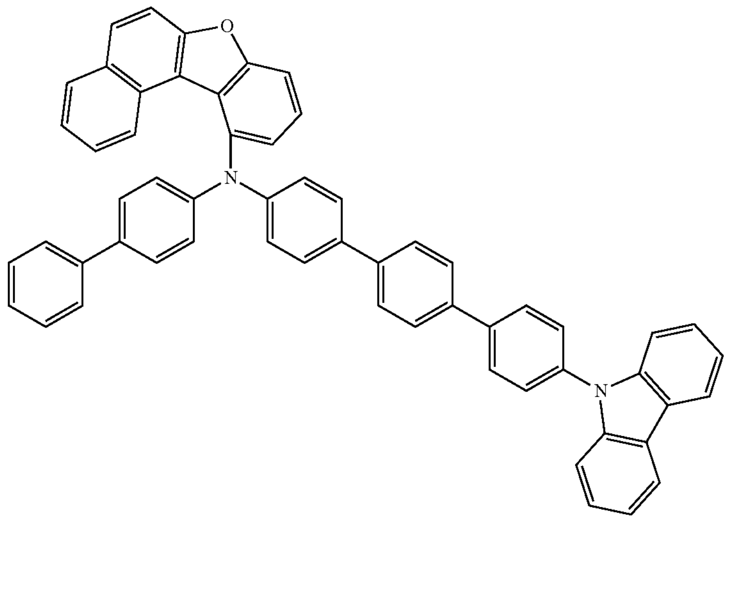

-continued
(589)
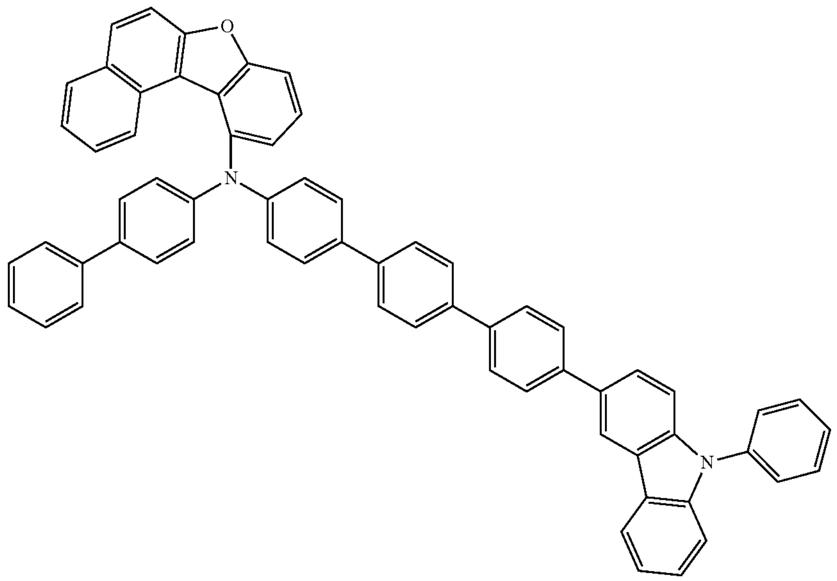
(590)
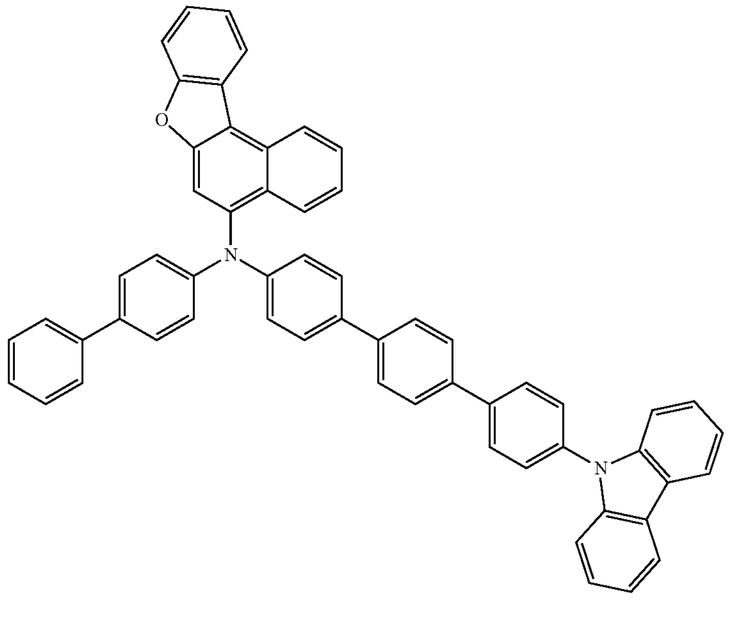

-continued
(591)
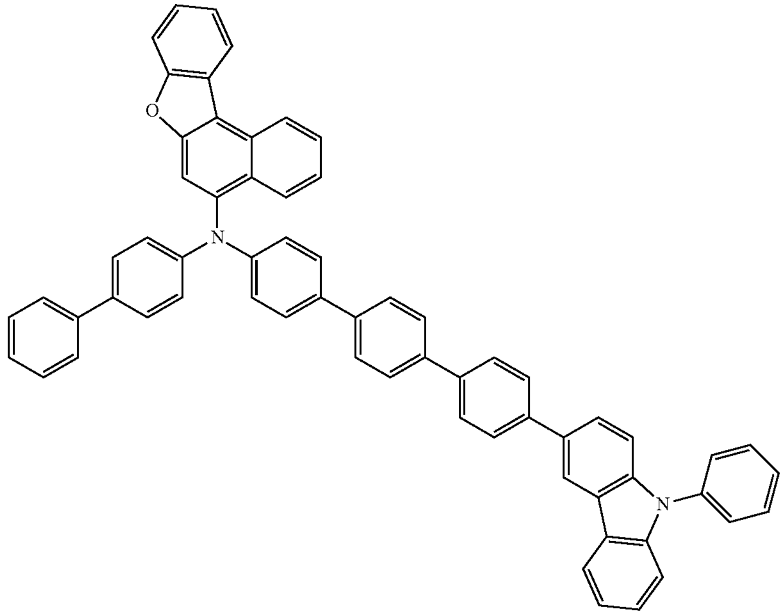
(592)
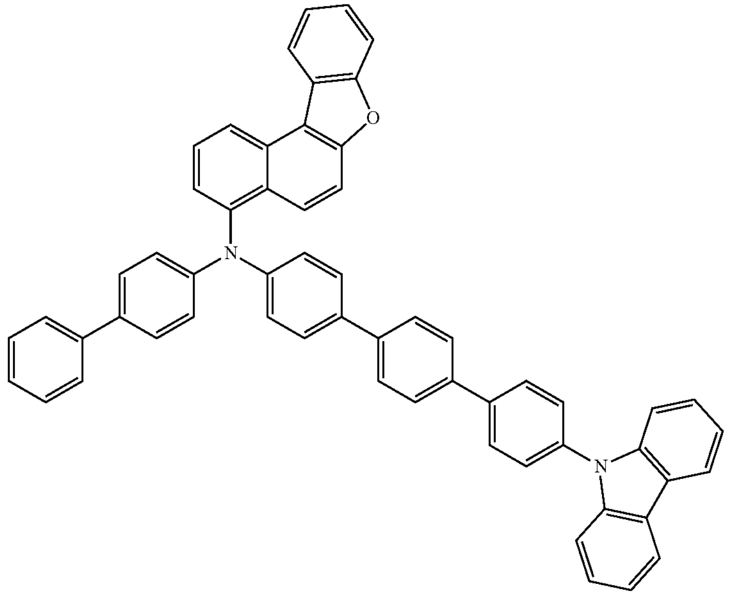

-continued
[Chemical Formula 44]
(593)
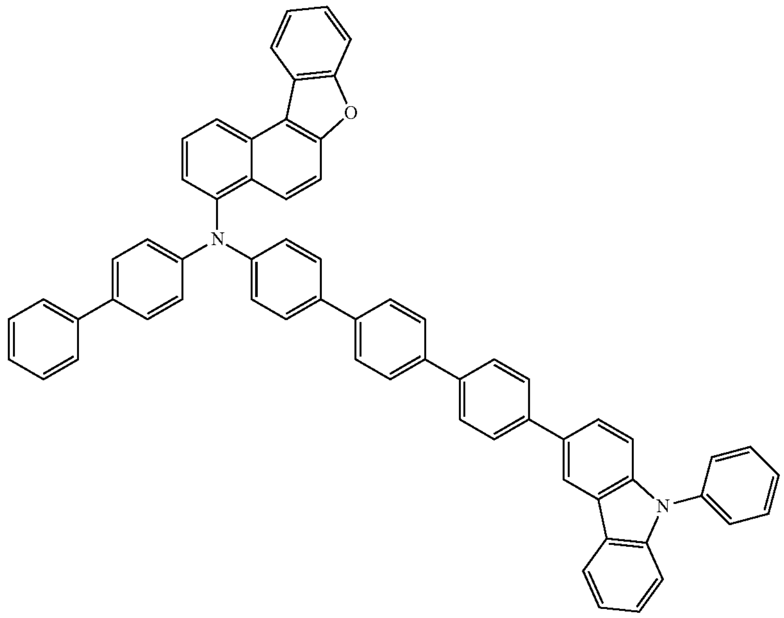
(594)
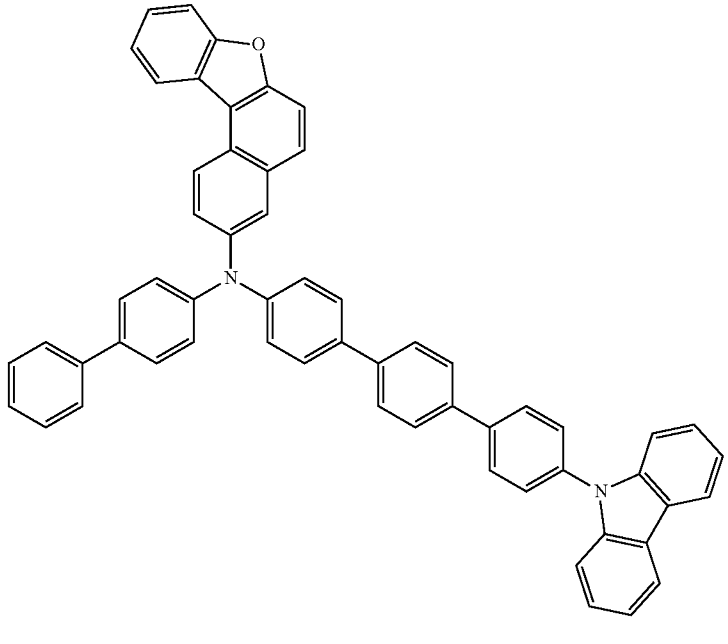

-continued
(595)
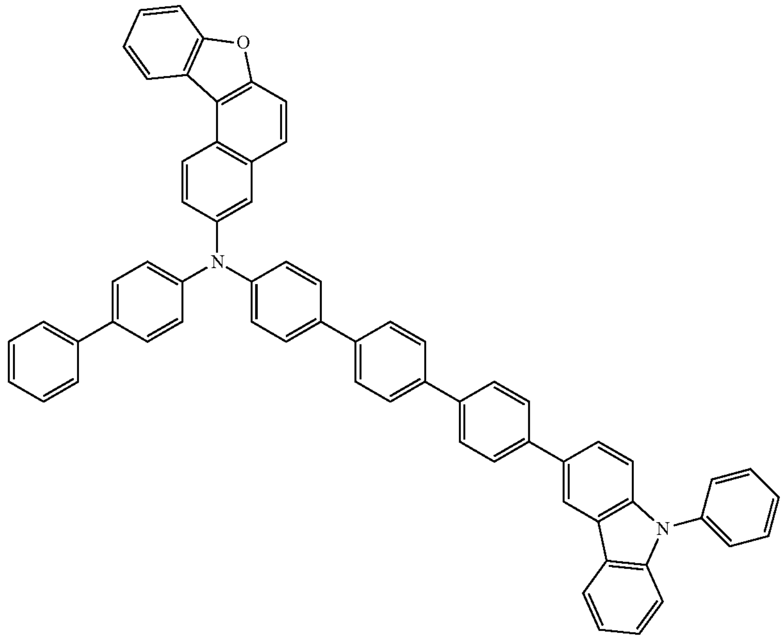
(596)
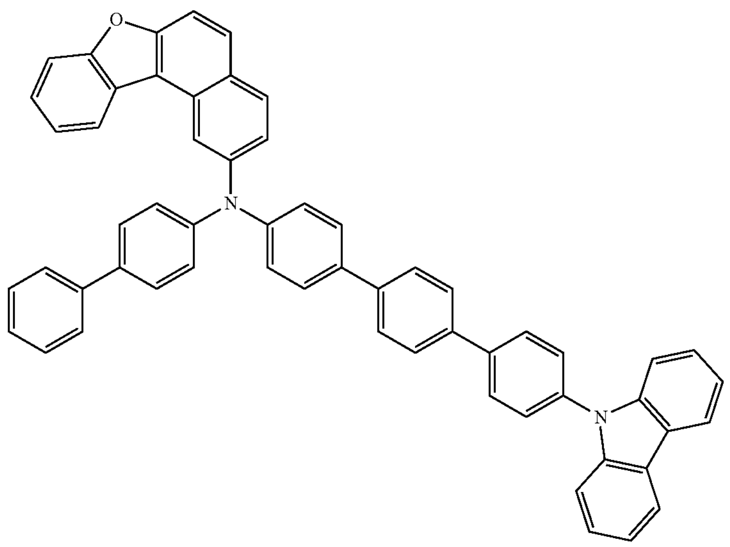

-continued
(597)
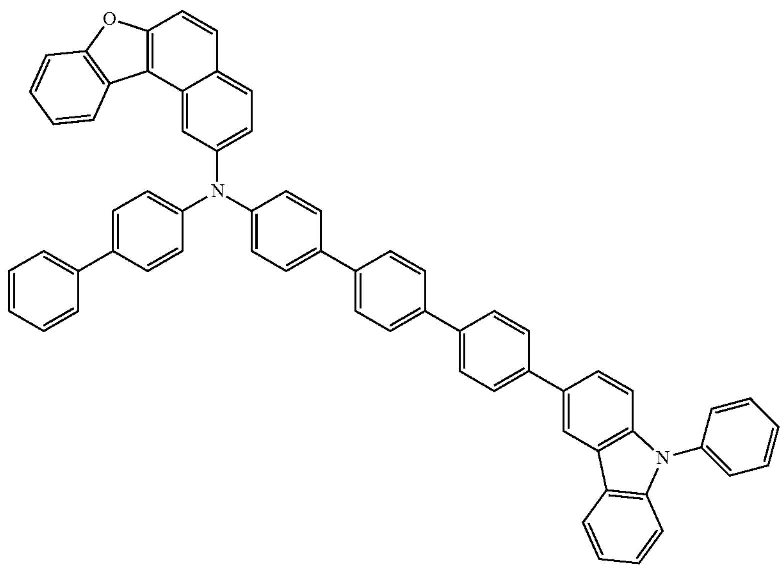
(598)
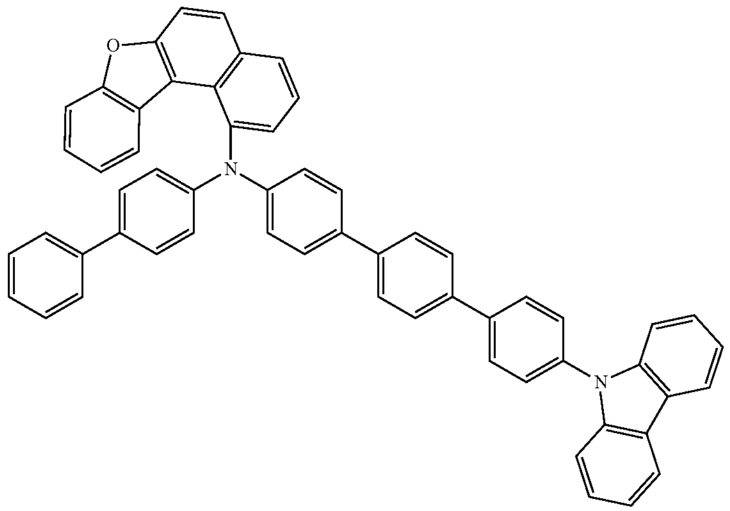
(599)
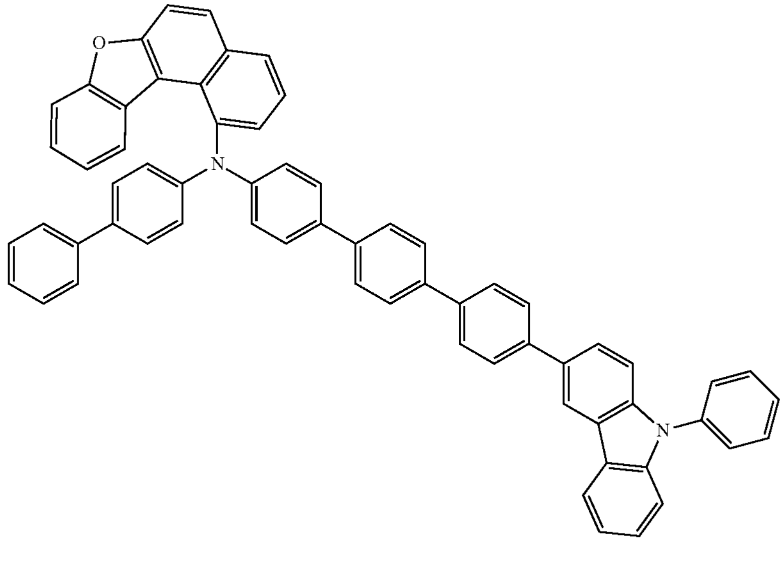

The above-described organic compounds can be synthesized by the following synthesis schemes, for example.

Here, synthesis methods of General Formula (G1) will be described by taking the cases where the group represented by General Formula (g1) is bonded to $R^9$ and where the group represented by General Formula (g1) is bonded to $R^0$ in General Formula (G1) above as examples. Note that in the case where the group represented by General Formula (g1) is bonded to $R^9$, General Formula (G1) above can be represented by General Formula (G1-1) below, and in the case where the group represented by General Formula (g1) is bonded to $R^0$, General Formula (G1) above can be represented by General Formula (G1-2) below. The descriptions of Cz, $R^0$ to $R^9$, $Ar^4$, $Ar^5$, $Ar^b$, n, and m in the organic compound represented by General Formula (G1-1) below and the organic compound represented by General Formula (G1-2) below are the same as the above descriptions thereof for General Formula (G1) and are therefore omitted.

[Chemical Formula 45]

(G1-1)

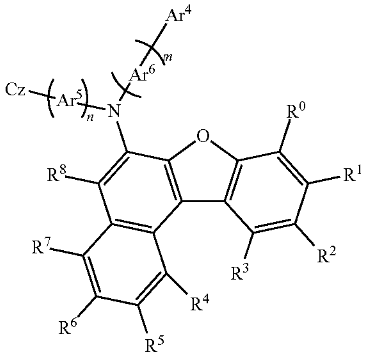

[Chemical Formula 46]

(G1-2)

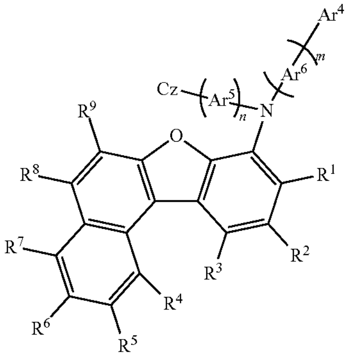

A variety of reactions can be applied to the method for synthesizing the organic compounds represented by General Formulae (G1-1) and (G1-2). For example, synthesis reactions described below enable the synthesis of the organic compounds represented by General Formulae (G1-1) and (G1-2).

<Method for Synthesizing Organic Compound Represented by General Formula (G1-1)>

The organic compound of the present invention represented by General Formula (G1-1) can be synthesized by Synthesis Schemes (a-1) to (a-3) below.

That is, a benzonaphthofuran compound (compound 1) is coupled with diarylamine (compound 2), whereby a benzonaphthofuranylamino compound (G1-1) can be obtained.

Alternatively, benzonaphthofuranylamine (compound 3) is coupled with a compound having an aryl skeleton (compound 4), whereby a benzonaphthofuranylamino compound (G1-1) can be obtained. Alternatively, benzonaphthofuranylamine (compound 5) is coupled with a compound having an aryl skeleton (compound 6), whereby a benzonaphthofuranylamino compound (G1-1) can be obtained. Synthesis Schemes (a-1) to (a-3) are shown below.

[Chemical Formula 47]

(a-1)

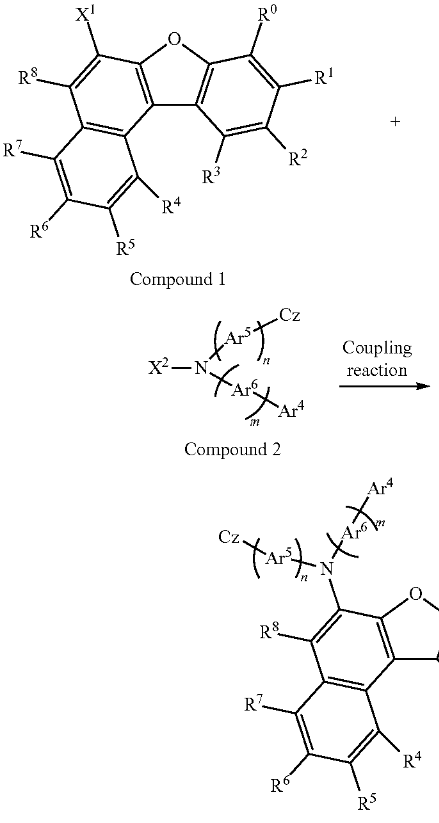

Compound 1

Compound 2

(G1-1)

[Chemical Formula 48]

(a-2)

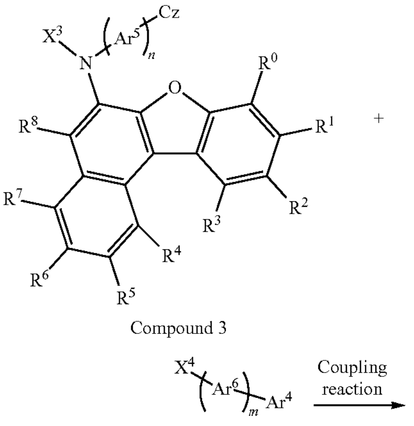

Compound 3

Compound 4

-continued

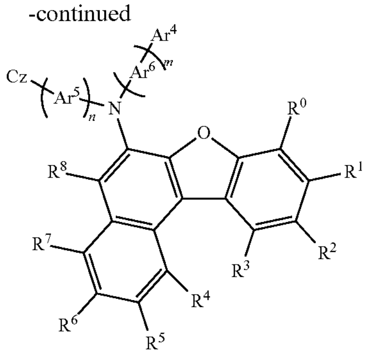

(G1-1)

[Chemical Formula 49]

(a-3)

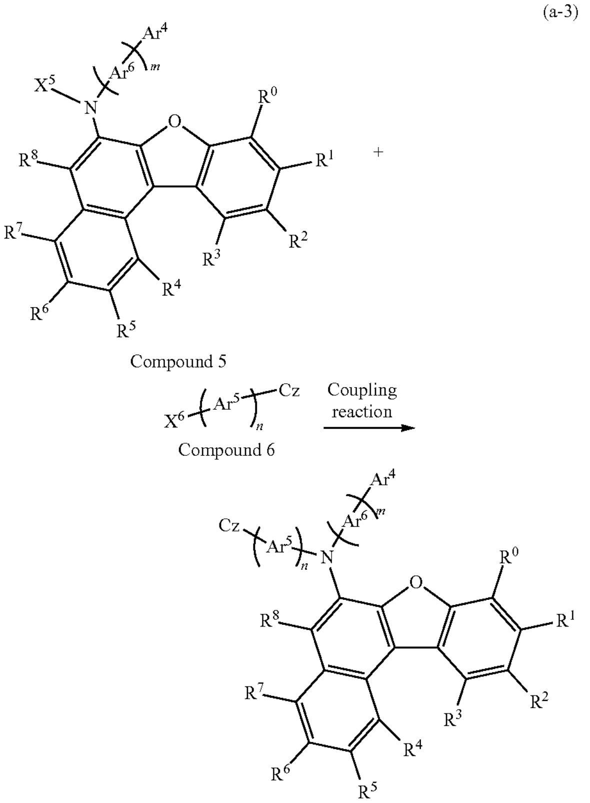

Compound 5

Compound 6

(G1-1)

In Synthesis Schemes (a-1) to (a-3), $R^0$ to $R^8$ each independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms, and Cz represents a substituted or unsubstituted carbazolyl group. Furthermore, $Ar^4$ represents any one of a substituted or unsubstituted aromatic hydrocarbon group having 6 to 60 carbon atoms and a substituted or unsubstituted carbazolyl group. In addition, $Ar^5$ and $Ar^6$ each independently represent a substituted or unsubstituted divalent aromatic hydrocarbon group having 6 to 54 carbon atoms. Moreover, n is any one integer of 1 to 3 and m is any one integer of 0 to 3; however, when $Ar^4$ is a carbazolyl group, m is any one integer of 1 to 3. Furthermore, a plurality of $Ar^5$ or $Ar^6$ may exist depending on the value of n or m; the plurality of $Ar^5$ or $Ar^6$ each independently represent a substituted or unsubstituted divalent aromatic hydrocarbon group having 6 to 54 carbon atoms. Furthermore, the sum of the numbers of carbon atoms of Cz and $Ar^5$ and the sum of the numbers of carbon atoms of $Ar^4$ and $Ar^6$ are each smaller than or equal to 60.

In Synthesis Schemes (a-1) to (a-3), $X^1$, $X^4$, and $X^6$ each independently represent chlorine, bromine, iodine, a triflate group, or the like; and $X^2$, $X^3$, and $X^5$ each independently represent hydrogen, an organotin group, or the like.

In the case where the reactions shown in Synthesis Schemes (a-1) to (a-3) are performed by the Buchwald-Hartwig reaction using a palladium catalyst, a palladium compound such as bis(dibenzylideneacetone)palladium(0), palladium(II) acetate, [1,1-bis(diphenylphosphino)ferrocene]palladium(II) dichloride, tetrakis(triphenylphosphine) palladium(0), or allylpalladium(II) chloride (dimer) can be used as a catalyst, and a ligand such as tri(tert-butyl) phosphine, tri(n-hexyl)phosphine, tricyclohexylphosphine, di(1-adamantyl)-n-butylphosphine, 2-dicyclohexylphosphino-2',6'-dimethoxybiphenyl, tri(ortho-tolyl)phosphine, or (S)-(6,6'-dimethoxybiphenyl-2,2'-diyl)bis(diisopropylphosphine) (abbreviation: cBRIDP) can be used. In the reaction, an organic base such as sodium tert-butoxide, an inorganic base such as potassium carbonate, cesium carbonate, or sodium carbonate, or the like can be used. In the reaction, toluene, xylene, benzene, tetrahydrofuran, dioxane, or the like can be used as a solvent. Note that reagents that can be used in the reaction are not limited to the above-described reagents.

Furthermore, in the case where the Ullmann reaction using copper or a copper compound is used in Synthesis Schemes (a-1) to (a-3), $X^1$, $X^4$, and $X^6$ each independently represent chlorine, bromine, or iodine, and $X^2$, $X^3$, and $X^5$ represent hydrogen. Copper or a copper compound can be used in the reaction. As the base to be used, an inorganic base such as potassium carbonate can be given. As the solvent that can be used in the reaction, 1,3-dimethyl-3,4,5,6-tetrahydro-2(1H)pyrimidinone (DMPU), toluene, xylene, benzene, and the like can be given. In the Ullmann reaction, when the reaction temperature is 100° C. or higher, an objective substance can be obtained in a shorter time in a higher yield; therefore, it is preferable to use DMPU or xylene having a high boiling point. A higher reaction temperature of 150° C. or higher is further preferred, and accordingly, DMPU is further preferably used. Reagents that can be used in the reaction are not limited to the above-described reagents.

<Method for Synthesizing Organic Compound Represented by General Formula (G1-2)>

The organic compound represented by General Formula (G1-2) can be synthesized as shown in Synthesis Schemes (b-1) to (b-3) below.

That is, a benzonaphthofuran compound (compound 11) is coupled with diarylamine (compound 12), whereby a benzonaphthofuranylamino compound (G1-2) can be obtained. Alternatively, benzonaphthofuranylamine (compound 13) is coupled with a compound having an aryl skeleton (compound 4), whereby a benzonaphthofuranylamino compound (G1-2) can be obtained. Alternatively, benzonaphthofuranylamine (compound 15) is coupled with a compound having an aryl skeleton (compound 6), whereby a benzonaphthofuranylamino compound (G1-2) can be obtained. Synthesis Schemes (b-1) to (b-3) are shown below.

[Chemical Formula 50]

(b-1)

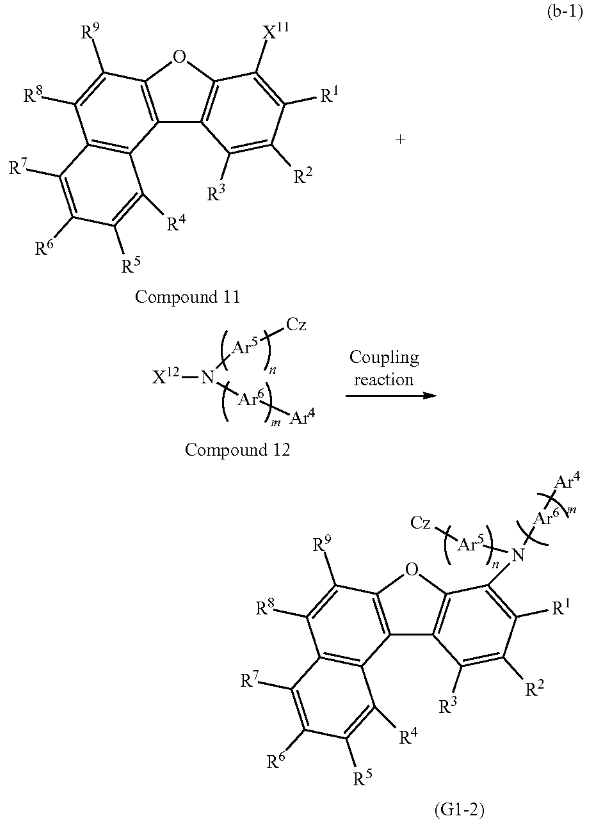

Compound 11

Compound 12

(G1-2)

[Chemical Formula 51]

(b-2)

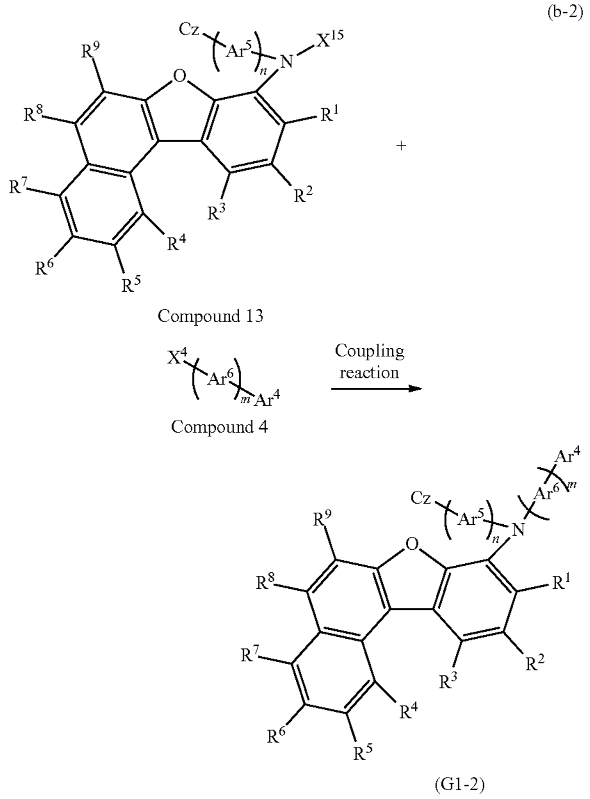

Compound 13

Compound 4

(G1-2)

-continued

[Chemical Formula 52]

(b-3)

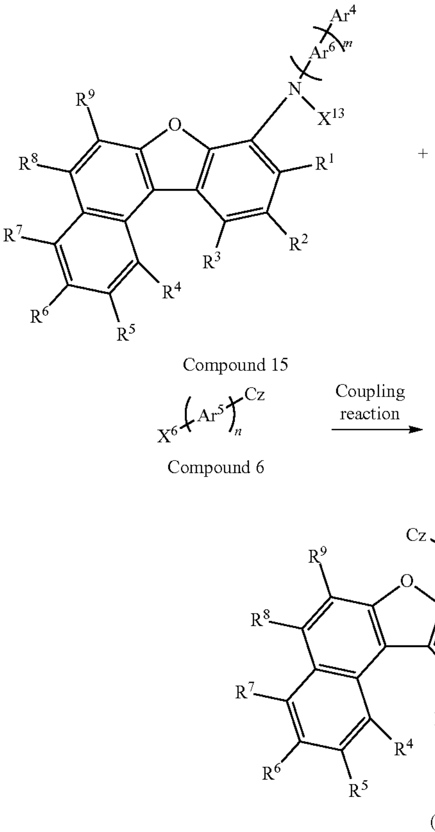

Compound 15

Compound 6

(G1-2)

In Synthesis Schemes (b-1) to (b-3), $R^1$ to $R^9$ each independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms, and Cz represents a substituted or unsubstituted carbazolyl group. Furthermore, $Ar^4$ represents any one of a substituted or unsubstituted aromatic hydrocarbon group having 6 to 60 carbon atoms and a substituted or unsubstituted carbazolyl group. In addition, $Ar^5$ and $Ar^6$ each independently represent any one of substituted or unsubstituted divalent aromatic hydrocarbon groups having 6 to 54 carbon atoms. Moreover, n is any one integer of 1 to 3 and m is any one integer of 0 to 3; however, when $Ar^4$ is a carbazolyl group, m is any one integer of 1 to 3. Furthermore, a plurality of $Ar^5$ or $Ar^6$ may exist depending on the value of n or m; the plurality of $Ar^5$ or $Ar^6$ each independently represent any one of substituted or unsubstituted divalent aromatic hydrocarbon groups having 6 to 54 carbon atoms. Furthermore, the sum of the numbers of carbon atoms of Cz and $Ar^5$ and the sum of the numbers of carbon atoms of $Ar^4$ and $Ar^6$ are each smaller than or equal to 60.

In Synthesis Schemes (b-1) to (b-3), $X^{11}$, $X^4$, and $X^6$ each independently represent chlorine, bromine, iodine, or a triflate group; and $X^{12}$, $X^{13}$, and $X^{15}$ each independently represent hydrogen, an organotin group, or the like.

In the case where the reactions shown in Synthesis Schemes (b-1) to (b-3) are performed by the Buchwald- Hartwig reaction using a palladium catalyst, a palladium compound such as bis(dibenzylideneacetone)palladium(0), palladium(II) acetate, [1,1-bis(diphenylphosphino)ferrocene]palladium(II) dichloride, tetrakis(triphenylphosphine) palladium(0), or allylpalladium(II) chloride (dimer) can be used as a catalyst, and a ligand such as tri(tert-butyl) phosphine, tri(n-hexyl)phosphine, tricyclohexylphosphine, di(1-adamantyl)-n-butylphosphine, 2-dicyclohexylphosphino-2',6'-dimethoxybiphenyl, tri(ortho-tolyl)phosphine, or (S)-(6,6'-dimethoxybiphenyl-2,2'-diyl)bis(diisopropylphosphine) (abbreviation: cBRIDP (registered trademark)) can be used. In the reaction, an organic base such as sodium tert-butoxide, an inorganic base such as potassium carbonate, cesium carbonate, or sodium carbonate, or the like can be used. In the reaction, toluene, xylene, benzene, tetrahydrofuran, dioxane, or the like can be used as a solvent. Reagents that can be used in the reaction are not limited to the above-described reagents.

Furthermore, in the case where the Ullmann reaction using copper or a copper compound is used in Synthesis Schemes (b-1) to (b-3), $X^1$, $X^4$, and $X^6$ each independently represent chlorine, bromine, or iodine, and $X^{12}$, $X^{13}$, and $X^{15}$ represent hydrogen. Copper or a copper compound can be used in the reaction. As the base to be used, an inorganic base such as potassium carbonate can be given. As the solvent that can be used in the reaction, 1,3-dimethyl-3,4,5,6-tetrahydro-2(1H)pyrimidinone (DMPU), toluene, xylene, benzene, and the like can be given. In the Ullmann reaction, when the reaction temperature is 100° C. or higher, an objective substance can be obtained in a shorter time in a higher yield; therefore, it is preferable to use DMPU or xylene having a high boiling point. A higher reaction temperature of 150° C. or higher is further preferred, and accordingly, DMPU is further preferably used. Reagents that can be used in the reaction are not limited to the above-described reagents.

The synthesis methods of General Formula for the cases where (g1) is bonded to $R^9$ in General Formula (G1) and where (g1) is bonded to $R^0$ in General Formula (G1) have been described so far. A similar synthesis method can be used for the cases where (g1) is bonded to $R^1$ to $R^8$ in General Formula (G1). In other words, the objective compound of General Formula (G1) can be synthesized by a coupling reaction between a benzonaphthofuran compound and an amine compound or a coupling reaction between a benzonaphthofuranylamine compound and a compound having an aryl group. The synthesis method of the compound represented by General Formula (G1) is not limited to these methods.

Examples of amine that can be used for the synthesis of the organic compound of one embodiment of the present invention are shown below. Among these, (700) to (739), (817) to (848), and (884) to (926) correspond to the above-described compounds 2 and 12, and (740) to (816), (849) to (883), and (927) to (945) correspond to the above-described compounds 3, 5, 13, and 15; these are organic compounds capable of synthesizing the organic compound of one embodiment of the present invention by a coupling reaction with an appropriate organic compound.

[Chemical Formula 53]

(700)

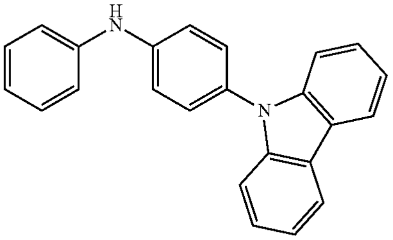

(701)

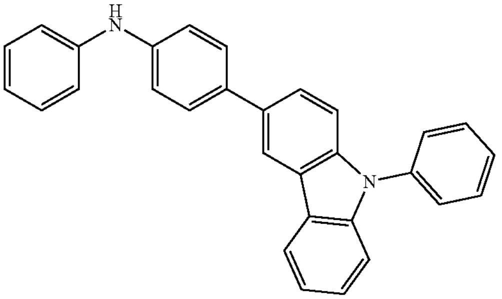

(702)

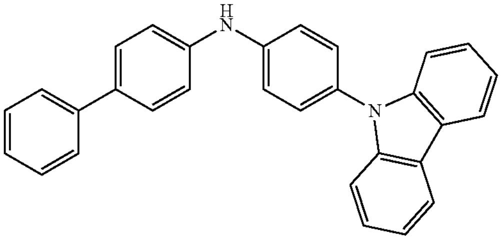

(703)

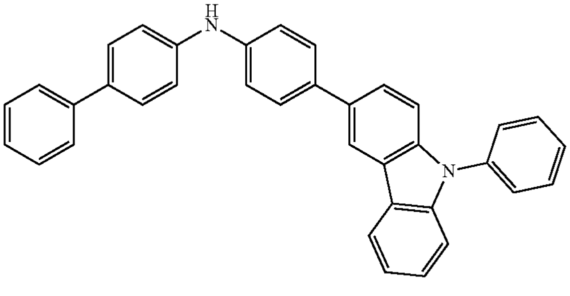

-continued
(704)
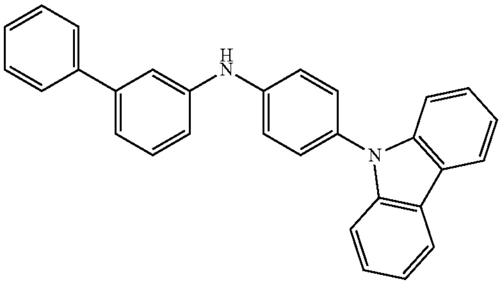
(705)
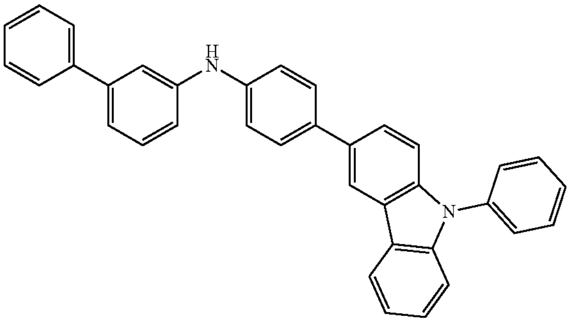
(706)
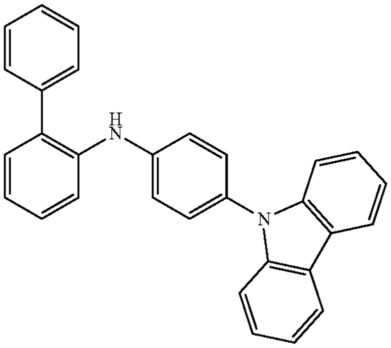
(707)
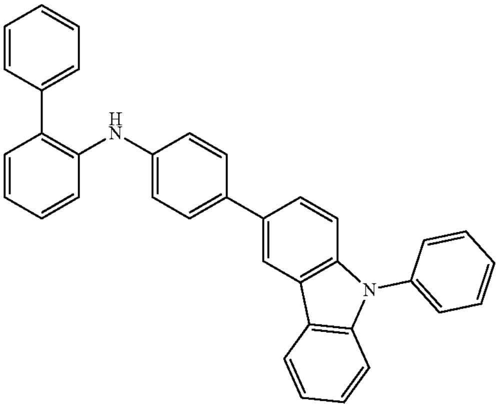
(708)
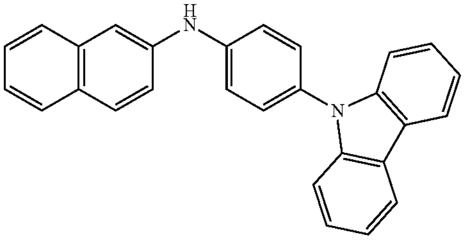
(709)
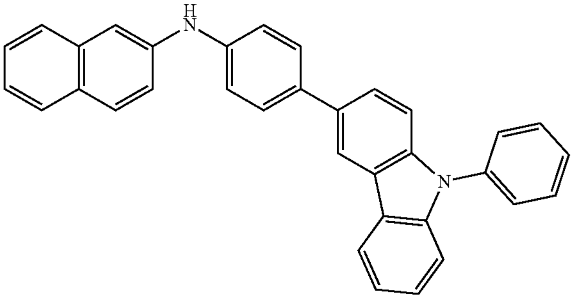
(710)
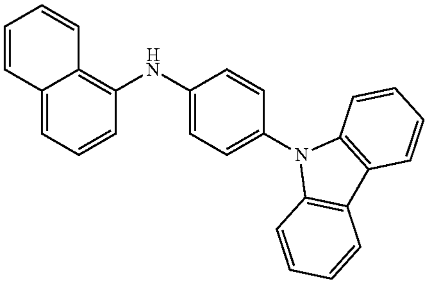
(711)
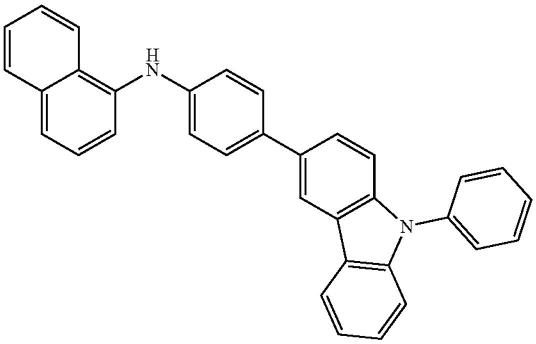

-continued
(712)
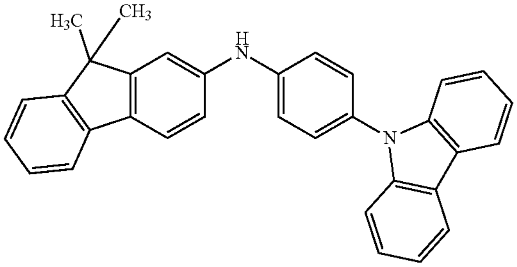
(713)
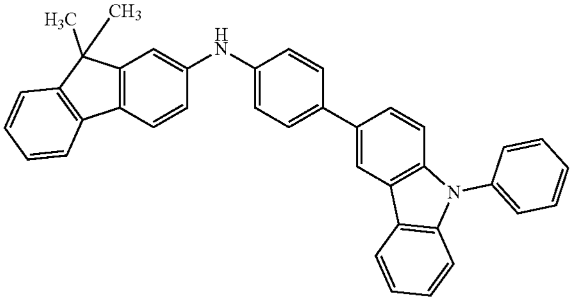
(714)
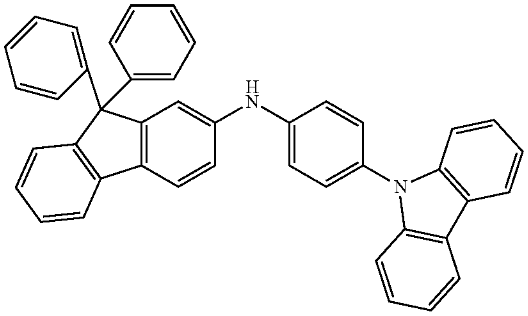
(715)
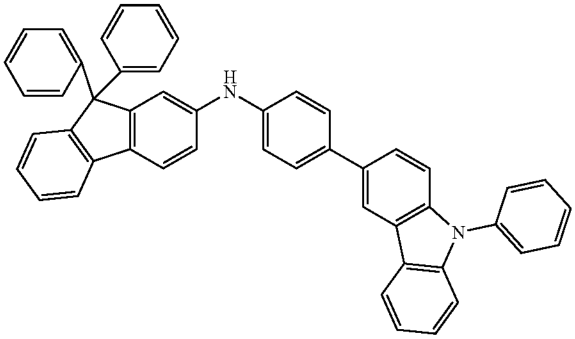
(716)
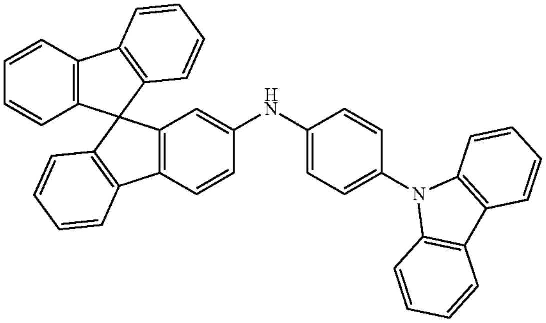
(717)
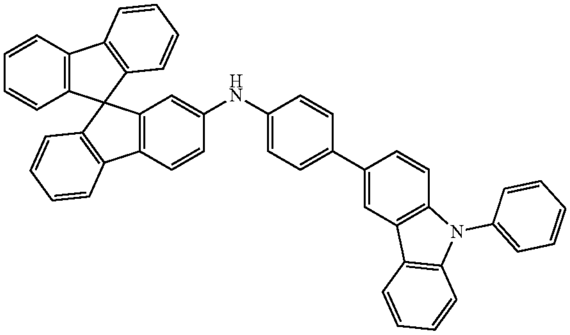
(718)
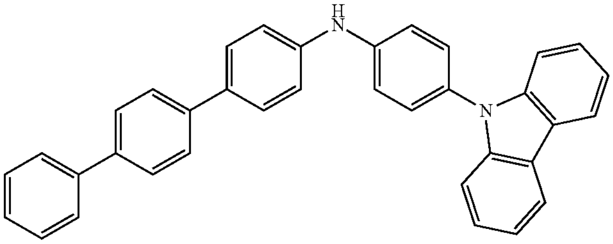
[Chemical Formula 54]
(719)
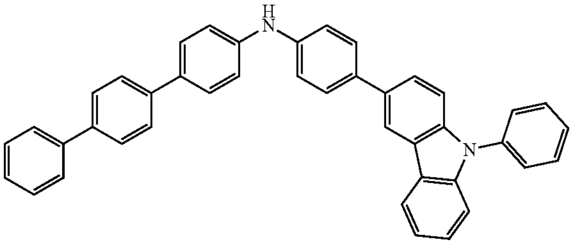
(720)
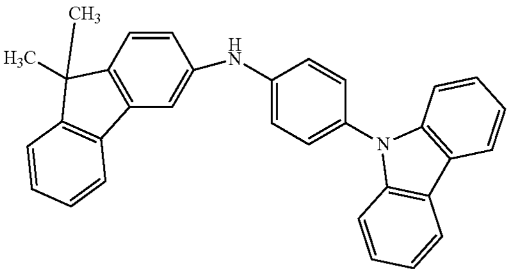

-continued
(721)
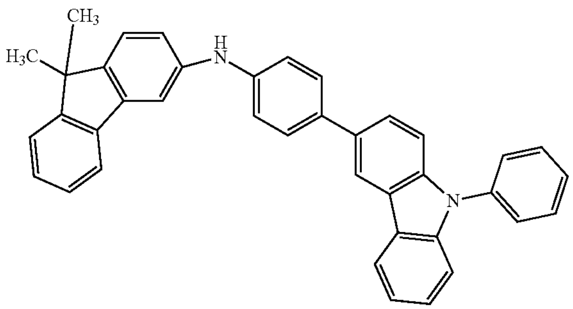
(722)
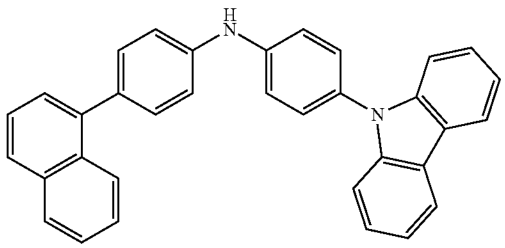
(723)
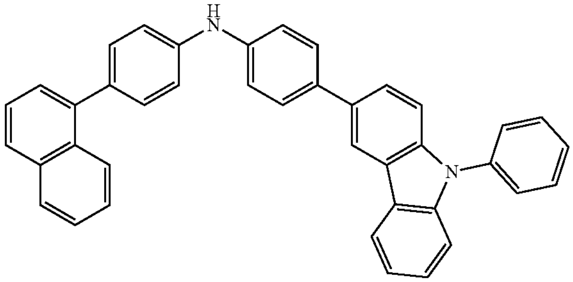
(724)
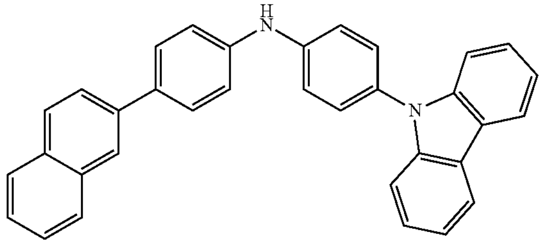
(725)
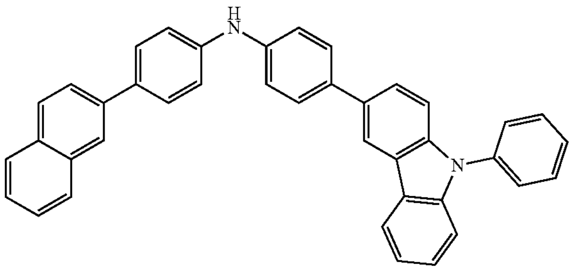
(726)
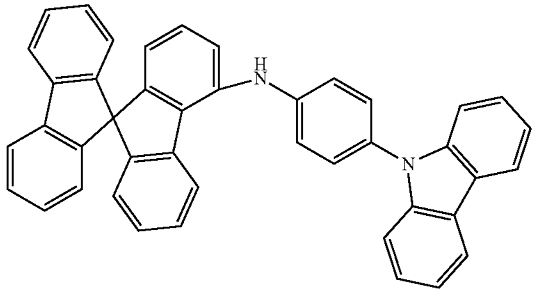
(727)
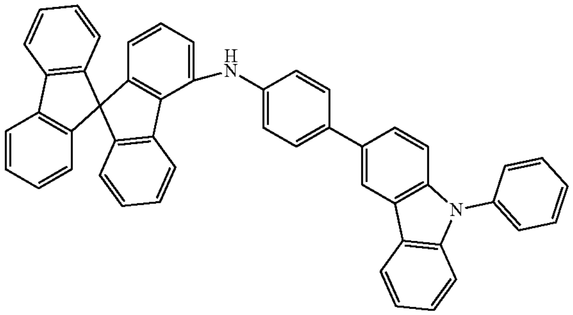
(728)
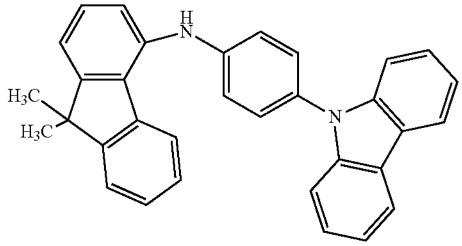

-continued
(729)
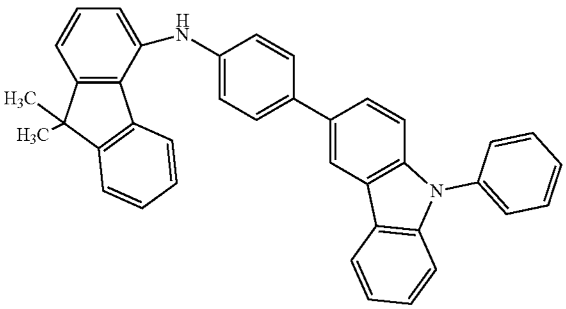
(730)
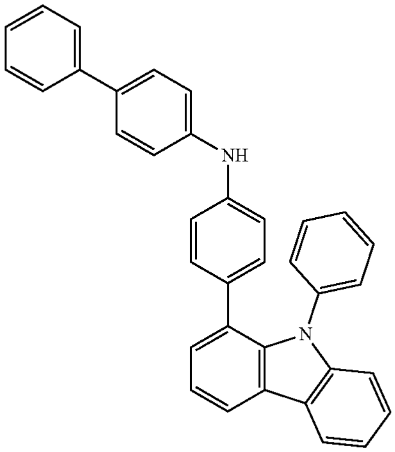
(731)
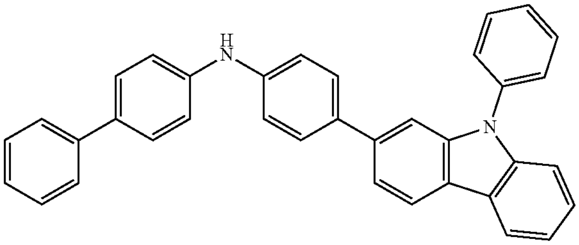
(732)
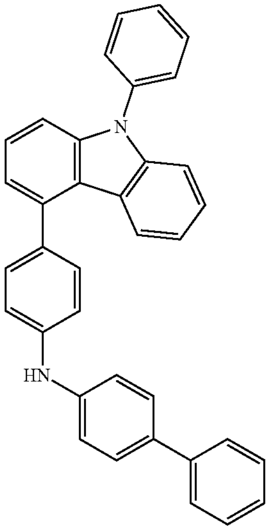
(734)
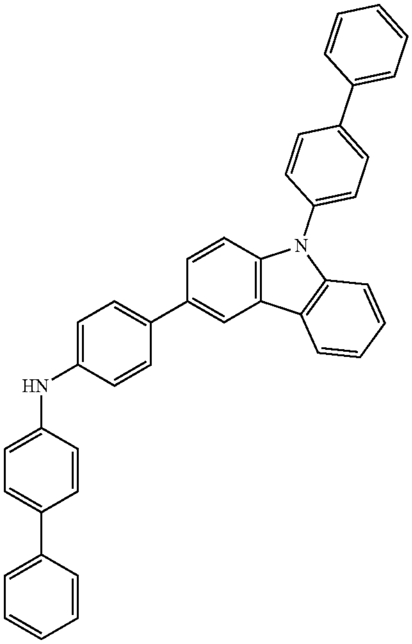
(735)
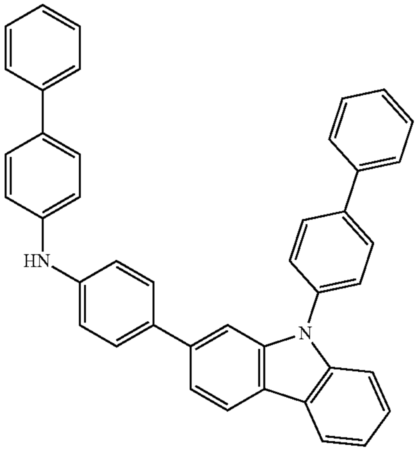

-continued
(736)
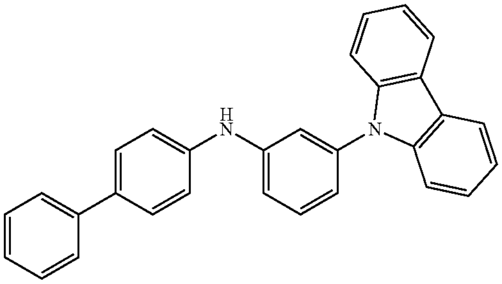
(737)
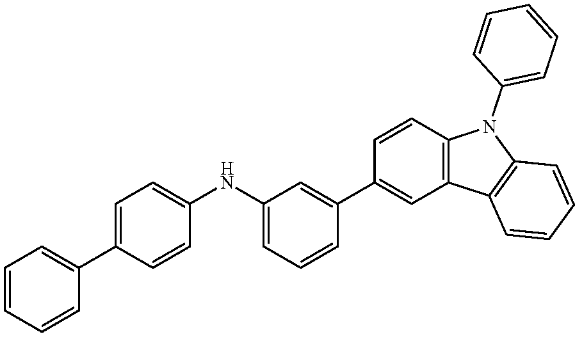
[Chemical Formula 55]
(738)
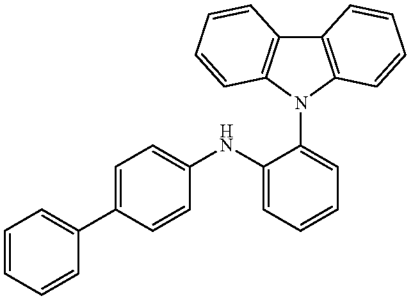
(739)
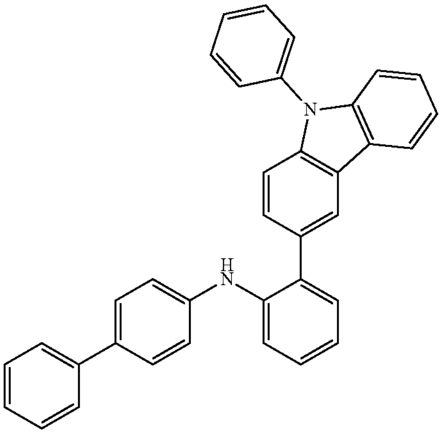
(740
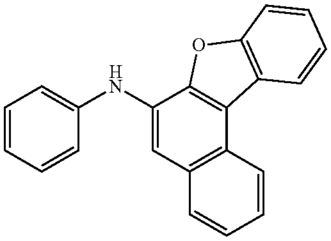
(741)
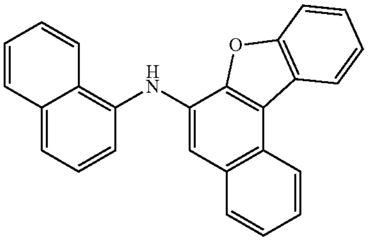
(742)
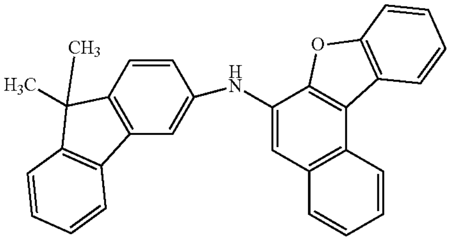
(743)
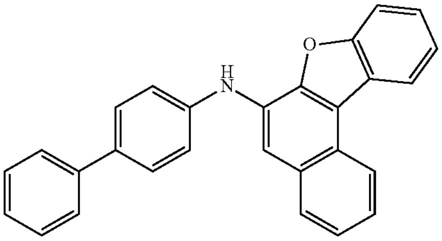
(744)
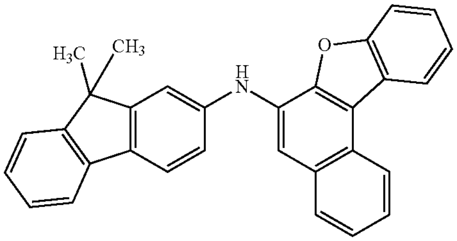
(745)
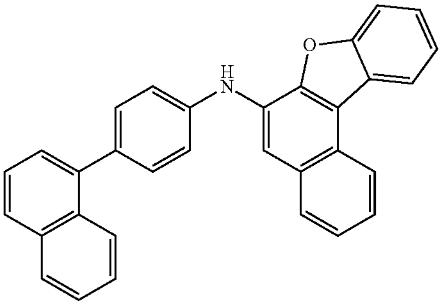

-continued
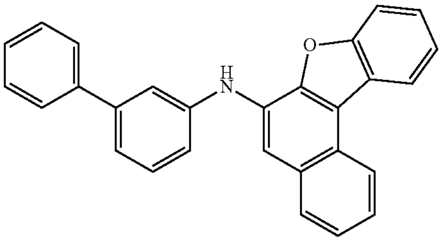
(746)
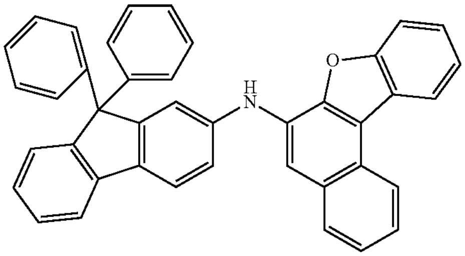
(747)
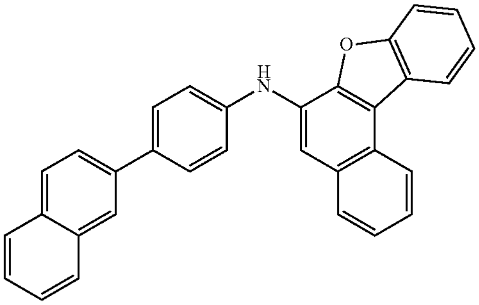
(748)
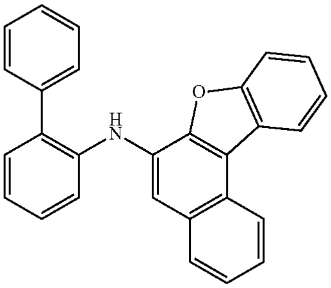
(749)
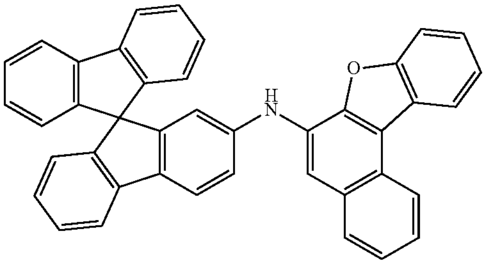
(750)
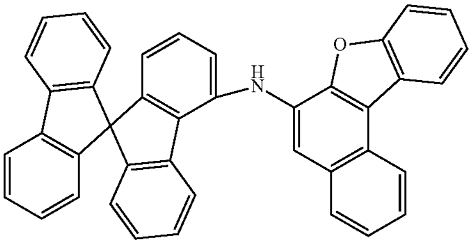
(751)
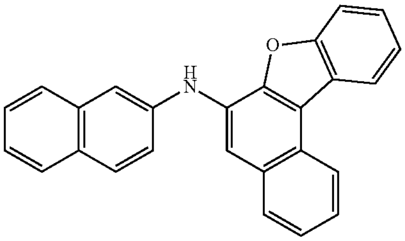
(752)
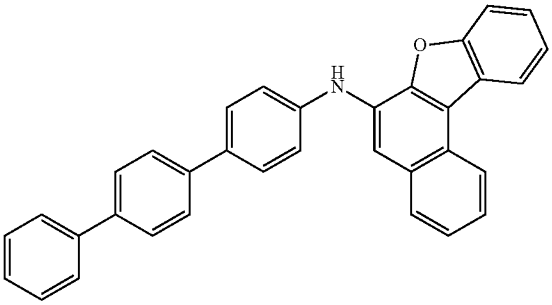
(753)
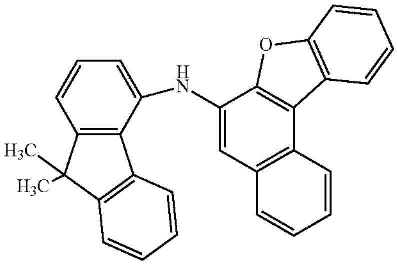
(754)
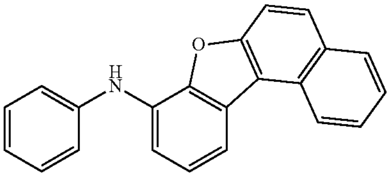
(755)

-continued
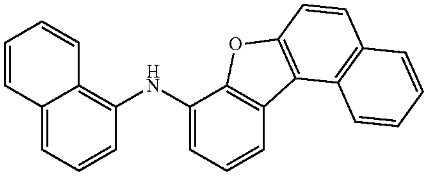
(756)
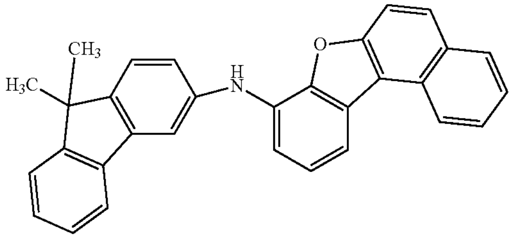
(757)
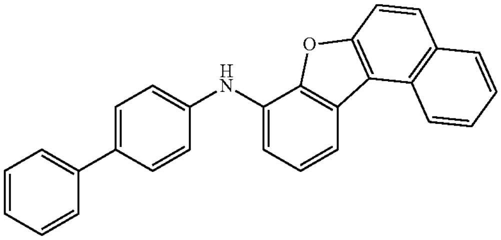
(758)
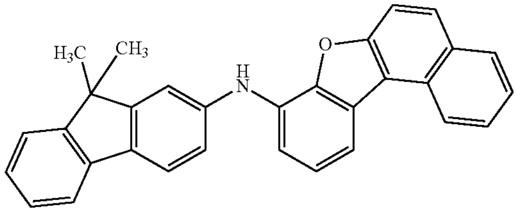
(759)
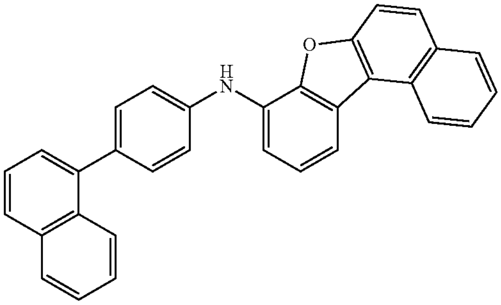
(760)
[Chemical Formula 56]
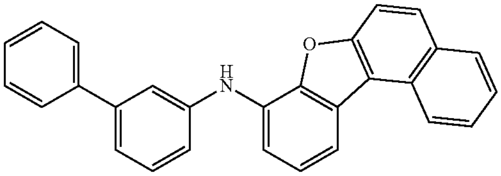
(761)
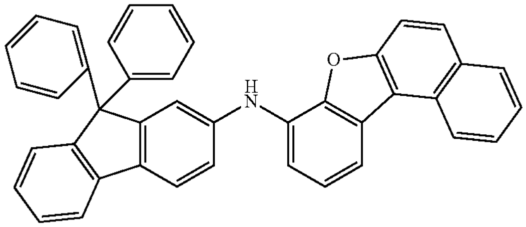
(762)
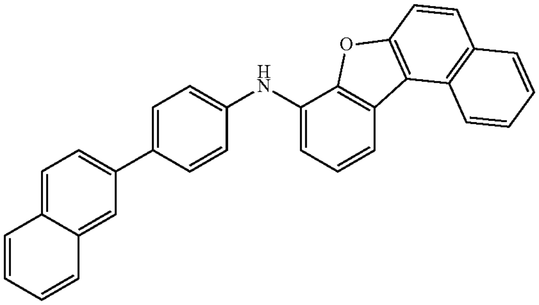
(763)
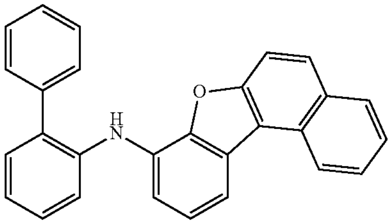
(764)

-continued
(765)
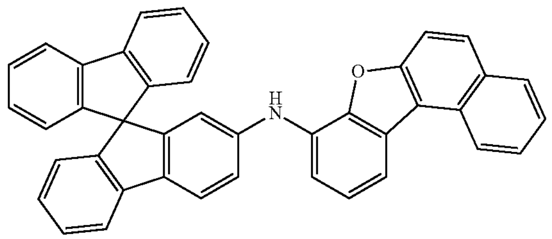
(766)
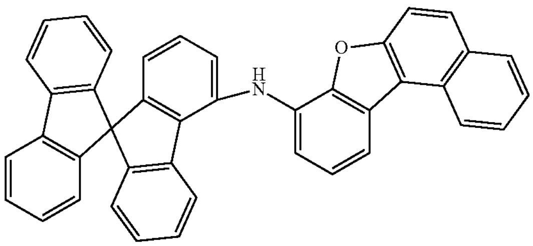
(767)
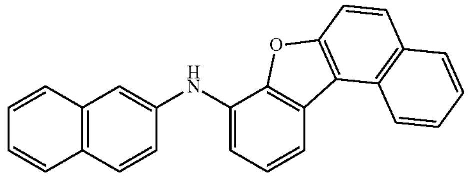
(768)
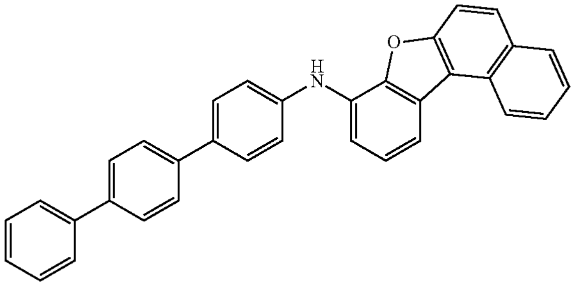
(769)
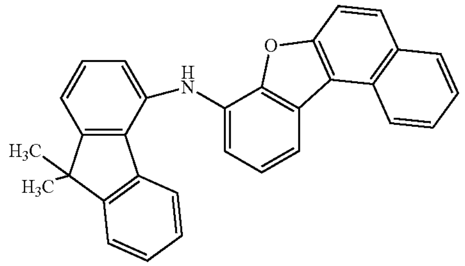
(770)
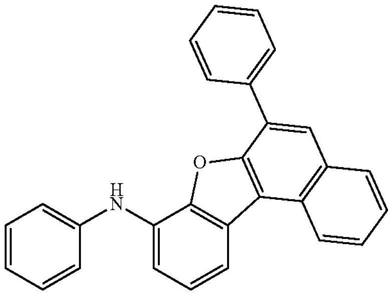
(771)
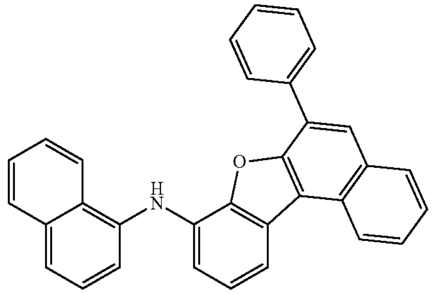
(772)
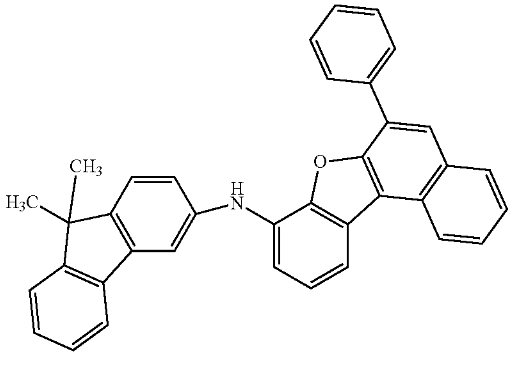
(773)
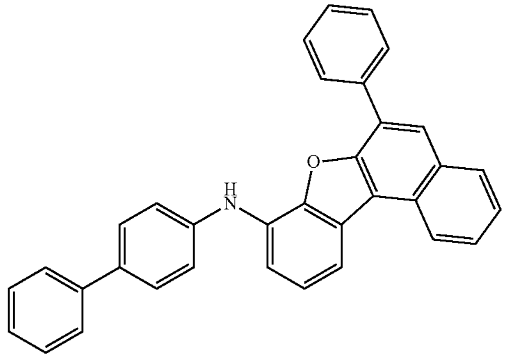
(774)
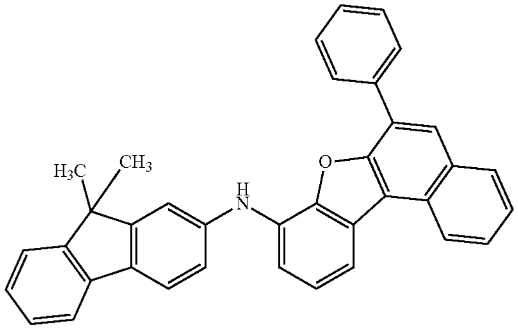

-continued
(775)
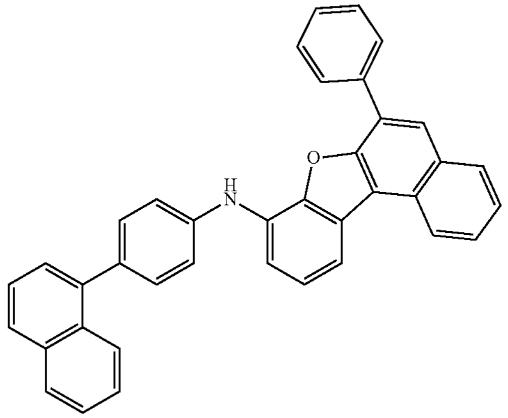
(776)
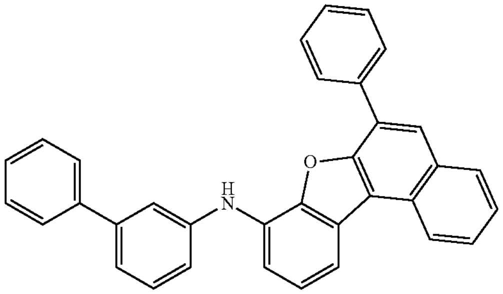
(777)
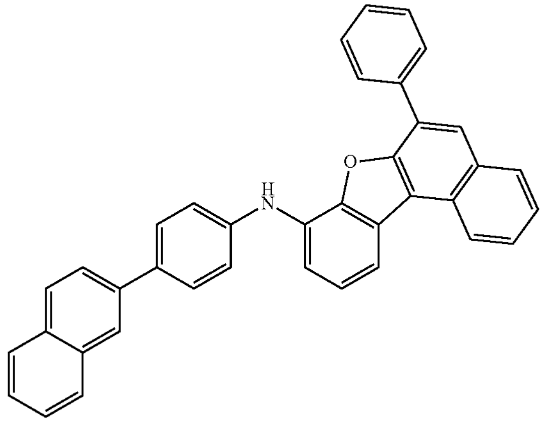
(778)
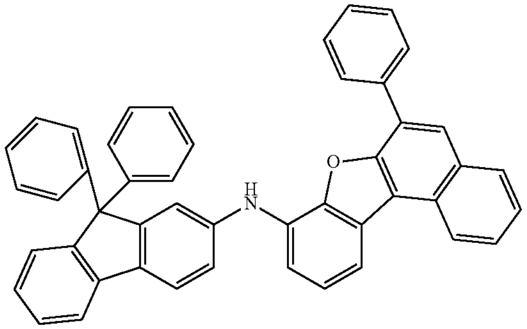
(779)
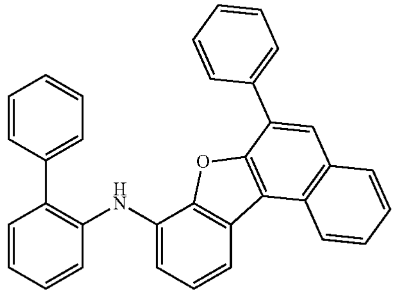
(780)
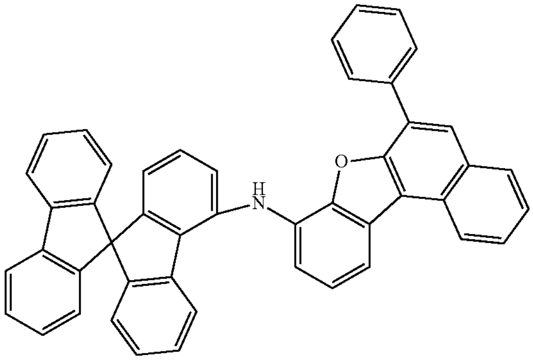
(781)
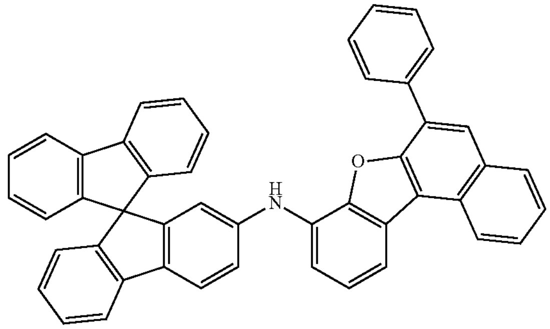
(782)
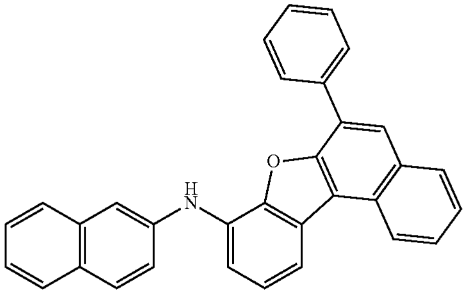

-continued
[Chemical Formula 57]
(783)
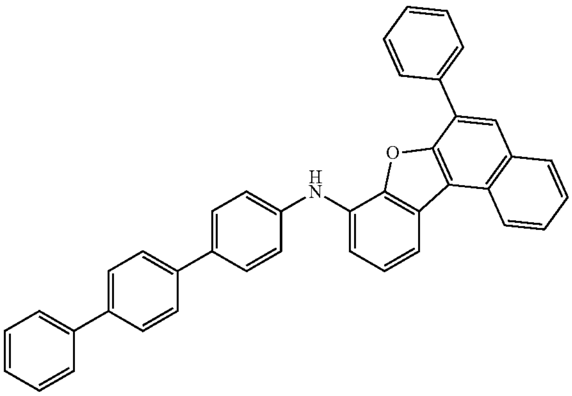
(784)
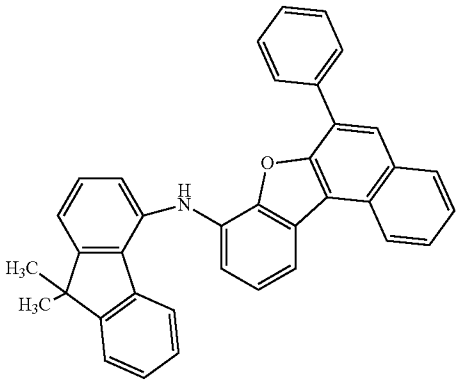
(785)
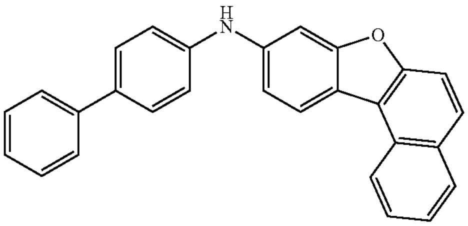
(786)
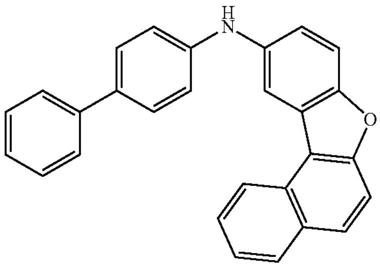
(787)
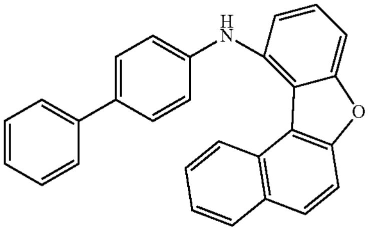
(788)
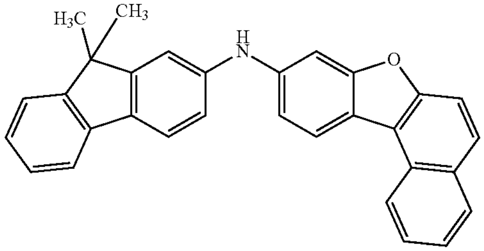
(789)
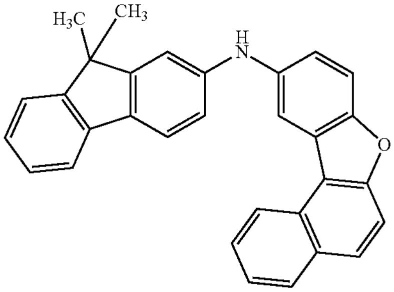
(790)
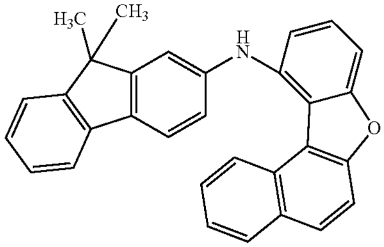
(791)
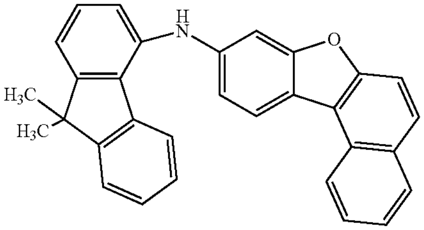
(792)
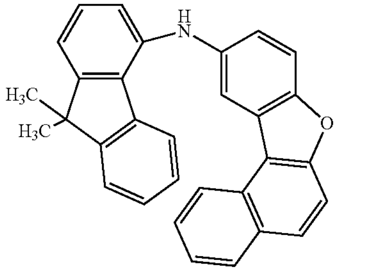

-continued
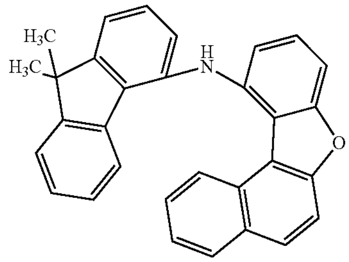
(793)
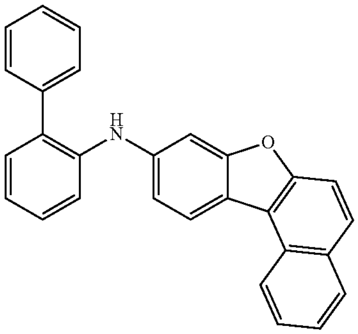
(794)
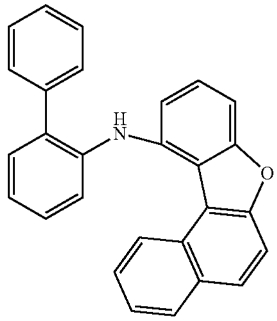
(795)
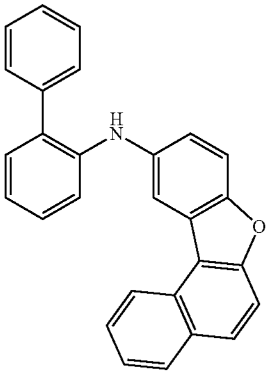
(796)
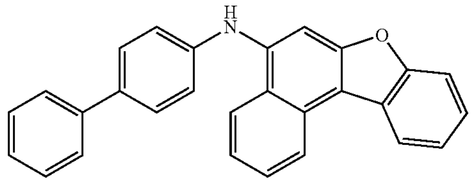
(797)
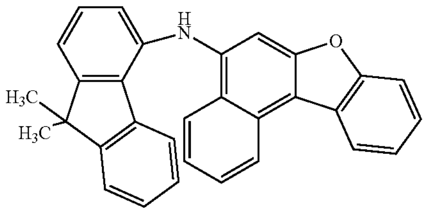
(798)
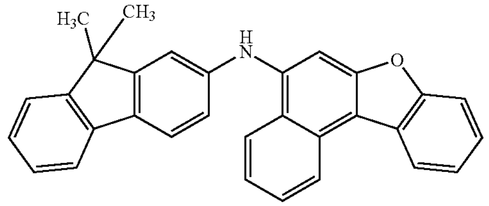
(799)
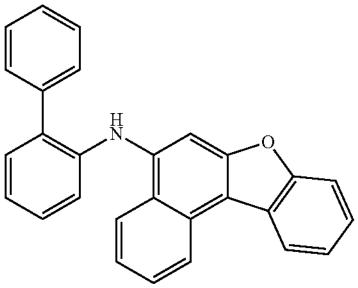
(800)
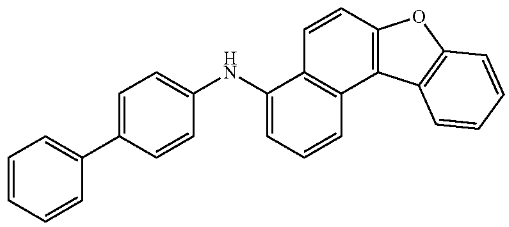
(801)
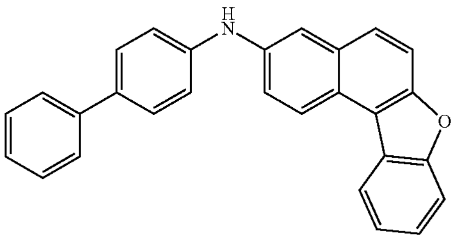
(802)

-continued
(803)
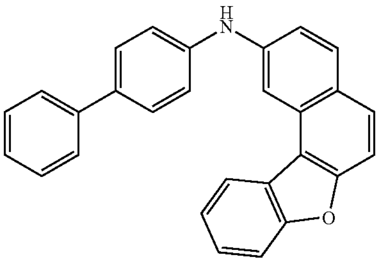
(804)
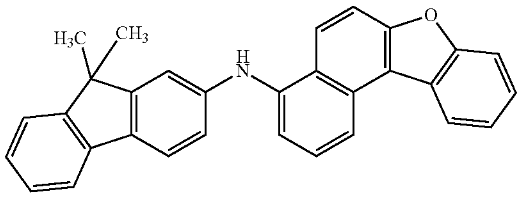
(805)
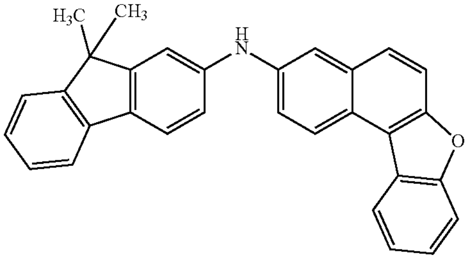
[Chemical Formula 58]
(806)
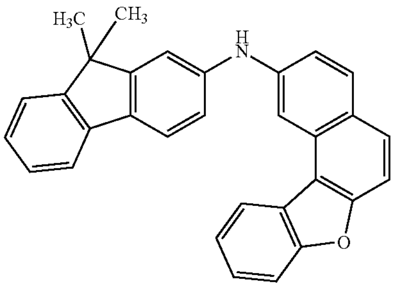
(807)
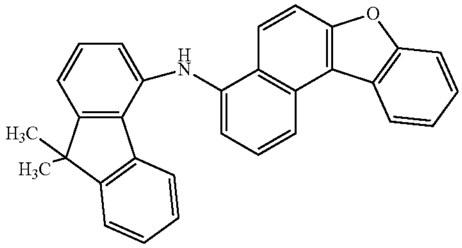
(808)
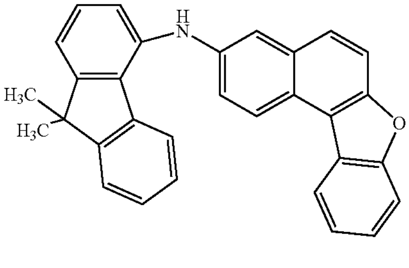
(809)
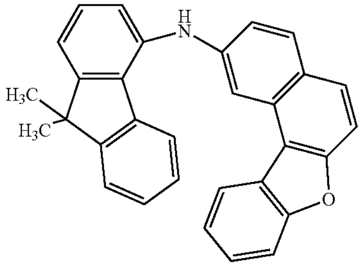
(810)
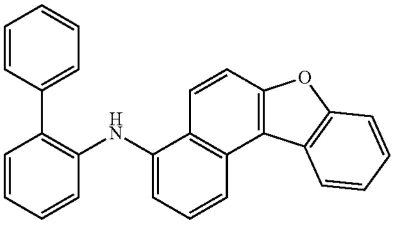
(811)
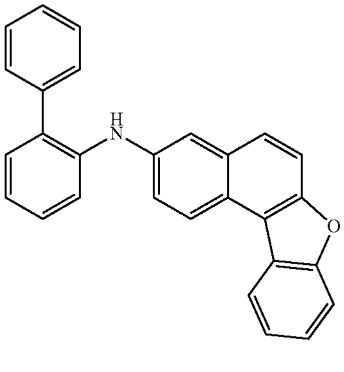

-continued
(812)
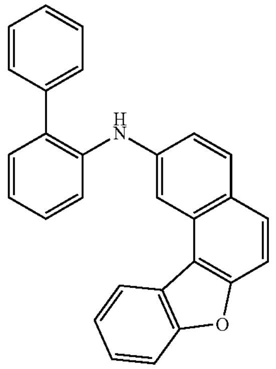
(813)
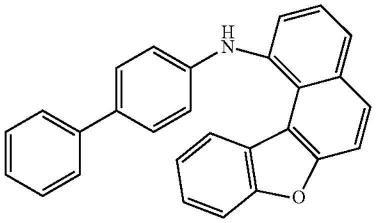
(814)
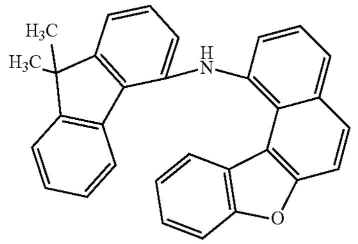
(815)
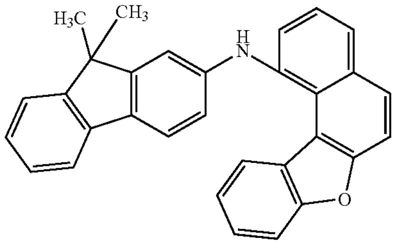
(816)
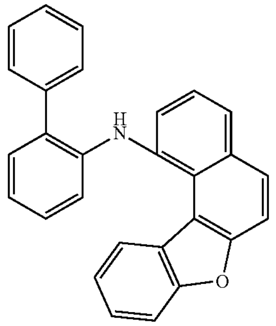
[Chemical Formula 59]
(817)
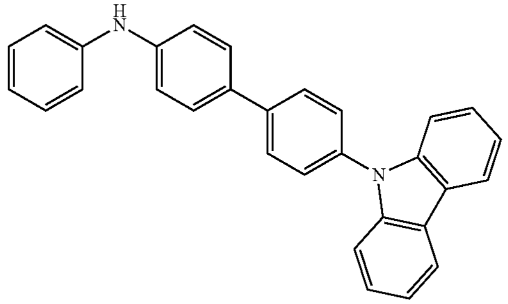
(818)
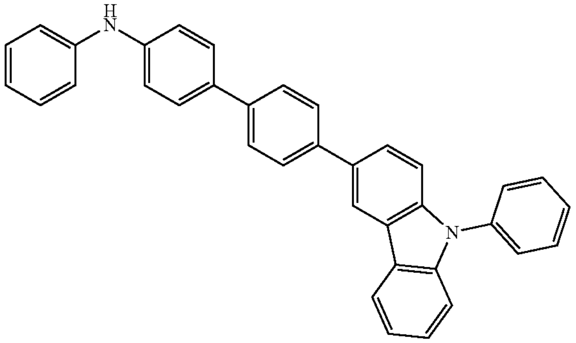

-continued
(819)
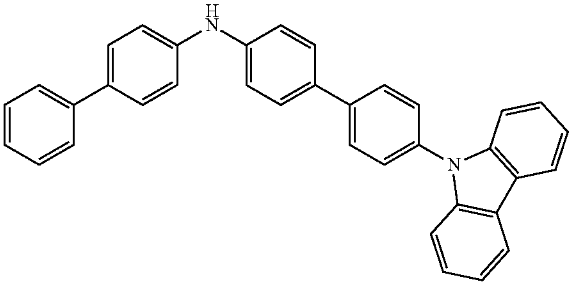
(820)
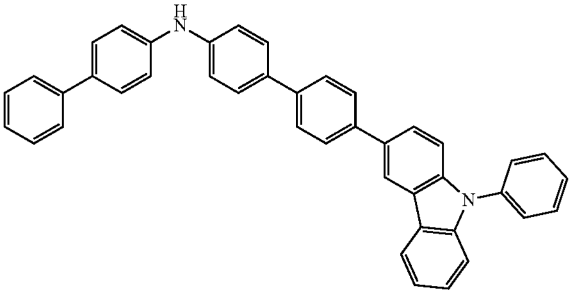
(821)
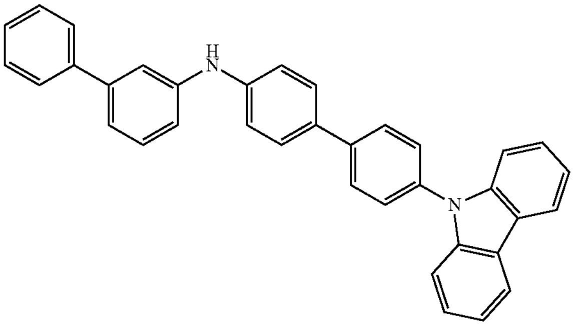
(822)
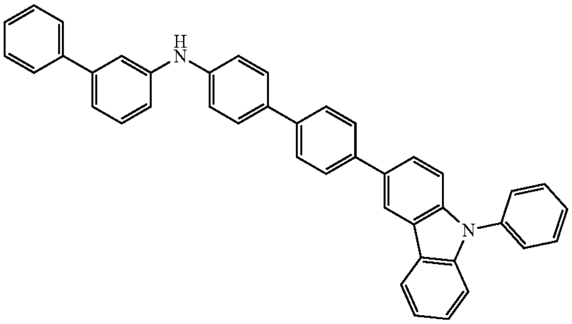
(823)
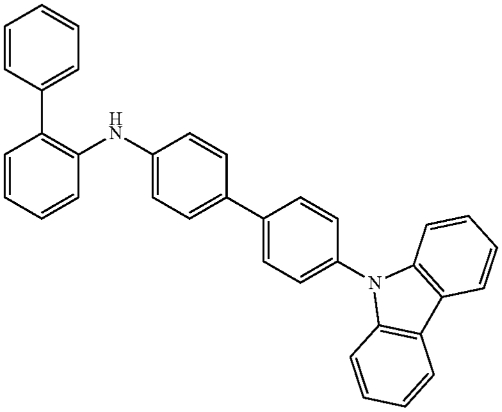
(824)
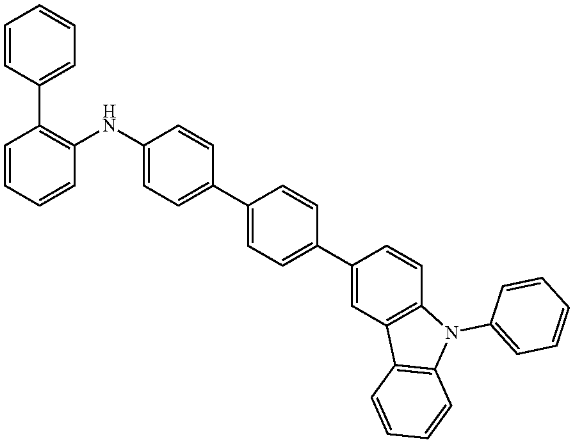
(825)
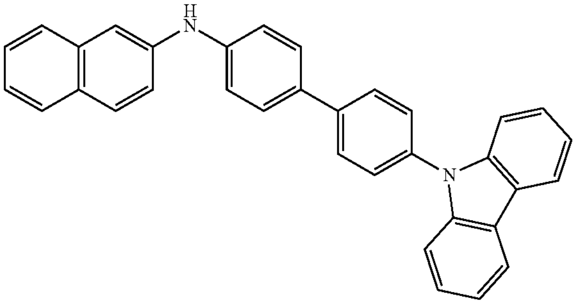
(826)
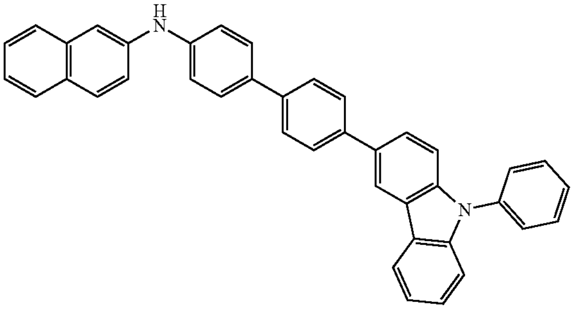

-continued
(827)
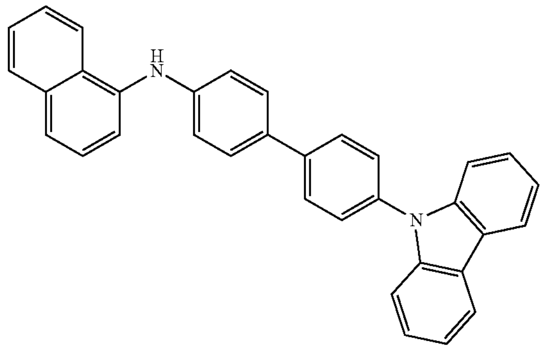
(828)
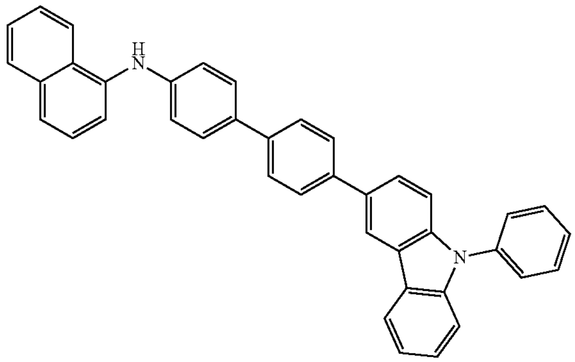
(829)
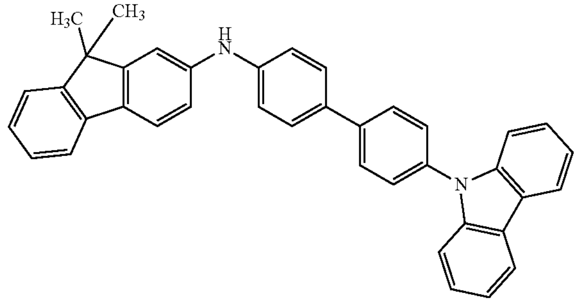
(830)
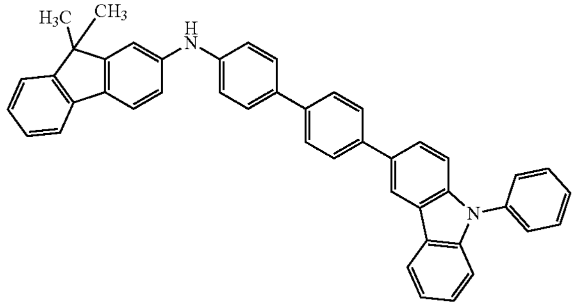
(831)
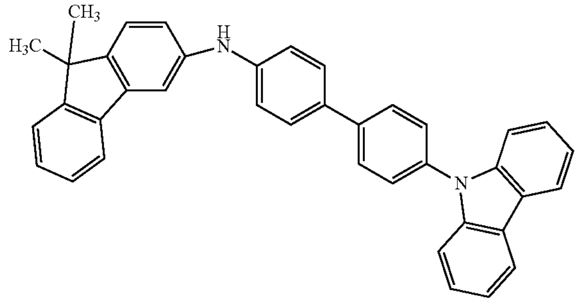
(832)
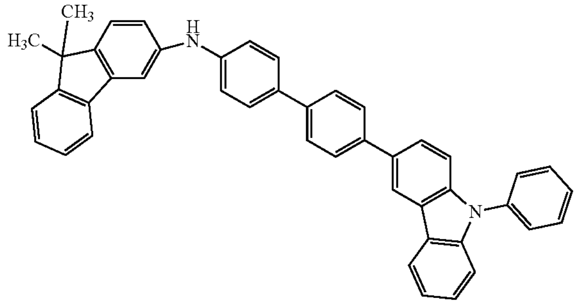
(833)
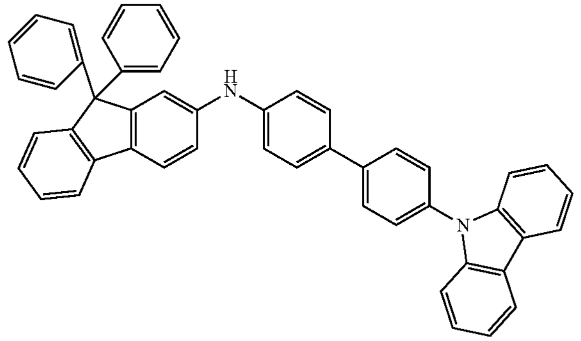
(834)
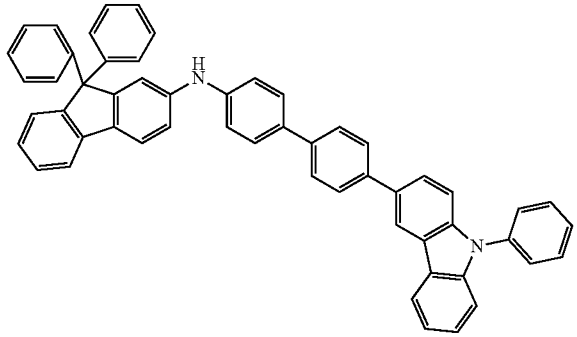

-continued
[Chemical Formula 60]
(835)
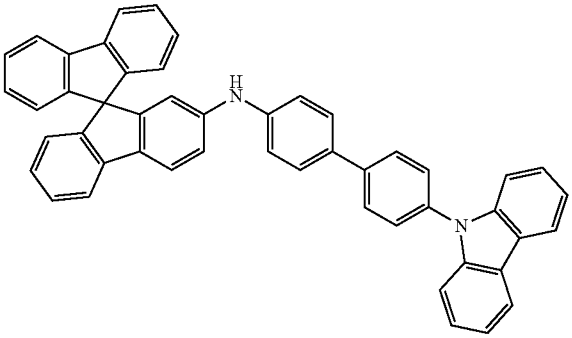
(836)
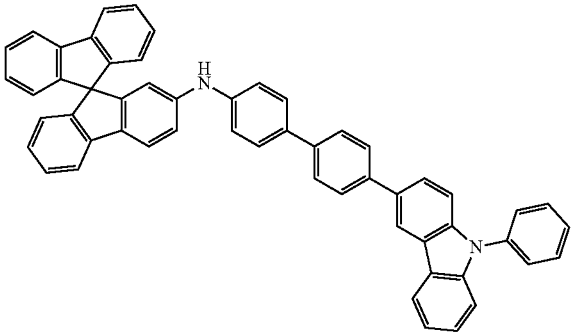
(837)
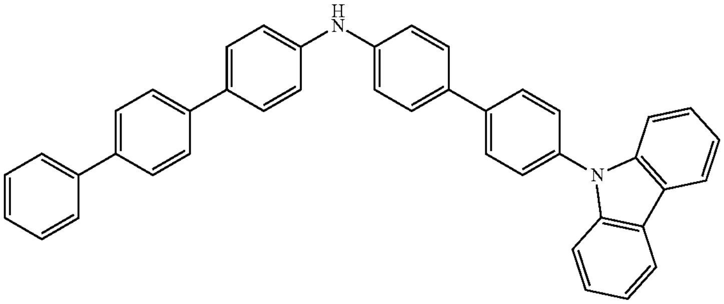
(839)
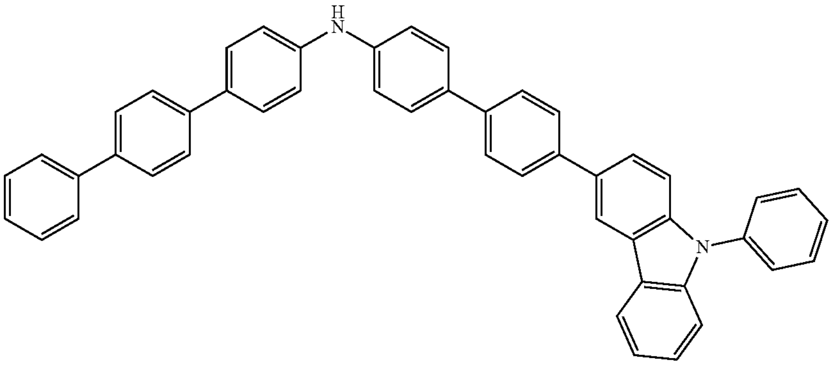
(840)
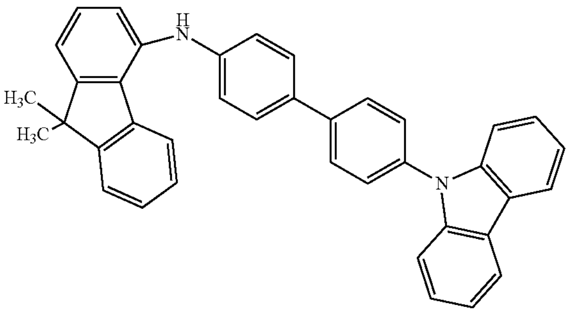
(841)
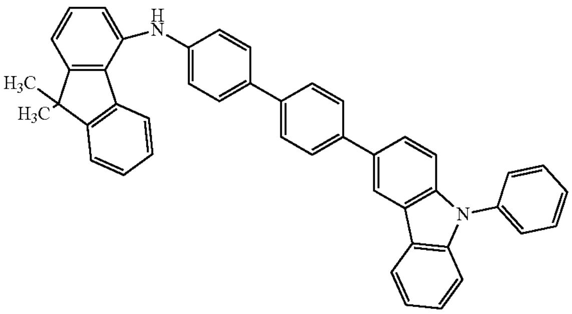

-continued
(842)
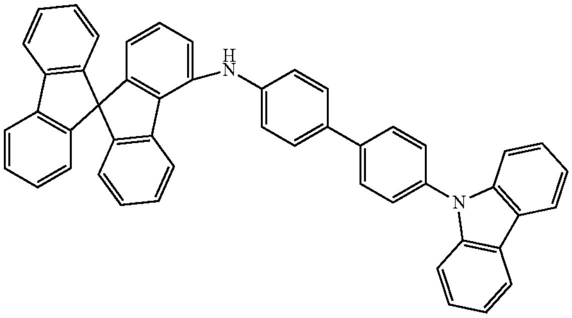
(843)
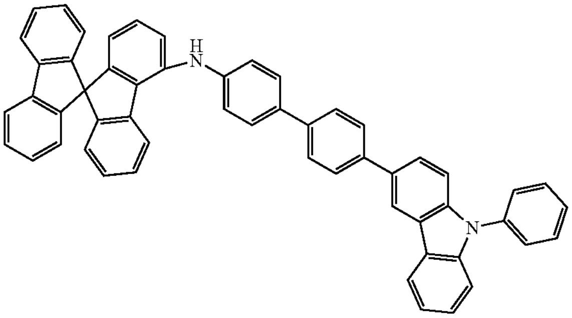
(844)
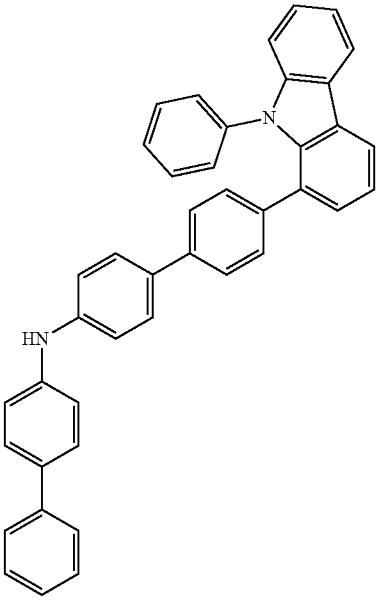
(845)
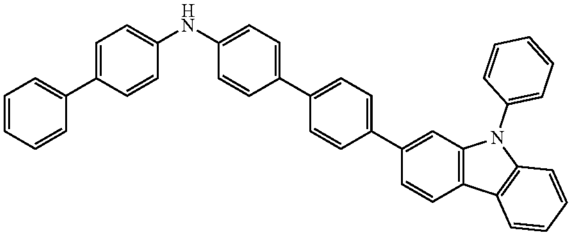
(846)
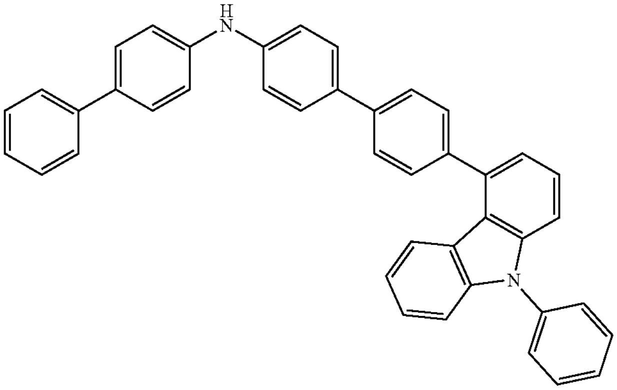

-continued
(847)
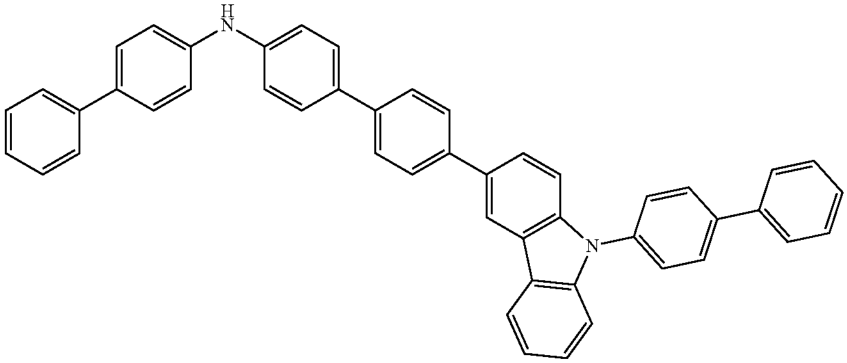
(848)
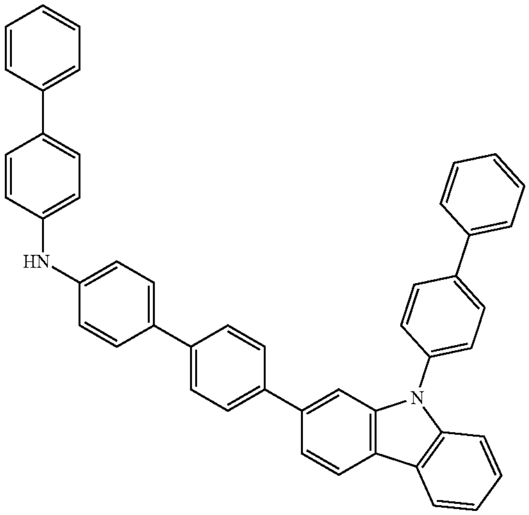
(849)
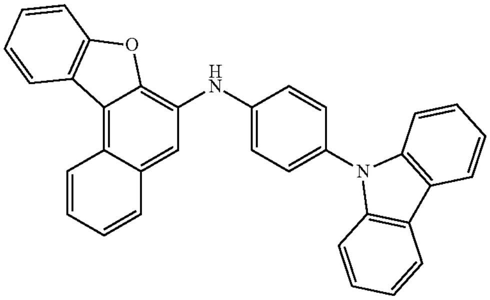
(850)
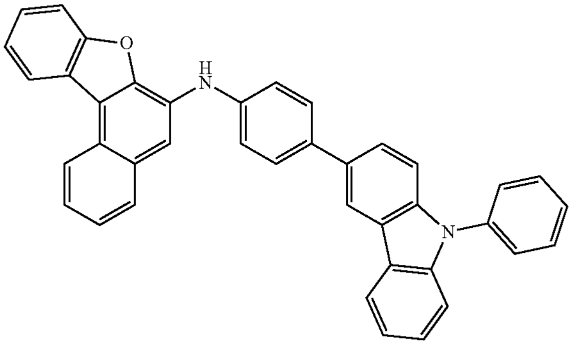
(851)
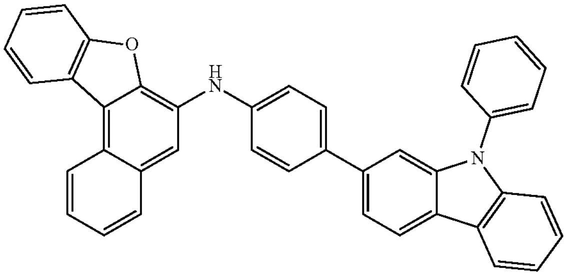

-continued
[Chemical Formula 61]
(852)
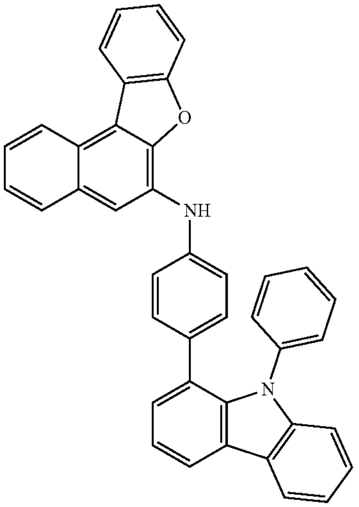
(853)
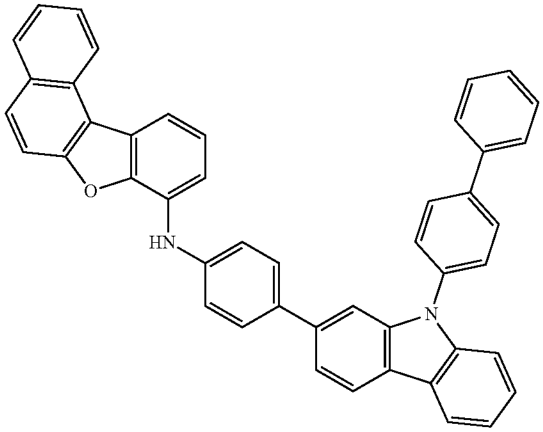
(854)
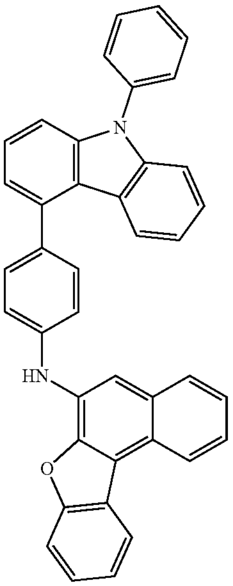
(855)
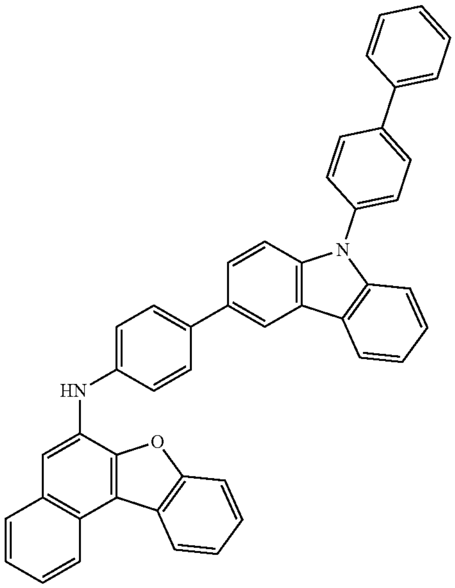
(856)
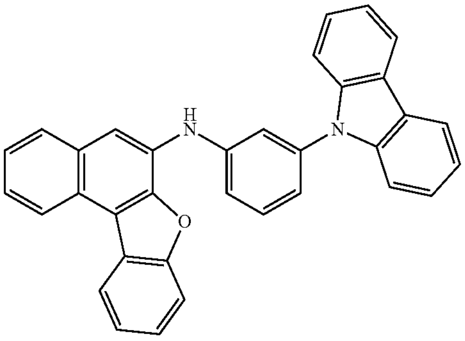
(857)
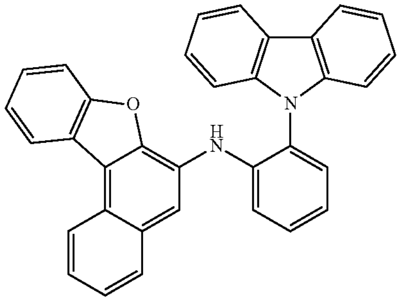

-continued
(858)
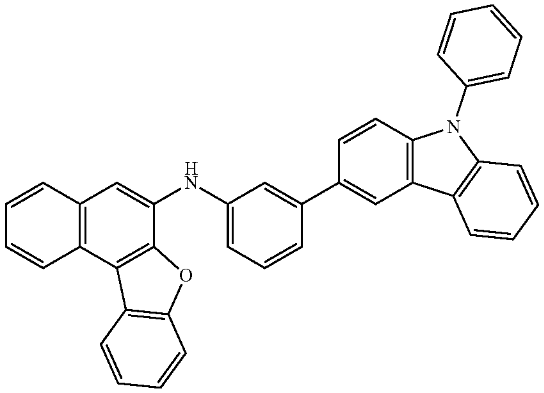
(859)
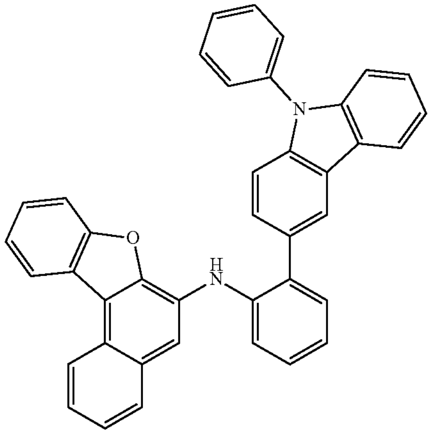
(860)
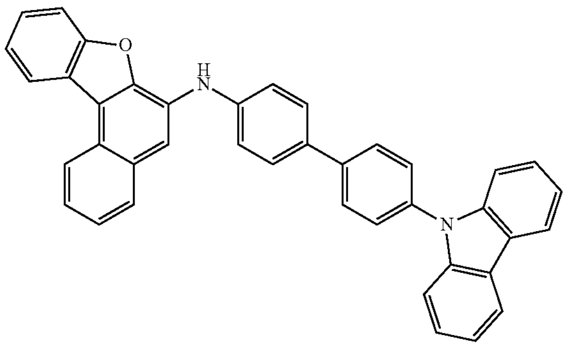
(861)
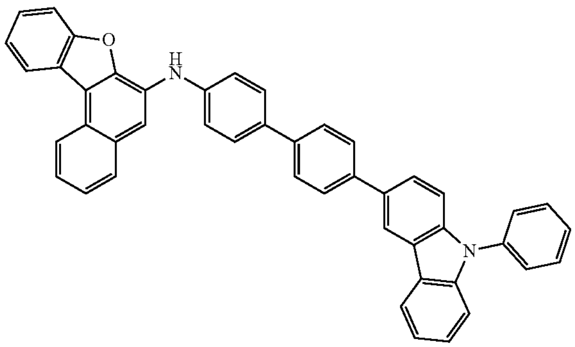
(862)
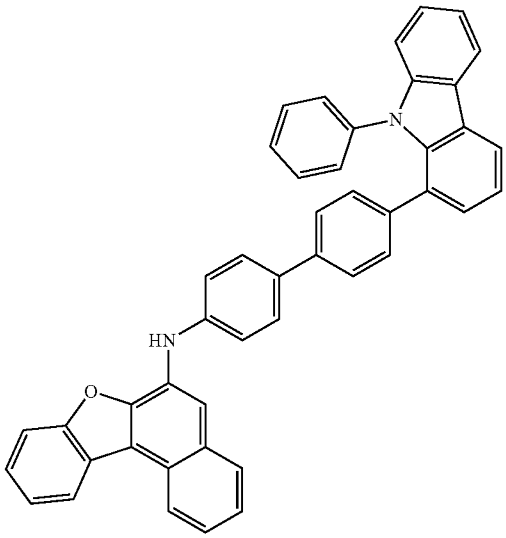
(863)
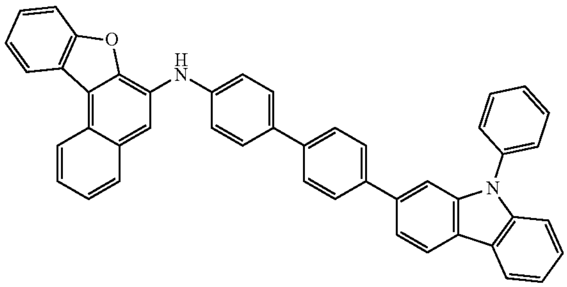

-continued
(864)
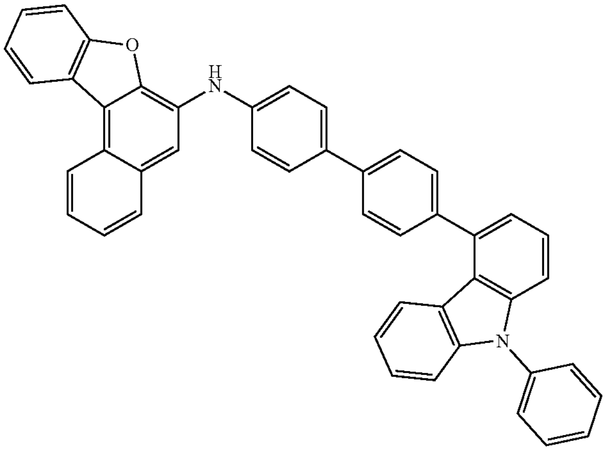
(865)
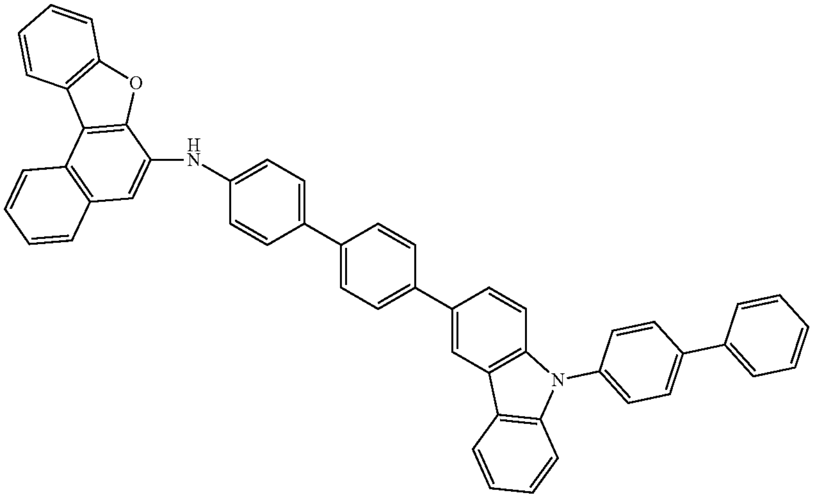
(866)
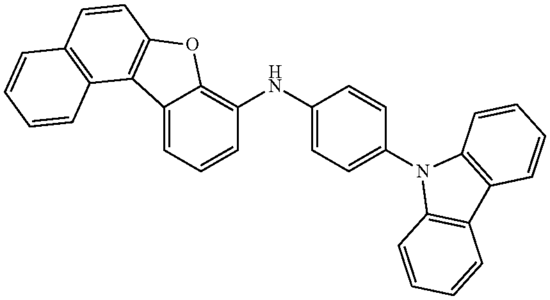
(867)
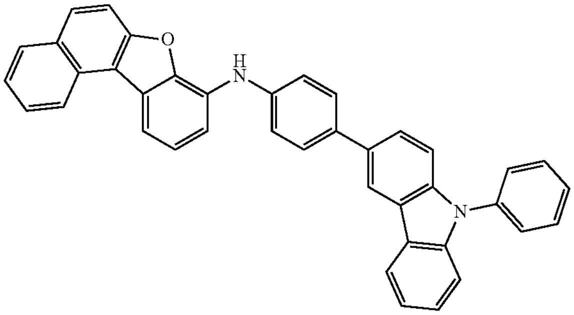
(868)
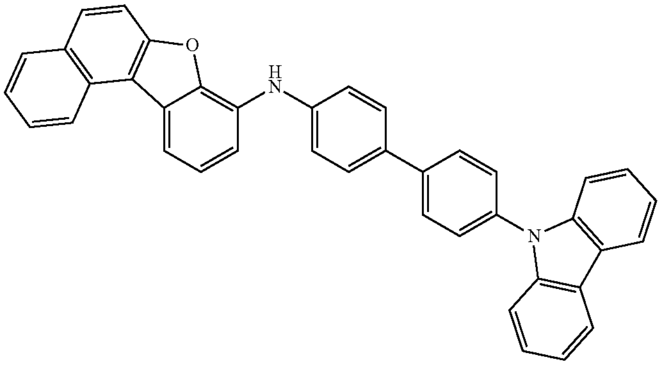

-continued
[Chemical Formula 62]
(869)
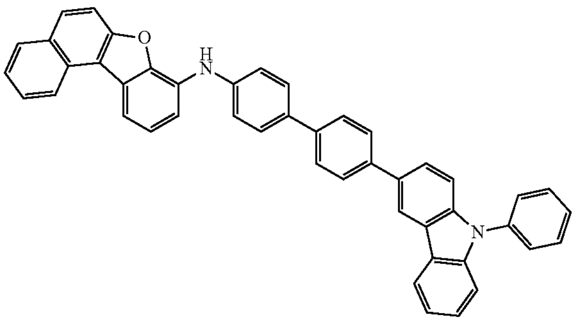
(870)
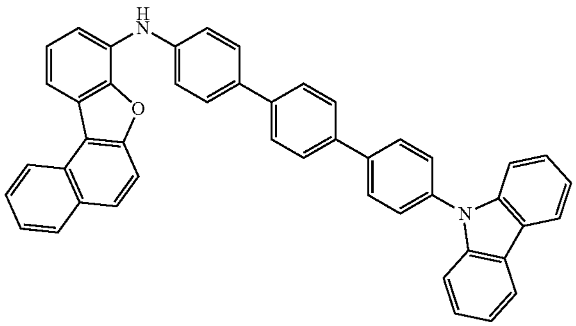
(871)
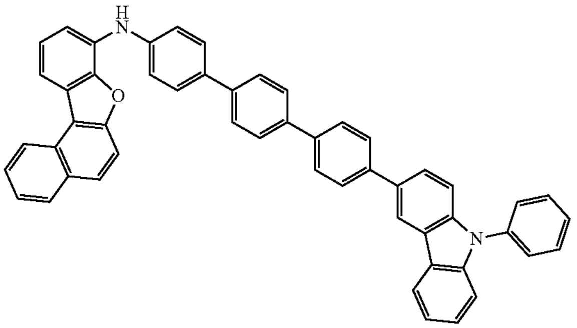
(872)
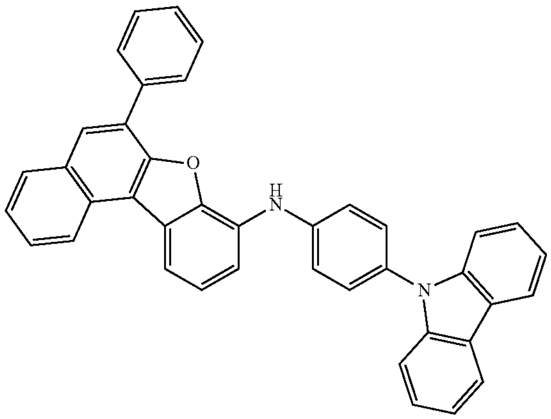
(873)
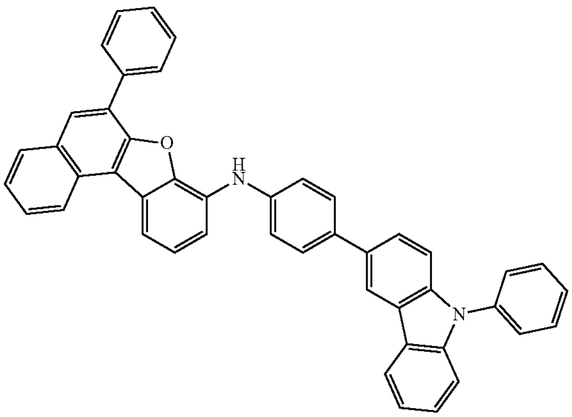
(874)
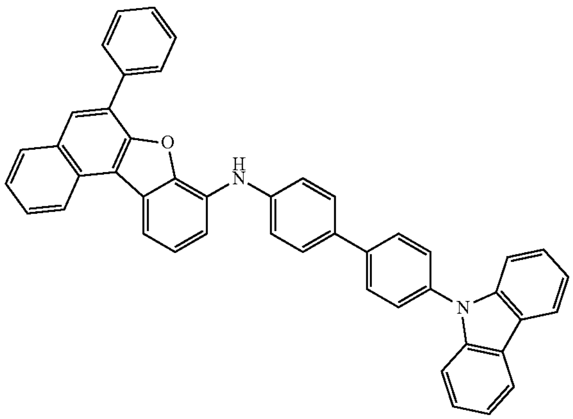

-continued
(875)
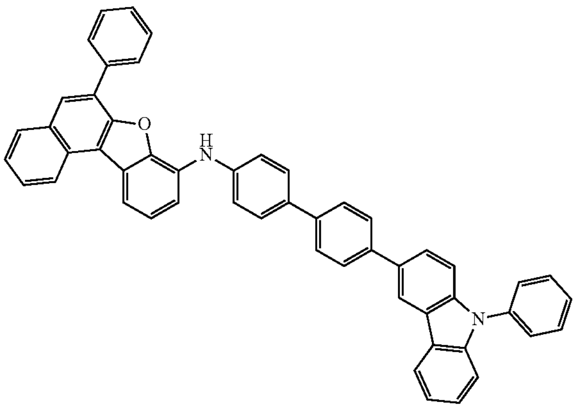
(876)
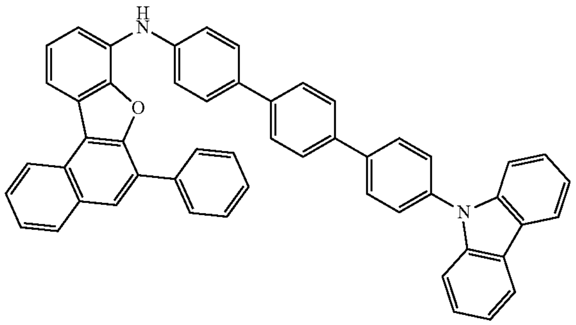
(877)
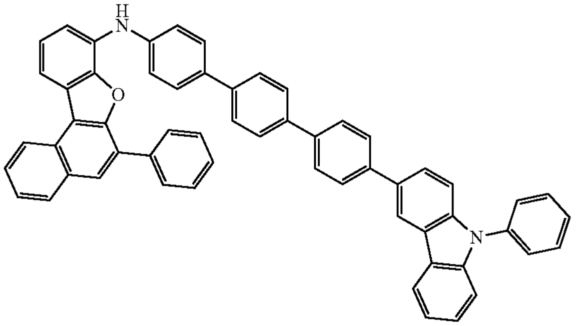
(878)
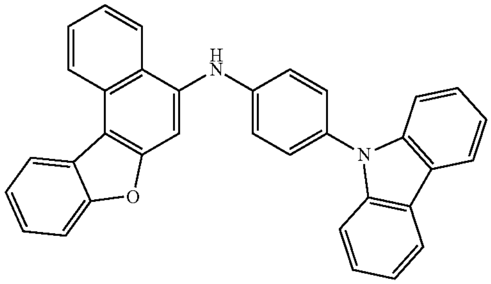
(879)
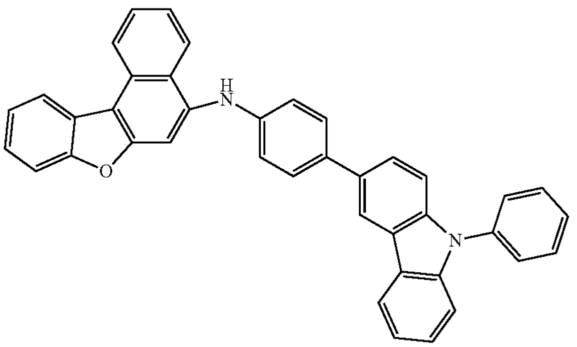
(880)
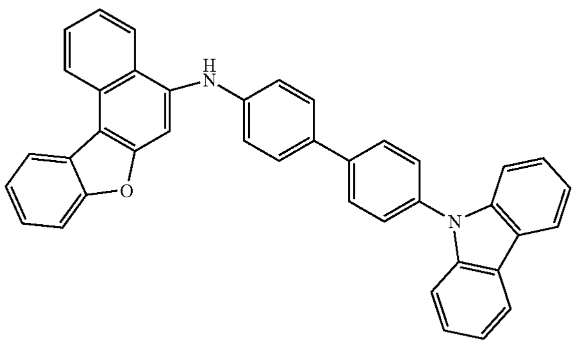
(881)
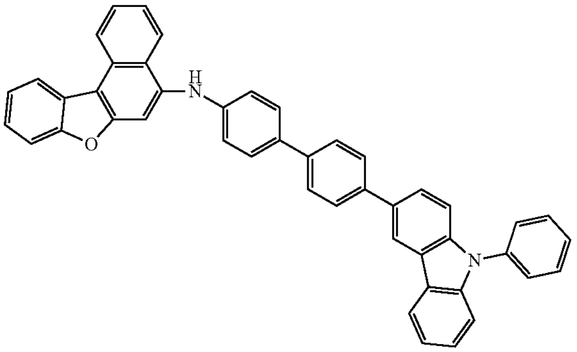
(882)
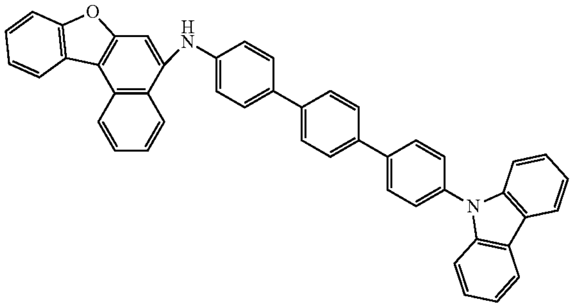

-continued
(883)
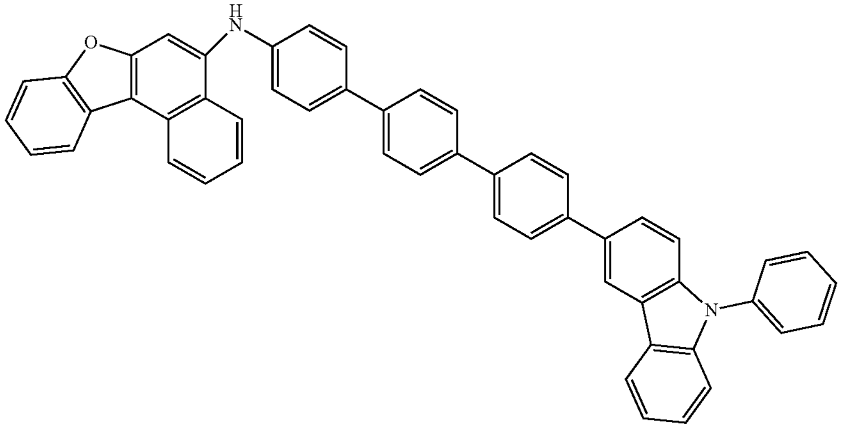
[Chemical Formula 63]
(884)
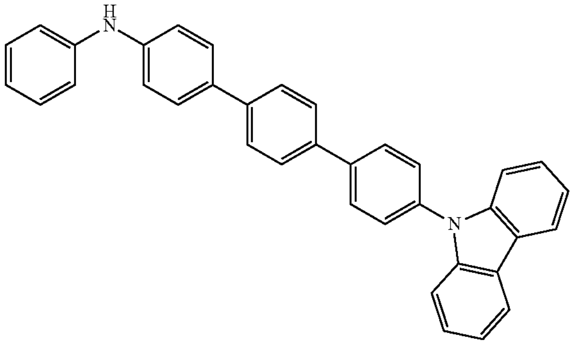
(885)
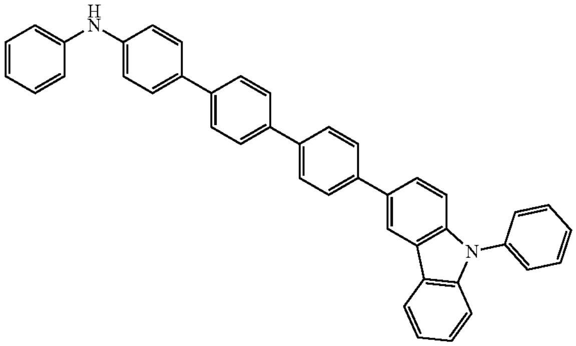
(886)
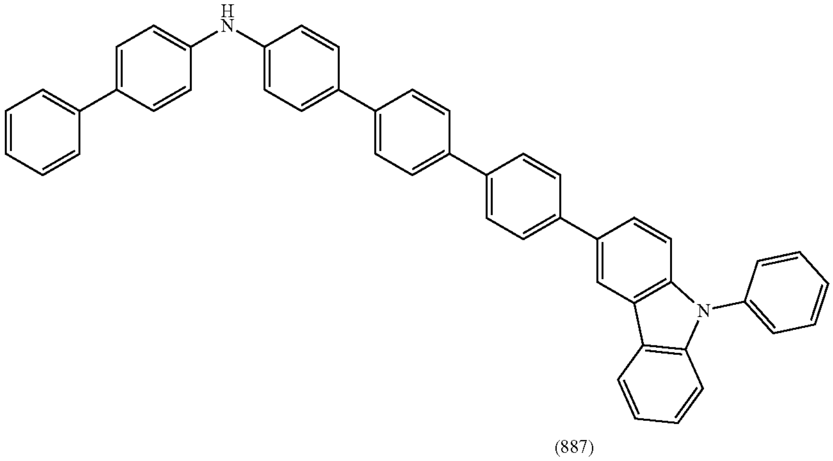
(887)
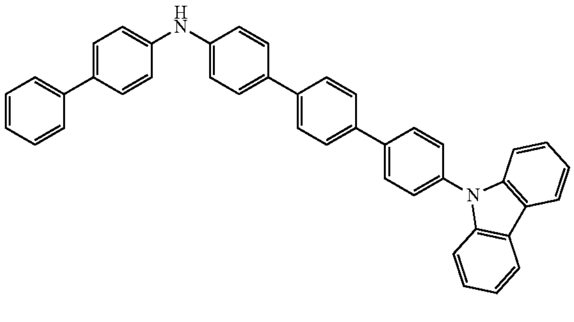
(888)
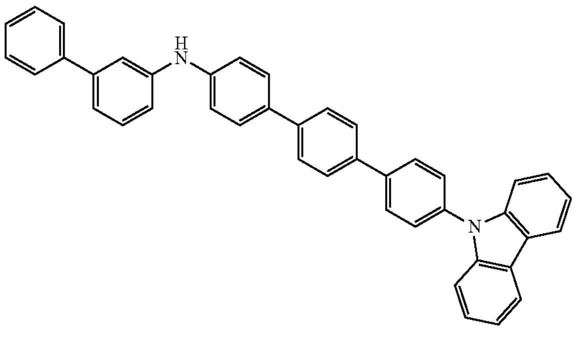

-continued
(889)
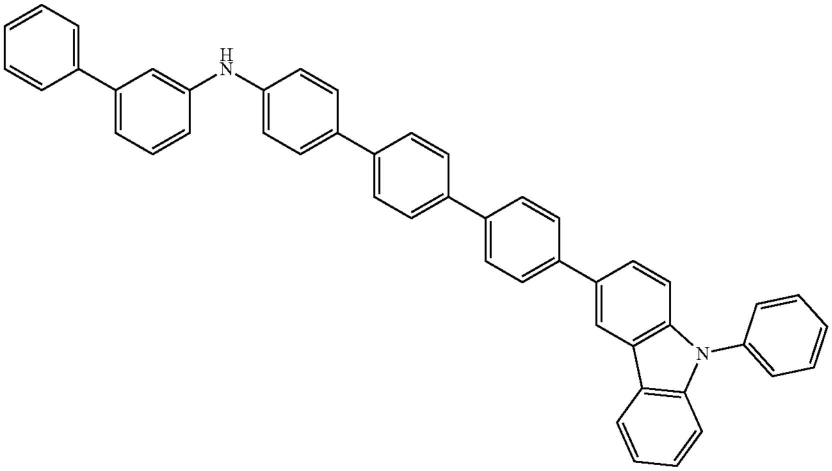
(890)
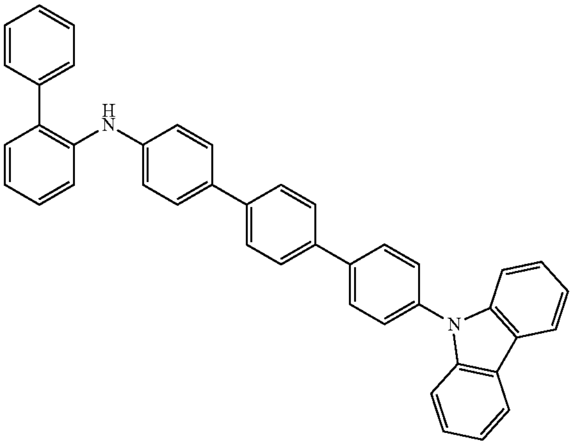
(891)
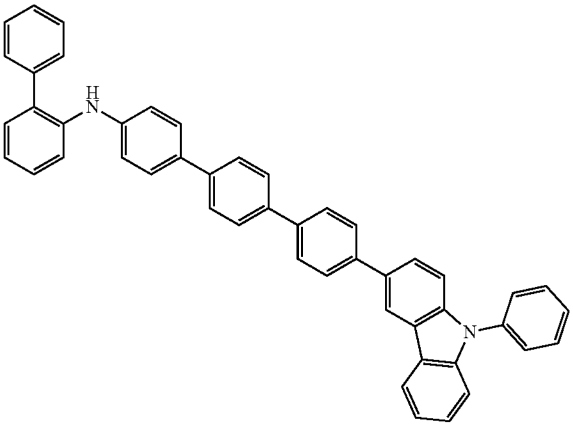
(892)
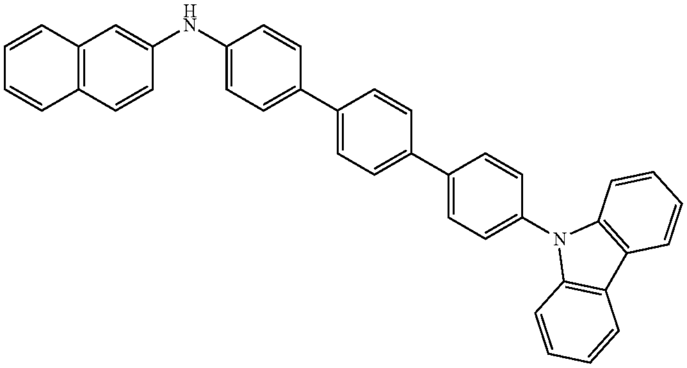

-continued
(893)
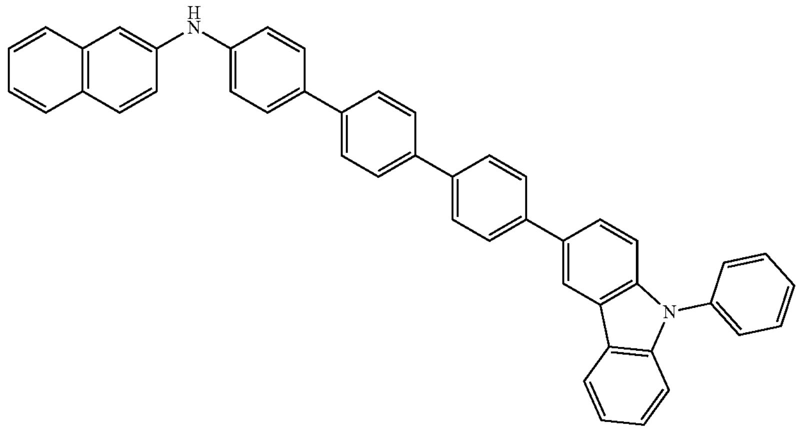
(894)
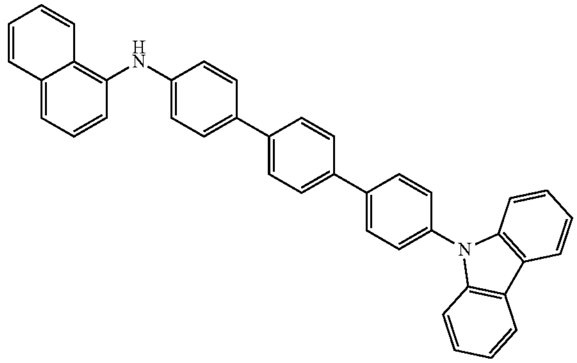
(895)
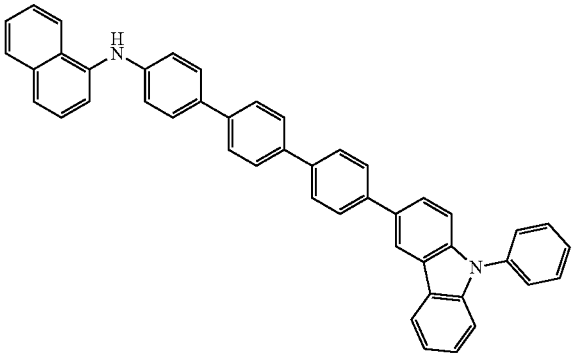
(896)
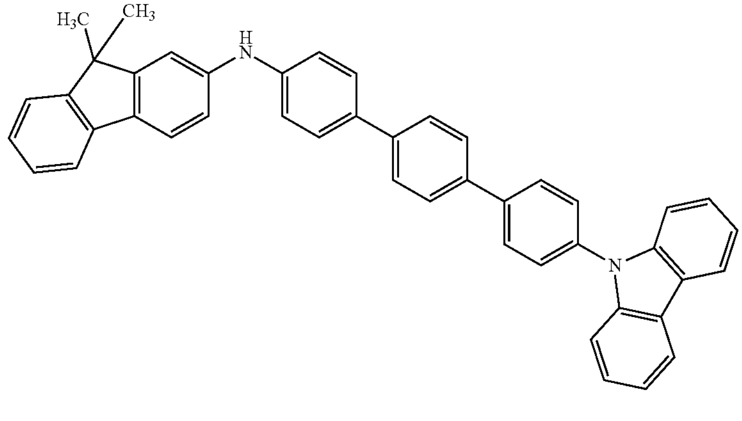

-continued
(897)
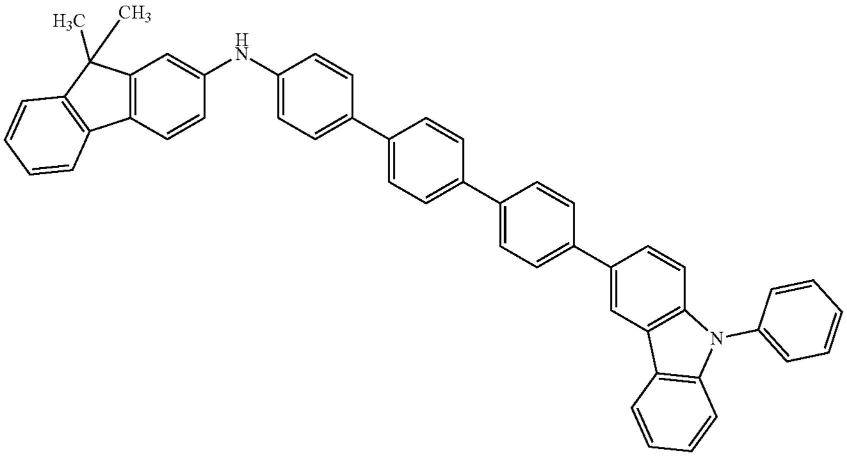
(898)
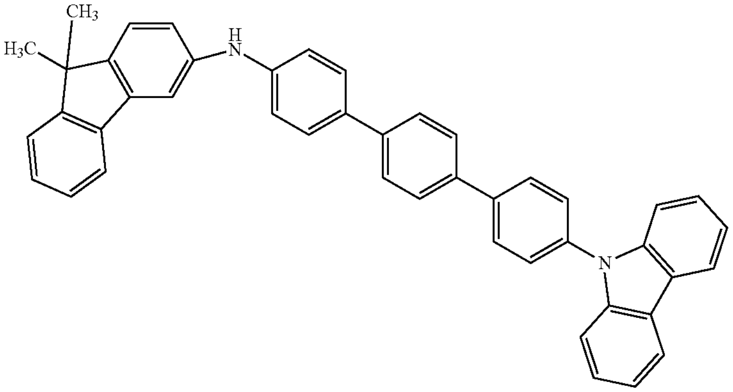
(899)
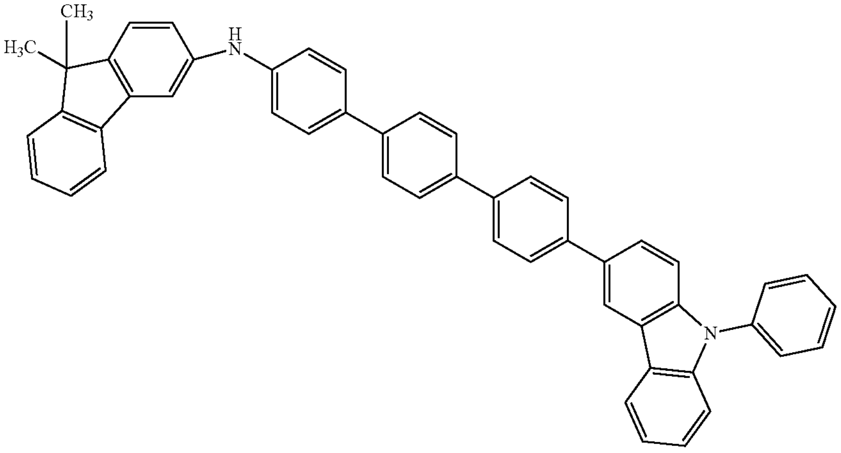

-continued
(900)
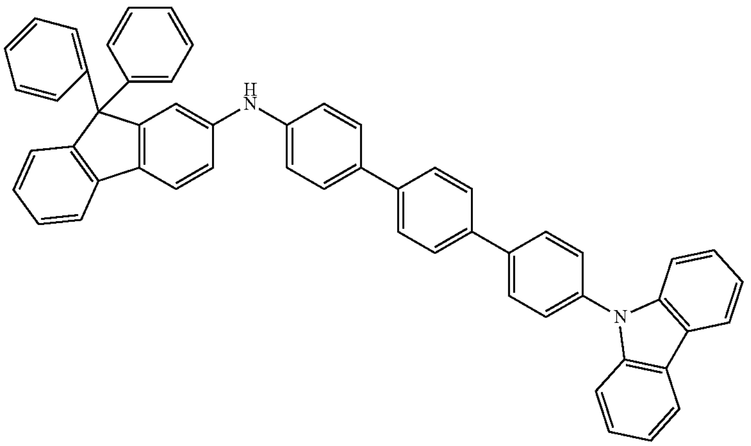
[Chemical Formula 64]
(901)
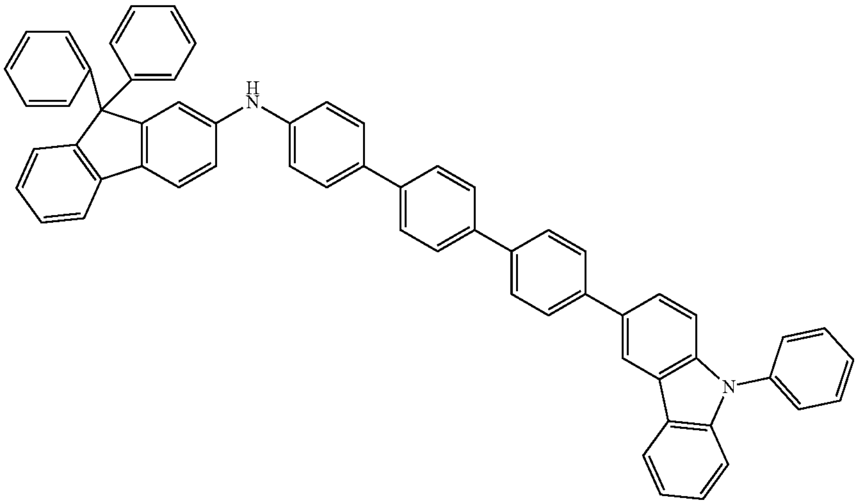
(902)
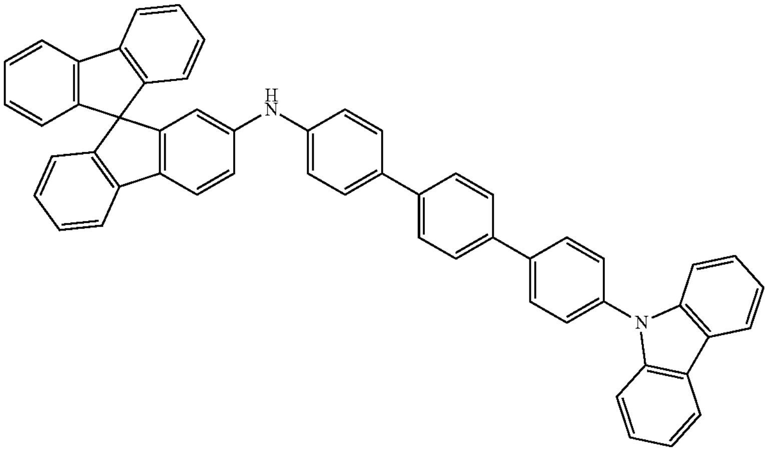

-continued
(903)
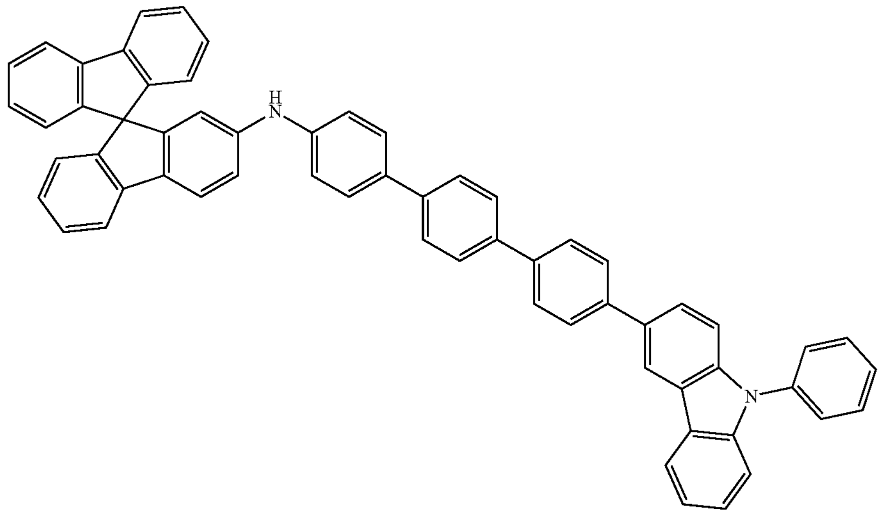
(904)
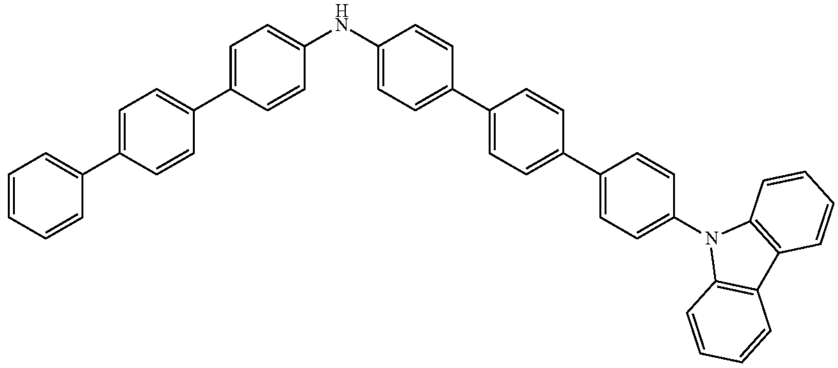
(905)
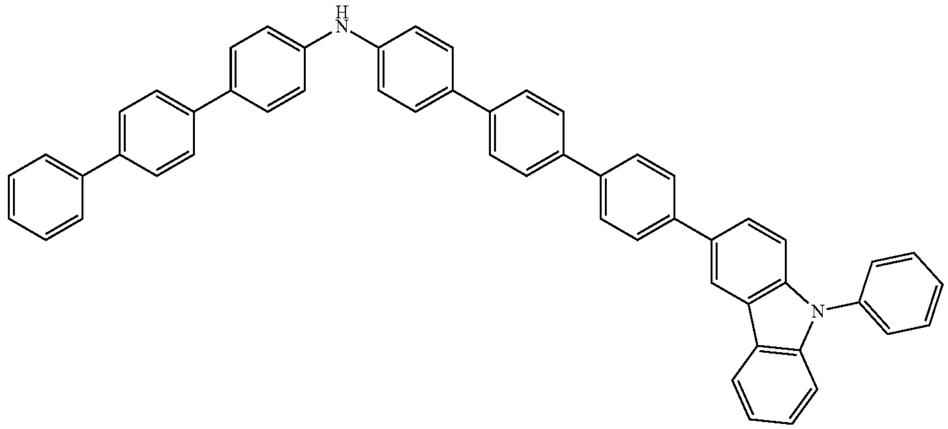

-continued
(906)
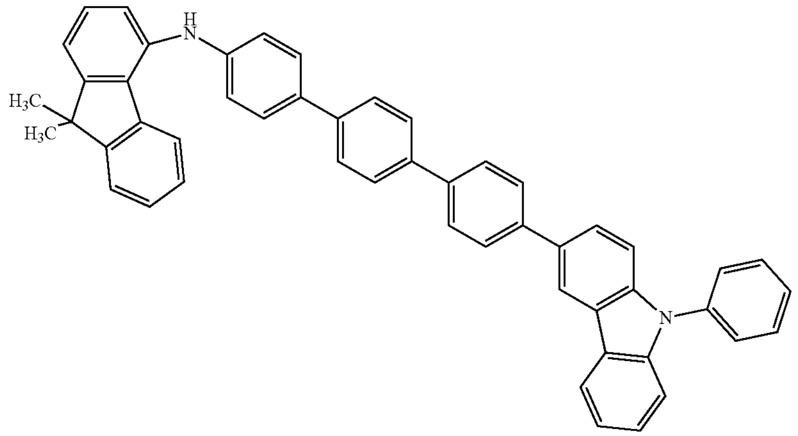
(907)
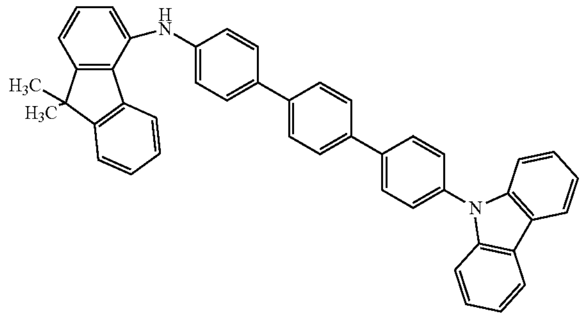
(908)
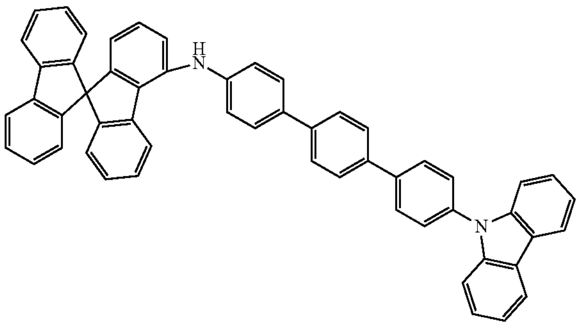
(909)
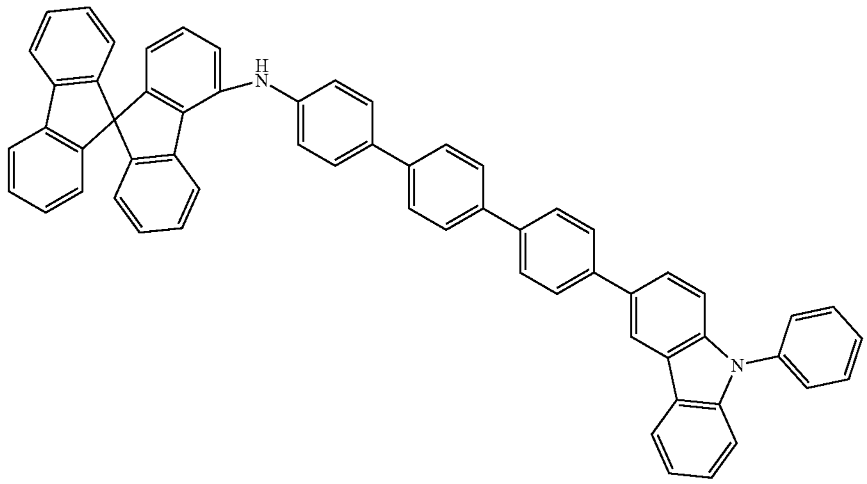

-continued
(910)
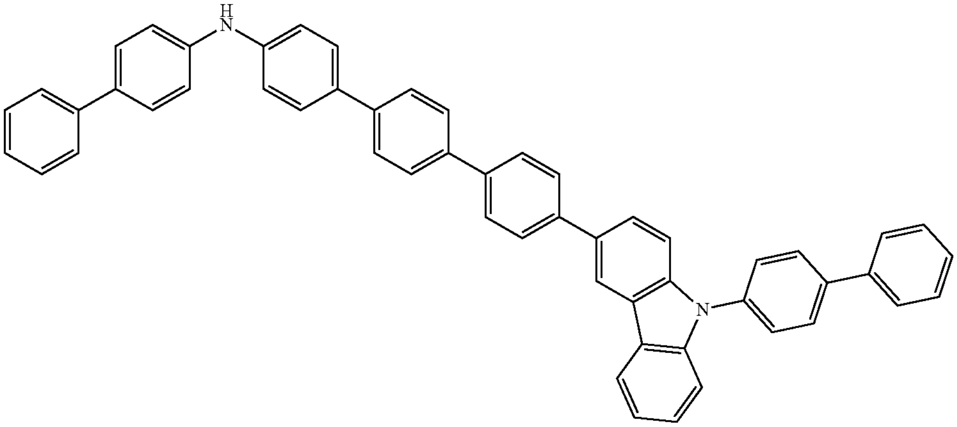
(911)
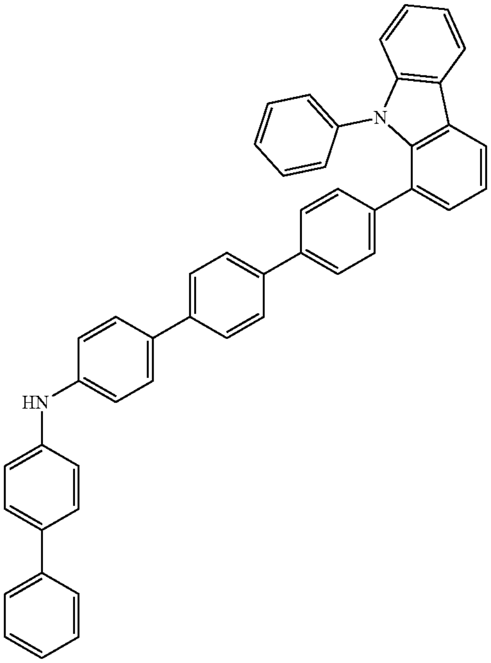
(912)
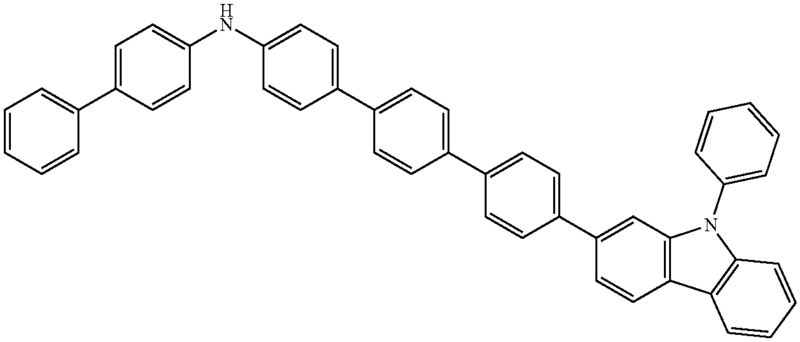

-continued
[Chemical Formula 65]
(913)
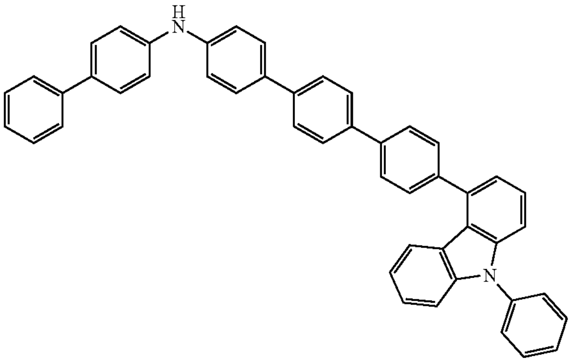
(914)
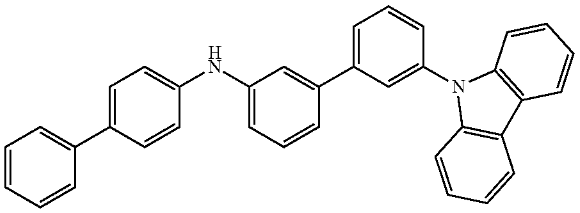
(915)
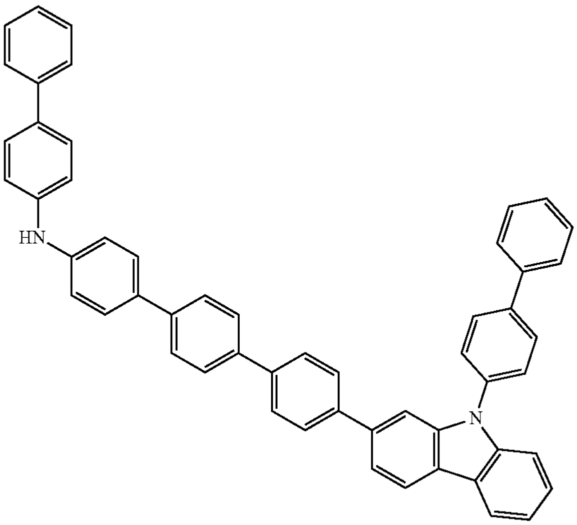
(916)
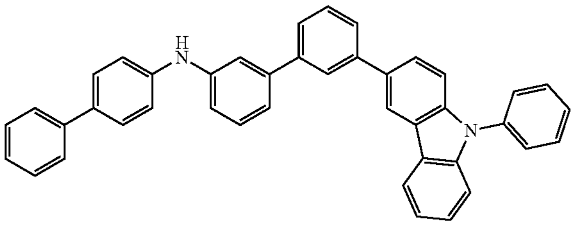
(917)
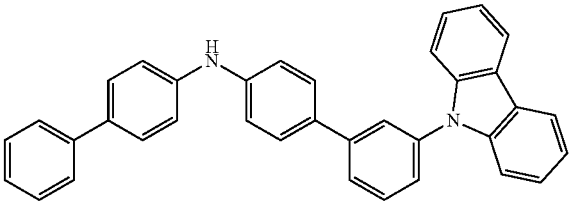
(918)
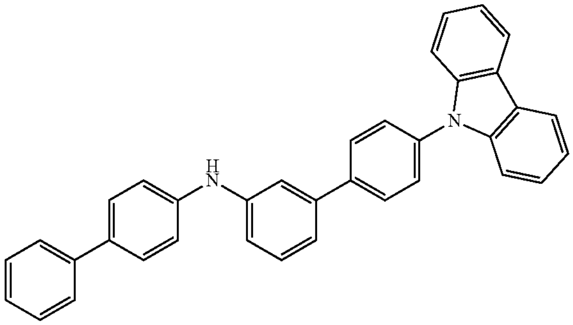

-continued
(919)
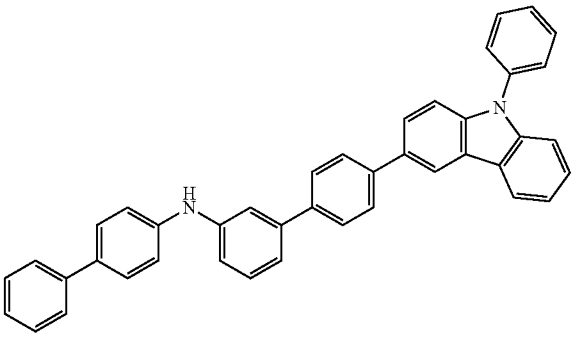
(920)
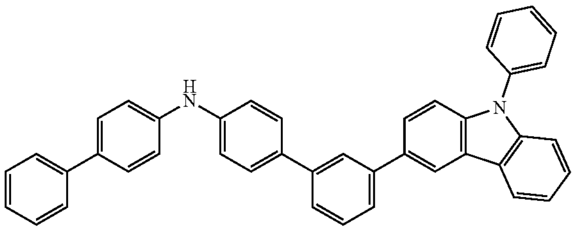
(921)
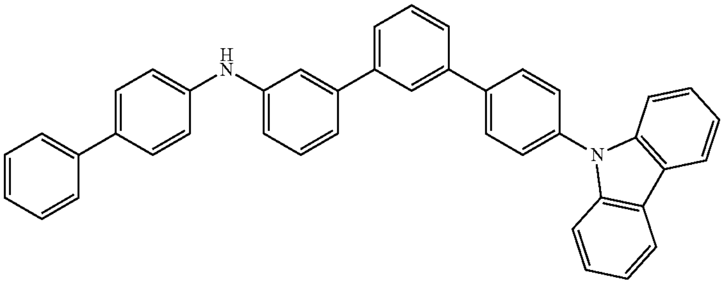
(922)
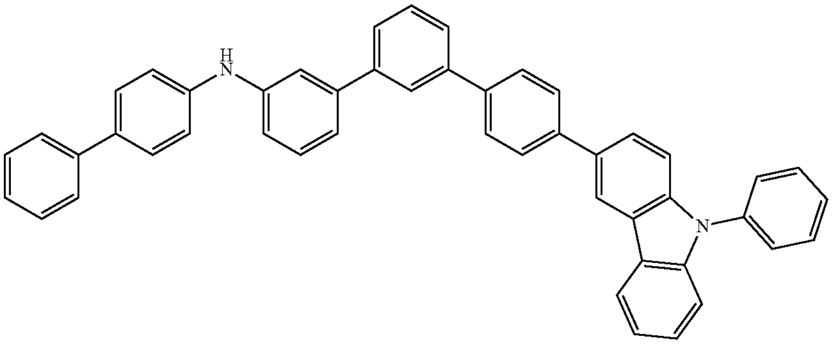
(923)
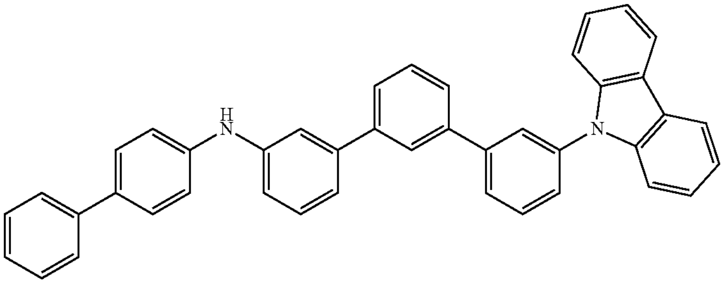
(924)
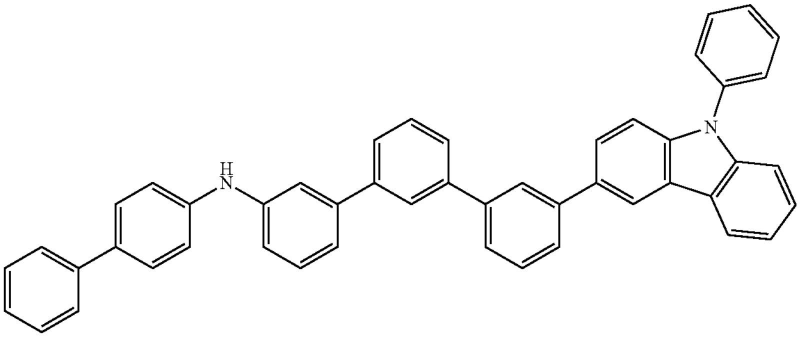

-continued
(925)
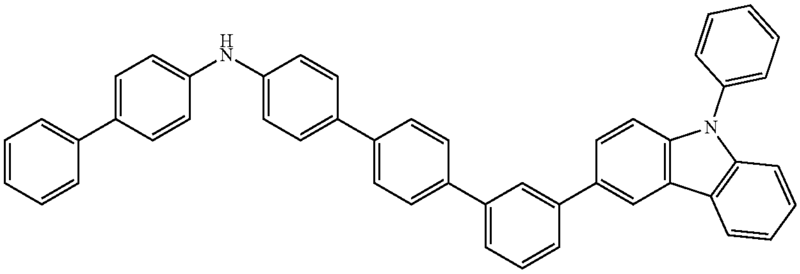
(926)
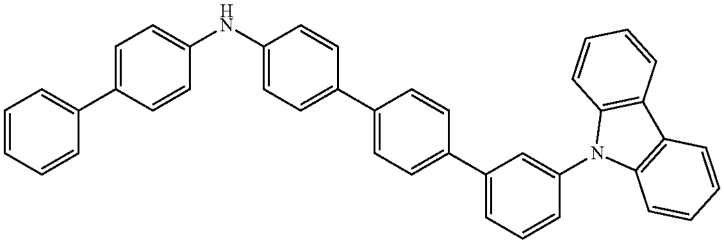
[Chemical Formula 66]
(927)
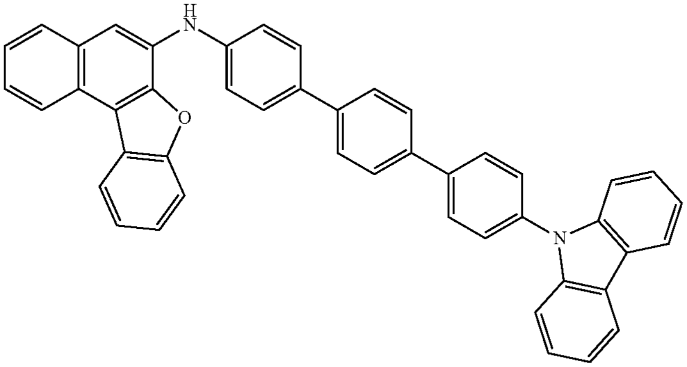
(928)
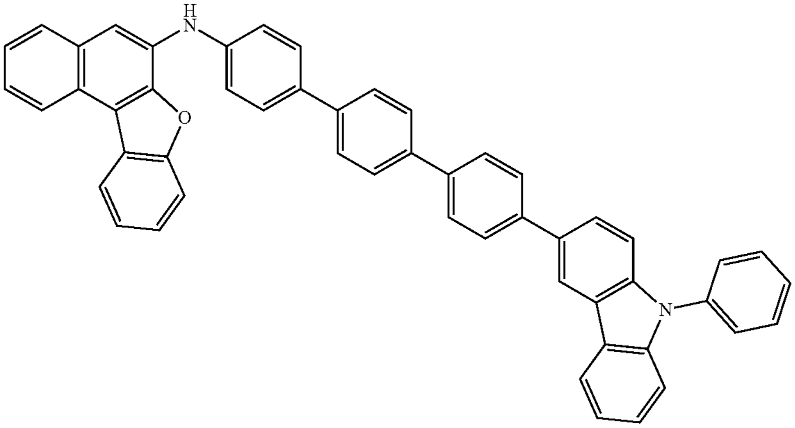

-continued
(929)
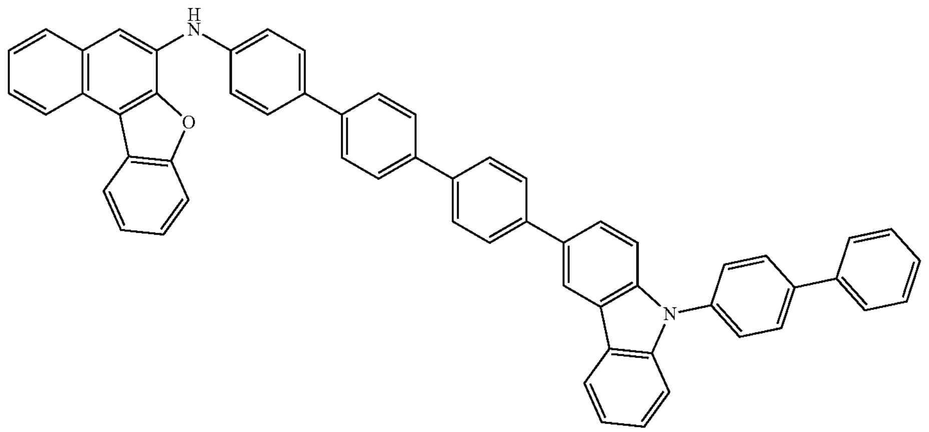
(930)
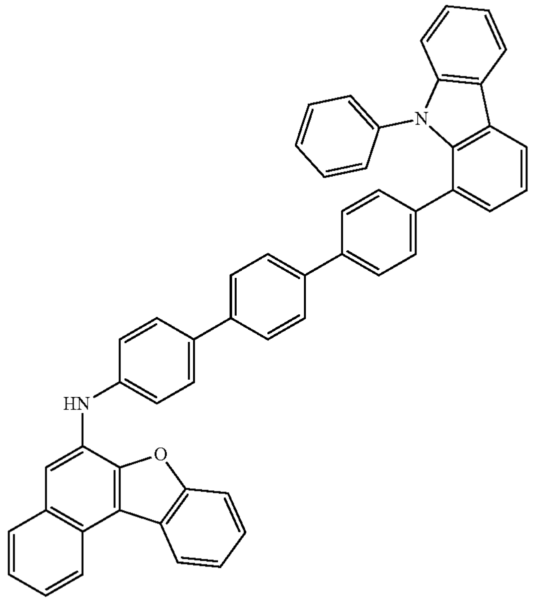
(931)
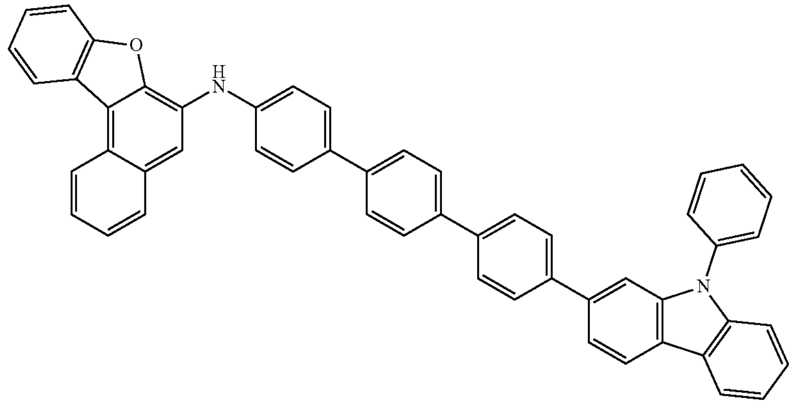

-continued
(932)
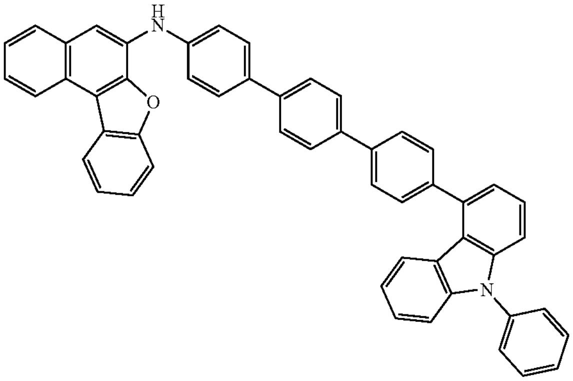
(933)
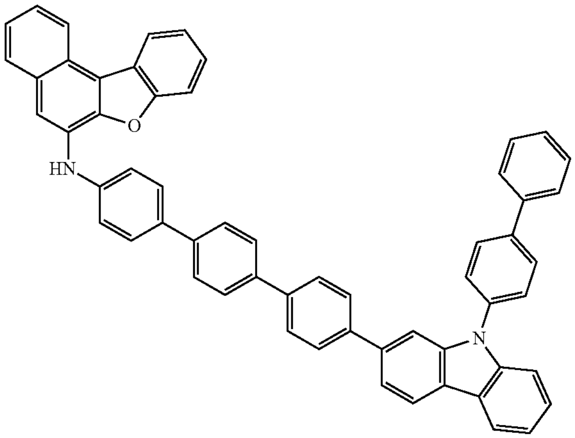
(934)
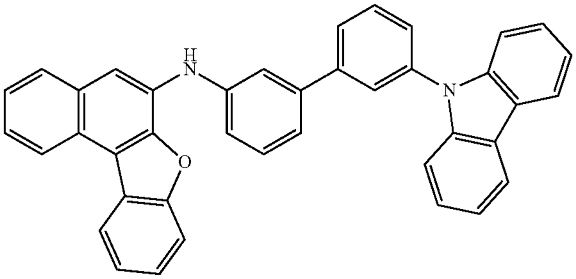
(935)
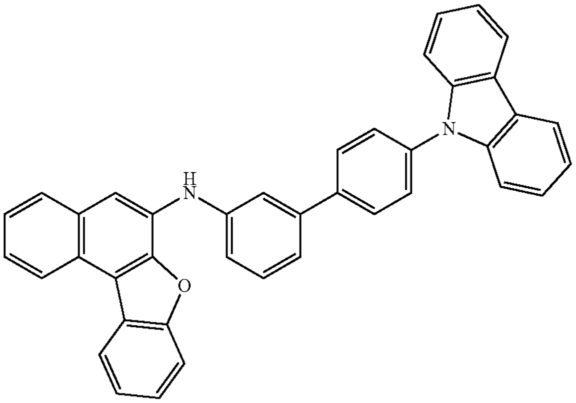
(936)
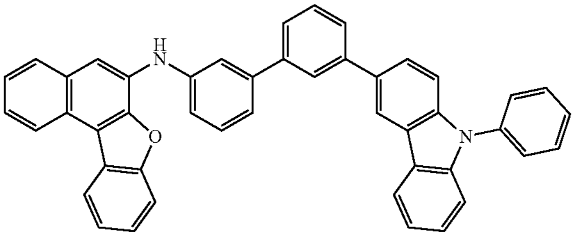
(937)
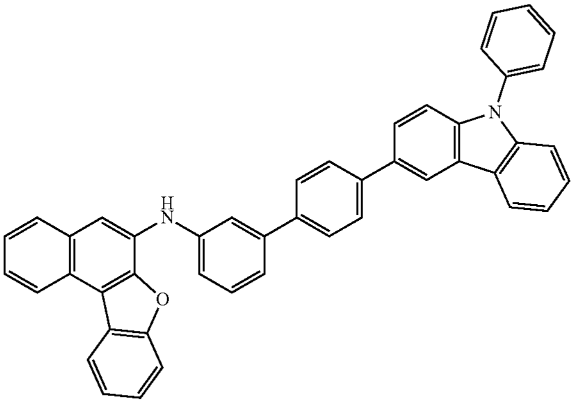
(938)
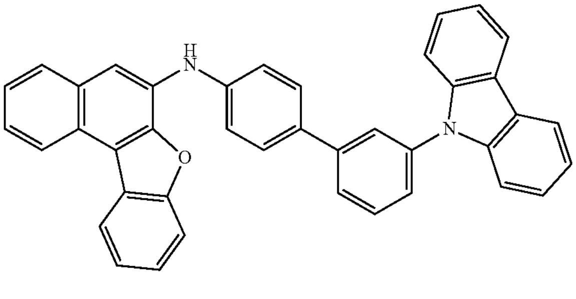
(939)
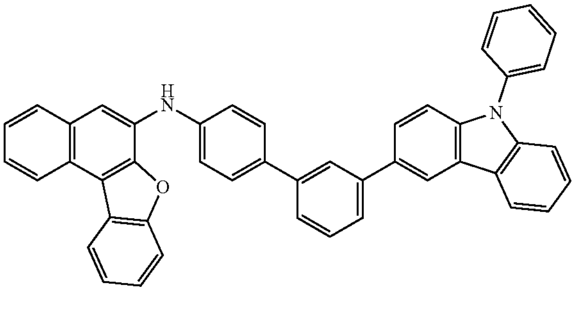

-continued (940)

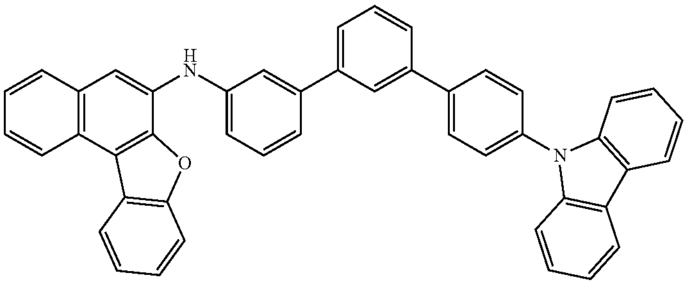

(941)

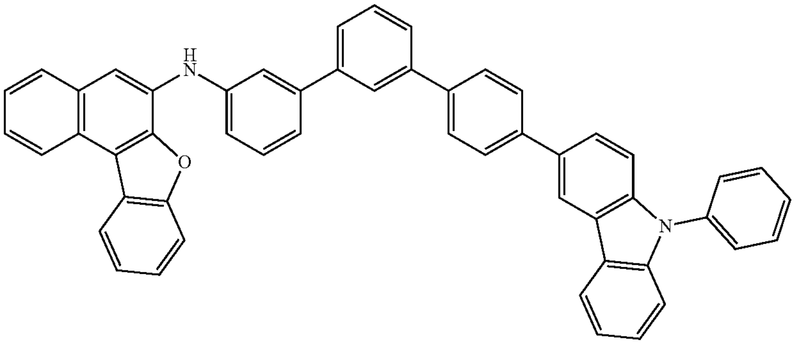

[Chemical Formula 67]

(942)

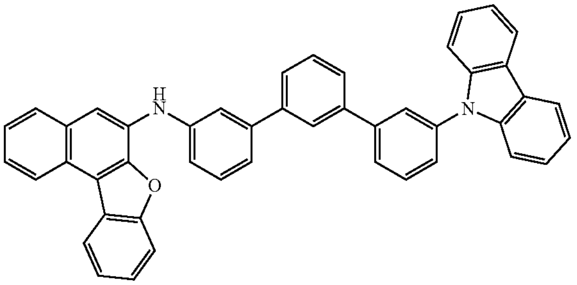

(943)

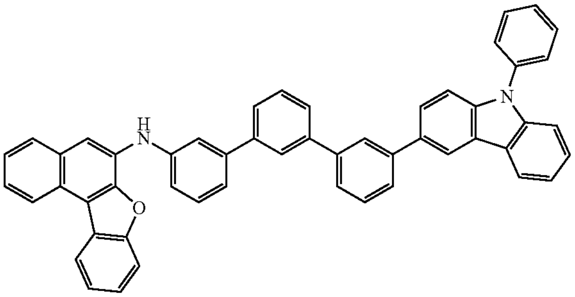

(944)

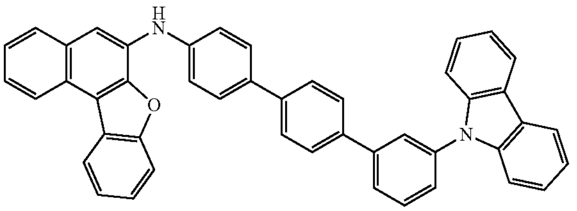

(945)

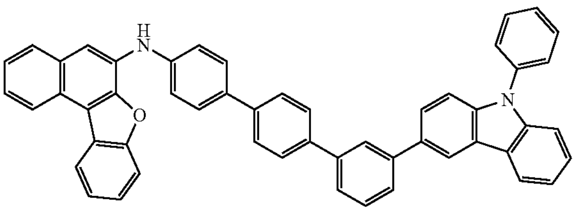

Embodiment 2

FIG. 1 illustrates a light-emitting element of one embodiment of the present invention. The light-emitting element of one embodiment of the present invention includes a first electrode 101, a second electrode 102, and an EL layer 103, and the above-described organic compound is contained in the EL layer.

The EL layer 103 includes a light-emitting layer 113 and may also include a hole-injection layer 111, a hole-transport layer 112, an electron-transport layer 114, an electron-injection layer 115, and the like. The organic compound of one embodiment of the present invention has a hole-transport property and thus is suitable for the hole-injection layer 111, the hole-transport layer 112, and the light-emitting layer 113.

The organic compound can also be used as a host material contained in the light-emitting layer 113. Furthermore, the organic compound and an electron-transport material may be deposited by co-evaporation so that an exciplex is formed of the electron-transport material and the organic compound. The exciplex having an appropriate emission wavelength allows efficient energy transfer to the light-emitting material, achieving a light-emitting element with a high efficiency and a long lifetime.

The above hole-transport material exhibits a good hole-transport property and therefore is effectively used in the hole-injection layer 111 or the hole-transport layer 112. In particular, the hole-transport material is suitably used in the case where the hole-injection layer 111 is provided between the hole-transport layer 112 and the first electrode 101 and includes an organic compound having an acceptor property, which facilitates the injection of holes from the electrode.

In the case where the injection of holes is performed using the organic compound having an acceptor property, a compound included in the hole-transport layer 112 in contact with the hole-injection layer 111 is preferably a hole-transport material with a relatively shallow HOMO level in order to facilitate the extraction of electrons by the organic compound having an acceptor property. However, holes cannot be easily injected into the light-emitting layer 113 from the hole-transport material with a shallow HOMO level, and when the light-emitting layer 113 is formed in contact with the hole-transport layer 112 made of the hole-transport material with a shallow HOMO level, carriers are accumulated at their interface, causing a decrease in the lifetime and efficiency of the light-emitting element. Thus, a layer containing the organic compound described in Embodiment 1 is provided between the light-emitting layer 113 and the hole-transport material with a shallow HOMO level, in which case holes can be easily injected into the light-emitting layer and the lifetime and efficiency of the light-emitting element can be improved.

That is, the hole-transport layer 112 includes a first hole-transport layer 112-1 and a second hole-transport layer 112-2 from the hole-injection layer 111 side, and the first hole-transport layer contains a first hole-transport material whereas the second hole-transport layer contains the above-described organic compound described in Embodiment 1. The light-emitting element in which the HOMO level of the organic compound described in Embodiment 1 is deeper than the HOMO level of the first hole-transport material is a preferable structure because the light-emitting element can have a long lifetime and a high efficiency. Note that the HOMO level of the first hole-transport material is preferably greater than or equal to −5.4 eV, in which case electrons can be easily extracted from the organic compound having an acceptor property.

The difference between the HOMO level of the first hole-transport material and the HOMO level of the organic compound described in Embodiment 1 of less than or equal to 0.3 eV, further preferably less than or equal to 0.2 eV is a preferable structure in order that holes can be easily injected from the first hole-transport layer 112-1 to the second hole-transport layer 112-2.

The hole-transport layer 112 may further include a third hole-transport layer 112-3 between the second hole-transport layer 112-2 and the light-emitting layer, and the third hole-transport layer 112-3 may contain a third hole-transport material. In that case, the HOMO level of the third hole-transport material is preferably deeper than the HOMO level of the organic compound described in Embodiment 1 included in the second hole-transport layer 112-2. Furthermore, the difference between the HOMO level of the third hole-transport material and the HOMO level of the organic compound described in Embodiment 1 included in the second hole-transport layer 112-2 is preferably less than or equal to 0.3 eV, further preferably less than or equal to 0.2 eV.

A structure in which the HOMO level of the third hole-transport material is deeper than or equal to the HOMO level of the host material is preferable in order that holes are appropriately transported to the light-emitting layer and the lifetime and efficiency can be favorable.

Note that in the case where the HOMO level of the light-emitting material is shallower (higher) than the HOMO level of the host material, many holes are injected into the light-emitting material depending on the HOMO level of the hole-transport layer, and furthermore, the holes are trapped in the light-emitting material, which might cause a decreased lifetime due to the movement of the light-emitting region. The use of the above-described structure of the light-emitting element is preferable in such a case. Examples of the element that is easily have such a structure include a blue fluorescent element. In particular, the structure of the present invention can be preferably used for an aromatic diamine compound that emits excellent blue fluorescence, more particularly a pyrenediamine compound, a naphthobisbenzofuran compound, and the like, achieving a light-emitting element with excellent lifetime, efficiency, and chromaticity.

Next, examples of specific structures and materials of the aforementioned light-emitting element will be described. As described above, the light-emitting element of one embodiment of the present invention includes the EL layer 103 that is positioned between the pair of electrodes (the first electrode 101 and the second electrode 102) and has a plurality of layers. The EL layer 103 includes at least the organic compound of one embodiment of the present invention. Note that there is no particular limitation on the layers included in the EL layer 103, and various layer structures such as a hole-injection layer, a hole-transport layer, an electron-transport layer, an electron-injection layer, a carrier-blocking layer, an exciton-blocking layer, and a charge-generation layer can be employed.

The first electrode 101 is preferably formed using any of metals, alloys, conductive compounds with a high work function (specifically, a work function of 4.0 eV or more), mixtures thereof, and the like. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Such conductive metal oxide films are usually formed by a sputtering method, but may be formed by application of a sol-gel method or the like. In an example of the formation method, indium oxide-zinc oxide is deposited by a sputtering method using a target obtained by adding 1 wt % to 20 wt % of zinc oxide to indium oxide. Furthermore, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used. Graphene can also be used. Note that when a composite material described later is used for a layer in contact with the first electrode 101 in the EL layer 103, an electrode material can be selected regardless of its work function.

Figure 1B:
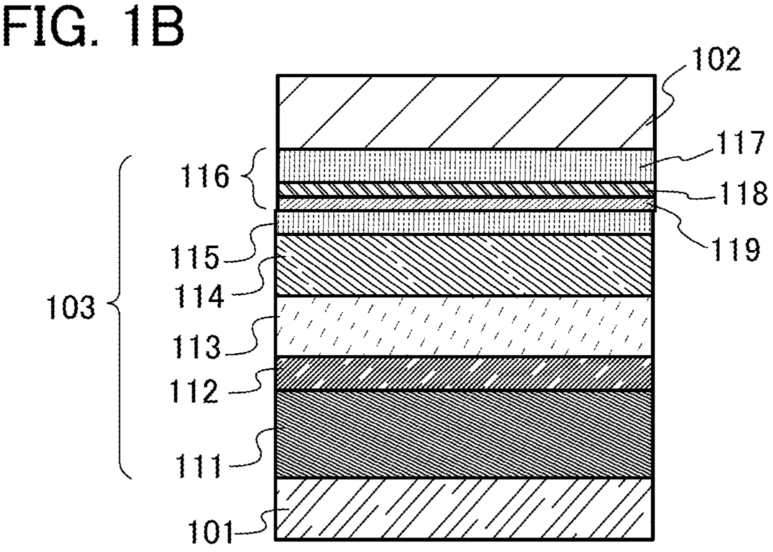

In this embodiment, two kinds of stacked-layer structures of the EL layer 103 are described: the structure including the electron-transport layer 114 and the electron-injection layer 115 in addition to the hole-injection layer 111, the hole-transport layer 112, and the light-emitting layer 113 as illustrated in FIG. 1(A); and the structure including the electron-transport layer 114, the electron-injection layer 115, and a charge-generation layer 116 in addition to the hole-injection layer 111, the hole-transport layer 112, and the light-emitting layer 113 as illustrated in FIG. 1(B). Materials forming the layers are specifically described below.

The hole-injection layer 111 is a layer containing a substance having an acceptor property. The structure of one embodiment of the present invention is preferably used in the case where an organic compound having an acceptor property is used. As the substance having an acceptor property, a compound including an electron-withdrawing group (a halogen group or a cyano group) can be used; for example, 7,7,8,8-tetracyano-2,3,5,6-tetrafluoroquinodimethane (abbreviation: F4-TCNQ), 3,6-difluoro-2,5,7,7,8,8-hexacyanoquinodimethane, chloranil, 2,3,6,7,10,11-hexacyano-1,4,5,8,9,12-hexaazatriphenylene (abbreviation: HAT-CN), or 1,3,4,5,7,8-hexafluorotetracyano-naphthoquinodimethane (abbreviation: F6-TCNNQ) can be used. The organic compound having an acceptor property is preferably a compound in which electron-withdrawing groups are bonded to a condensed aromatic ring having a plurality of heteroatoms, like HAT-CN, because it is thermally stable. A [3]radialene derivative including an electron-withdrawing group (in particular, a cyano group or a halogen group such as a fluoro group) has a very high electron-accepting property and thus is preferable; specific examples include α,α',α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], and α,α',α"-1,2,3-cyclopropanetriylidenetris[2,3,4,5,6-pentafluorobenzeneacetonitrile]. As the substance having an acceptor property, molybdenum oxide, vanadium oxide, ruthenium oxide, tungsten oxide, manganese oxide, or the like can be used, other than the above-described organic compounds. Alternatively, the hole-injection layer 111 can be formed using a phthalocyanine-based complex compound such as phthalocyanine (abbreviation: $H_2Pc$) or copper phthalocyanine (CuPC), an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD), or a high molecular compound such as poly(3,4-ethylenedioxythiophene)/poly(styrenesulfonic acid) (PEDOT/PSS). The substance having an acceptor property can extract electrons from an adjacent hole-transport layer (or hole-transport material) when an electric field is applied.

In the case where the organic compound having an acceptor property is not used for the hole-injection layer 111, molybdenum oxide, vanadium oxide, ruthenium oxide, tungsten oxide, manganese oxide, or the like can be used as the substance having an acceptor property. Alternatively, the hole-injection layer 111 can be formed using a phthalocyanine-based compound such as phthalocyanine (abbreviation: $H_2Pc$) or copper phthalocyanine (CuPC), an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD), or a high molecular compound such as poly(3,4-ethylenedioxythiophene)/poly(styrenesulfonic acid) (PEDOT/PSS).

Alternatively, a composite material in which a substance having a hole-transport property contains an acceptor substance can be used for the hole-injection layer 111. By using a composite material in which a substance having a hole-transport property contains an acceptor substance, a material used to form an electrode can be selected regardless of its work function. In other words, besides a material having a high work function, a material having a low work function can also be used for the first electrode 101. Examples of the acceptor substance include an organic compound having an acceptor property, such as 7,7,8,8-tetracyano-2,3,5,6-tetrafluoroquinodimethane (abbreviation: F4-TCNQ), chloranil, or 1,3,4,5,7,8-hexafluorotetracyano-naphthoquinodimethane (abbreviation: F6-TCNNQ), and a transition metal oxide. Alternatively, an oxide of a metal belonging to Group 4 to Group 8 in the periodic table can be used. As the oxide of a metal belonging to Group 4 to Group 8 in the periodic table, vanadium oxide, niobium oxide, tantalum oxide, chromium oxide, molybdenum oxide, tungsten oxide, manganese oxide, rhenium oxide, or the like is preferably used because their electron-accepting property is high. Among these, molybdenum oxide is especially preferable since it is stable in the air, has a low hygroscopic property, and is easy to handle.

As the substance having a hole-transport property which is used for the composite material, any of a variety of organic compounds such as aromatic amine compounds, carbazole derivatives, aromatic hydrocarbons, and high molecular compounds (e.g., oligomers, dendrimers, or polymers) can be used. Note that the substance having a hole-transport property which is used for the composite material is preferably a substance having a hole mobility of $10^{-6}$ $cm^2/Vs$ or more. Note that the organic compound of one embodiment of the present invention can also be suitably used. The organic compounds that can be used as the substance having a hole-transport property in the composite material are specifically given below.

Examples of the aromatic amine compounds that can be used for the composite material include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B). Specific examples of the carbazole derivative include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene. Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Besides, pentacene, coronene, or the like can be used. The aromatic hydrocarbon may have a vinyl skeleton. Examples of the aromatic hydrocarbon having a vinyl group are 4,4'-bis(2,2-diphenylvinyl)biphenyl (abbreviation: DPVBi) and 9,10-bis[4-(2,2-diphenylvinyl) phenyl]anthracene (abbreviation: DPVPA). Note that the organic compound of one embodiment of the present invention can also be used.

A high molecular compound such as poly(N-vinylcarbazole) (abbreviation: PVK), poly(4-vinyltriphenylamine) (abbreviation: PVTPA), poly[N-(4-{N'-[4-(4-diphenylamino) phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: poly-TPD) can also be used.

The formation of the hole-injection layer 111 can improve the hole-injection property, whereby a light-emitting element having a low driving voltage can be obtained. The organic compound having an acceptor property is an easy-to-use material because evaporation is easy and its film can be easily formed.

The hole-transport layer 112 contains a hole-transport material. The hole-transport material preferably has a hole mobility of $1\times10^{-6}$ $cm^2/Vs$ or more. The hole-transport layer 112 preferably includes the hole-transport material of one embodiment of the present invention. When the organic compound of one embodiment of the present invention described in Embodiment 1 is contained in the hole-transport layer 112, a light-emitting element with a long lifetime and a favorable efficiency can be provided.

Particularly when the organic compound having an acceptor property is used for the hole-injection layer 111, at least the hole-transport layer 112 consists of two layers of a first hole-transport layer 112-1 and a second hole-transport layer 112-2, a first hole-transport material with a relatively shallow HOMO level is used for the first hole-transport layer 112-1, and the organic compound described in Embodiment 1 is contained in the second hole-transport layer; as a result, a light-emitting element with a long lifetime and a high efficiency can be provided.

Although the difference between the LUMO level of the organic compound having an acceptor property and the HOMO level of the first hole-transport material is not particularly limited because it depends on the strength of the acceptor property of the organic compound having an acceptor property, holes can be injected when the difference between the levels is less than or equal to approximately 1 eV. Since the LUMO level of HAT-CN is estimated to be −4.41 eV by cyclic voltammetry measurement, in the case where HAT-CN is used as the organic compound having an acceptor property, the HOMO level of the first hole-transport material is preferably greater than or equal to −5.4 eV. Note that if the HOMO level of the first hole-transport material is too high, the hole-injection property for the second hole-transport material deteriorates. In addition, since the work function of an anode such as ITO is approximately −5 eV, the use of a material whose HOMO level is higher than −5 eV as the first hole-transport material brings a disadvantage. Therefore, the HOMO level of the first hole-transport material is preferably less than or equal to −5.0 eV.

A third hole-transport layer 112-3 may be formed between the second hole-transport layer and the light-emitting layer. The third hole-transport layer 112-3 includes a third hole-transport material.

The first hole-transport layer 112-1, the second hole-transport layer 112-2, and the third hole-transport layer 112-3 are described above and not repeatedly described. Note that the hole-transport material included in each hole-transport layer may be selected from the aforementioned materials having hole-transport properties or other various materials having hole-transport properties so that the layers have an appropriate relationship.

The light-emitting layer 113 is a layer including the light-emitting material. As the light-emitting material, fluorescent materials, phosphorescent materials, substances exhibiting thermally activated delayed fluorescence (TADF), or other light-emitting materials may be used. Furthermore, the light-emitting layer 113 may be a single layer or include a plurality of layers containing different light-emitting materials. Note that one embodiment of the present invention is further preferably used in the case where the light-emitting layer 113 emits fluorescence, specifically, blue fluorescence.

Examples of the material that can be used as a fluorescent substance in the light-emitting layer 113 are described below. Fluorescent substances other than those given below can also be used.

Examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9H-carbazol-9-yl) phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N,N-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N,N-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA) coumarin 545T, N,N'-diphenylquinacridone, (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl) tetracene-5,11-diamine (abbreviation: p-mPhTD), 7,14-diphenyl-N,N,N',N-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H- benzo[j]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and N,N-(pyrene--1,6-diyl)bis[6,N-diphenylbenzo[b]naphtho[1,2-d]furan)-8-amine](abbreviation: 1,6BnfAPrn-03). Condensed aromatic diamine compounds typified by pyrenediamine compounds such as 1,6FLPAPrn, 1,6mMemFLPAPrn, and 1,6BnfAPrn-03 are particularly preferable because of their high hole-trapping properties, high emission efficiency, and high reliability.

Examples of the material that can be used as a phosphorescent substance in the light-emitting layer 113 are as follows.

The examples include organometallic iridium complexes having 4H-triazole skeletons, such as tris{2-[5-(2-methylphenyl)-4-(2,6-dimethylphenyl)-4H-1,2,4-triazol-3-yl-κN2]phenyl-κC}iridium(III) (abbreviation: $[Ir(mpptz\text{-}dmp)_3]$), tris(5-methyl-3,4-diphenyl-4H-1,2,4-triazolato)iridium(III) (abbreviation: $[Ir(Mptz)_3]$), and tris[4-(3-biphenyl)-5-isopropyl-3-phenyl-4H-1,2,4-triazolato]iridium(III) (abbreviation: $[Ir(iPrptz\text{-}3b)_3]$); organometallic iridium complexes having 1H-triazole skeletons, such as tris[3-methyl-1-(2-methylphenyl)-5-phenyl-1H-1,2,4-triazolato]iridium(III) (abbreviation: $[Ir(Mptz1\text{-}mp)_3]$) and tris(1-methyl-5-phenyl-3-propyl-1H-1,2,4-triazolato)iridium(III) (abbreviation: $[Ir(Prptz1\text{-}Me)_3]$); organometallic iridium complexes having imidazole skeletons, such asfac-tris[(1-(2,6-diisopropylphenyl)-2-phenyl-1H-imidazole]iridium(III) (abbreviation: $[Ir(iPrpmi)_3]$) and tris[3-(2,6-dimethylphenyl)-7-methylimidazo[1,2-]phenanthridinato]iridium(III) (abbreviation: $[Ir(dmpimpt\text{-}Me)_3]$); and organometallic iridium complexes in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: $[Ir(CF_3ppy)_2(pic)]$), and bis[2-(4',6'-difluorophenyl)pyridinato-N,$C^{2'}$]iridium(III) acetylacetonate (abbreviation: FIr(acac)). These are compounds emitting blue phosphorescence and have an emission peak at 440 nm to 520 nm.

Other examples include organometallic iridium complexes having pyrimidine skeletons, such as tris(4-methyl-6-phenylpyrimidinato)iridium(III) (abbreviation: $[Ir(mppm)_3]$), tris(4-t-butyl-6-phenylpyrimidinato)iridium(III) (abbreviation: $[Ir(tBuppm)_3]$), (acetylacetonato)bis(6-methyl-4-phenylpyrimidinato)iridium(III) (abbreviation: $[Ir(mppm)_2(acac)]$), (acetylacetonato)bis(6-tert-butyl-4-phenylpyrimidinato)iridium(III) (abbreviation: $[Ir(tBuppm)_2(acac)]$), (acetylacetonato)bis[6-(2-norbornyl)-4-phenylpyrimidinato]iridium(III) (abbreviation: $[Ir(nbppm)_2(acac)]$), (acetylacetonato)bis[5-methyl-6-(2-methylphenyl)-4-phenylpyrimidinato]iridium(III) (abbreviation: $[Ir(mpmppm)_2(acac)]$), and (acetylacetonato)bis(4,6-diphenylpyrimidinato)iridium(III) (abbreviation: $[Ir(dppm)_2(acac)]$); organometallic iridium complexes having pyrazine skeletons, such as (acetylacetonato)bis(3,5-dimethyl-2-phenylpyrazinato)iridium(III) (abbreviation: $[Ir(mppr\text{-}Me)_2(acac)]$) and (acetylacetonato)bis(5-isopropyl-3-methyl-2-phenylpyrazinato)iridium(III) (abbreviation: $[Ir(mppr\text{-}iPr)_2(acac)]$); organometallic iridium complexes having pyridine skeletons, such as tris(2-phenylpyridinato-N,$C^{2'}$)iridium(III) (abbreviation: $[Ir(ppy)_3]$), bis(2-phenylpyridinato-N,$C^{2'}$)iridium(III) acetylacetonate (abbreviation: $[Ir(ppy)_2(acac)]$), bis(benzo[h]quinolinato)iridium(III) acetylacetonate (abbreviation: $[Ir(bzq)_2(acac)]$), tris(benzo[h]quinolinato)iridium(III) (abbreviation: $[Ir(bzq)_3]$), tris(2-phenylquinolinato-N,$C^{2'}$)iridium(III) (abbreviation: $[Ir(pq)_3]$), and bis(2-phenylquinolinato-N,$C^{2'}$)iridium(III) acetylacetonate (abbreviation: $[Ir(pq)_2(acac)]$); and rare earth metal complexes such as tris(acetylacetonato)(monophenanthroline)terbium(III) (abbreviation: $[Tb(acac)_3(Phen)]$). These are mainly compounds emitting green phosphorescence and have an emission peak at 500 nm to 600 nm. Note that organometallic iridium complexes having pyrimidine skeletons have distinctively high reliability and emission efficiency and thus are especially preferable.

Other examples include organometallic iridium complexes having pyrimidine skeletons, such as (diisobutyrylmethanato)bis[4,6-bis(3-methylphenyl)pyrimidinato]iridium(III) (abbreviation: $[Ir(5mdppm)_2(dibm)]$), bis[4,6-bis(3-methylphenyl)pyrimidinato](dipivaloylmethanato)iridium(III) (abbreviation: $[Ir(5mdppm)_2(dpm)]$), bis[4,6-di(naphthalen-1-yl)pyrimidinato](dipivaloylmethanato)iridium(III) (abbreviation: $[Ir(d1npm)_2(dpm)]$); organometallic iridium complexes having pyrazine skeletons, such as (acetylacetonato)bis(2,3,5-triphenylpyrazinato)iridium(III) (abbreviation: $[Ir(tppr)_2(acac)]$), bis(2,3,5-triphenylpyrazinato)(dipivaloylmethanato)iridium(III) (abbreviation: $[Ir(tppr)_2(dpm)]$), and (acetylacetonato)bis[2,3-bis(4-fluorophenyl)quinoxalinato]iridium(III) (abbreviation: $[Ir(Fdpq)_2(acac)]$); organometallic iridium complexes having pyridine skeletons, such as tris(1-phenylisoquinolinato-N,$C^{2'}$)iridium(III) (abbreviation: $[Ir(piq)_3]$) and bis(1-phenylisoquinolinato-N,$C^{2'}$)iridium(III) acetylacetonate (abbreviation: $[Ir(piq)_2(acac)]$); platinum complexes such as 2,3,7,8,12,13,17,18-octaethyl-21H,23H-porphyrin platinum(II) (abbreviation: PtOEP); and rare earth metal complexes such as tris(1,3-diphenyl-1,3-propanedionato)(monophenanthroline)europium(III) (abbreviation: $[Eu(DBM)_3(Phen)]$) and tris[1-(2-thenoyl)-3,3,3-trifluoroacetonato](monophenanthroline)europium(III) (abbreviation: $[Eu(TTA)_3(Phen)]$). These are compounds emitting red phosphorescence and have an emission peak at 600 nm to 700 nm. Furthermore, organometallic iridium complexes having pyrazine skeletons can provide red light emission with favorable chromaticity.

Besides the above phosphorescent compounds, known phosphorescent materials may be selected and used.

As the TADF material, a fullerene, a derivative thereof, an acridine, a derivative thereof, an eosin derivative, or the like can be used. Other examples include a metal-containing porphyrin containing magnesium (Mg), zinc (Zn), cadmium (Cd), tin (Sn), platinum (Pt), indium (In), palladium (Pd), or the like. Examples of the metal-containing porphyrin include a protoporphyrin-tin fluoride complex ($SnF_2$(Proto IX)), a mesoporphyrin-tin fluoride complex ($SnF_2$(Meso IX)), a hematoporphyrin-tin fluoride complex ($SnF_2$(Hemato IX)), a coproporphyrin tetramethyl ester-tin fluoride complex ($SnF_2$(Copro III-4Me)), an octaethylporphyrin-tin fluoride complex ($SnF_2$(OEP)), an etioporphyrin-tin fluoride complex ($SnF_2$(Etio I)), and an octaethylporphyrin-platinum chloride complex ($PtCl_2$(OEP)), which are expressed by the following structural formulae.

[Chemical Formula 68]
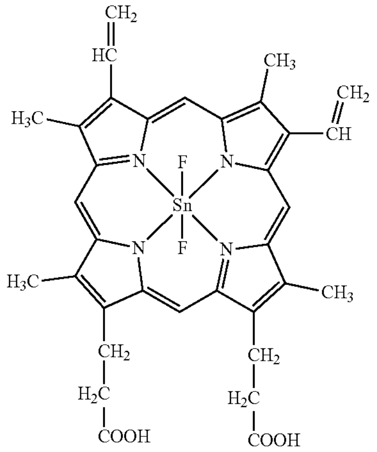
SnF2(Proto IX)
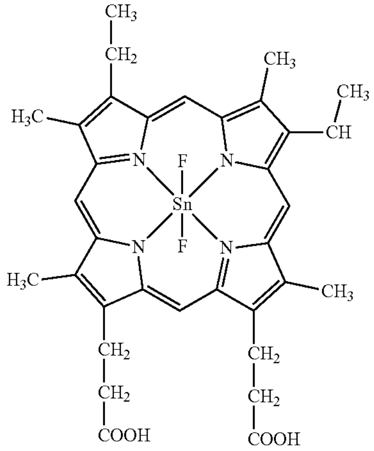
SnF2(Meso IX)
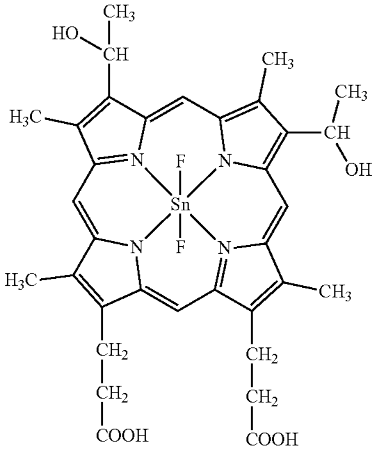
SnF2(Hemato IX)
-continued
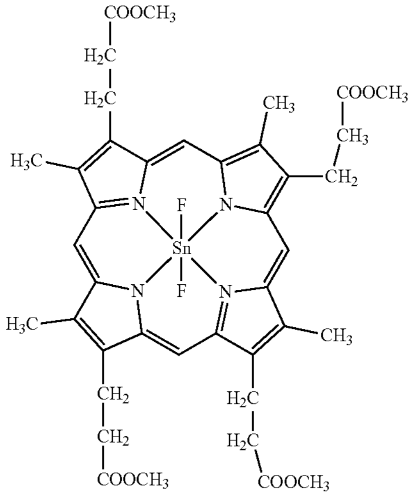
SnF2(Copro III-4Me)
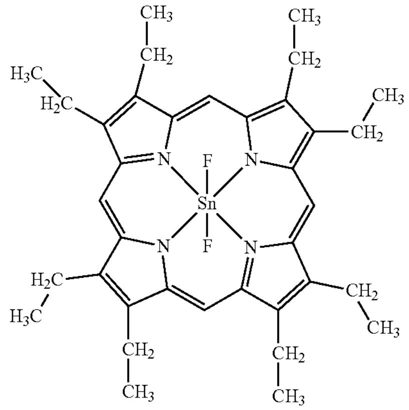
SnF2(OEP)
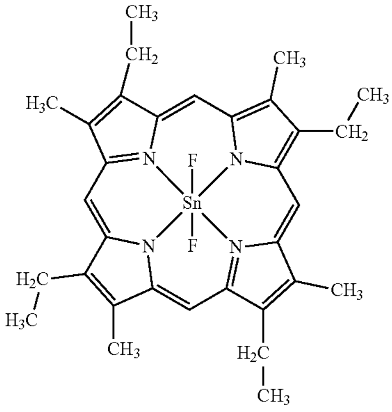
SnF2(Etio 1)

-continued

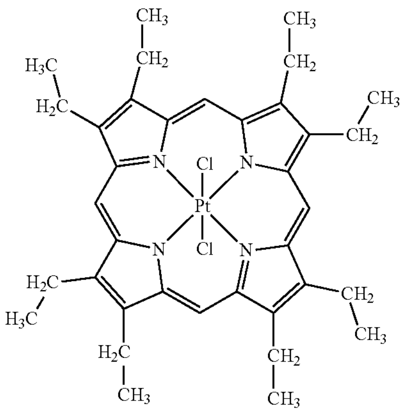

$PtCl_2OEP$

[Chemical Formula 69]

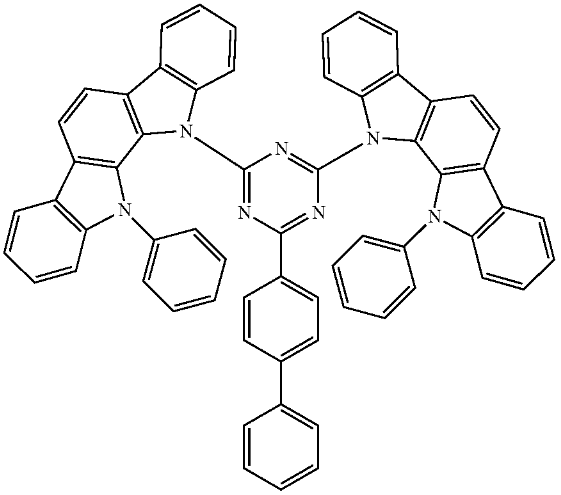

PIC-TRZ

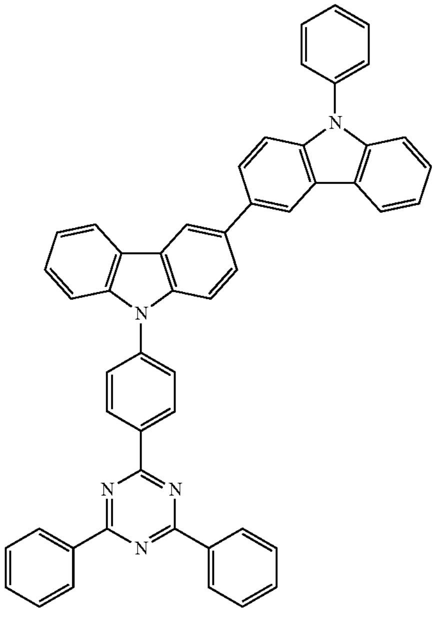

PCCzPTzn

Alternatively, a heterocyclic compound having both a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA), which are represented by the following structural formulae, can be used. The heterocyclic compound is preferable because of having both a high electron-transport property and a high hole-transport property owing to a π-electron rich heteroaromatic ring and a π-electron deficient heteroaromatic ring. Note that a substance in which the π-electron rich heteroaromatic ring and the π-electron deficient heteroaromatic ring are directly bonded to each other is particularly preferable because the donor property of the π-electron rich heteroaromatic ring and the acceptor property of the π-electron deficient heteroaromatic ring are both increased and the energy difference between the $S_1$ level and the $T_1$ level becomes small, so that thermally activated delayed fluorescence can be obtained with high efficiency. Note that an aromatic ring to which an electron-withdrawing group such as a cyano group is bonded may be used instead of the it-electron deficient heteroaromatic ring.

-continued

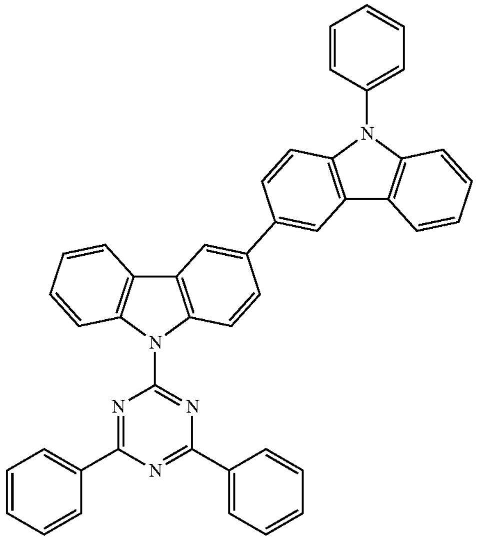

PCCzTzn

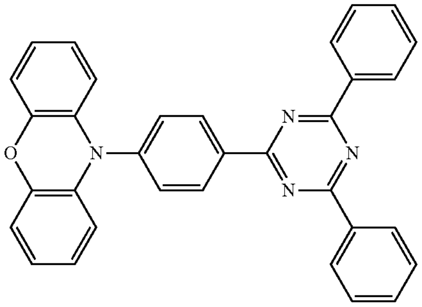

PXZ-TRZ

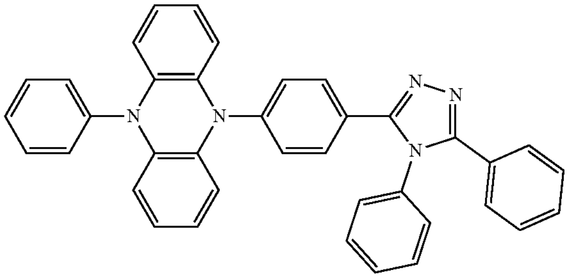

PPZ-3TPT

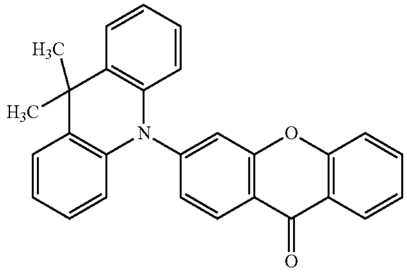

ACRXTN

-continued

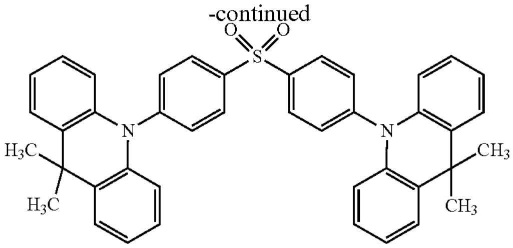

DMAC-DPS

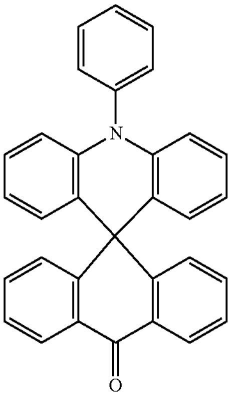

ACRSA

As the host material in the light-emitting layer, various carrier-transport materials such as materials with an electron-transport property and materials with a hole-transport property can be used.

Examples of a material having a hole-transport property include a compound having an aromatic amine skeleton, such as 4,4'-bis[N-(1-naphthyl)-N-phenylamino]biphenyl (abbreviation: NPB), N,N-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); a compound having a thiophene skeleton, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and a compound having a furan skeleton, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

Among the above, the compound having an aromatic amine skeleton and the compound having a carbazole skeleton are preferable because these have favorable reliability, have high hole-transport properties, and contribute to a reduction in driving voltage. The organic compound described in Embodiment 1 can also be suitably used.

Examples of materials having an electron-transport property include metal complexes such as bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 2-[3'-(9,9-dimethyl-9H-fluoren-2-yl)-1,1'-biphenyl-3-yl]-4,6-diphenyl-1,3,5-triazine (abbreviation: mFBPTzn), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: COl1), 2,2',2"-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), and 2-{4-[9,10-di(naphthalen-2-yl)-2-anthryl]phenyl}-1-phenyl-1H-benzoimidazole (abbreviation: ZADN); heterocyclic compounds having diazine skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II); and heterocyclic compounds having pyridine skeletons, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compounds having diazine skeletons and the heterocyclic compounds having pyridine skeletons are highly reliable and preferred. In particular, the heterocyclic compounds having diazine (pyrimidine or pyrazine) skeletons have a high electron-transport property and contribute to a decrease in drive voltage.

In the case where a fluorescent substance is used as the light-emitting material, a material having an anthracene skeleton is suitably used as the host material. The use of a substance having an anthracene skeleton as the host material for the fluorescent substance makes it possible to obtain a light-emitting layer with high emission efficiency and high durability. Most of materials having an anthracene skeleton have a deep HOMO level; therefore, such a material can be suitably used in one embodiment of the present invention. Among the substances having an anthracene skeleton, a substance with a diphenylanthracene skeleton, in particular, a substance with a 9,10-diphenylanthracene skeleton, is chemically stable and thus is preferably used as the host material. The host material preferably has a carbazole skeleton so that the hole-injection and hole-transport properties can be increased; further preferably, the host material has a benzocarbazole skeleton in which a benzene ring is further condensed to carbazole so that the HOMO level thereof can be shallower than that of carbazole by approximately 0.1 eV and thus holes can enter the host material easily. In particular, the host material preferably includes a dibenzocarbazole skeleton so that the HOMO level thereof can be shallower than that of carbazole by approximately 0.1 eV and thus holes can enter the host material easily, the hole-transport property can be improved, and the heat resistance can be increased. Accordingly, a substance that has both a 9,10-diphenylanthracene skeleton and a carbazole skeleton (or a benzocarbazole or dibenzocarbazole skeleton) is further preferable as the host material. Note that in terms of the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN) 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)biphenyl-4'-yl}anthracene (abbreviation: FLPPA). In particular, CzPA, cgDBCzPA, 2mBnfPPA, and PCzPA are preferable choices because of their excellent characteristics.

Note that the light-emitting element of one embodiment of the present invention is particularly preferably applied to a light-emitting element that emits blue fluorescence.

Note that the host material may be a mixture of a plurality of kinds of substances, and in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be 1:9 to 9:1.

An exciplex may be formed by these mixed materials. It is preferable that the combination of these materials be selected so as to form an exciplex that emits light with a wavelength overlapping with that of the lowest energy absorption band of the light-emitting material, in which case energy is transferred smoothly and light emission can be obtained efficiently. The use of the structure is preferable in terms of reduction in driving voltage as well.

The electron-transport layer 114 is a layer containing a substance with an electron-transport property. As the substance having an electron-transport property, it is possible to use any of the above-listed substances having electron-transport properties that can be used as the host material.

A layer containing an alkali metal, an alkaline earth metal, or a compound thereof such as lithium fluoride (LiF), 8-hydroxyquinolinolato-lithium (abbreviation: Liq), cesium fluoride (CsF), or calcium fluoride ($CaF_2$) may be provided as the electron-injection layer 115 between the electron-transport layer 114 and the second electrode 102. For example, a layer that is formed using a substance having an electron-transport property and that contains an alkali metal, an alkaline earth metal, or a compound thereof, or an electride can be used as the electron-injection layer 115. Examples of the electride include a substance in which electrons are added at high concentration to a mixed oxide of calcium and aluminum.

Instead of the electron-injection layer 115, the charge-generation layer 116 may be provided (FIG. 1(B)). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing a hole-transport material. When a potential is applied to the p-type layer 117, electrons are injected into the electron-transport layer 114 and holes are injected into the second electrode 102 serving as a cathode; thus, the light-emitting element operates.

Note that the charge-generation layer 116 preferably includes one or both of an electron-relay layer 118 and an electron-injection buffer layer 119 in addition to the p-type layer 117.

The electron-relay layer 118 contains at least the substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is preferably between the LUMO level of the acceptor substance in the p-type layer 117 and the LUMO level of a substance contained in a layer of the electron-transport layer 114 that is in contact with the charge-generation layer 116. As a specific value of the energy level, the LUMO level of the substance having an electron-transport property in the electron-relay layer 118 is preferably higher than or equal to −5.0 eV, further preferably higher than or equal to −5.0 eV and lower than or equal to −3.0 eV. Note that as the substance having an electron-transport property in the electron-relay layer 118, a phthalocyanine-based material or a metal complex having a metal-oxygen bond and an aromatic ligand is preferably used.

For the electron-injection buffer layer 119, a substance having a high electron-injection property, such as an alkali metal, an alkaline earth metal, a rare earth metal, or a compound thereof (an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)), can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound of the above metal (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)). Note that as the substance having an electron-transport property, a material similar to the above-described material used for the electron-transport layer 114 can be used.

For the second electrode 102, any of metals, alloys, electrically conductive compounds, and mixtures thereof which have a low work function (specifically, a work function of 3.8 eV or less) can be used, for example. Specific examples of such a cathode material are elements belonging to Group 1 or 2 of the periodic table, such as alkali metals (e.g., lithium (Li) and cesium (Cs)), magnesium (Mg), calcium (Ca), and strontium (Sr), alloys thereof (e.g., MgAg and AlLi), rare earth metals such as europium (Eu) and ytterbium (Yb), and alloys thereof. However, when the electron-injection layer is provided between the second electrode 102 and the electron-transport layer, for the second electrode 102, any of a variety of conductive materials such as Al, Ag, ITO, or indium oxide-tin oxide containing silicon or silicon oxide can be used regardless of the work function. Films of these conductive materials can be formed by a dry method such as a vacuum evaporation method or a sputtering method, an inkjet method, a spin coating method, or the like. In addition, the films may be formed by a wet method using a sol-gel method, or by a wet method using paste of a metal material.

Any of a variety of methods can be used to form the EL layer 103 regardless of whether it is a dry process or a wet process. For example, a vacuum evaporation method, a gravure printing method, an offset printing method, a screen printing method, an inkjet method, or a spin coating method may be used.

The electrodes or the layers described above may be formed by different methods.

The structure of the layers provided between the first electrode 101 and the second electrode 102 is not limited to the above-described structure. Preferably, a light-emitting region where holes and electrons recombine is positioned away from the first electrode 101 and the second electrode 102 so as to prevent quenching due to the proximity of the light-emitting region and a metal used for electrodes and carrier-injection layers.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer closer to the recombination region in the light-emitting layer 113, are formed using a material having a wider band gap than the light-emitting material of the light-emitting layer or the light-emitting material included in the light-emitting layer.

Next, an embodiment of a light-emitting element with a structure in which a plurality of light-emitting units are stacked (also referred to as a stacked element or a tandem element) is described with reference to FIG. 1(C). This light-emitting element is a light-emitting element in which a plurality of light-emitting units are provided between an anode and a cathode. One light-emitting unit has substantially the same structure as the EL layer 103 illustrated in FIG. 1(A). In other words, the light-emitting element illustrated in FIG. 1(C) is a light-emitting element including a plurality of light-emitting units; each of the light-emitting elements illustrated in FIG. 1(A) and FIG. 1B is a light-emitting element including a single light-emitting unit.

Figure 1C:
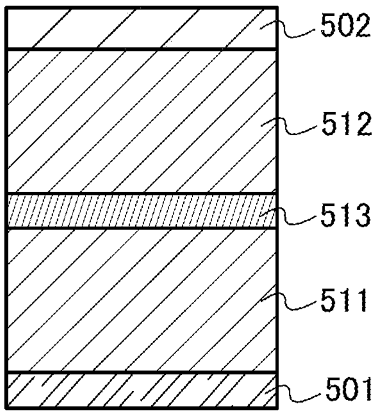

In FIG. 1C, a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond, respectively, to the first electrode 101 and the second electrode 102 illustrated in FIG. 1(A), and the materials given in the description for FIG. 1(A) can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the first electrode 501 and the second electrode 502. That is, in FIG. 1(C), the charge-generation layer 513 injects electrons into the first light-emitting unit 511 and holes into the second light-emitting unit 512 when a voltage is applied so that the potential of the anode becomes higher than the potential of the cathode.

The charge-generation layer 513 preferably has a structure similar to that of the charge-generation layer 116 described with reference to FIG. 1(B). Since the composite material of an organic compound and a metal oxide is superior in carrier-injection property and carrier-transport property, low-voltage driving or low-current driving can be achieved. Note that when a surface of a light-emitting unit on the anode side is in contact with the charge-generation layer 513, the charge-generation layer 513 can also serve as a hole-injection layer in the light-emitting unit and a hole-injection layer is not necessarily formed in the light-emitting unit.

In the case where the electron-injection buffer layer 119 is provided in the charge-generation layer 513, the electron-injection buffer layer 119 serves as the electron-injection layer in the light-emitting unit on the anode side and thus the light-emitting unit on the anode side does not necessarily need an electron-injection layer.

The light-emitting element having two light-emitting units is described with reference to FIG. 1(C); however, the present invention can be similarly applied to a light-emitting element in which three or more light-emitting units are stacked. With a plurality of light-emitting units partitioned by the charge-generation layer 513 between a pair of electrodes as in the light-emitting element according to this embodiment, it is possible to provide a long-life element which can emit high luminance light with the current density kept low. Moreover, a low-power-consumption light-emitting device driven at a low voltage can be achieved.

Furthermore, when emission colors of light-emitting units are made different, light emission of a desired color can be obtained from the light-emitting element as a whole. For example, in a light-emitting element having two light-emitting units, the emission colors of the first light-emitting unit may be red and green and the emission color of the second light-emitting unit may be blue, so that the light-emitting element can emit white light as the whole element.

The above-described electrodes and layers such as the EL layer 103, the first light-emitting unit 511, the second light-emitting unit 512, and the charge-generation layer can be deposited by a method such as an evaporation method (including a vacuum evaporation method), a droplet discharge method (also referred to as an ink-jet method), a coating method, or a gravure printing method. A low molecular material, a middle molecular material (including an oligomer and a dendrimer), or a high molecular material may be included in the layers and electrodes.

Embodiment 3

In this embodiment, a light-emitting device using the light-emitting element described in Embodiment 2 will be described.

Figures 2A, 2B:
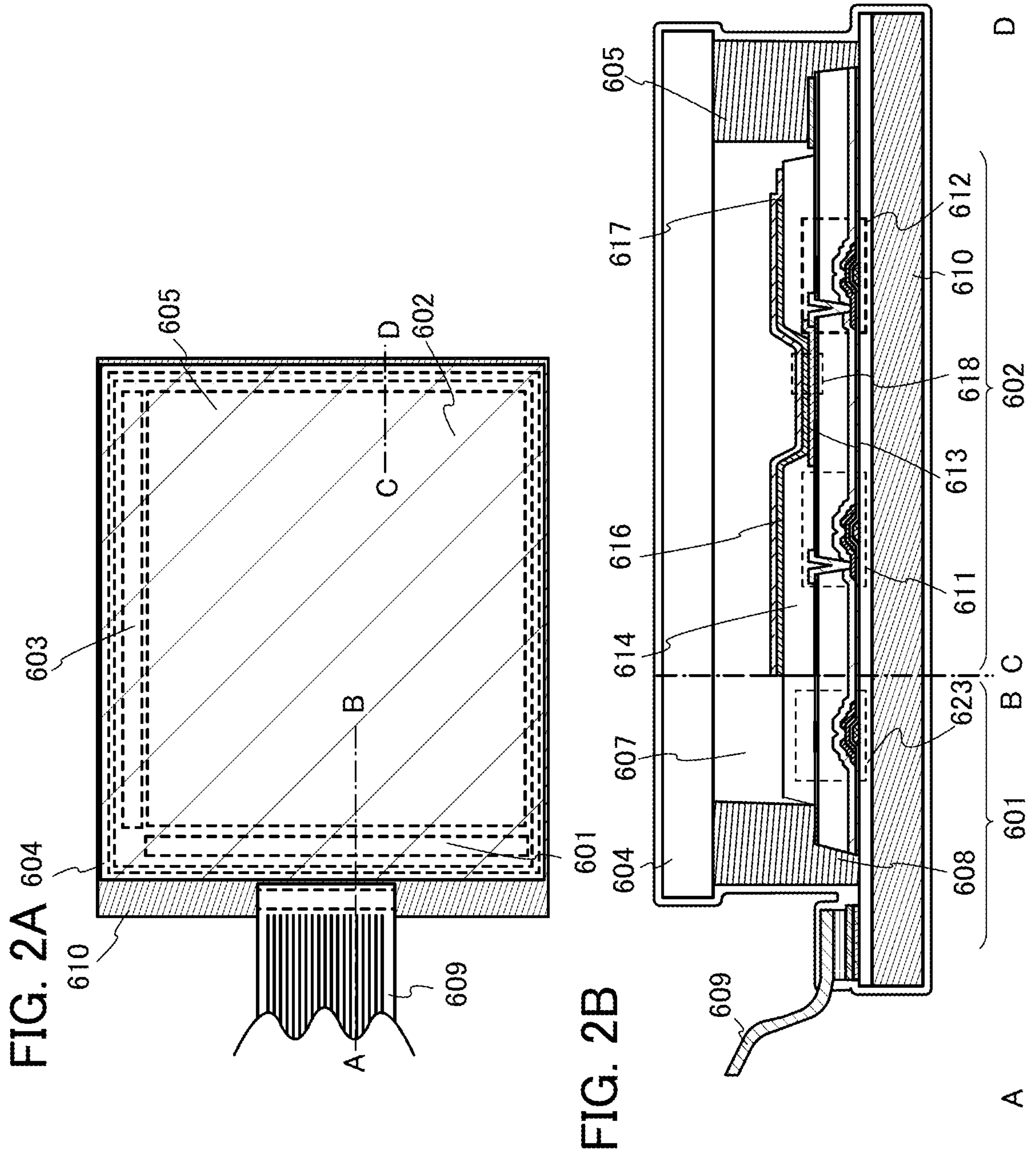
FIGS. 2(A) and 2(B) are conceptual diagrams of an active matrix light-emitting device.

In this embodiment, a light-emitting device fabricated using the light-emitting element described in Embodiment 2 will be described with reference to FIG. 2. Note that FIG. 2(A) is a top view illustrating the light-emitting device, and FIG. 2(B) is a cross-sectional view taken along A-B and C-D in FIG. 2(A). This light-emitting device includes a driver circuit portion (source line driver circuit) 601, a pixel portion 602, and a driver circuit portion (gate line driver circuit) 603, which are for controlling light emission of a light-emitting element and are illustrated with dotted lines. Furthermore, 604 denotes a sealing substrate, 605 denotes a sealant, and the inside surrounded by the sealant 605 is a space 607.

Note that a lead wiring 608 is a wiring for transmitting signals to be input to the source line driver circuit 601 and the gate line driver circuit 603 and receives a video signal, a clock signal, a start signal, a reset signal, and the like from an FPC (flexible printed circuit) 609 serving as an external input terminal. Although only the FPC is illustrated here, a printed wiring board (PWB) may be attached to this FPC. The light-emitting device in this specification includes not only the light-emitting device itself but also the device provided with the FPC or the PWB.

Next, a cross-sectional structure will be described with reference to FIG. 2(B). The driver circuit portion and the pixel portion are formed over an element substrate 610. Here, the source line driver circuit 601, which is the driver circuit portion, and one pixel of the pixel portion 602 are illustrated.

The element substrate 610 may be fabricated using a substrate containing glass, quartz, an organic resin, a metal, an alloy, a semiconductor, or the like, or a plastic substrate formed of FRP (Fiber Reinforced Plastic), PVF (polyvinyl fluoride), polyester, an acrylic resin, or the like.

The structure of transistors used in pixels and driver circuits is not particularly limited. For example, an inverted staggered transistor or a staggered transistor may be used. Furthermore, top-gate transistors or bottom-gate transistors may be used. A semiconductor material used for the transistors is not particularly limited, and for example, silicon, germanium, silicon carbide, gallium nitride, or the like can be used. Alternatively, an oxide semiconductor containing at least one of indium, gallium, and zinc, such as In—Ga—Zn-based metal oxide, may be used.

There is no particular limitation on the crystallinity of a semiconductor material used for the transistors, and any of an amorphous semiconductor or a semiconductor having crystallinity (a microcrystalline semiconductor, a polycrystalline semiconductor, a single-crystal semiconductor, and a semiconductor partly including crystal regions) may be used. A semiconductor having crystallinity is preferably used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. The use of an oxide semiconductor material having a wider band gap than silicon can reduce the off-state current of the transistors.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such a material as the semiconductor layer makes it possible to achieve a highly reliable transistor with a reduced change in electrical characteristics.

Charge accumulated in a capacitor through a transistor including the above-described semiconductor layer can be retained for a long time because of the low off-state current of the transistor. The use of such a transistor in pixels allows a driver circuit to stop while the gray level of an image displayed on each display region is maintained. As a result, an electronic device with significantly reduced power consumption can be achieved.

For stable characteristics of the transistor or the like, a base film is preferably provided. The base film can be formed to be a single-layer or a stacked-layer using an inorganic insulating film such as a silicon oxide film, a silicon nitride film, a silicon oxynitride film, or a silicon nitride oxide film. The base film can be formed by a sputtering method, a CVD (Chemical Vapor Deposition) method (e.g., a plasma CVD method, a thermal CVD method, or an MOCVD (Metal Organic CVD) method), an ALD (Atomic Layer Deposition) method, a coating method, a printing method, or the like. Note that the base film is not necessarily provided when not needed.

Note that an FET 623 is illustrated as a transistor formed in the driver circuit portion 601. The driver circuit can be formed using various circuits such as a CMOS circuit, a PMOS circuit, and an NMOS circuit. Although a driver-integrated type in which the driver circuit is formed over the substrate is described in this embodiment, the driver circuit is not necessarily formed over the substrate and can be formed outside.

The pixel portion 602 is formed with a plurality of pixels including a switching FET 611, a current control FET 612, and a first electrode 613 electrically connected to a drain of the current control FET 612; however, without being limited thereto, a pixel portion in which three or more FETs and a capacitor are combined may be employed.

Note that an insulator 614 is formed to cover an end portion of the first electrode 613. The insulator 614 can be formed using a positive photosensitive acrylic resin film here.

In order to improve the coverage with an EL layer or the like to be formed later, the insulator 614 is formed so as to have a curved surface with curvature at its upper end portion or lower end portion. For example, in the case where a positive photosensitive acrylic resin is used as a material for the insulator 614, only the upper end portion of the insulator 614 preferably has a curved surface with a curvature radius (0.2 μm to 3 μm). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material with a high work function is desirably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stacked layer of a titanium nitride film and a film containing aluminum as its main component, a three-layer structure of a titanium nitride film, a film containing aluminum as its main component, and a titanium nitride film, or the like can be used. Note that the stacked-layer structure achieves low wiring resistance, a favorable ohmic contact, and a function as an anode.

The EL layer 616 is formed by any of a variety of methods such as an evaporation method using an evaporation mask, an inkjet method, and a spin coating method. The EL layer 616 has the structure described in Embodiment 1. Alternatively, a material included in the EL layer 616 may be a low molecular compound or a high molecular compound (including an oligomer or a dendrimer).

As a material used for the second electrode 617, which is formed over the EL layer 616 and functions as a cathode, a material with a low work function (e.g., Al, Mg, Li, Ca, or an alloy or a compound thereof (e.g., MgAg, MgIn, or AlLi)) is preferably used. Note that in the case where light generated in the EL layer 616 passes through the second electrode 617, it is preferable to use, for the second electrode 617, a stacked layer of a thin metal film and a transparent conductive film (e.g., ITO, indium oxide containing zinc oxide at 2 wt % to 20 wt %, indium tin oxide containing silicon, or zinc oxide (ZnO)).

Note that a light-emitting element is formed with the first electrode 613, the EL layer 616, and the second electrode 617. The light-emitting element is the light-emitting element described in Embodiment 2. A plurality of light-emitting elements are formed in the pixel portion, and the light-emitting device of this embodiment may include both the light-emitting element described in Embodiment 2 and a light-emitting element having a different structure.

The sealing substrate 604 and the element substrate 610 are attached to each other using the sealant 605, so that a structure is employed in which a light-emitting element 618 is provided in the space 607 surrounded by the element substrate 610, the sealing substrate 604, and the sealant 605. The space 607 is filled with a filler; it is filled with an inert gas (e.g., nitrogen or argon) in some cases, and filled with the sealant in some cases. The structure of the sealing substrate in which a recessed portion is formed and a desiccant is provided is preferable because deterioration due to the influence of moisture can be inhibited.

Note that an epoxy-based resin or glass frit is preferably used for the sealant 605. Furthermore, these materials are preferably materials that transmit moisture or oxygen as little as possible. As the material used for the sealing substrate 604, in addition to a glass substrate and a quartz substrate, a plastic substrate formed of FRP (Fiber Reinforced Plastics), PVF (polyvinyl fluoride), polyester, an acrylic resin, or the like can be used.

Although not illustrated in FIG. 2, a protective film may be provided over the second electrode. The protective film may be formed using an organic resin film or an inorganic insulating film. The protective film may be formed so as to cover an exposed portion of the sealant 605. The protective film may be provided so as to cover surfaces and side surfaces of the pair of substrates and exposed side surfaces of a sealing layer, an insulating layer, and the like.

For the protective film, a material that is not easily transmit an impurity such as water can be used. Thus, diffusion of an impurity such as water from the outside into the inside can be effectively inhibited.

As a material included in the protective film, an oxide, a nitride, a fluoride, a sulfide, a ternary compound, a metal, a polymer, or the like can be used; for example, it is possible to use a material containing aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide, or the like; a material containing aluminum nitride, hafnium nitride, silicon nitride, tantalum nitride, titanium nitride, niobium nitride, molybdenum nitride, zirconium nitride, gallium nitride, or the like; or a material containing a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method that enables favorable step coverage. One such method is an atomic layer deposition (ALD) method. A material that can be formed by an ALD method is preferably used for the protective film. With the use of an ALD method, a dense protective film with reduced defects such as cracks and pinholes or with a uniform thickness can be formed. Furthermore, damage caused to a process member in forming the protective film can be reduced.

For example, by an ALD method, a uniform protective film with few defects can be formed even on a surface with a complex uneven shape or upper, side, and lower surfaces of a touch panel.

As described above, the light-emitting device fabricated using the light-emitting element described in Embodiment 2 can be obtained.

For the light-emitting device in this embodiment, the light-emitting element described in Embodiment 2 is used and thus a light-emitting device having favorable characteristics can be obtained. Specifically, since the light-emitting element described in Embodiment 2 is a light-emitting element having a long lifetime, the light-emitting device can have high reliability. Since the light-emitting device using the light-emitting element described in Embodiment 2 has high emission efficiency, the light-emitting device can have low power consumption.

Figure 3A:
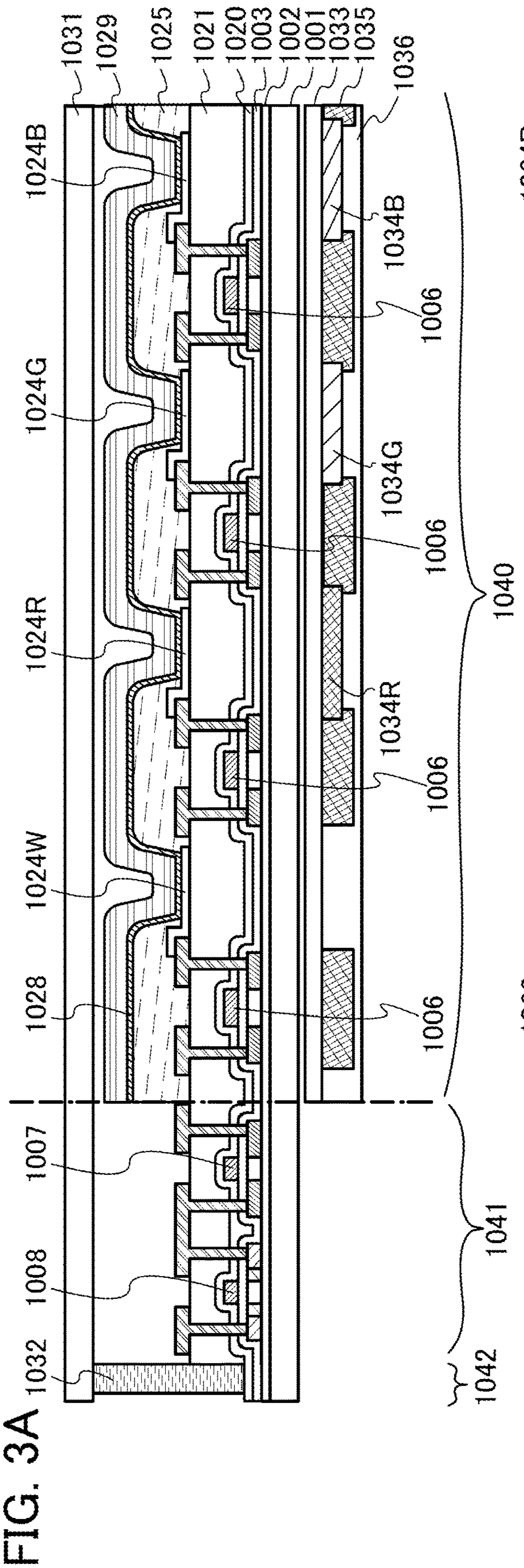
FIGS. 3(A) and 3(B) are conceptual diagrams of active matrix light-emitting devices.

FIG. 3 illustrates examples of a light-emitting device in which full color display is achieved by formation of a light-emitting element exhibiting white light emission and provision of coloring layers (color filters) and the like. FIG. 3(A) illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of the light-emitting elements, a partition 1025, an EL layer 1028, a second electrode 1029 of the light-emitting elements, a sealing substrate 1031, a sealant 1032, and the like.

In FIG. 3(A), coloring layers (a red coloring layer 1034R, a green coloring layer 1034G, and a blue coloring layer 1034B) are provided on a transparent base material 1033. A black layer (black matrix) 1035 may be additionally provided. The transparent base material 1033 provided with the coloring layers and the black matrix is positioned and fixed to the substrate 1001. Note that the coloring layers and the black matrix 1035 are covered with an overcoat layer 1036. In FIG. 3(A), a light-emitting layer from which light is emitted to the outside without passing through the coloring layer and light-emitting layers from which light is emitted to the outside, passing through the coloring layers of the respective colors are shown. Since light that does not pass through the coloring layer is white and light that passes through the coloring layer is red, green, or blue, an image can be expressed with pixels of the four colors.

Figure 3B:
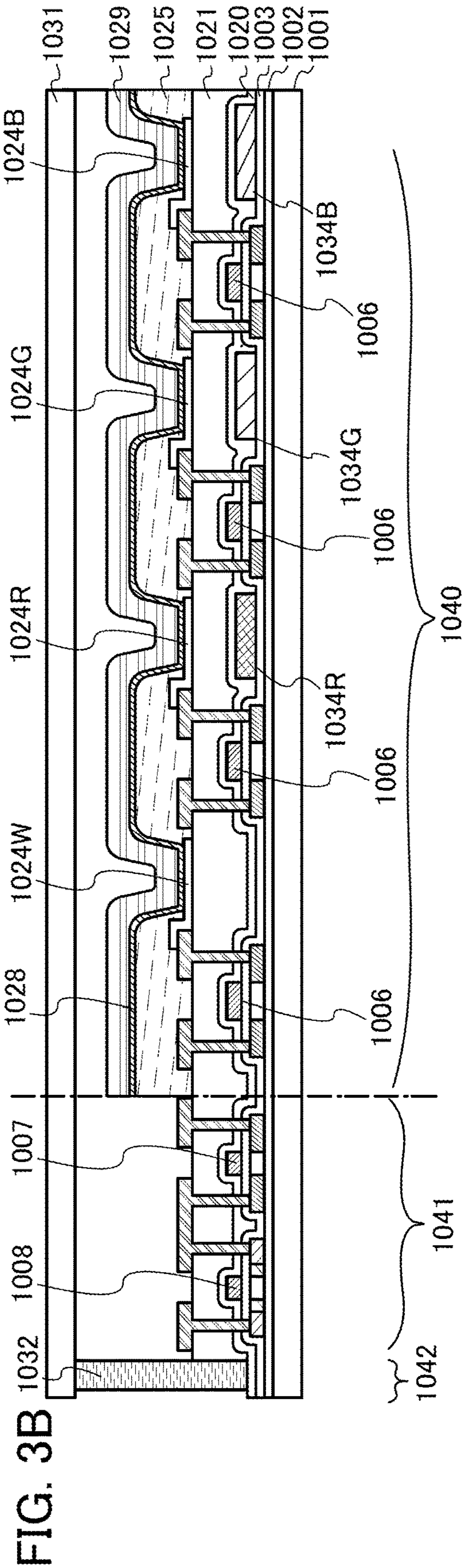

FIG. 3(B) illustrates an example in which the coloring layers (the red coloring layer 1034R, the green coloring layer 1034G, and the blue coloring layer 1034B) are formed between the gate insulating film 1003 and the first interlayer insulating film 1020. The coloring layers may be provided between the substrate 1001 and the sealing substrate 1031 in this manner.

Figure 4:
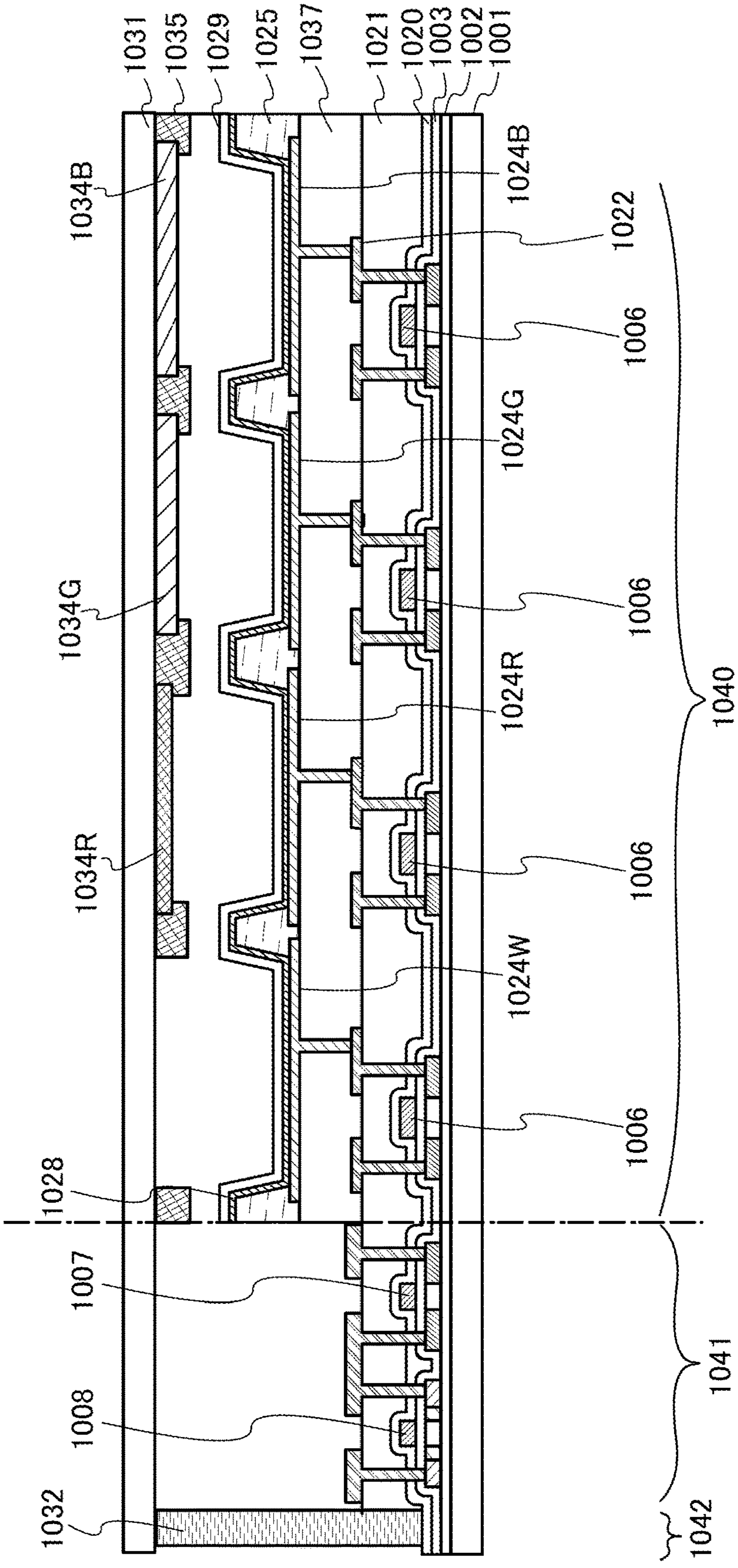
FIG. 4 A conceptual diagram of an active matrix light-emitting device.

The above-described light-emitting device is a light-emitting device having a structure in which light is extracted to the substrate 1001 side where the FETs are formed (a bottom-emission type), but a light-emitting device having a structure in which light emission is extracted to the sealing substrate 1031 side (a top-emission type) may be formed. FIG. 4 illustrates a cross-sectional view of a top-emission light-emitting device. In this case, a substrate that does not transmit light can be used as the substrate 1001. The top-emission light-emitting device is formed in a manner similar to that of the bottom-emission light-emitting device until a connection electrode which connects the FET and the anode of the light-emitting element is formed. Then, a third interlayer insulating film 1037 is formed to cover an electrode 1022. This insulating film may have a planarization function. The third interlayer insulating film 1037 can be formed using a material similar to that for the second interlayer insulating film or using any other known materials.

The first electrodes 1024W, 1024R, 1024G, and 1024B of the light-emitting elements are anodes here, but may be cathodes. Furthermore, in the case of the top-emission light-emitting device illustrated in FIG. 4, the first electrodes are preferably reflective electrodes. The structure of the EL layer 1028 is such a structure as the structure of the EL layer 103 described in Embodiment 1 and an element structure with which white light emission can be obtained.

In the case of such a top-emission structure as in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer 1036. Note that a light-transmitting substrate is used as the sealing substrate 1031. Although an example in which full color display is performed using four colors of red, green, blue, and white is shown here, there is no particular limitation and full color display may be performed using four colors of red, yellow, green, and blue or three colors of red, green, and blue.

In the top-emission-type light-emitting device, a microcavity structure can be favorably employed. Alight-emitting element with a microcavity structure can be obtained with the use of a reflective electrode as the first electrode and a semi-transmissive and semi-reflective electrode as the second electrode. The light-emitting element with a microcavity structure includes at least an EL layer between the reflective electrode and the semi-transmissive and semi-reflective electrode, which includes at least a light-emitting layer serving as a light-emitting region.

Note that the reflective electrode is a film having a visible light reflectivity of 40% to 100%, preferably 70% to 100%, and a resistivity of $1\times10^{-2}$ cm or lower. In addition, the semi-transmissive and semi-reflective electrode is a film having a visible light reflectivity of 20% to 80%, preferably 40% to 70%, and a resistivity of $1\times10^{-2}$ 92 cm or lower.

Light emitted from the light-emitting layer included in the EL layer is reflected and resonated by the reflective electrode and the semi-transmissive and semi-reflective electrode.

In the light-emitting element, by changing thicknesses of the transparent conductive film, the above-described composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light); therefore, the optical path length between the reflective electrode and the light-emitting layer is preferably adjusted to $(2n-1)\lambda/4$ (n is a natural number of 1 or larger and $\lambda$ is a wavelength of light emission to be amplified). By adjusting the optical path length, the phases of the first reflected light and the first incident light can be aligned with each other and the light emitted from the light-emitting layer can be further amplified.

Note that in the above structure, the EL layer may have a structure including a plurality of light-emitting layers or may have a structure including a single light-emitting layer. In combination with the tandem light-emitting element described above, for example, it can be used in a structure where a light-emitting element is provided with a plurality of EL layers, a charge-generation layer is provided between the EL layers, and each EL layer includes a plurality of light-emitting layers or a single light-emitting layer.

With the microcavity structure, emission intensity of a specific wavelength in the front direction can be increased, whereby power consumption can be reduced. Note that in the case of a light-emitting device which displays images with subpixels of four colors, red, yellow, green, and blue, the light-emitting device can have favorable characteristics because a microcavity structure suitable for wavelengths of the corresponding colors can be employed in each subpixel, in addition to the effect of an improvement in luminance owing to yellow light emission.

For the light-emitting device in this embodiment, the light-emitting element described in Embodiment 2 is used and thus a light-emitting device having favorable characteristics can be obtained. Specifically, since the light-emitting element described in Embodiment 2 is a light-emitting element having a long lifetime, the light-emitting device can have high reliability. Since the light-emitting device using the light-emitting element described in Embodiment 2 has high emission efficiency, the light-emitting device can have low power consumption.

Figure 5A:
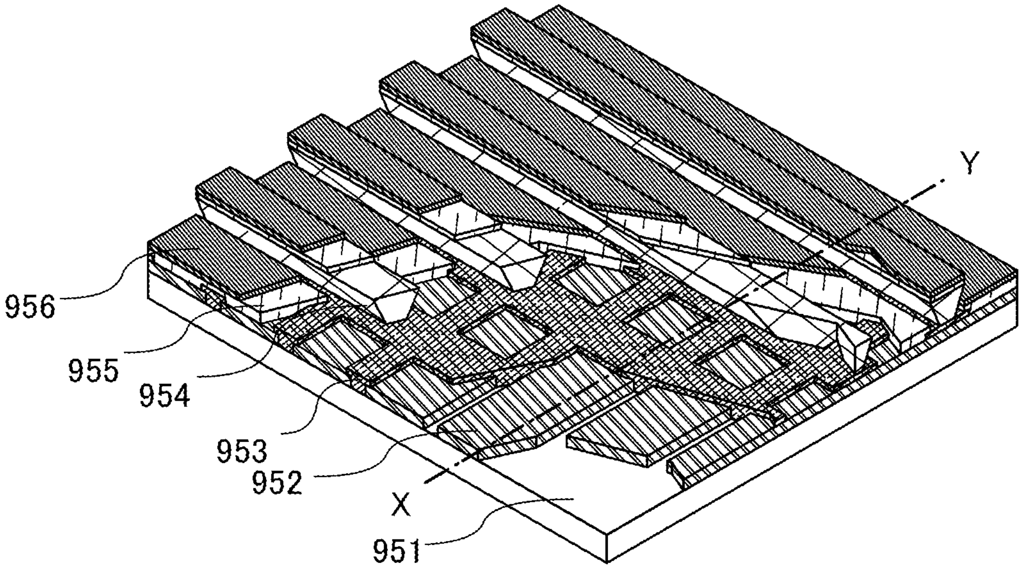
FIGS. 5(A) and 5(B) are conceptual diagrams of a passive matrix light-emitting device.
Figure 5B:
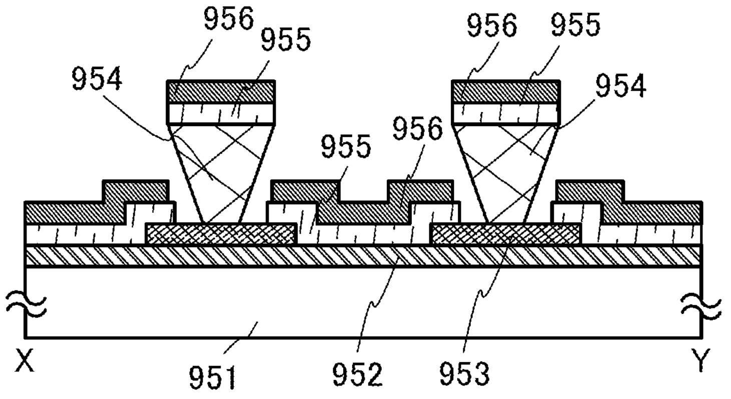

The active matrix light-emitting device is described above, whereas a passive matrix light-emitting device is described below. FIG. 5 illustrates a passive matrix light-emitting device fabricated using the present invention. Note that FIG. 5(A) is a perspective view illustrating the light-emitting device, and FIG. 5(B) is a cross-sectional view taken along X-Y in FIG. 5(A). In FIG. 5, over a substrate 951, an EL layer 955 is provided between an electrode 952 and an electrode 956. An end portion of the electrode 952 is covered with an insulating layer 953. A partition layer 954 is provided over the insulating layer 953. Sidewalls of the partition layer 954 are aslope such that the distance between one sidewall and the other sidewall is gradually narrowed toward the surface of the substrate. That is, a cross section in the short side direction of the partition layer 954 is a trapezoidal shape, and the lower side (the side facing the same direction as the plane direction of the insulating layer 953 and touching the insulating layer 953) is shorter than the upper side (the side facing the same direction as the plane direction of the insulating layer 953, and not touching the insulating layer 953). By providing the partition layer 954 in this manner, defects of the light-emitting element due to static charge or the like can be prevented. The passive-matrix light-emitting device also uses the light-emitting element described in Embodiment 2; thus, the light-emitting device can have favorable reliability or low power consumption.

Since many minute light-emitting elements arranged in a matrix can each be controlled in the light-emitting device described above, the light-emitting device can be suitably used as a display device for displaying images.

This embodiment can be freely combined with any of the other embodiments.

Embodiment 4

Figure 6A:
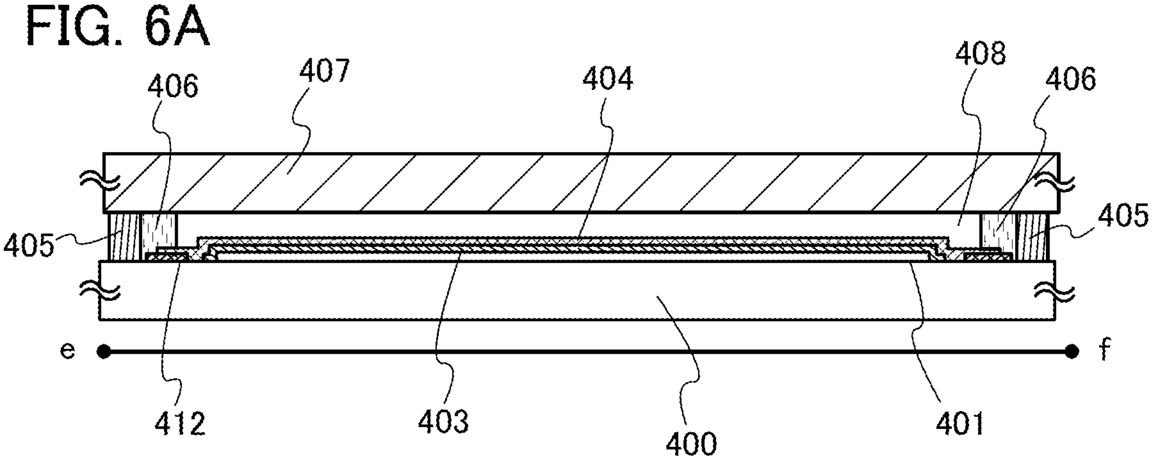
FIGS. 6(A) and 6(B) are diagrams illustrating a lighting device.
Figure 6B:
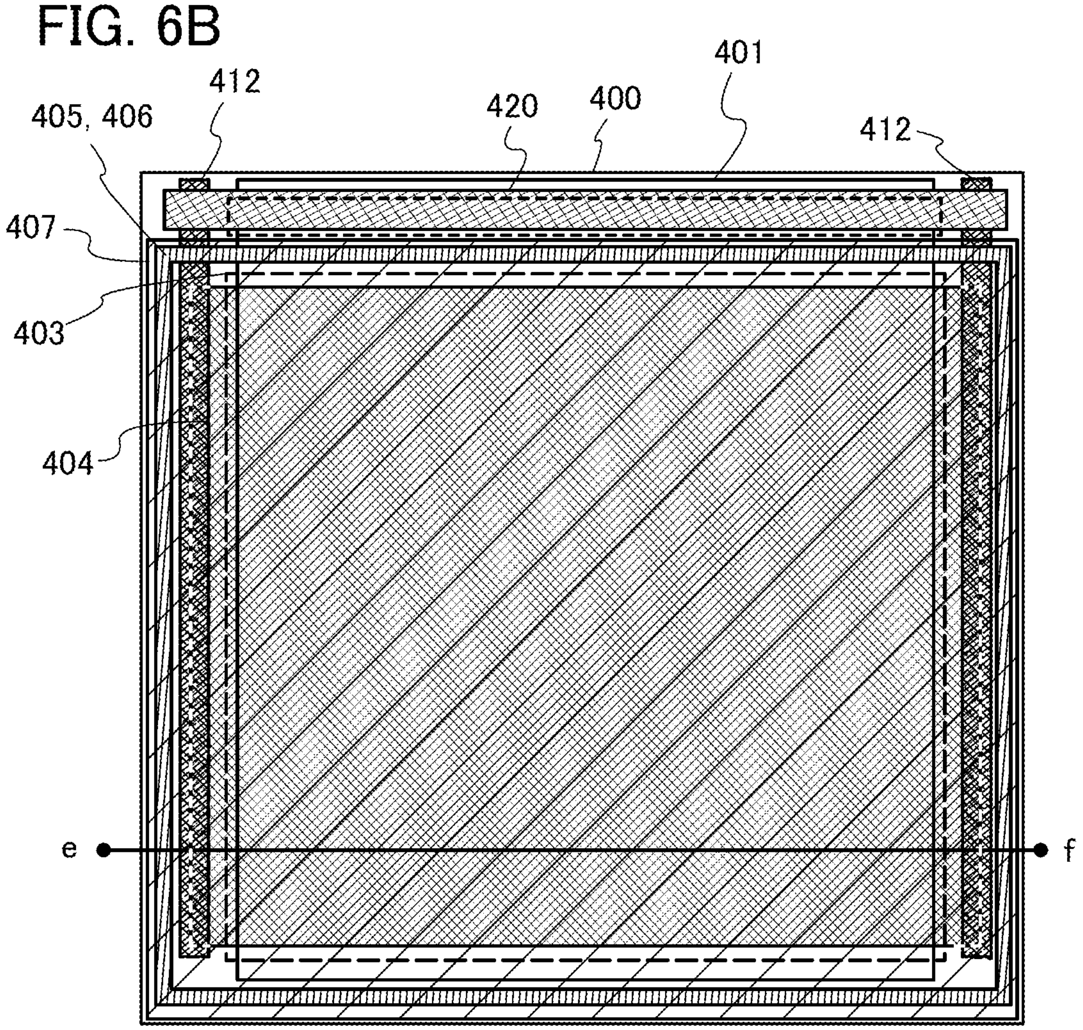

In this embodiment, an example in which the light-emitting element described in Embodiment 2 is used for a lighting device will be described with reference to FIG. 6. FIG. 6(B) is a top view of the lighting device, and FIG. 6(A) is a cross-sectional view taken along e-f in FIG. 6(B).

In the lighting device in this embodiment, a first electrode 401 is formed over a substrate 400 which is a support and has a light-transmitting property. The first electrode 401 corresponds to the first electrode 101 in Embodiment 1. In the case where light emission is extracted from the first electrode 401 side, the first electrode 401 is formed with a material having a light-transmitting property.

A pad 412 for supplying a voltage to a second electrode 404 is formed over the substrate 400.

An EL layer 403 is formed over the first electrode 401. The EL layer 403 has a structure corresponding to that of the EL layer 103 in Embodiment 1, or the structure in which the light-emitting units 511 and 512 are combined with the charge-generation layer 513. Note that for these structures, the corresponding description can be referred to.

The second electrode 404 is formed to cover the EL layer 403. The second electrode 404 corresponds to the second electrode 102 in Embodiment 1. In the case where light-emission is extracted from the first electrode 401 side, the second electrode 404 is formed with a material having high reflectivity. The second electrode 404 is supplied with a voltage when connected to the pad 412.

As described above, the lighting device described in this embodiment includes a light-emitting element including the first electrode 401, the EL layer 403, and the second electrode 404. Since the light-emitting element is a light-emitting element with high emission efficiency, the lighting device in this embodiment can be a lighting device with low power consumption.

The substrate 400 over which the light-emitting element having the above structure is formed is fixed to a sealing substrate 407 with sealants 405 and 406 and sealing is performed, whereby the lighting device is completed. It is possible to use only either the sealant 405 or 406. In addition, the inner sealant 406 (not illustrated in FIG. 6(B)) can be mixed with a desiccant, which enables moisture adsorption, resulting in improved reliability.

When parts of the pad 412 and the first electrode 401 are provided to extend to the outside of the sealants 405 and 406, those can serve as external input terminals. An IC chip 420 mounted with a converter or the like may be provided over the external input terminals.

The lighting device described in this embodiment uses the light-emitting element described in Embodiment 2 as an EL element; thus, the light-emitting device can have favorable reliability. Furthermore, the light-emitting device can have low power consumption.

Embodiment 5

In this embodiment, examples of electronic devices each partly including the light-emitting element described in Embodiment 2 are described. The light-emitting element described in Embodiment 2 is a light-emitting element having a favorable lifetime and favorable reliability. As a result, the electronic devices described in this embodiment can be electronic devices each including a light-emitting portion with favorable reliability.

Examples of electronic devices to which the light-emitting element is applied include a television devices (also referred to as TV or television receivers), monitors for computers and the like, cameras such as digital cameras and digital video cameras, digital photo frames, mobile phones (also referred to as portable telephones or portable telephone devices), portable game machines, portable information terminals, audio playback devices, and large game machines such as pin-ball machines. Specific examples of these electronic devices are shown below.

Figure 7A:
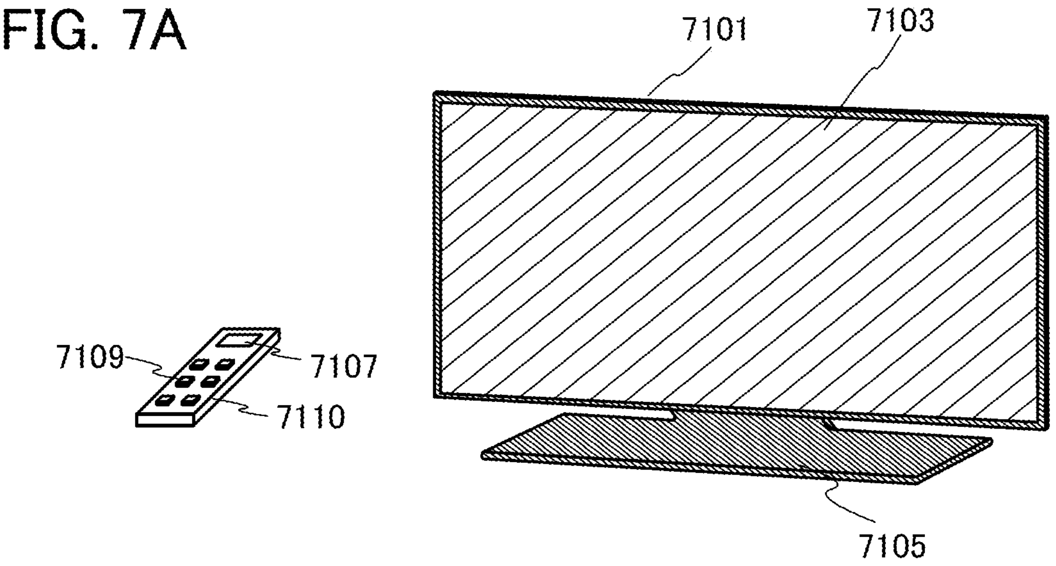
Figure 7A:
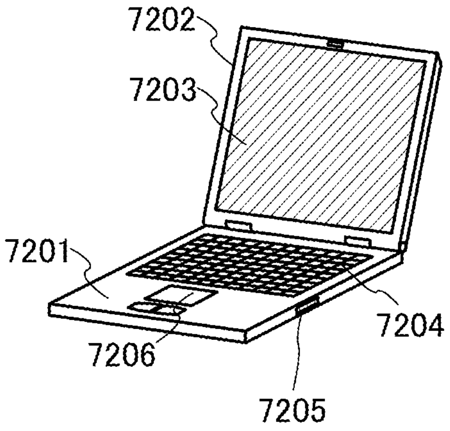
Figure 7A:
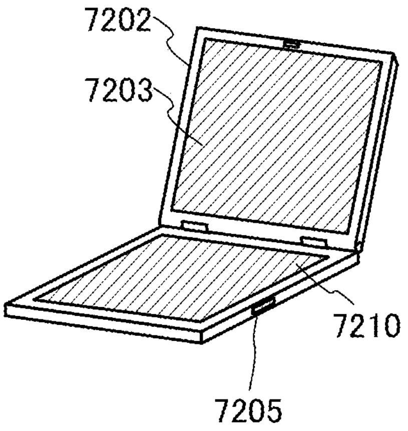

FIG. 7(A) illustrates an example of a television device. In the television device, a display portion 7103 is incorporated in a housing 7101. Here, a structure in which the housing 7101 is supported by a stand 7105 is shown. Images can be displayed on the display portion 7103, and the light-emitting elements described in Embodiment 2 are arranged in a matrix in the display portion 7103.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, a structure may be employed in which the remote controller 7110 is provided with a display portion 7107 for displaying data output from the remote controller 7110.

Note that the television device has a structure of including a receiver, a modem, and the like. With the use of the receiver, a general television broadcast can be received, and moreover, when the television device is connected to a communication network with or without a wire via the modem, one-way (from a sender to a receiver) or two-way (between a sender and a receiver or between receivers) data communication can be performed.

FIG. 7(B1) is a computer which includes a main body 7201, a housing 7202, a display portion 7203, a keyboard 7204, an external connection port 7205, a pointing device 7206, and the like. Note that this computer is fabricated using the light-emitting elements described in Embodiment 2 arranged in a matrix in the display portion 7203. The computer in FIG. 7(B1) may be such a mode as illustrated in FIG. 7(B2). The computer in FIG. 7(B2) is provided with a second display portion 7210 instead of the keyboard 7204 and the pointing device 7206. The second display portion 7210 is of a touch-panel type, and input can be performed by operating display for input displayed on the second display portion 7210 with a finger or a dedicated pen. The second display portion 7210 can also display images other than the display for input. The display portion 7203 may also be a touch panel. Connecting the two screens with a hinge can prevent troubles such as a crack in or damage to the screens caused when the computer is stored or carried.

Figure 7C:
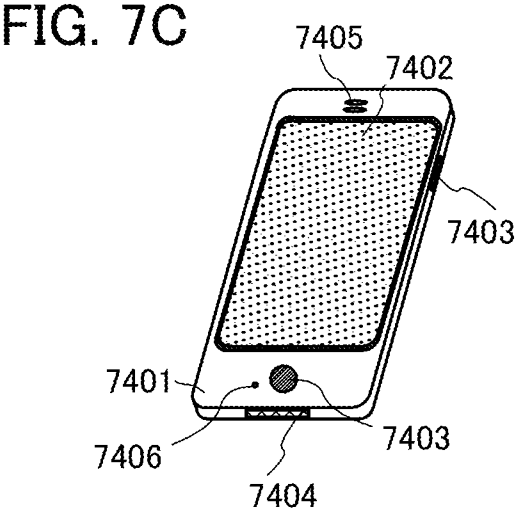

FIG. 7(C) illustrates an example of a portable terminal. A mobile phone includes operation buttons 7403, an external connection port 7404, a speaker 7405, a microphone 7406, and the like in addition to a display portion 7402 incorporated in a housing 7401. Note that a mobile phone 7400 includes the display portion 7402 which is fabricated by arranging the light-emitting elements described in Embodiment 2 in a matrix.

The portable terminal illustrated in FIG. 7(C) may have a structure in which information can be input by touching the display portion 7402 with a finger or the like. In this case, operations such as making a call and creating an e-mail can be performed by touching the display portion 7402 with a finger or the like.

The display portion 7402 has mainly three screen modes. The first one is a display mode mainly for displaying images, and the second one is an input mode mainly for inputting data such as text. The third one is a display+input mode in which two modes of the display mode and the input mode are combined.

For example, in the case of making a call or creating an e-mail, a text input mode mainly for inputting text is selected for the display portion 7402 so that an operation of inputting text displayed on the screen may be performed. In this case, it is preferable to display a keyboard or number buttons on almost the entire screen of the display portion 7402.

When a sensing device including a sensor for sensing inclination, such as a gyroscope sensor or an acceleration sensor, is provided inside the portable terminal, screen display of the display portion 7402 can be automatically changed by determining the orientation of the portable terminal (vertically or horizontally).

The screen modes are changed by touching the display portion 7402 or operating the operation buttons 7403 of the housing 7401. Alternatively, the screen modes can be changed depending on the kind of image displayed on the display portion 7402. For example, when a signal of an image displayed on the display portion is moving image data, the screen mode is changed to the display mode, and when the signal is text data, the screen mode is changed to the input mode.

Moreover, in the input mode, when input by the touch operation of the display portion 7402 is not performed for a certain period while a signal sensed by an optical sensor in the display portion 7402 is sensed, the screen mode may be controlled so as to be changed from the input mode to the display mode.

The display portion 7402 can also function as an image sensor. For example, an image of a palm print, a fingerprint, or the like is taken when the display portion 7402 is touched with the palm or the finger, whereby personal authentication can be performed. Furthermore, by using a backlight which emits near-infrared light or a sensing light source which emits near-infrared light in the display portion, an image of a finger vein, a palm vein, or the like can be taken.

Note that the structures described in this embodiment can be combined with the structures described in Embodiment 1 to Embodiment 4 as appropriate.

As described above, the application range of the light-emitting device including the light-emitting element described in Embodiment 2 is wide so that this light-emitting device can be applied to electronic devices in a variety of fields. With the use of the light-emitting element described in Embodiment 2, an electronic device with high reliability can be obtained.

Figure 8A:
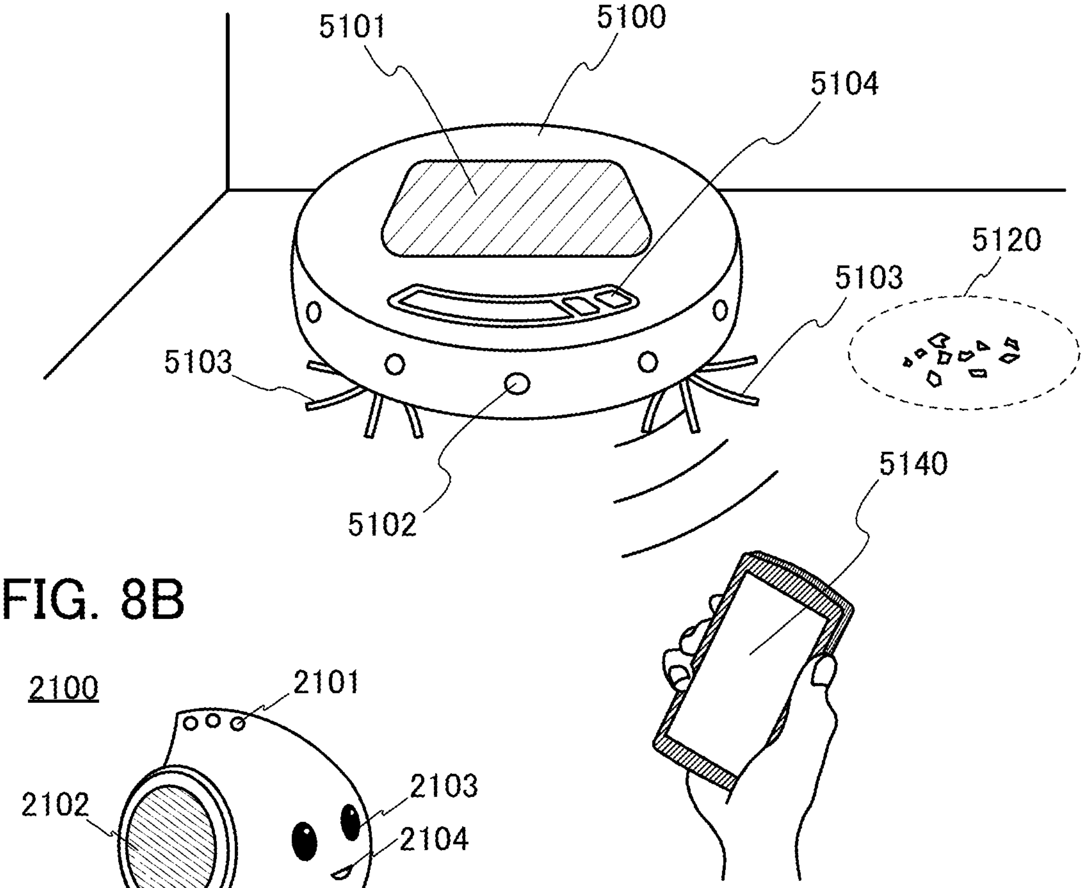
FIGS. 8(A) to 8(C) are diagrams illustrating electronic devices.

FIG. 8(A) is a schematic view illustrating an example of a cleaning robot.

A cleaning robot 5100 includes a display 5101 placed on its top surface, a plurality of cameras 5102 placed on its side surface, a brush 5103, and operation buttons 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. In addition, the cleaning robot 5100 has a wireless communication means.

The cleaning robot 5100 is self-propelled, detects dust 5120, and sucks up the dust through the inlet provided on the bottom surface.

The cleaning robot 5100 can judge whether there is an obstacle such as a wall, furniture, or a step by analyzing images taken by the cameras 5102. When an object that is likely to be caught in the brush 5103, such as a wire, is detected by image analysis, the rotation of the brush 5103 can be stopped.

The display 5101 can display the remaining capacity of a battery, the amount of vacuumed dust, and the like. The display 5101 may display a path on which the cleaning robot 5100 has run. The display 5101 may be a touch panel, and the operation buttons 5104 may be provided on the display 5101.

The cleaning robot 5100 can communicate with a portable electronic device 5140 such as a smartphone. The portable electronic device 5140 can display images taken by the cameras 5102. Accordingly, an owner of the cleaning robot 5100 can monitor the room even from the outside. The display on the display 5101 can be checked by the portable electronic device such as a smartphone.

The light-emitting device of one embodiment of the present invention can be used for the display 5101.

Figure 8B:
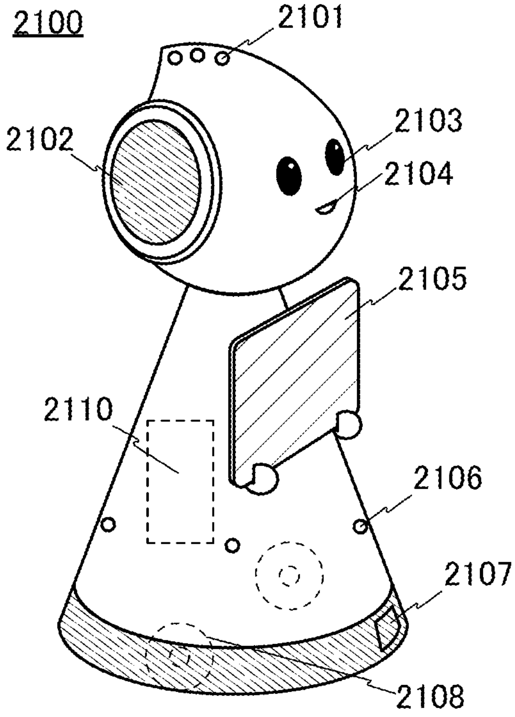

A robot 2100 illustrated in FIG. 8(B) includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect the presence of an obstacle in the direction where the robot 2100 advances with the moving mechanism 2108. The robot 2100 can move safely by recognizing the surroundings with the upper camera 2103, the lower camera 2106, and the obstacle sensor 2107. The light-emitting device of one embodiment of the present invention can be used for the display 2105.

Figure 8C:
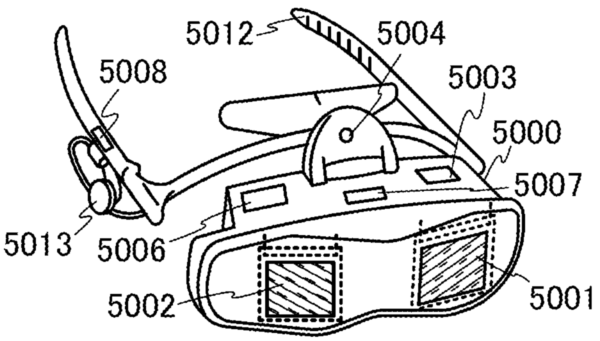

FIG. 8(C) shows an example of a goggle-type display. The goggle-type display includes, for example, a housing 5000, a display portion 5001, a speaker 5003, an LED lamp 5004, an operation keys 5005 (including a power switch or an operation switch), a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared ray), a microphone 5008, a display portion 5002, a support 5012, and an earphone 5013.

The light-emitting device of one embodiment of the present invention can be used for the display portion 5001 and the second display portion 5002.

Figure 9:
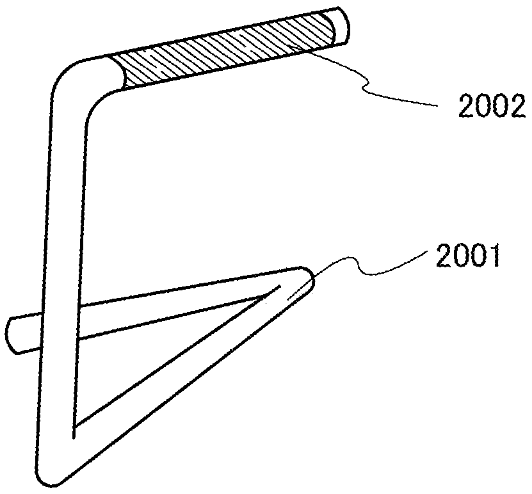
FIG. 9 A diagram illustrating a lighting device.

FIG. 9 illustrates an example in which the light-emitting element described in Embodiment 2 is used for a table lamp which is a lighting device. The table lamp illustrated in FIG. 9 includes a housing 2001 and a light source 2002, and the lighting device described in Embodiment 3 may be used for the light source 2002.

Figure 10:
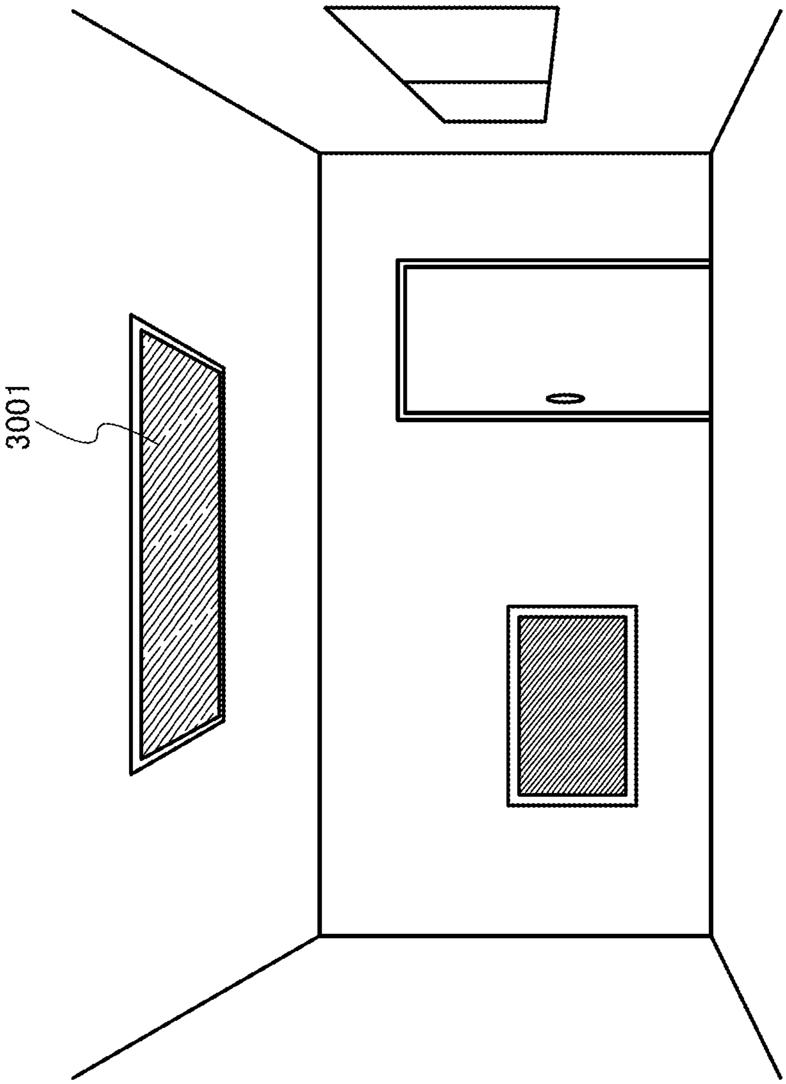
FIG. 10 A diagram illustrating a lighting device.

FIG. 10 illustrates an example in which the light-emitting element described in Embodiment 2 is used for an indoor lighting device 3001. Since the light-emitting element described in Embodiment 2 is a light-emitting element having high reliability, the lighting device can have high reliability. Furthermore, the light-emitting element described in Embodiment 2 can have a larger area, and thus can be used for a large-area lighting device. Furthermore, the light-emitting element described in Embodiment 2 is thin, and thus can be used for a lighting device having a reduced thickness.

Figure 11:
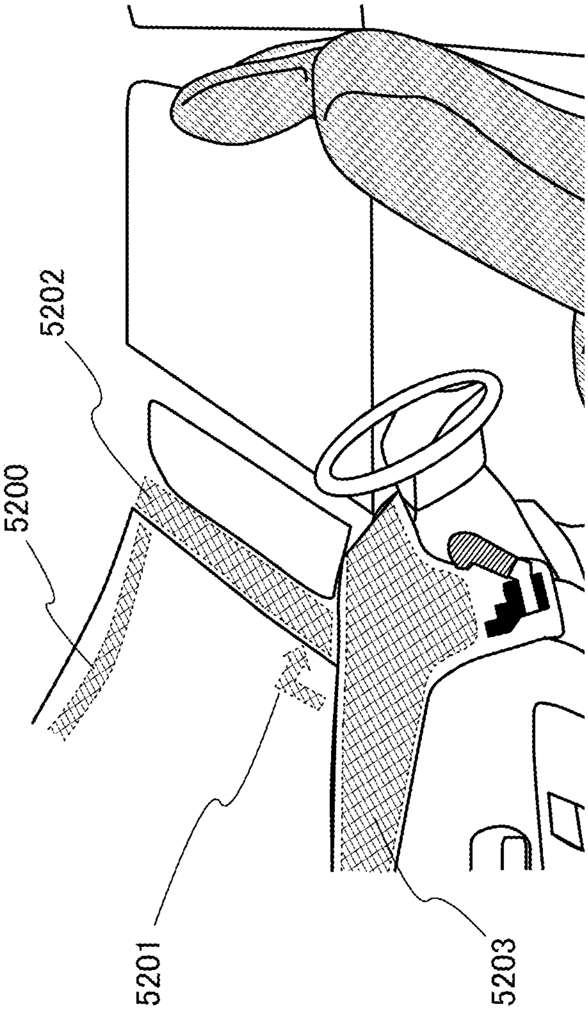
FIG. 11 A diagram illustrating in-vehicle display devices and lighting devices.

The light-emitting element described in Embodiment 2 can also be incorporated in an automobile windshield or an automobile dashboard. FIG. 11 illustrates one mode in which the light-emitting element described in Embodiment 2 is used for a windshield and a dashboard of an automobile. A display region 5200 to a display region 5203 are displays provided using the light-emitting element described in Embodiment 2.

The display region 5200 and the display region 5201 are display devices provided in the automobile windshield, in which the light-emitting elements described in Embodiment 2 are incorporated. When the light-emitting elements described in Embodiment 2 are fabricated using electrodes having light-transmitting properties as a first electrode and a second electrode, what is called see-through display devices, through which the opposite side can be seen, can be obtained. See-through display devices can be provided without hindering the vision even when being provided in the automobile windshield. Note that in the case where a driving transistor or the like is provided, a transistor having a light-transmitting property, such as an organic transistor using an organic semiconductor material or a transistor using an oxide semiconductor, is preferably used.

The display region 5202 is a display device provided in a pillar portion, in which the light-emitting elements described in Embodiment 2 are incorporated. The display region 5202 can compensate for the view hindered by the pillar by displaying an image taken by an imaging means provided on the car body. Similarly, the display region 5203 provided in the dashboard portion can compensate for the view hindered by the car body by displaying an image taken by an imaging means provided on the outside of the automobile. Thus, blind areas can be compensated for and the safety can be enhanced. Showing an image so as to compensate for the area that cannot be seen makes it possible to confirm safety more naturally and comfortably.

The display region 5203 can provide a variety of kinds of information by displaying navigation data, a speedometer, a tachometer, a mileage, a fuel meter, a gearshift state, air-condition setting, and the like. The content or layout of the display can be changed freely in accordance with the preference of a user. Note that such information can also be provided on the display region 5200 to the display region 5202. The display region 5200 to the display region 5203 can also be used as lighting devices.

Figure 12A:
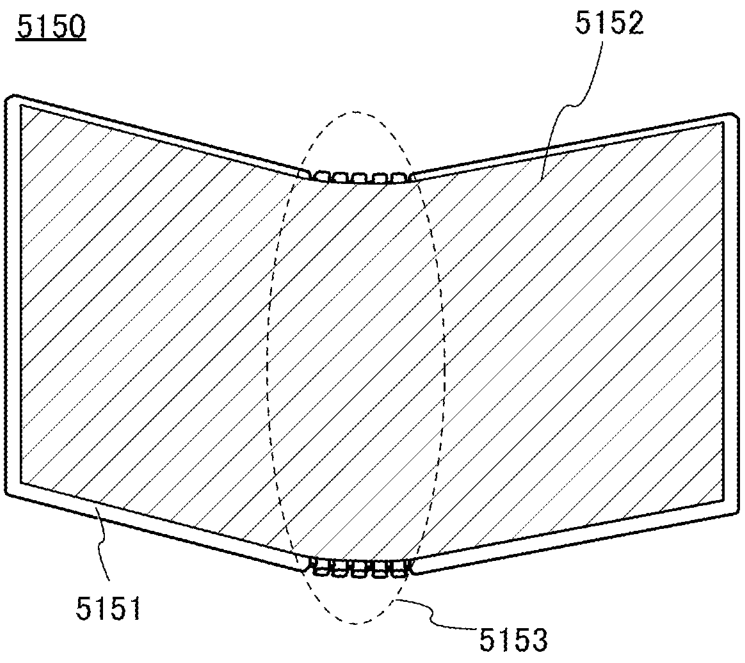
FIGS. 12(A) and 12(B) are diagrams illustrating an electronic device.
Figure 12B:
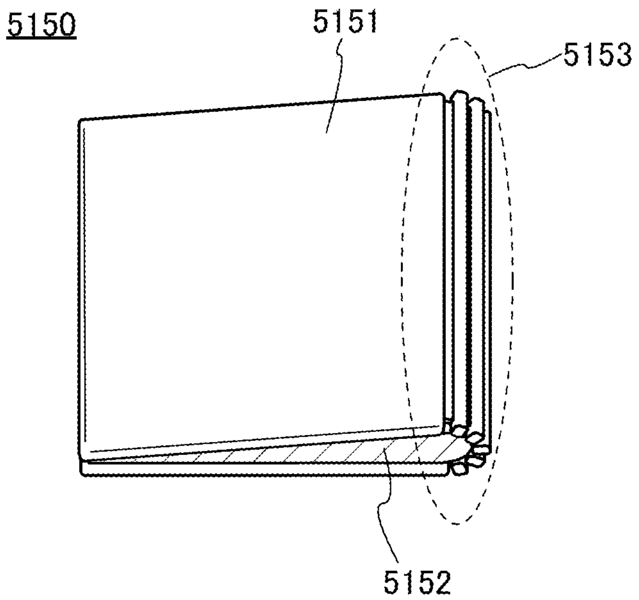

FIGS. 12(A) and 12(B) illustrate a foldable portable information terminal 5150. The foldable portable information terminal 5150 includes a housing 5151, a display region 5152, and a bend portion 5153. FIG. 12(A) illustrates the portable information terminal 5150 that is opened. FIG. 12(B) illustrates the portable information terminal that is folded. The portable information terminal 5150 is compact in size and has excellent portability when folded, despite its large display region 5152.

The display region 5152 can be folded in half with the bend portion 5153. The bend portion 5153 includes a flexible member and a plurality of supporting members, and when the display region is folded, the flexible member expands and the bend portion 5153 has a radius of curvature of 2 mm or more, preferably 3 mm or more.

Note that the display region 5152 may be a touch panel (an input/output device) controlling a touch sensor (an input device). The light-emitting device of one embodiment of the present invention can be used for the display region 5152.

Figure 13A:
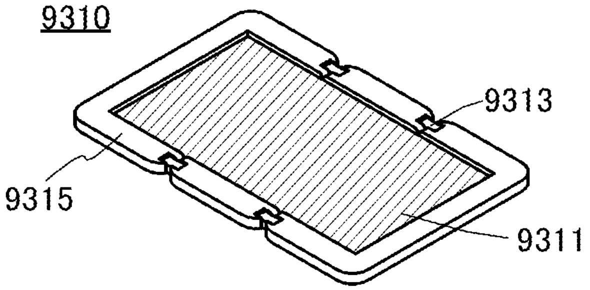
FIGS. 13(A) to 13(C) are diagrams illustrating an electronic device.
Figure 13B:
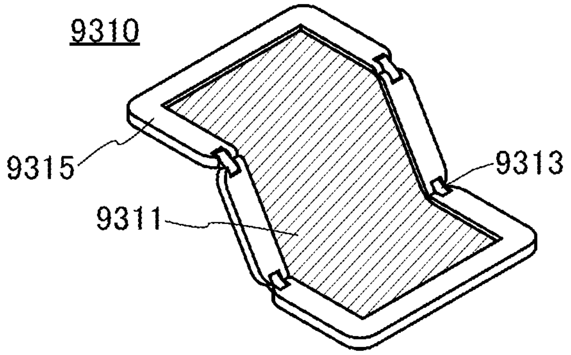
Figure 13C:
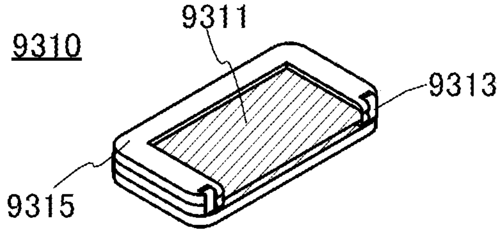

FIGS. 13(A) to 13(C) illustrate a foldable portable information terminal 9310. FIG. 13(A) illustrates the portable information terminal 9310 that is opened. FIG. 13(B) illustrates the portable information terminal 9310 which is in the state of being changed from one of an opened state and a folded state to the other. FIG. 13(C) illustrates the portable information terminal 9310 that is folded. The portable information terminal 9310 is excellent in portability when folded, and is excellent in display browsability when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. A light-emitting device of one embodiment of the present invention can be used for the display panel 9311.

Example 1

In this example, a synthesis method of N-[4'-(9H-carbazol-9-yl)-1,1'-biphenyl-4-yl]-N-(1,1'-biphenyl-4-yl)-6-phenylbenzo[b]naphtho[1,2-d]furan-8-amine (abbreviation: YGBBiBnf), which is an organic compound of one embodiment of the present invention, is described in detail. The structural formula of YGBBiBnf is shown below.

[Chemical Formula 70]

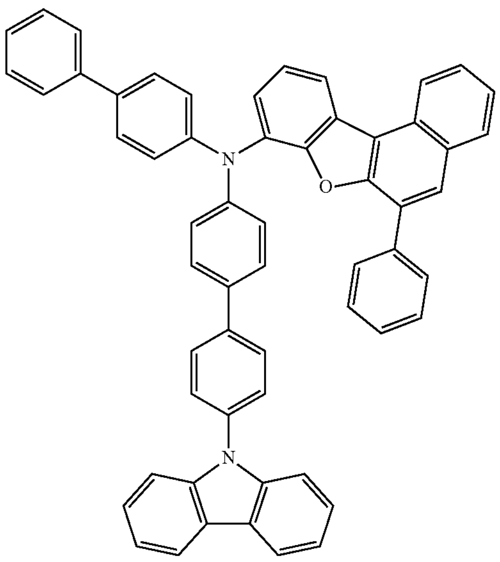

YGBBiBnf

Step 1: Synthesis of 4'-(9H-carbazol-9-yl)bis(1,1'-biphenyl-4-yl)amine

Into a 200-mL three-neck flask, 1.6 g (5.0 mmol) of N-(4-bromophenyl)-4-biphenylamine, 1.4 g (5.0 mmol) of 4-(9H-carbazol-9-yl)benzeneboronic acid, 46 mg (0.15 mmol) of tri(ortho-tolyl)phosphine, 7.5 mL of an aqueous solution of potassium carbonate (2.0 mmol/L), 20 mL of toluene, and 5 mL of ethanol were put. This mixture was degassed under reduced pressure, and the air in the flask was replaced with nitrogen. After this mixture was heated to 60° C., 11 mg (50 μmol) of palladium(II) acetate was added and the mixture was stirred at 80° C. for 7.5 hours. After the stirring, the precipitated solid was collected by suction filtration, and the obtained solid was washed with toluene, ethanol, and water. The washed solid was extracted with toluene with the use of a Soxhlet extractor, and the obtained solution was concentrated to give 1.5 g of a white solid in a yield of 63%. The synthesis scheme of Step 1 is shown below.

[Chemical Formula 71]

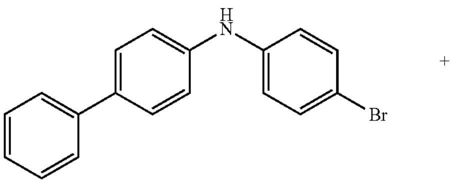

-continued

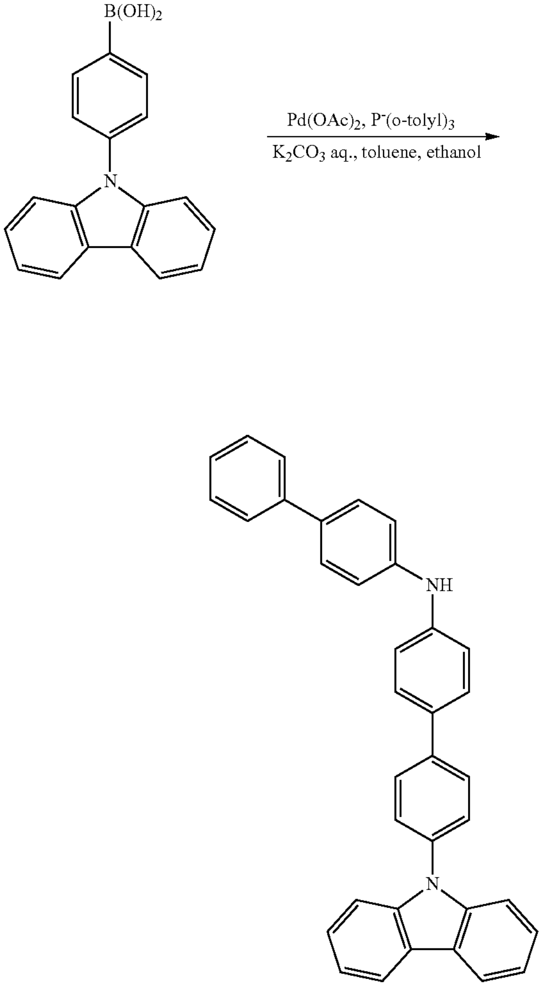

Step 2: Synthesis of N-[4'-(9H-carbazol-9-yl)-1,1'-biphenyl-4-yl]-N-(1,1'-biphenyl-4-yl)-6-phenylbenzo[b]naphtho[1,2-d]furan-8-amine (abbreviation: YGBBiBnf)

Into a 200-mL three-neck flask, 1.4 g (2.9 mmol) of 4'-(9H-carbazol-9-yl)bis(1,1'-biphenyl-4-yl)amine obtained in Step 1, 1.2 g (2.9 mmol) of 8-iodo-6-phenylbenzo[b]naphtho[1,2,d]furan, 0.10 g (0.25 mmol) of 2-dicyclohexylphosphine-2',6'-dimethoxybiphenyl (abbreviation: s-phos), 0.59 g (6.1 mmol) of sodium tert-butoxide, and 30 mL of xylene were put; this mixture was degassed under reduced pressure; and then the air in the system was replaced with nitrogen. To this mixture, 71 mg (0.12 mmol) of palladium(II) acetate was added, and this mixture was stirred at 80° C. for 13 hours. After the stirring, the precipitated solid was removed by suction filtration, and the obtained filtrate was filtered through alumina, Florisil (Wako Pure Chemical Industries, Ltd., Catalog No. 066-05265), and Celite (Wako Pure Chemical Industries, Ltd., Catalog No. 537-02305). A solid was obtained by concentration of the obtained filtrate and was recrystallized with toluene to give 1.5 g of a white solid in a yield of 65%. The synthesis scheme of Step 2 is shown below.

[Chemical Formula 72]

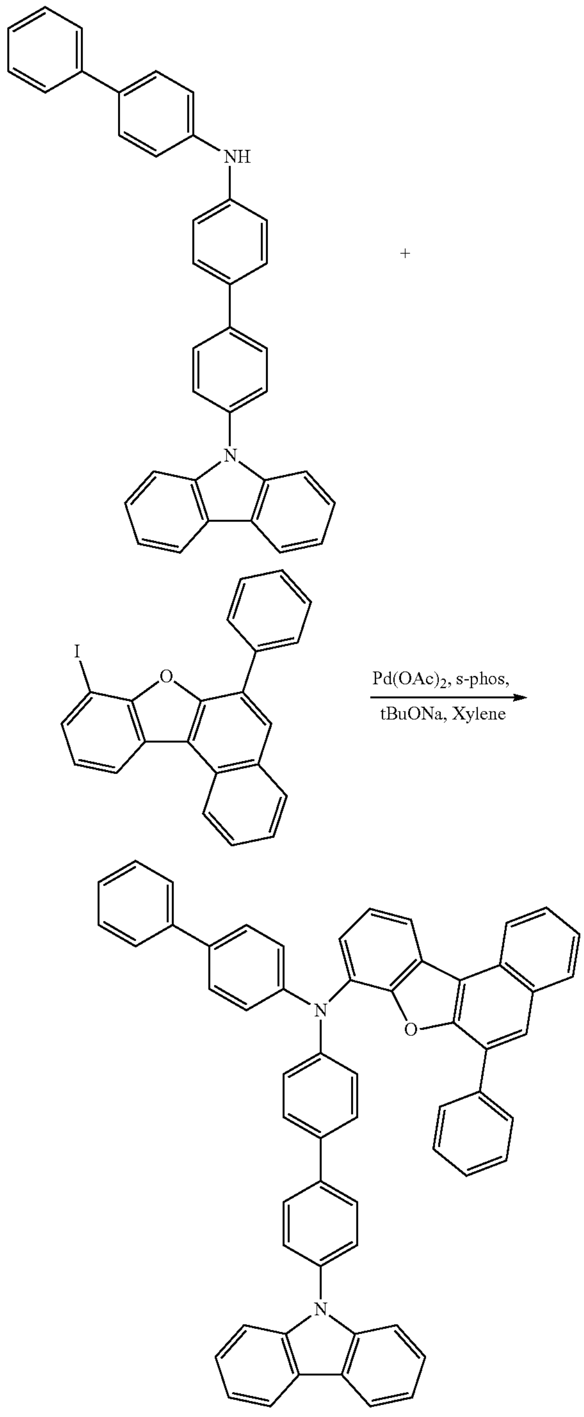

YGBBiBnf

Figure 14A:
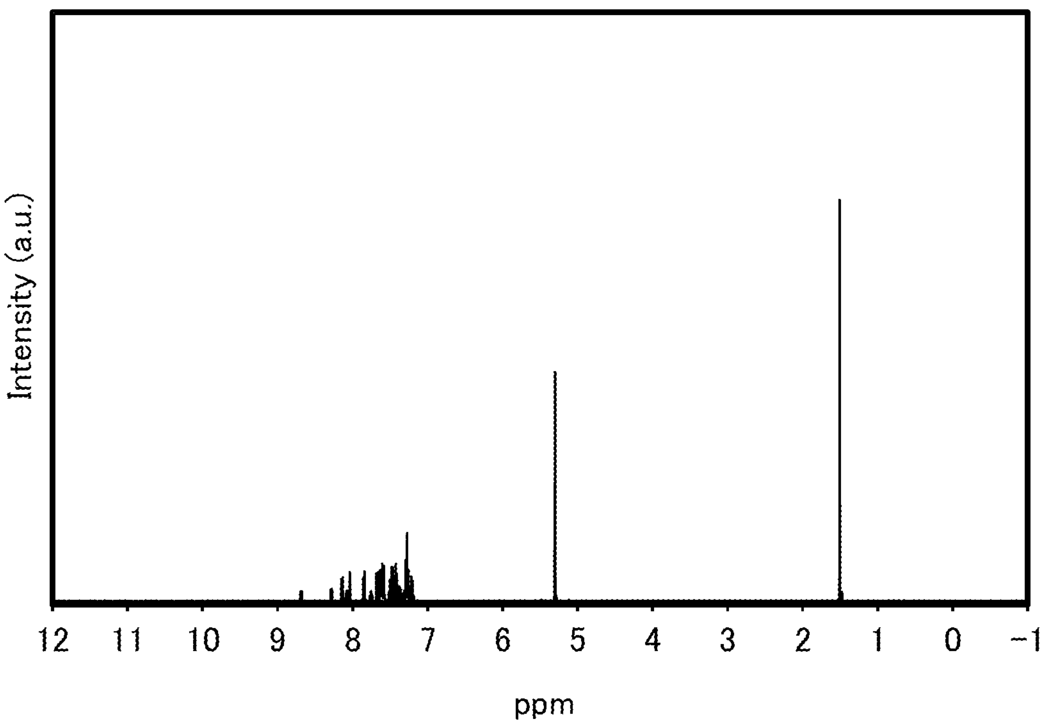
FIGS. 14(A) and 14(B) show a $^1$H NMR spectrum of YGBBiBnf.
Figure 14B:
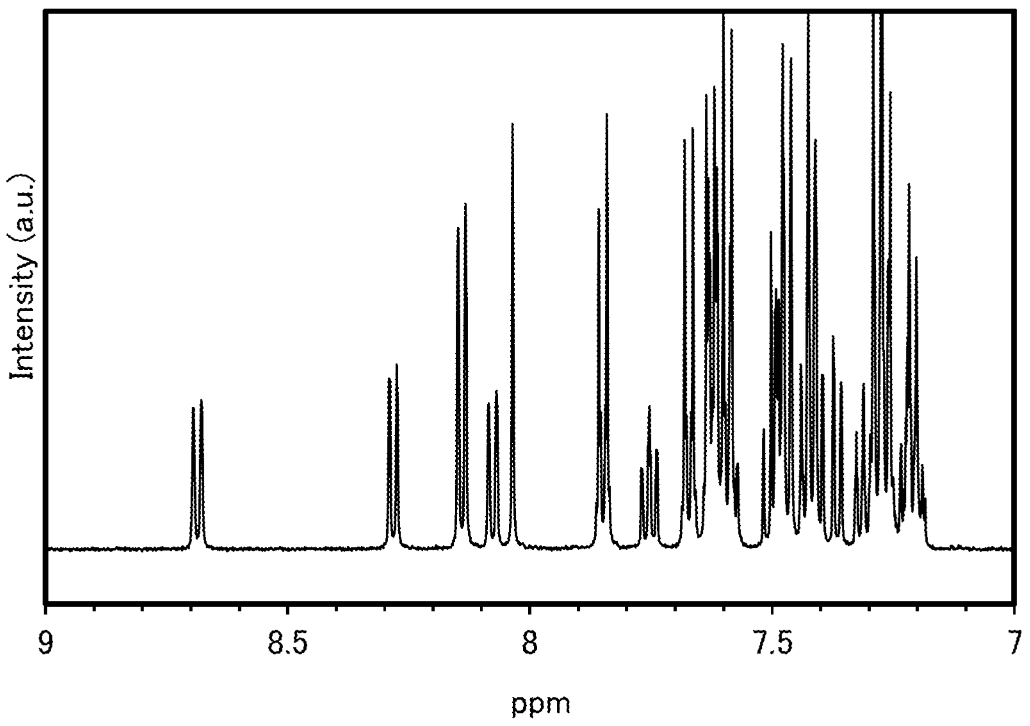

FIG. 14 shows $^1$H NMR data of the obtained solid, whose numerical data is given below. These indicate that N-[4'-(9H-carbazol-9-yl)-1,1'-biphenyl-4-yl]-N-(1,1'-biphenyl-4-yl)-6-phenylbenzo[h]naphtho[1,2-d]furan-8-amine (abbreviation: YGBBiBnf) was obtained.

$^1$H NMR (dichloromethane-d2, 500 MHz): δ=7.18-7.23 (m, 3H), 7.25-7.29 (m, 6H), 7.31 (t, J=7.5 Hz, 1H), 7.37 (d, J=8.0 Hz, 1H), 7.40-7.52 (m, 9H), 7.58-7.64 (m, 7H), 7.68 (d, J=8.5 Hz, 2H), 7.75 (td, J1=7.5 Hz, J2=1.0 Hz, 1H), 7.85 (d, J=8.5 Hz, 2H), 8.04 (s, 1H), 8.08 (d, J=8.0 Hz, 1H), 8.14 (d, J=7.5 Hz, 2H) 8.28 (dd, J1=8.0 Hz, J2=1 Hz, 1H), 8.69 (d, J=8.0 Hz, 1H)

The obtained solid was purified by sublimation. The sublimation purification was conducted by heating the solid to 340° C. to 350° C. at an argon flow rate of 10 mL/min under a pressure of 2.2 Pa. After the sublimation purification, 1.2 g of a light yellow solid, which is an objective compound, was obtained at a collection rate of 84%.

Figure 15:
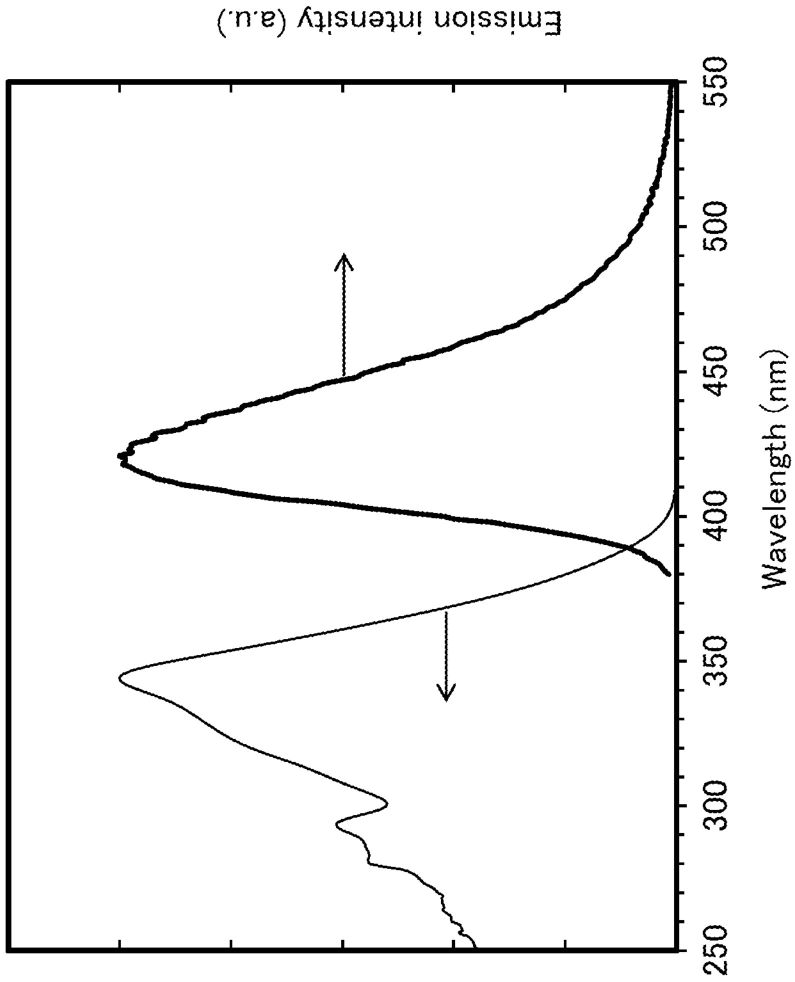
FIG. 15 An absorption spectrum and an emission spectrum of a toluene solution of YGBBiBnf.
Figure 16:
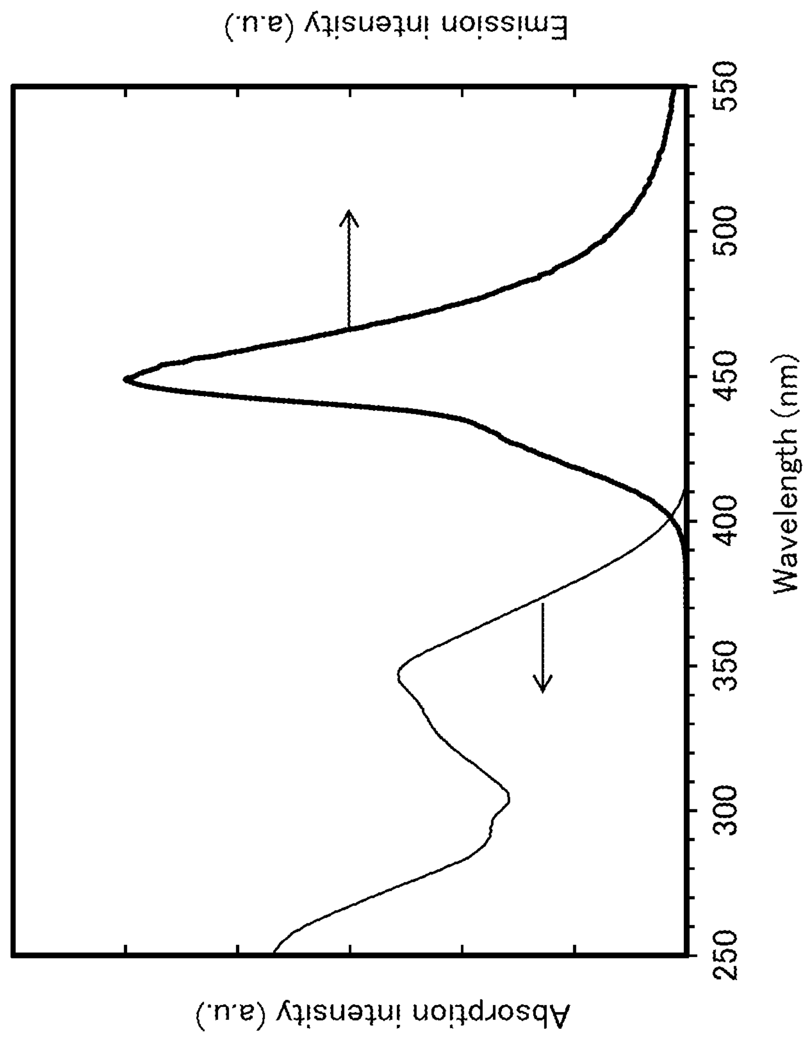
FIG. 16 An absorption spectrum and an emission spectrum of a thin film of YGBBiBnf.

Next, the measurement results of the absorption spectrum and the emission spectrum of the toluene solution of YGBBiBnf are shown in FIG. 15. In addition, the absorption spectrum and the emission spectrum of the thin film are shown in FIG. 16. The solid thin film was formed over a quartz substrate by a vacuum evaporation method. For the measurement of the absorption spectrum of the toluene solution, an ultraviolet-visible light spectrophotometer (V550, manufactured by JASCO Corporation) was used, and the spectrum of toluene alone in a quartz cell was subtracted. For the measurement of the absorption spectrum of the thin film, a spectrophotometer (U4100 Spectrophotometer, manufactured by Hitachi High-Technologies Corporation) was used. For the measurement of the emission spectra, a fluorescence spectrophotometer (FS920 manufactured by Hamamatsu Photonics K.K.) was used.

FIG. 15 shows that the toluene solution of YGBBiBnf has an absorption peak at around 344 nm and an emission wavelength peak at 421 nm (excitation wavelength: 344 nm). Furthermore, FIG. 16 shows that the thin film of YGBBiBnf has absorption peaks at around 347 nm, 330 nm, 298 nm, and 252 nm, and emission wavelength peaks at around 430 nm and 449 nm (excitation wavelength: 360 nm). These results indicate that YGBBiBnf emits blue light and can also be used as a host for a light-emitting substance or a host for a substance that emits fluorescence in the visible region.

Furthermore, the thin film of YGBBiBnf was found to be a high-quality film that is not easily aggregated even in the air and is hardly changed in shape.

Next, the HOMO level and the LUMO level of YGBBiBnf calculated on the basis of cyclic voltammetry (CV) measurement are shown. The calculation method is shown below.

An electrochemical analyzer (model No. ALS model 600A or 600C, manufactured by BAS Inc.) was used as a measurement apparatus. A solution for the CV measurement was prepared in the following manner: tetra-n-butylammonium perchlorate (n-Bu4NClO4, produced by Tokyo Chemical Industry Co., Ltd., catalog No. T0836) as a supporting electrolyte was dissolved in dehydrated dimethylformamide (DMF, produced by Sigma-Aldrich Co. LLC., 99.8%, catalog No. 22705-6) as a solvent at a concentration of 100 mmol/L, and the object to be measured was dissolved therein at a concentration of 2 mmol/L. A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag+ electrode (RE7 reference electrode for non-aqueous solvent, manufactured by BAS Inc.) was used as a reference electrode. Note that the measurement was performed at room temperature (20 to 25° C.). The scan speed in the CV measurement was fixed to 0.1 V/sec, and an oxidation potential Ea [V] and a reduction potential Ec [V] with respect to the reference electrode were measured. Ea was an intermediate potential of an oxidation-reduction wave, and Ec was an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]=−4.94−Ec.

CV measurement was repeated 100 times, and the oxidation-reduction wave in the hundredth cycle was compared with the oxidation-reduction wave in the first cycle to examine the electrical stability of the compound.

As a result, the HOMO level of YGBBiBnf was found to be −5.56 eV, and the LUMO level was found to be −2.51 eV. This measurement results revealed that YGBBiBnf is an organic compound having a relatively deep HOMO level. Accordingly, also in the case where an organic compound having a deep HOMO level is used as a host material of a light-emitting layer, a favorable hole-injection property to the host material can be exhibited. In addition, when the oxidation-reduction wave was repeatedly measured and the waveform of the first cycle was compared with that of the hundredth cycle, 81% of the peak intensity was maintained in the oxidation potential Ea [V] measurement, and 95% of the peak intensity was maintained in the reduction potential Ec [eV] measurement, which confirmed that YGBBiBnf had extremely high resistance to oxidation and reduction.

Differential scanning calorimetry (DSC) of YGBBiBnf was performed with Pyris1DSC manufactured by PerkinElmer, Inc. The DSC was performed in the following manner: the temperature was raised from −10° C. to 320° C. at a temperature rising rate of 40° C./min and held at the temperature for three minutes, and then the temperature was decreased to −10° C. at a temperature decreasing rate of 100° C./min and held at −10° C. for three minutes. This operation was performed twice in succession. It was revealed from the result of the second cycle of the DSC measurement that the glass transition point of YGBBiBnf was 159° C., that is, YGBBiBnf was a substance with extremely high heat resistance.

Then, thermogravimetry-differential thermal analysis (TG-DTA) of YGBBiBnf was performed. The measurement was performed using a high vacuum differential type differential thermal balance (TG-DTA2410SA, produced by Bruker AXS K.K.). The measurement was performed under atmospheric pressure at a temperature rising rate of 10° C./min under a nitrogen stream (flow rate: 200 mL/min). In the thermogravimetry-differential thermal analysis, the temperature (decomposition temperature) at which the weight obtained by thermogravimetry was reduced by 5% of the weight at the beginning of the measurement was found to be 500° C. or higher, which shows that YGBBiBnf is a substance with high heat resistance.

Example 2

In this example, a synthesis method of N-[4"-(9H-carbazol-9-yl)1,1':4',1"-terphenyl-4-yl]-N-(1,1'-biphenyl-4-yl)-6-phenylbenzo[b]naphtho[1,2-d]furan-8-amine (abbreviation: YGTBiBnf), which is an organic compound of one embodiment of the present invention, is described in detail. The structural formula of YGTBiBnf is shown below.

[Chemical Formula 73]

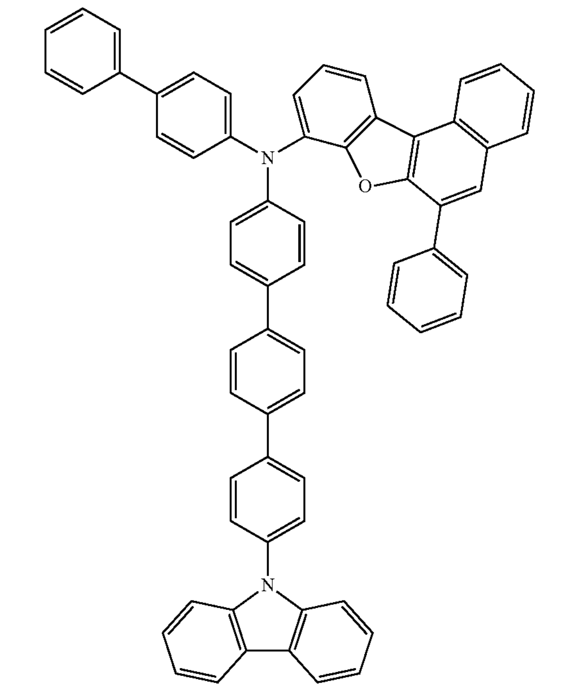

YGTBiBnf

Step 1: Synthesis of N-(1,1'-biphenyl-4-yl)-4"-(9H-carbazol-9-yl)(1,1';4',1"-terphenyl-4-yl)amine Into a 200-mL three-neck flask, 1.6 g (5.0 mmol) of N-(4-bromophenyl)-4-biphenylamine, 1.8 g (5.0 mmol) of 4'-(9H-carbazol-9-yl)-1,1'-biphenyl-4-boronic acid, 46 mg (0.15 mmol) of tri(ortho-tolyl)phosphine, 7.5 mL of an aqueous solution of potassium carbonate (2.0 mmol/L), 40 mL of toluene, and 10 mL of ethanol were put; this mixture was degassed under reduced pressure; and then the air in the flask was replaced with nitrogen. After this mixture was heated to 60° C., 12 mg (50 μmol) of palladium(II) acetate was added and this mixture was stirred at 80° C. for 12 hours. After the stirring, the precipitated solid was collected by suction filtration, and the obtained solid was washed with toluene, ethanol, and water. The washed solid was washed with toluene with the use of a Soxhlet extractor to give 1.8 g of an objective light gray solid in a yield of 63%. The synthesis scheme of Step 1 is shown below.

[Chemical Formula 74]

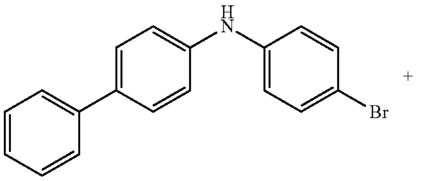

-continued

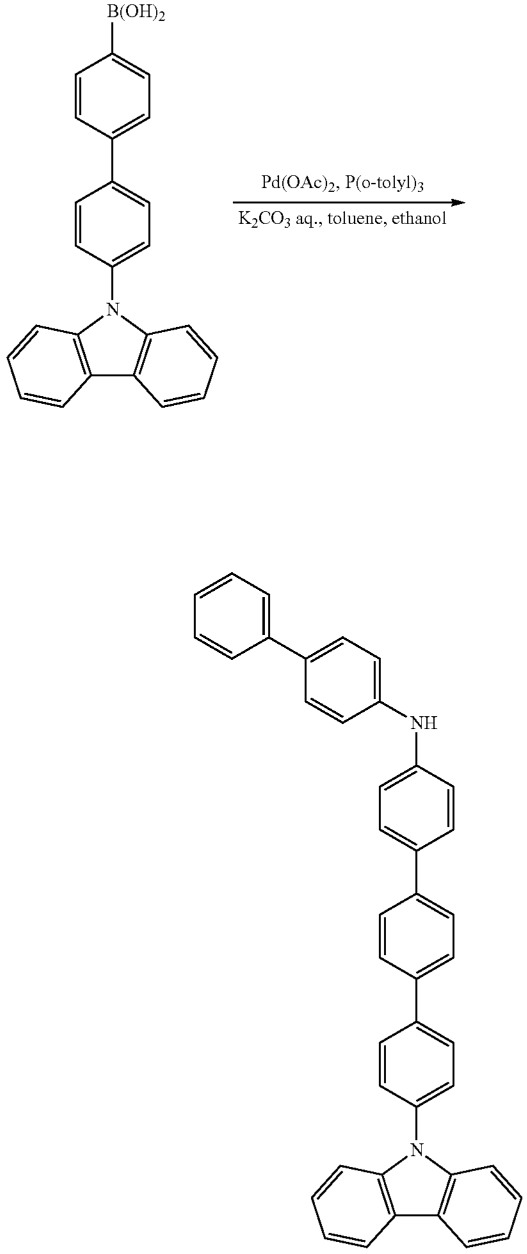

Step 2: Synthesis of N-[4"-(9H-carbazol-9-yl)1,1':4',1"-terphenyl-4-yl]-N-(1,1'-biphenyl-4-yl)-6-phenylbenzo[b]naphtho[1,2-d]furan-8-amine (abbreviation: YGTBiBnf)

Into a 200-mL three-neck flask, 1.8 g (3.2 mmol) of N-(1,1'-biphenyl-4-yl)-4"-(9H-carbazol-9-yl)(1,1';4',1"-terphenyl-4-yl)amine obtained in Step 1, 1.3 g (3.2 mmol) of 8-iodo-6-phenylbenzo[b]naphtho[1,2,d]furan, 0.13 g (0.32 mmol) of 2-dicyclohexylphosphine-2',6'-dimethoxybiphenyl (abbreviation: s-phos), 0.62 g (6.4 mmol) of sodium tert-butoxide, and 32 mL of xylene were put; this mixture was degassed under reduced pressure; and then the air in the flask was replaced with nitrogen. To this mixture, 92 mg (0.16 mmol) of palladium(II) acetate was added, and this mixture was stirred at 80° C. for 3 hours. After the stirring, the reaction was checked by thin layer chromatography, and it was found that the raw material was left. To this mixture, 67 mg (0.16 mmol) of s-phos and 90 mg (0.16 mmol) of palladium(II) acetate were added, and the mixture was further stirred while heating at 100° C. for 13 hours. The precipitated solid was removed by suction filtration, the obtained filtrate was filtered through alumina, Florisil (Wako Pure Chemical Industries, Ltd., Catalog No. 066-05265), and Celite (Wako Pure Chemical Industries, Ltd., Catalog No. 537-02305), and the obtained filtrate was concentrated. The solid obtained after the concentration was purified by silica gel chromatography using a given solvent to give 1.5 g of an objective solid in a yield of 65%. The synthesis scheme of Step 2 is shown below.

[Chemical Formula 75]

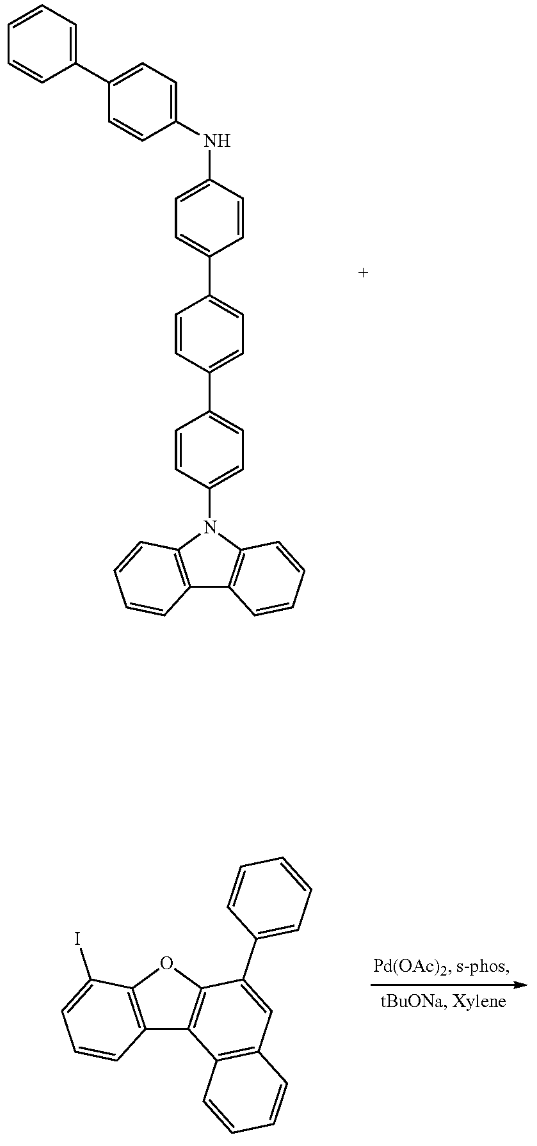

-continued

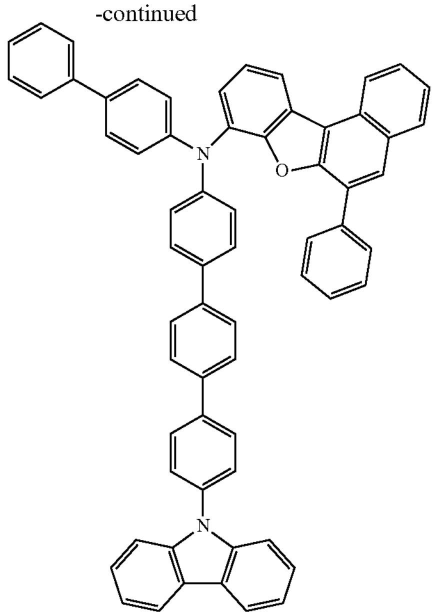

YGTBiBnf

Figure 17A:
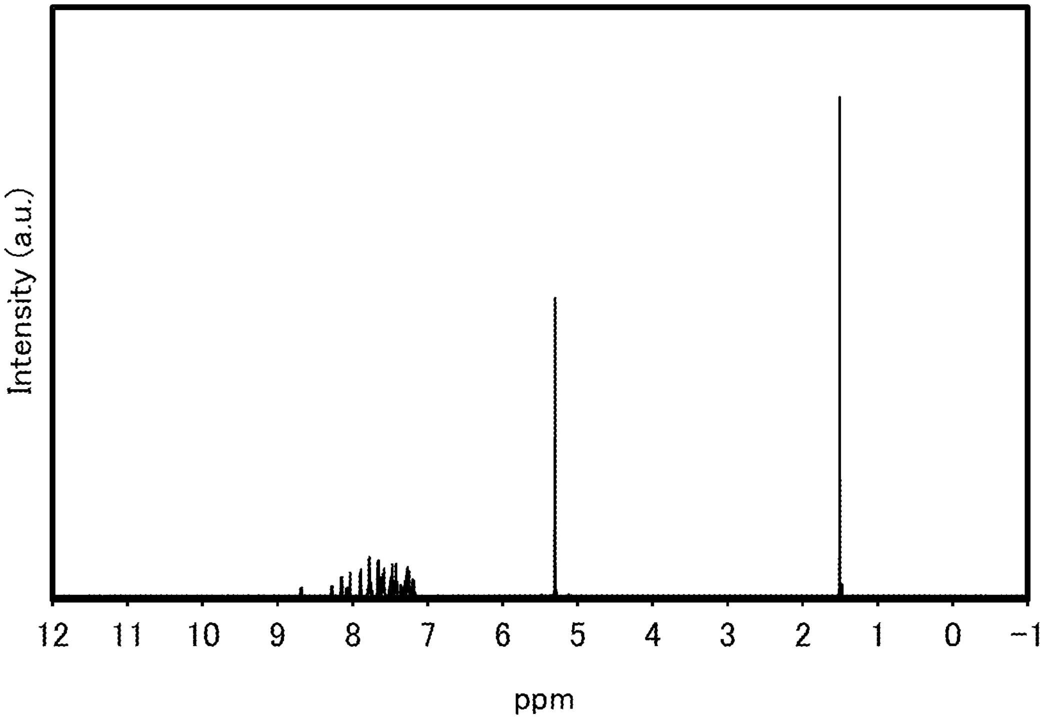
FIGS. 17(A) and 17(B) show a $^1$H NMR spectrum of YGTBiBnf.
Figure 17B:
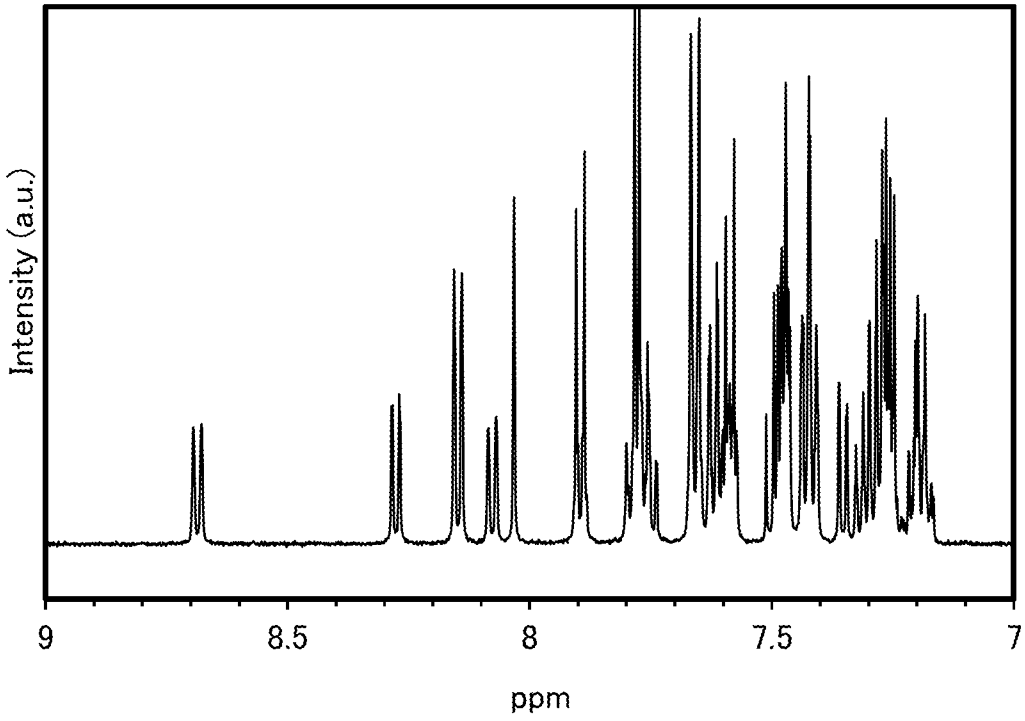

FIG. 17 shows $^{1}$H NMR data of the obtained solid, whose numerical data is given below. These indicate that N-[4"-(9H-carbazol-9-yl)1,1':4',1"-terphenyl-4-yl]-N-(1,1'-biphenyl-4-yl)-6-phenylbenzo[b]naphtho[1,2-d]furan-8-amine (abbreviation: YGTBiBnf) was obtained.

$^{1}$H NMR (dichloromethane-d2, 500 MHz): δ=7.16-7.23 (m, 3H), 7.25-7.33 (m, 7H), 7.35 (d, J=8.0 Hz, 1H), 7.42 (tt, J1=7.0, J2=1.0 Hz, 4H), 7.46-7.51 (m, 5H), 7.57-7.63 (m, 5H), 7.66 (d, J=8.5 Hz, 4H), 7.74-7.80 (m, 5H), 7.90 (d, J=8.5 Hz, 2H), 8.03 (s, 1H), 8.08 (d, J=8.0 Hz, 1H), 8.15 (d, J=8.0 Hz, 2H), 8.28 (dd, J1=8.5 Hz, J2=1.5 Hz, 1H), 8.69 (d, J=8.0 Hz, 1H)

Sublimation purification was performed on 1.5 g of the obtained solid. The sublimation purification was conducted by heating the solid to 370° C. under a pressure of $1.8\times10^{-2}$ Pa. After the sublimation purification, 1.0 g of a light yellow solid, which is an objective compound, was obtained at a collection rate of 69%.

Figure 18:
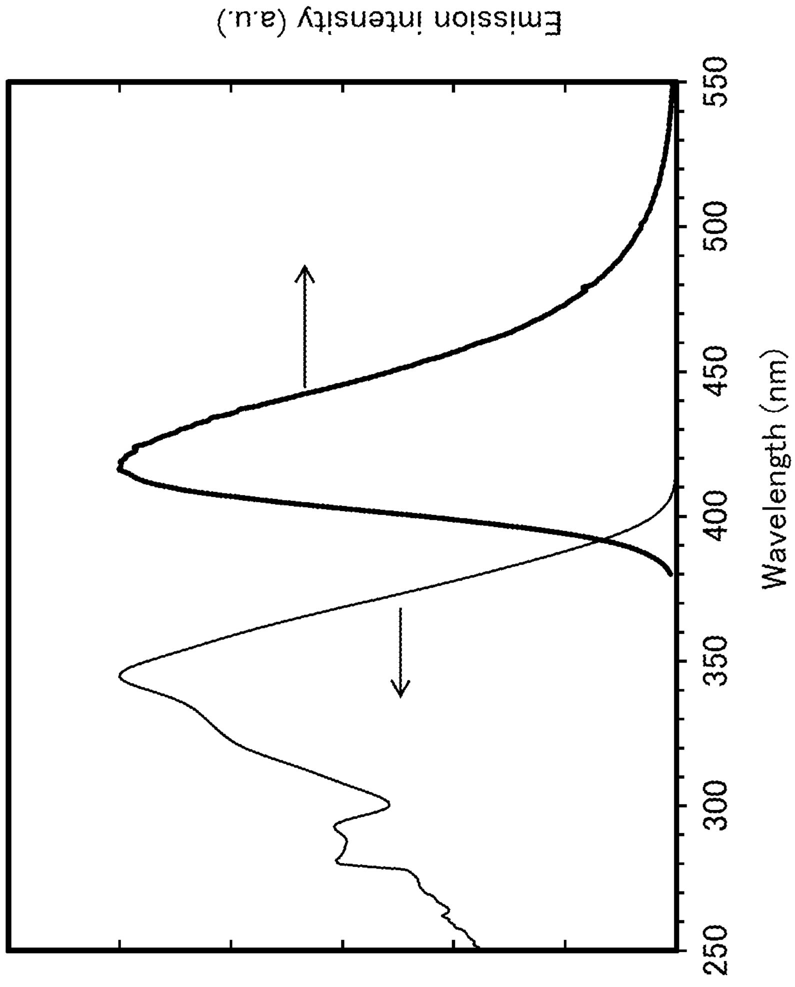
FIG. 18 An absorption spectrum and an emission spectrum of a toluene solution of YGTBiBnf.
Figure 19:
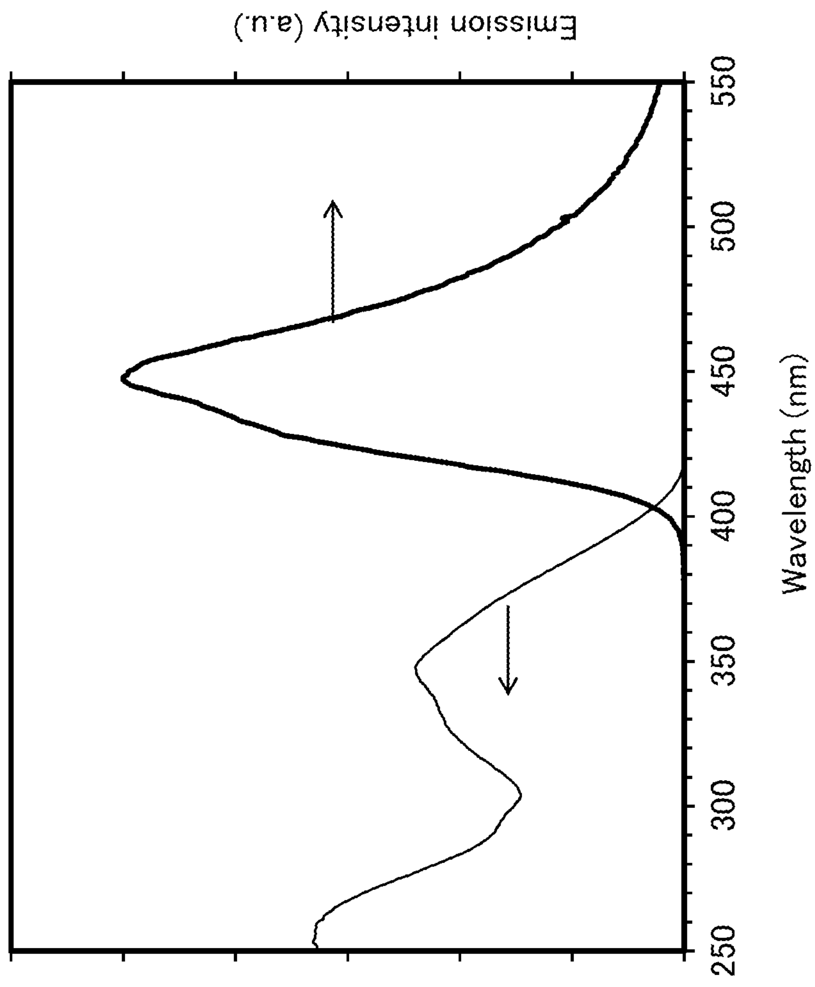
FIG. 19 An absorption spectrum and an emission spectrum of a thin film of YGTBiBnf.

Next, the measurement results of the absorption spectrum and the emission spectrum of the toluene solution of YGTBiBnf are shown in FIG. 18 and FIG. 19. The measurement was performed in a manner similar to that in Example 1.

FIG. 18 shows that the toluene solution of YGTBiBnf has an absorption peak at around 345 nm and an emission wavelength peak at 416 nm (excitation wavelength: 345 nm). Furthermore, FIG. 19 shows that the thin film of YGTBiBnf has absorption peaks at around 368 nm, 348 nm, 325 nm, 297 nm, and 257 nm, and emission wavelength peaks at around 430 nm and 448 nm (excitation wavelength: 360 nm). These results indicate that YGTBiBnf emits blue light and can also be used as a host for a light-emitting substance or a host for a substance that emits fluorescence in the visible region.

Furthermore, the thin film of YGTBiBnf was found to be a high-quality film that is not easily aggregated even in the air and is hardly changed in shape.

Next, the HOMO level and the LUMO level of YGTBiBnf calculated on the basis of cyclic voltammetry (CV) measurement are shown. The calculation method is similar to that in Example 1.

As a result, the HOMO level of YGTBiBnf was found to be −5.55 eV, and the LUMO level was found to be −2.51 eV. This measurement results revealed that YGTBiBnf is an organic compound having a relatively deep HOMO level. Accordingly, also in the case where an organic compound having a deep HOMO level is used as a host material of a light-emitting layer, a favorable hole-injection property to the host material of the light-emitting layer can be exhibited. In addition, when the oxidation-reduction wave was repeatedly measured and the waveform of the first cycle was compared with that of the hundredth cycle, 81% of the peak intensity was maintained in the oxidation potential Ea [V] measurement, and 93% of the peak intensity was maintained in the reduction potential Ec [eV] measurement, which confirmed that YGTBiBnf had extremely high resistance to oxidation and reduction.

Furthermore, DSC measurement of YGTBiBnf was performed. The DSC measurement was performed in a manner similar to that in Example 1. It was revealed from the result of the second cycle of the DSC measurement that the glass transition point of YGTBiBnf was 167° C., that is, YGTBiBnf was a substance with extremely high heat resistance.

Then, TG-DTA of YGTBiBnf was performed. The measurement was performed in a manner similar to that in Example 1. By this, the temperature (decomposition temperature) at which the weight obtained by thermogravimetry was reduced by 5% of the weight at the beginning of the measurement was found to be 500° C. or higher, which shows that YGTBiBnf is a substance with high heat resistance.

Example 3

In this example, a synthesis method of N-(1,1'-biphenyl-4-yl)-6-phenyl-N-[4-(9-phenylcarbazol-3-yl)phenyl]benzo[b]naphtho[d]furan-8-amine (abbreviation: PCBBiBnf), which is an organic compound of the present invention, is described in detail. The structural formula of PCBBiBnf is shown below.

[Chemical Formula 76]

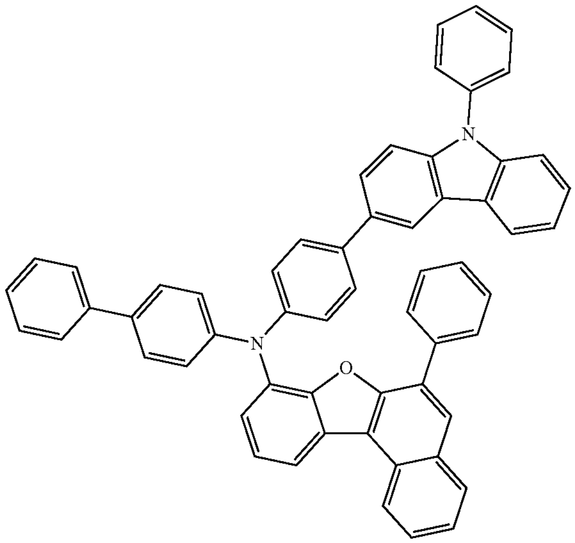

PCBBiBnf

Step 1: Synthesis of N-(1,1'-biphenyl-4-yl)-6-phenyl-N-[4-(9-phenylcarbazol-3-yl)phenyl]benzo[b]naphtho[d]furan-8-amine (abbreviation: PCBBiBnf)

Into a 500-mL four-neck flask equipped with a reflux pipe, 13 g (30 mmol) of 8-iodo-6-phenylbenzo[b]naphtho[1,2,d]furan, 15 g (32 mmol) of 4-(9-phenyl-9H-carbazol-3-yl)-4'-phenyldiphenylamine, 7.8 g (0.14 mol) of potassium hydroxide, 2.4 g (1.2 mmol) of a 10 wt % toluene solution of tri(t-butyl)phosphine, 210 mL of toluene, and 0.17 g (0.30 mmol) of bis(dibenzylideneacetone)palladium(II) were put, and the air in the system was replaced with nitrogen. This mixture was stirred at 110° C. for 29 hours. Toluene was added to this mixture so that the solid is dissolved, and the obtained organic layer was washed with water. Activated carbon was added to the obtained organic layer, and suction filtration was performed. The obtained filtrate was concentrated to give a brown solid. The obtained solid was dissolved in toluene, and isopropyl alcohol was dropped to give a light yellow solid. This solid was dissolved in toluene, and isopropyl alcohol was dropped to obtain a crystal, that is, 20 g of an objective light yellow crystal in a yield of 86%. The synthesis scheme of Step 1 is shown below.

[Chemical Formula 77]

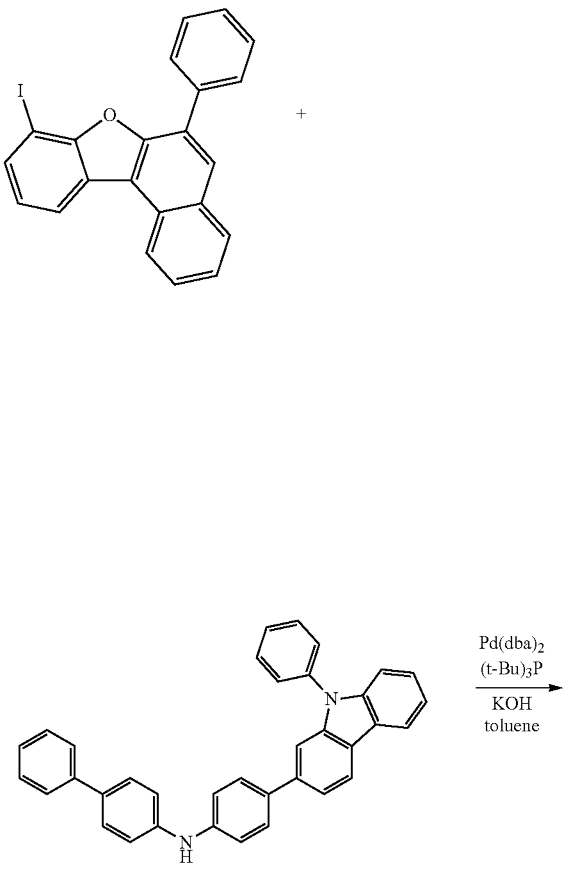

-continued

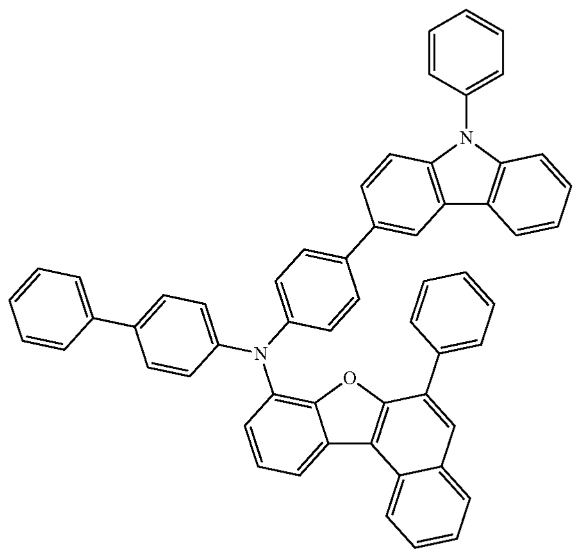

Figure 20A:
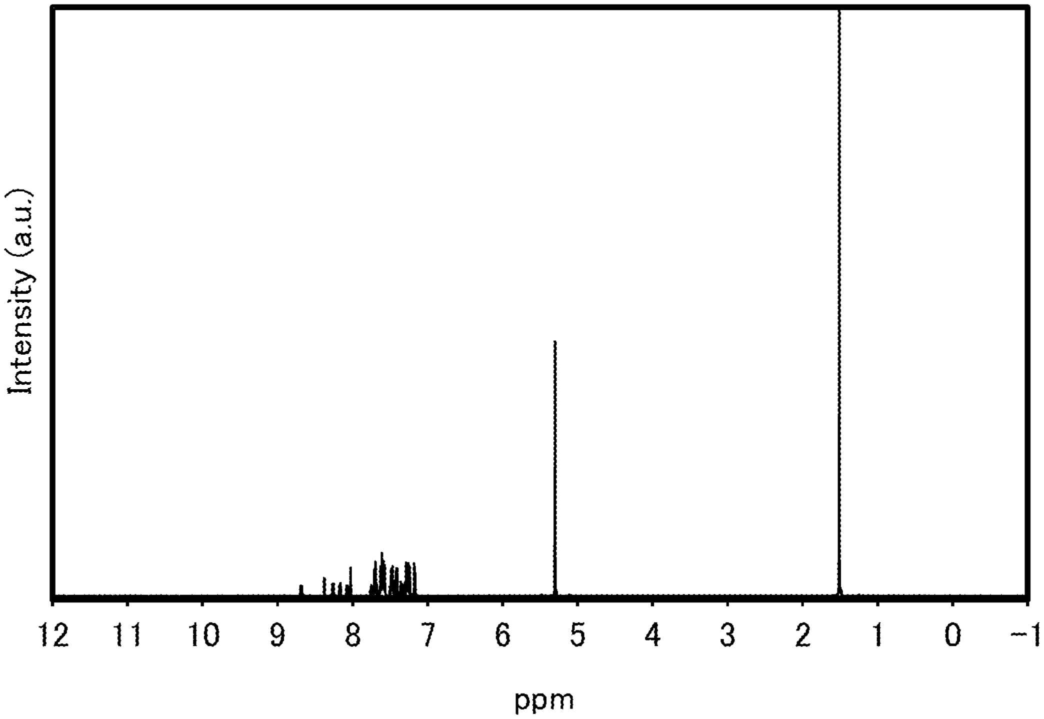
FIGS. 20(A) and 20(B) show a $^1$H NMR spectrum of PCBBiBnf.
Figure 20B:
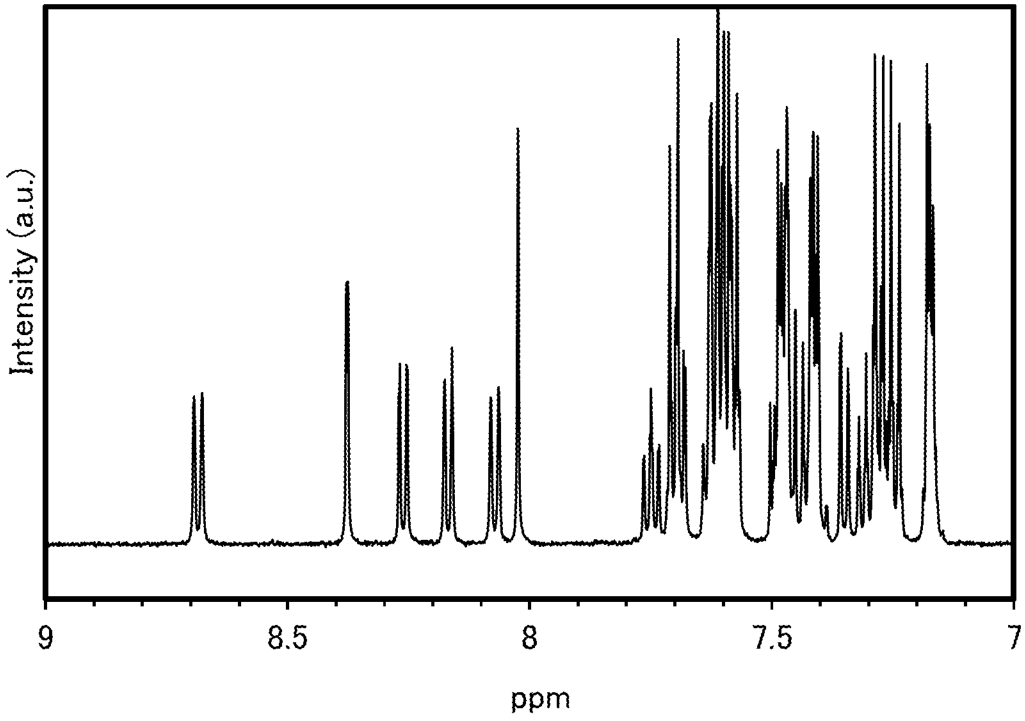

FIG. 20 shows $^1H$ NMR data of the obtained solid, whose numerical data is given below. These indicate that N-(1,1'-biphenyl-4-yl)-6-phenyl-N-[4-(9-phenylcarbazol-3-yl)phenyl]benzo[b]naphtho[d]furan-8-amine (abbreviation: PCBBiBnf) was obtained. The measurement results of $^1H$ NMR are shown below.

$^1H$ NMR (dichloromethane-d2, 500 MHz): δ=7.15-7.19 (m, 3H), 7.25 (d, J=8.5 Hz, 2H) 7.26-7.29 (m, 3H), 7.31 (dt, J1=7.5 Hz, J2=1 Hz, 1H), 7.35 (dd, J1=8.0 Hz, J2=1 Hz, 1H), 7.39-7.50 (m, 9H), 7.57-7.64 (m, 9H), 7.69 (dd, J1=8.0 Hz, J2=1.5 Hz, 1H), 7.70 (d, J=8.5 Hz, 2H), 7.76 (td, J1=7.0 Hz, J2=1.5 Hz, 11H), 8.02 (s, 1H), 8.07 (d, J=8.5 Hz, 11H), 8.17 (d, J=7.5 Hz, 1H), 8.26 (dd, J1=8.0 Hz, J2=1.5 Hz, 1H), 8.38 (sd, J=1.0 Hz, 1H), 8.69 (d, J=8.0 Hz, 11H)

Sublimation purification was performed on 17 g of the obtained solid. The sublimation purification was conducted by heating the solid at 300° C. under a pressure of 2.0 Pa for 1 hour and 10 minutes and then heating the solid at 360° C. for 2 hours and 40 minutes. After the sublimation purification, 15.5 g of an objective light yellow solid was obtained at a collection rate of 91%.

Figure 21:
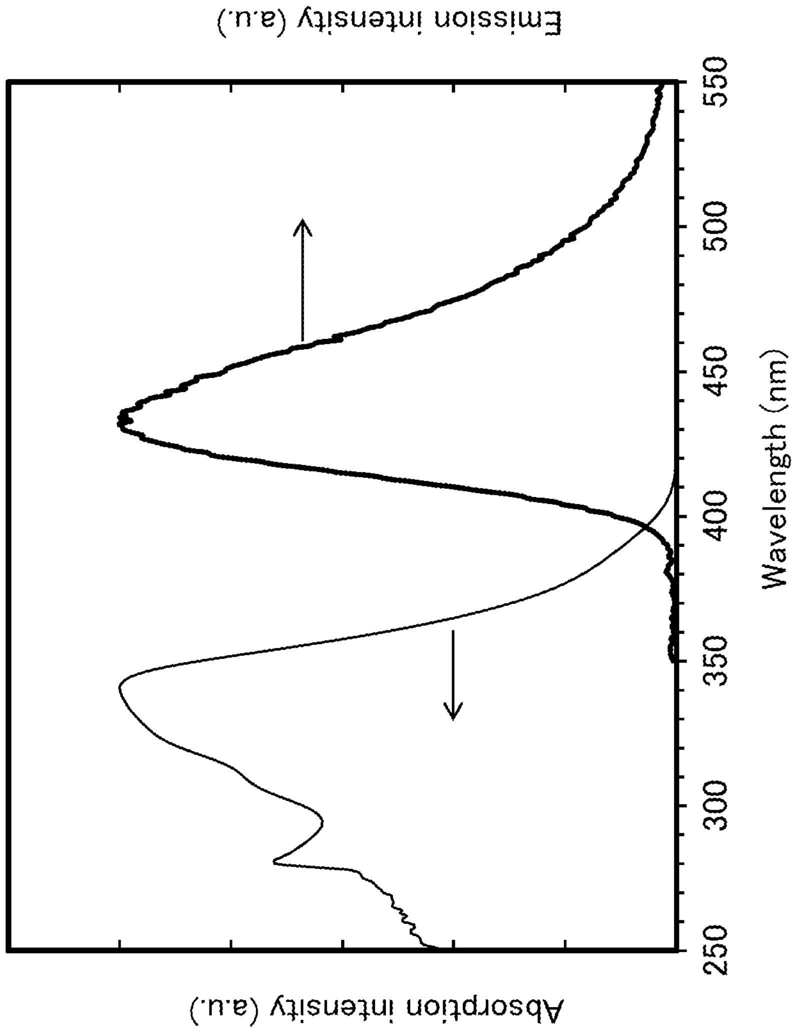
FIG. 21 An absorption spectrum and an emission spectrum of a toluene solution of PCBBiBnf.
Figure 22:
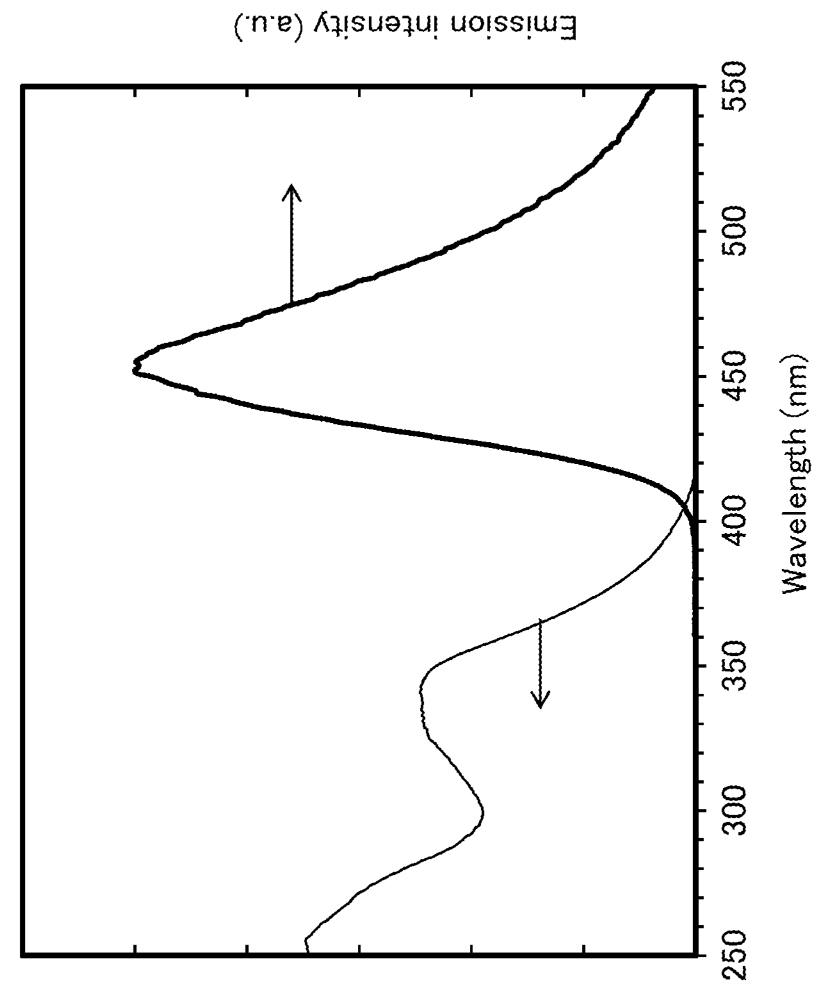
FIG. 22 An absorption spectrum and an emission spectrum of a thin film of PCBBiBnf.

Next, the measurement results of the absorption spectrum and the emission spectrum of the toluene solution of PCBBiBnf are shown in FIG. 21 and FIG. 22. The measurement was performed in a manner similar to that in Example 1.

FIG. 21 shows that the toluene solution of PCBBiBnf has an absorption peak at around 341 nm and an emission wavelength peak at 432 nm (excitation wavelength: 341 nm). Furthermore, FIG. 22 shows that the thin film of PCBBiBnf has absorption peaks at around 376 nm, 336 nm, 272 nm, and 254 nm, and emission wavelength peaks at around 430 nm and 449 nm (excitation wavelength: 360 nm). These results indicate that PCBBiBnf emits blue light and can also be used as a host for a light-emitting substance or a host for a substance that emits fluorescence in the visible region.

Furthermore, the thin film of PCBBiBnf was found to be a high-quality film that is not easily aggregated even in the air and is hardly changed in shape.

Next, the HOMO level and the LUMO level of PCBBiBnf calculated on the basis of cyclic voltammetry (CV) measurement are shown. The calculation method is similar to that in Example 1.

As a result, the HOMO level of PCBBiBnf was found to be −5.47 eV, and the LUMO level was found to be −2.50 eV. This measurement results revealed that PCBBiBnf is an organic compound having a relatively deep HOMO level. Accordingly, also in the case where an organic compound having a deep HOMO level is used as a host material of a light-emitting layer, a favorable hole-injection property to the host material can be exhibited. In addition, when the oxidation-reduction wave was repeatedly measured and the waveform of the first cycle was compared with that of the hundredth cycle, 90% of the peak intensity was maintained in the oxidation potential Ea [V] measurement, and 94% of the peak intensity was maintained in the reduction potential Ec [eV] measurement, which confirmed that PCBBiBnf had extremely high resistance to oxidation and reduction.

Furthermore, DSC measurement of PCBBiBnf was performed. The DSC measurement was performed in a manner similar to that in Example 1. It was revealed from the result of the second cycle of the DSC measurement that the glass transition point of PCBBiBnf was 153° C., that is, PCBBiBnf was a substance with extremely high heat resistance.

Then, TG-DTA of PCBBiBnf was performed. The measurement was performed in a manner similar to that in Example 1. By this, the temperature (decomposition temperature) at which the weight obtained by thermogravimetry was reduced by 5% of the weight at the beginning of the measurement was found to be 492° C., which shows that PCBBiBnf is a substance with high heat resistance.

Example 4

In this example, a light-emitting element 1 and a light-emitting element 2 of one embodiment of the present invention described in Embodiment 2 will be described. The structural formulae of organic compounds used in the light-emitting element 1 and the light-emitting element 2 are shown below.

[Chemical Formula 78]

(i)

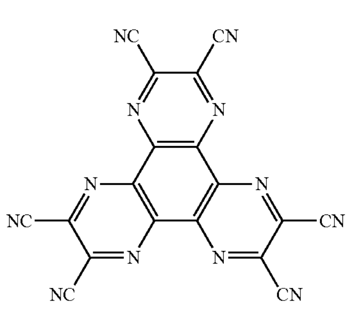

HAT—CN

-continued
(ii)
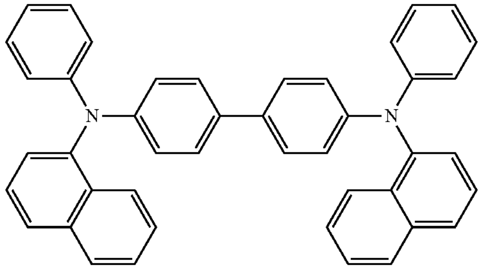
NPB
(iii)
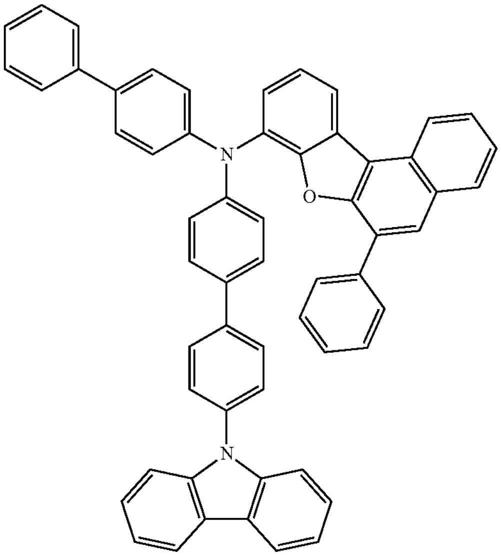
YGBBiBnf
(iv)
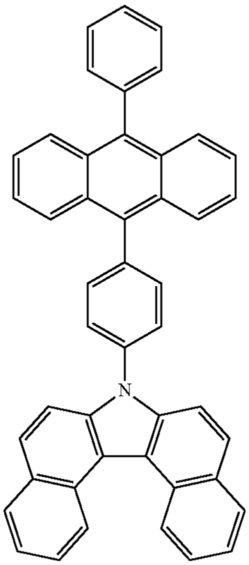
cgDBCzPA
-continued
(v)
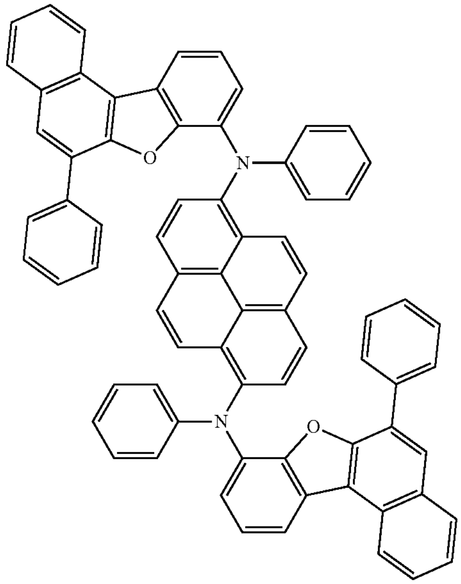
1,6BnfAPrn-03
(vi)
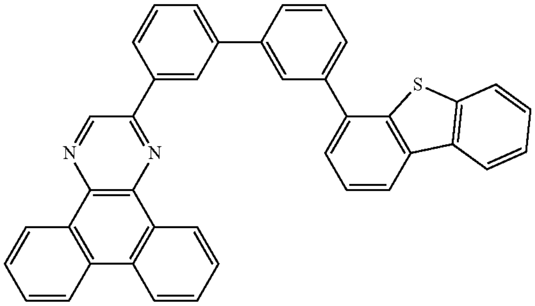
2mDBTBPDBq-II
(vii)
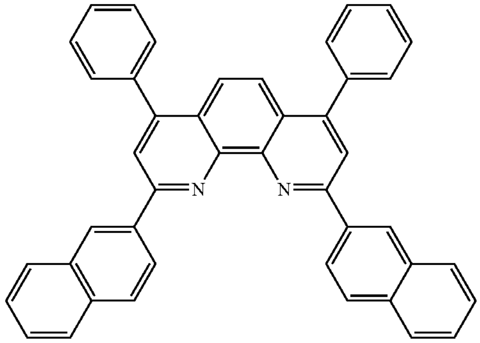
NBPhen -continued (viii)

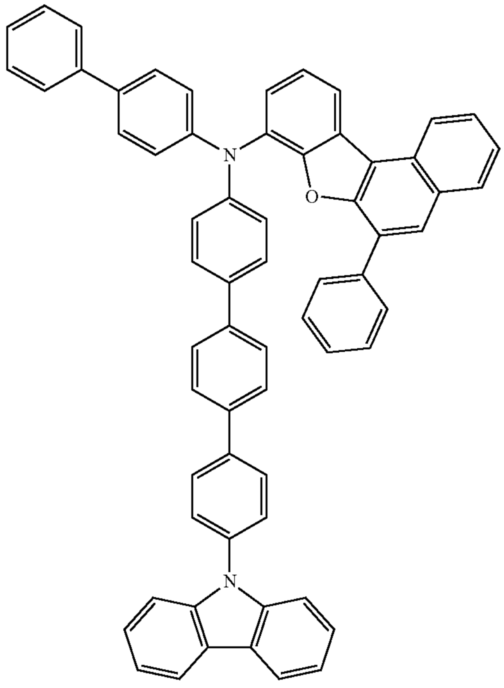

YGTBiBnf (ix)

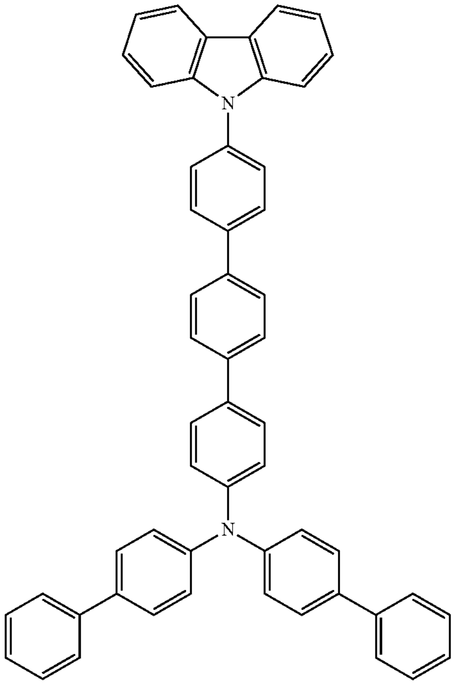

YGTBi1BP (Fabrication Method of Light-Emitting Element 1)

First, a film of indium tin oxide containing silicon oxide (ITSO) was formed over a glass substrate by a sputtering method, so that the first electrode 101 was formed. Note that the thickness was 70 nm and the area of the electrode was 2 mm×2 mm.

Next, in pretreatment for forming the light-emitting element over the substrate, the surface of the substrate was washed with water and baked at 200° C. for 1 hour, and then UV ozone treatment was performed for 370 seconds.

After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Then, the substrate over which the first electrode 101 was formed was fixed to a substrate holder provided in the vacuum evaporation apparatus so that the surface over which the first electrode 101 was formed faced downward; and over the first electrode 101, 2,3,6,7,10,11-hexacyano-1,4,5,8,9,12-hexaazatriphenylene (abbreviation: HAT-CN) represented by Structural Formula (i) above was evaporated to 5 nm by an evaporation method using resistance heating, so that the hole-injection layer 111 was formed.

Next, 4,4'-bis[N-(1-naphthyl)-N-phenylamino]biphenyl (abbreviation: NPB) represented by Structural Formula (ii) above was deposited to a thickness of 20 nm over the hole-injection layer 111 by evaporation, whereby the first hole-transport layer 112-1 was formed; and N-[4'-(9H-carbazol-9-yl)-1,1'-biphenyl-4-yl]-N-(1,1'-biphenyl-4-yl)-6-phenylbenzo[b]naphtho[1,2-d]furan-8-amine (abbreviation: YGBBiBnf) represented by Structural Formula (iii) above was deposited to a thickness of 10 nm over the first hole-transport layer 112-1 by evaporation, whereby the second hole-transport layer 112-2 was formed.

Subsequently, 7-[4-(10-phenyl-9-anthryl)phenyl]-7H-dibenzo[cg]carbazole (abbreviation: cgDBCzPA) represented by Structural Formula (iv) above and N,N-(pyrene-1,6-diyl)bis[(6,N-diphenylbenzo[b]naphtho[1,2-d]furan)-8-amine] (abbreviation: 1,6BnfAPrn-03) represented by Structural Formula (v) above were deposited to 25 nm by co-evaporation at a weight ratio of 1:0.03 (=cgDBCzPA:1,6BnfAPrn-03), whereby the light-emitting layer 113 was formed.

After that, over the light-emitting layer 113, 2-[3'-(dibenzothiophen-4-yl)biphenyl-3-yl]dibenzo[f,h]quinoxaline (abbreviation: 2mDBTBPDBq-II) represented by Structural Formula (vi) above was deposited by evaporation to a thickness of 15 nm, and then 2,9-bis(naphthalen-2-yl)-4,7-diphenyl-1,10-phenanthroline (abbreviation: NBPhen) represented by Structural Formula (vii) above was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the second electrode 102, whereby the light-emitting element 1 of this example was fabricated.

(Fabrication Method of Light-Emitting Element 2)

The light-emitting element 2 was fabricated in a manner similar to that of the light-emitting element 1 except that N-[4"-(9H-carbazol-9-yl)1,1':4',1"-terphenyl-4-yl]-N-(1,1'-biphenyl-4-yl)-6-phenylbenzo[b]naphtho[1,2-d]furan-8-amine (abbreviation: YGTBiBnf) represented by Structural Formula (viii) above was used instead of YGBBiBnf in the second hole-transport layer 112-2.

(Fabrication Method of Comparative Light-Emitting Element 1)

The comparative light-emitting element 1 was fabricated in a manner similar to that of the light-emitting element 1 except that 4,4'-diphenyl-4"-[4'-(carbazol-9-yl)biphenyl-4-yl]triphenylamine (abbreviation: YGTBi1BP) represented by Structural Formula (ix) above was used instead of YGBBiBnf in the second hole-transport layer 112-2.

The element structures of the light-emitting element 1, the light-emitting element 2, and the comparative light-emitting element 1 are listed in the following table.

TABLE 1

| | Hole-injection layer | Hole-transport layer 1 | Hole-transport layer 2 | Light-emitting layer | Electron-transport layer | | Electron-injection layer |
|---|---|---|---|---|---|---|---|
| | 5 nm | 20 nm | 10 nm | 25 nm | 15 nm | 10 nm | 1 nm |
| Light-emitting element 1 | HAT-CN | NPB | YGBBiBnf | cgDBCzPA: | 2mDBTBPDBq-II | NBPhen | LiF |
| Light-emitting element 2 | | | YGTBiBnf | 1,6BnfAPrn-03 | | | |
| Comparative light-emitting element 1 | | | YGTBi1BP | (1:0.03) | | | |

The light-emitting element 1, the light-emitting element 2, and the comparative light-emitting element 1 were subjected to sealing with a glass substrate (a sealant was applied to surround the element, followed by UV treatment and one-hour heat treatment at 80° C. at the time of sealing) in a glove box containing a nitrogen atmosphere so that the light-emitting elements are not exposed to the air, and then the initial characteristics and reliabilities of these light-emitting elements were measured. Note that the measurement was performed at room temperature.

Figure 23:
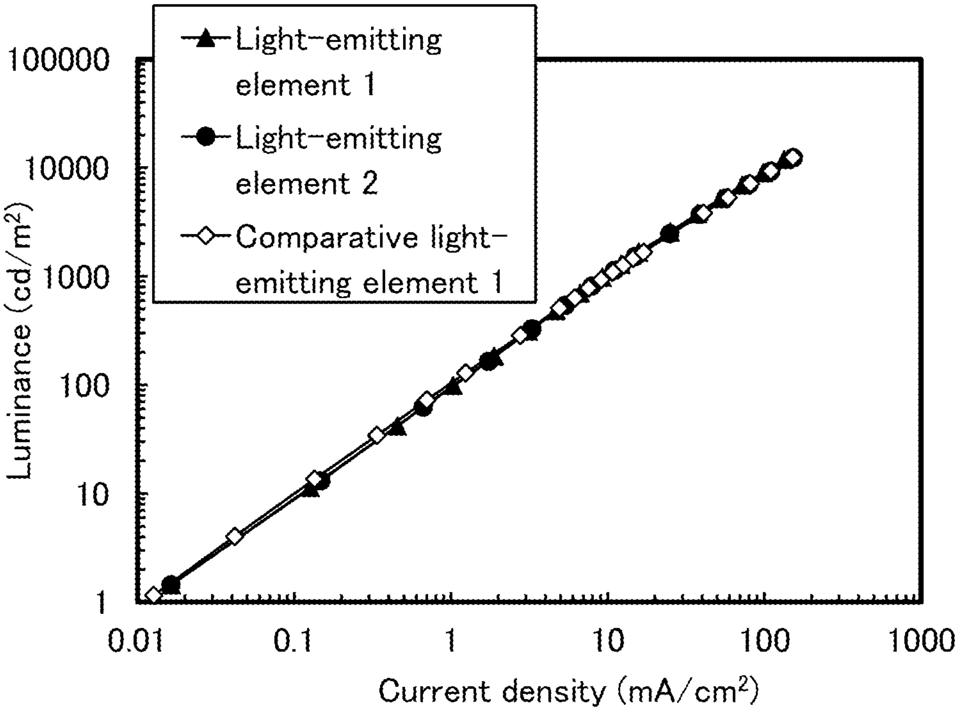
FIG. 23 Luminance-current density characteristics of a light-emitting element 1, a light-emitting element 2, and a comparative light-emitting element 1.
Figure 24:
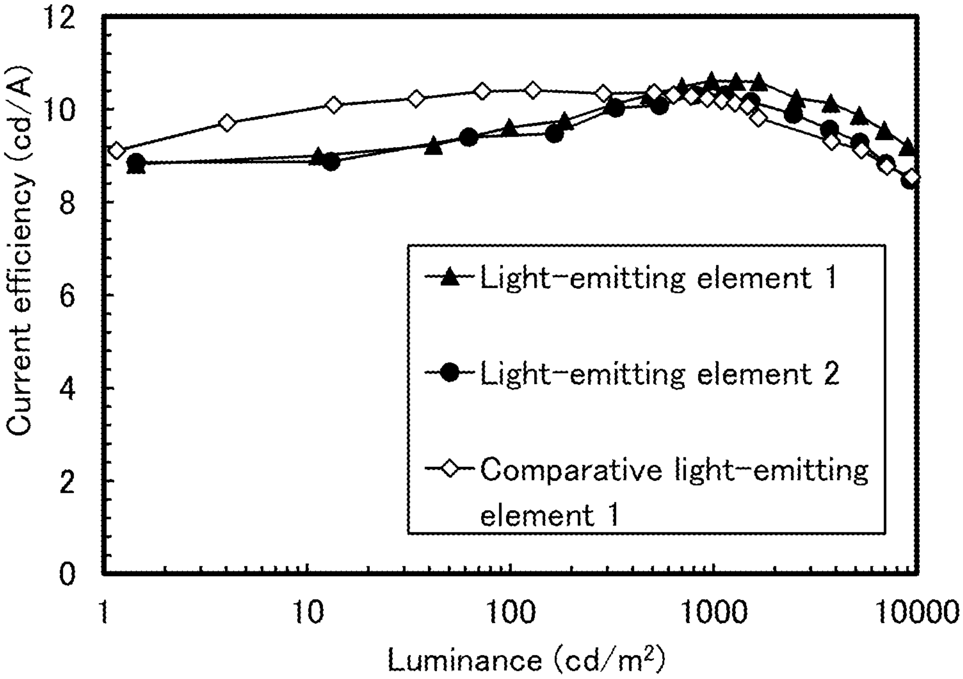
FIG. 24 Current efficiency-luminance characteristics of the light-emitting element 1, the light-emitting element 2, and the comparative light-emitting element 1.
Figure 25:
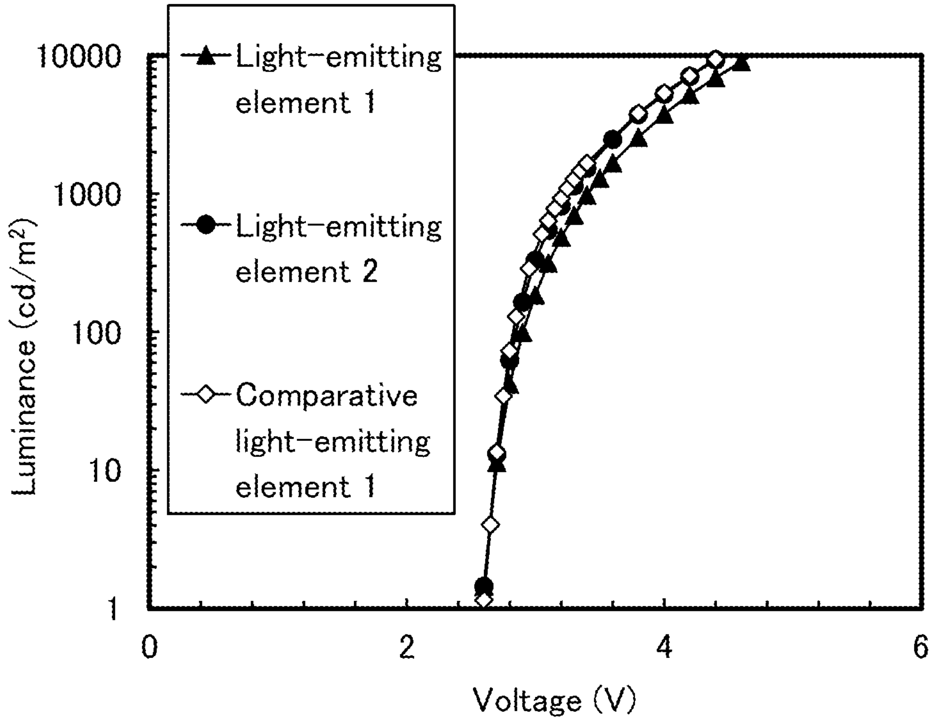
FIG. 25 Luminance-voltage characteristics of the light-emitting element 1, the light-emitting element 2, and the comparative light-emitting element 1.
Figure 26:
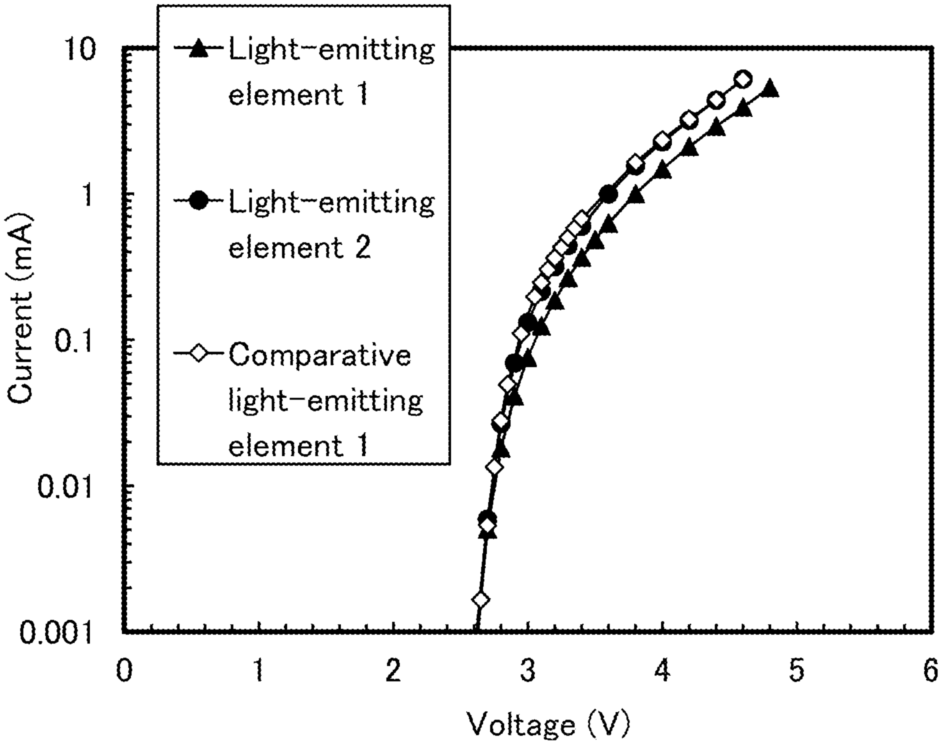
FIG. 26 Current-voltage characteristics of the light-emitting element 1, the light-emitting element 2, and the comparative light-emitting element 1.
Figure 27:
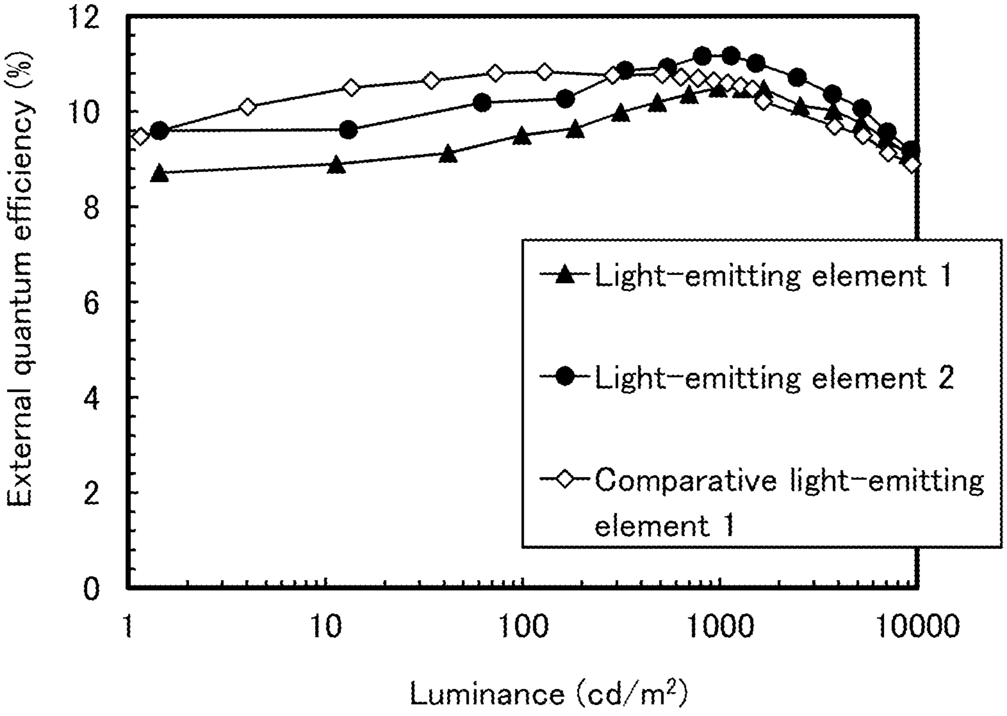
FIG. 27 External quantum efficiency-luminance characteristics of the light-emitting element 1, the light-emitting element 2, and the comparative light-emitting element 1.
Figure 28:
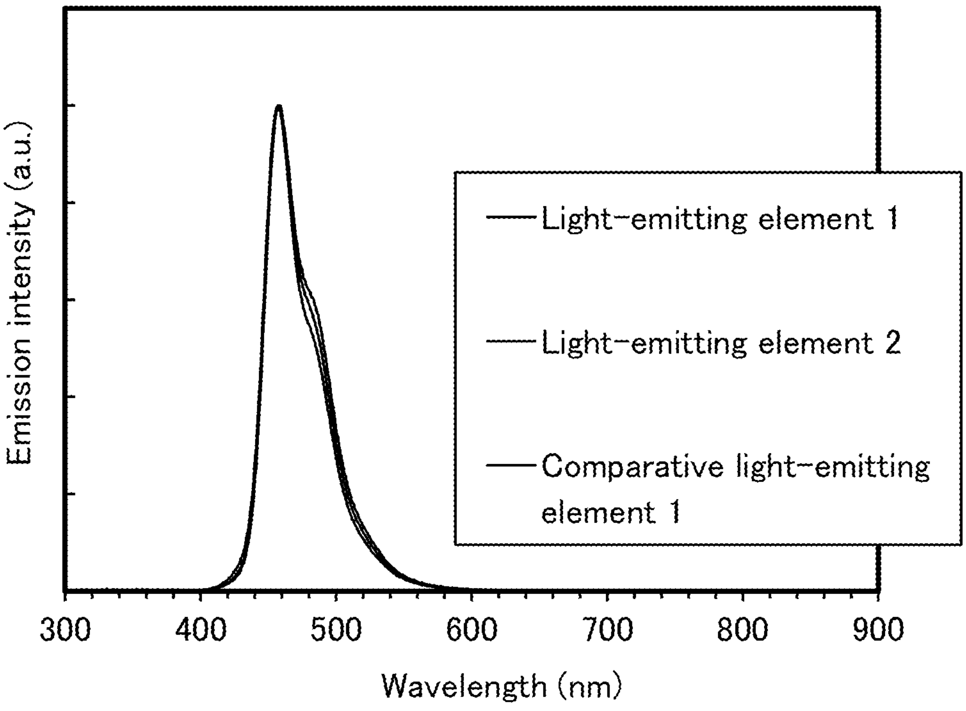
FIG. 28 Emission spectra of the light-emitting element 1, the light-emitting element 2, and the comparative light-emitting element 1.

FIG. 23 shows the luminance-current density characteristics of the light-emitting element 1, the light-emitting element 2, and the comparative light-emitting element 2; FIG. 24 shows the current efficiency-luminance characteristics thereof, FIG. 25 shows the luminance-voltage characteristics thereof; FIG. 26 shows the current-voltage characteristics thereof; FIG. 27 shows the external quantum efficiency-luminance characteristics thereof; and FIG. 28 shows the emission spectra thereof. In addition, Table 2 shows the main characteristics of each of the light-emitting elements at around 1000 cd/m$^2$.

TABLE 2

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting element 1 | 3.4 | 0.37 | 9.2 | 0.14 | 0.13 | 10.6 | 10.5 |
| Light-emitting element 2 | 3.3 | 0.44 | 11.0 | 0.14 | 0.11 | 10.3 | 11.2 |
| Comparative light-emitling element 1 | 3.2 | 0.36 | 9.1 | 0.14 | 0.12 | 10.2 | 10.6 |

It was found from FIG. 22 to FIG. 28 and Table 2 that the light-emitting element 1 and the light-emitting element 2, which are one embodiment of the present invention, were blue light-emitting elements with favorable characteristics such as driving voltage and emission efficiency.

Figure 29:
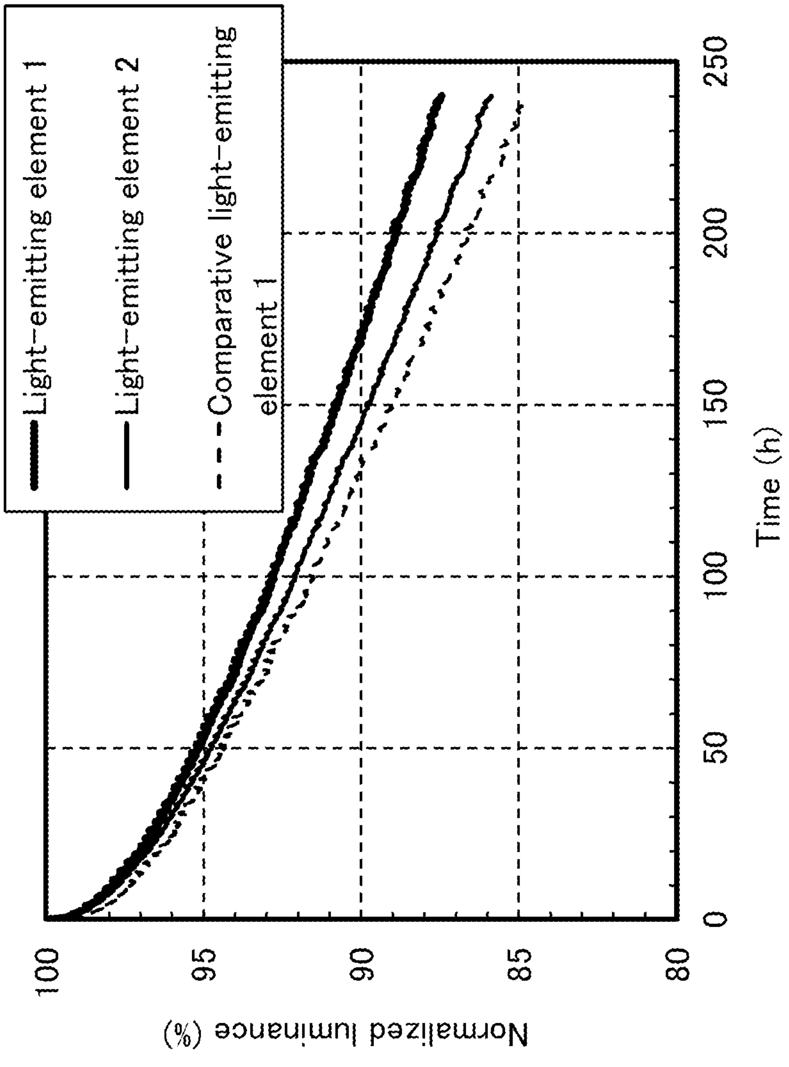
FIG. 29 A graph showing a change in luminance over driving time at a current density of 50 $mA/cm^2$ of the light-emitting element 1, the light-emitting element 2, and the comparative light-emitting element 1.

A graph showing a change in luminance over driving time at a current density of 50 mA/cm$^2$ is shown in FIG. 29. As shown in FIG. 29, decreases in luminance over driving time of the light-emitting element 1 and the light-emitting element 2, which are light-emitting elements of one embodiment of the present invention, were smaller than that of the comparative light-emitting element 1, showing that the use of the organic compound of one embodiment of the present invention, which has a benzonaphthofuranyl group instead of a biphenyl group as a substituent of the amine, provides the long-lifetime light-emitting elements.

Example 5

In this example, a light-emitting element 3 and a light-emitting element 4 of one embodiment of the present invention described in Embodiment 2 will be described. The structural formulae of organic compounds used in the light-emitting element 3 and the light-emitting element 4 are shown below.

[Chemical Formula 79]

(i)

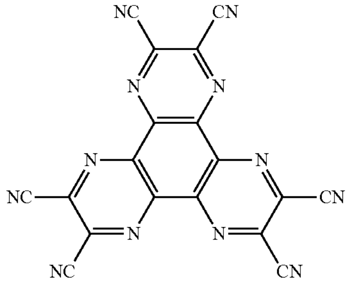

HAT-CN

-continued (ii)

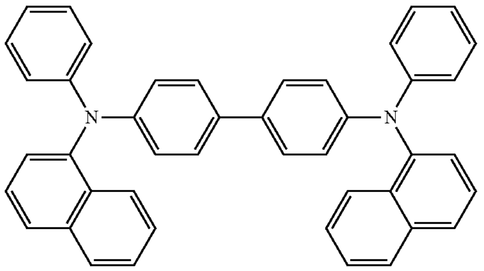

NPB

-continued
(iii)
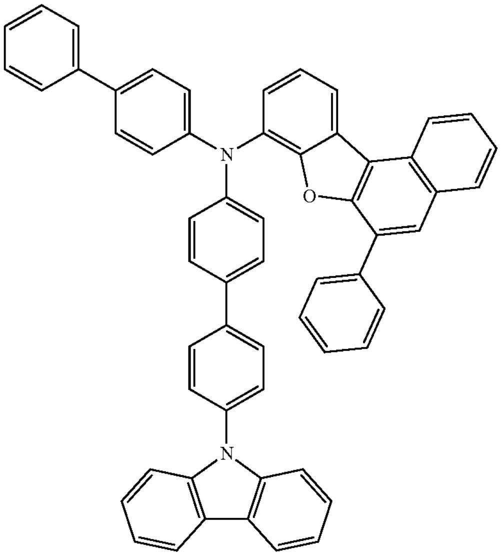
YGBBiBnf
(iv)
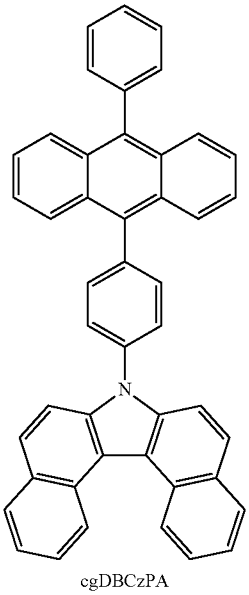
cgDBCzPA
-continued
(v)
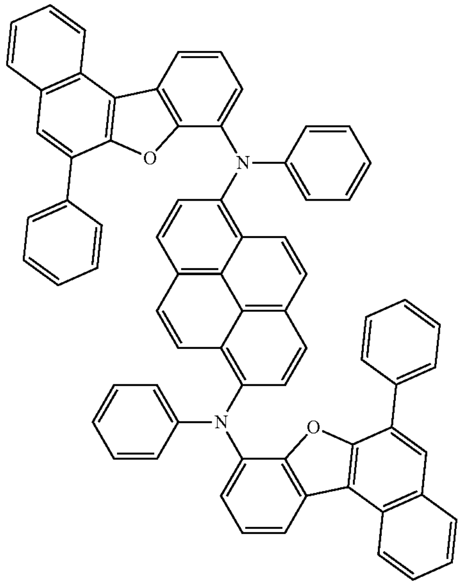
1,6BnfAPrn-03
(vi)
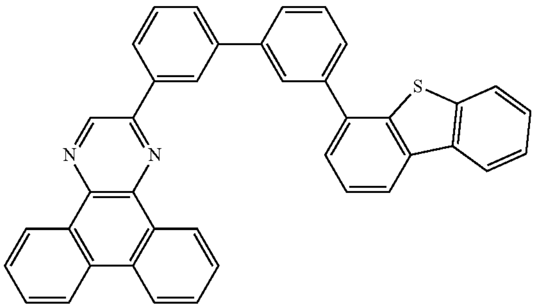
2mDBTBPDBq-II
(vii)
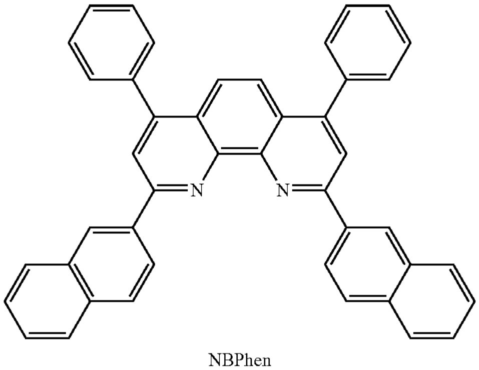
NBPhen -continued (viii)

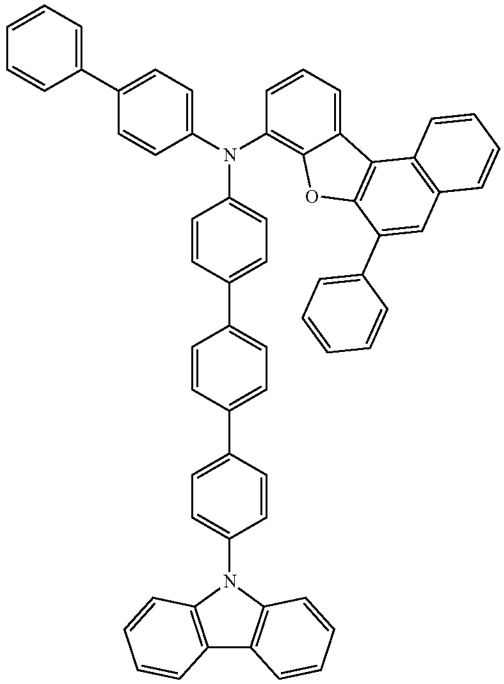

YGTBiBnf (x)

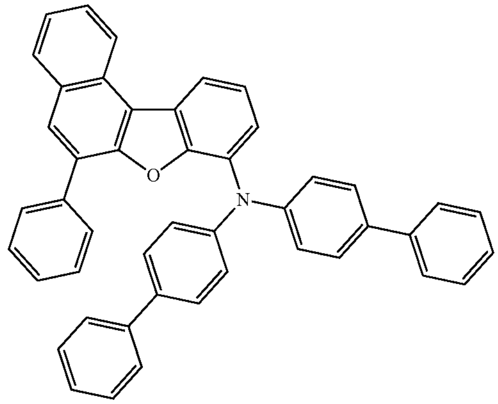

BBABnf (Fabrication Method of Light-Emitting Element 3)

First, a film of indium tin oxide containing silicon oxide (ITSO) was formed over a glass substrate by a sputtering method, so that the first electrode 101 was formed. Note that the thickness was 70 nm and the area of the electrode was 2 mm×2 mm.

Next, in pretreatment for forming the light-emitting element over the substrate, the surface of the substrate was washed with water and baked at 200° C. for 1 hour, and then UV ozone treatment was performed for 370 seconds.

After that, the substrate was transferred into a vacuum evaporation apparatus in which the pressure was reduced to approximately 104 Pa, vacuum baking at 170° C. for 30 minutes was performed in a heating chamber in the vacuum evaporation apparatus, and then the substrate was cooled down for approximately 30 minutes.

Then, the substrate over which the first electrode 101 was formed was fixed to a substrate holder provided in the vacuum evaporation apparatus so that the surface over which the first electrode 101 was formed faced downward; and over the first electrode 101, 2,3,6,7,10,11-hexacyano-1,4,5,8,9,12-hexaazatriphenylene (abbreviation: HAT-CN) represented by Structural Formula (i) above was evaporated to 5 nm by an evaporation method using resistance heating, so that the hole-injection layer 111 was formed.

Next, 4,4'-bis[N-(1-naphthyl)-N-phenylamino]biphenyl (abbreviation: NPB) represented by Structural Formula (ii) above was deposited to a thickness of 20 nm over the hole-injection layer 111 by evaporation, whereby the first hole-transport layer 112-1 was formed; and N-[4'-(9H-carbazol-9-yl)-1,1'-biphenyl-4-yl]-N-(1,1'-biphenyl-4-yl)-6-phenylbenzo[b]naphtho[1,2-d]furan-8-amine (abbreviation: YGBBiBnf) represented by Structural Formula (iii) above was deposited to a thickness of 10 nm over the first hole-transport layer 112-1 by evaporation, whereby the second hole-transport layer 112-2 was formed.

Subsequently, 7-[4-(10-phenyl-9-anthryl)phenyl]-7H-dibenzo[c,g]carbazole (abbreviation: cgDBCzPA) represented by Structural Formula (iv) above and N,N-(pyrene-1,6-diyl)bis[(6,N-diphenylbenzo[b]naphtho[1,2-d]furan)-8-amine] (abbreviation: 1,6BnfAPrn-03) represented by Structural Formula (v) above were deposited to 25 nm by co-evaporation at a weight ratio of 1:0.03 (=cgDBCzPA:1,6BnfAPrn-03), whereby the light-emitting layer 113 was formed.

After that, over the light-emitting layer 113, 2-[3'-(dibenzothiophen-4-yl)biphenyl-3-yl]dibenzo[f,h]quinoxaline (abbreviation: 2mDBTBPDBq-II) represented by Structural Formula (vi) above was deposited by evaporation to a thickness of 15 nm, and then 2,9-bis(naphthalen-2-yl)-4,7-diphenyl-1,10-phenanthroline (abbreviation: NBPhen) represented by Structural Formula (vii) above was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the second electrode 102, whereby the light-emitting element 1 of this example was fabricated.

(Fabrication Method of Light-Emitting Element 4)

The light-emitting element 4 was fabricated in a manner similar to that of the light-emitting element 3 except that N-[4"-(9H-carbazol-9-yl)1,1':4',1"-terphenyl-4-yl]-N-(1,1'-biphenyl-4-yl)-6-phenylbenzo[b]naphtho[1,2-d]furan-8-amine (abbreviation: YGTBiBnf) represented by Structural Formula (viii) above was used instead of YGBBiBnf in the second hole-transport layer 112-2.

(Fabrication Method of Comparative Light-Emitting Element 2)

The comparative light-emitting element 2 was fabricated in a manner similar to that of the light-emitting element 3 except that N,N-bis(4-biphenyl)-6-phenylbenzo[b]naphtho[1,2-d]furan-8-amine (abbreviation: BBABnf) represented by Structural Formula (x) above was used instead of YGBBiBnf in the second hole-transport layer 112-2.

The element structures of the light-emitting element 3, the light-emitting element 4, and the comparative light-emitting element 2 are listed in the following table.

TABLE 3

| | Hole-injection layer | Hole-transport layer | | Light-emitting layer | Electron-transport layer | | Electron-injection layer |
|---|---|---|---|---|---|---|---|
| | | 1 | 2 | | | | |
| | 5 nm | 20 nm | 10 nm | 25 nm | 15 nm | 10 nm | 1 nm |
| Light-emitting element 3 | HAT-CN | NPB | YGBBiBnf | cgDBCzPA: 1,6BnfAPrn-03 (1:0.03) | 2mDBTBPDBq-II | NBPhen | LiF |
| Light-emitting element 4 | | | YGTBiBnf | | | | |
| Comparative light-emitting element 2 | | | BBABnf | | | | |

The light-emitting element 3, the light-emitting element 4, and the comparative light-emitting element 2 were subjected to sealing with a glass substrate (a sealant was applied to surround the element, followed by UV treatment and one-hour heat treatment at 80° C. at the time of sealing) in a glove box containing a nitrogen atmosphere so that the light-emitting elements are not exposed to the air, and then the initial characteristics of these light-emitting elements were measured. Note that the measurement was performed at room temperature.

Figure 30:
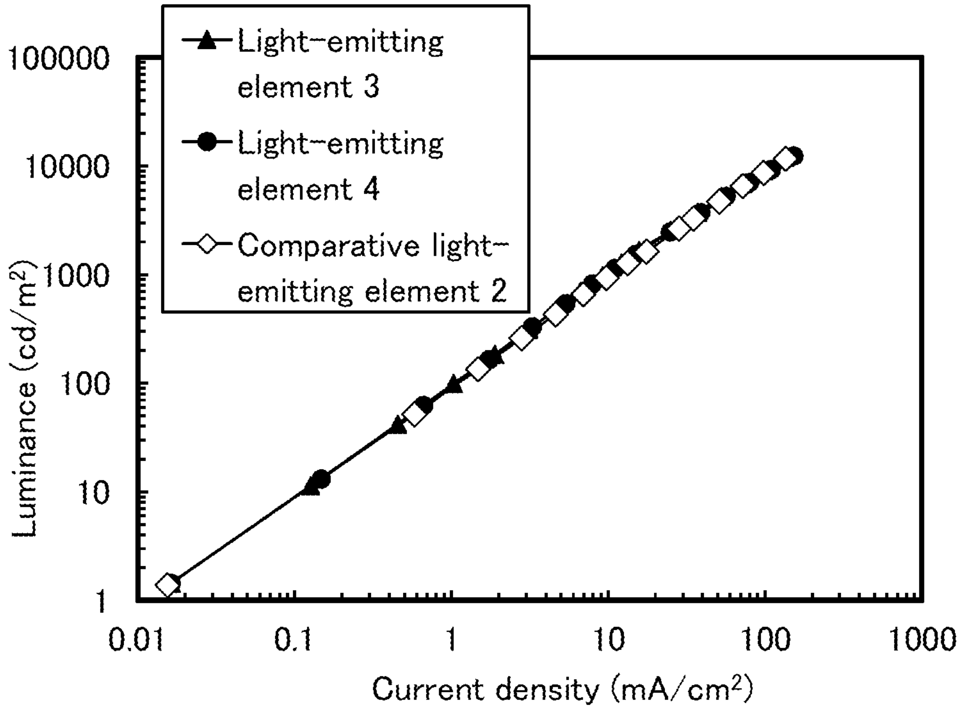
FIG. 30 Luminance-current density characteristics of a light-emitting element 3, a light-emitting element 4, and a comparative light-emitting element 2.
Figure 31:
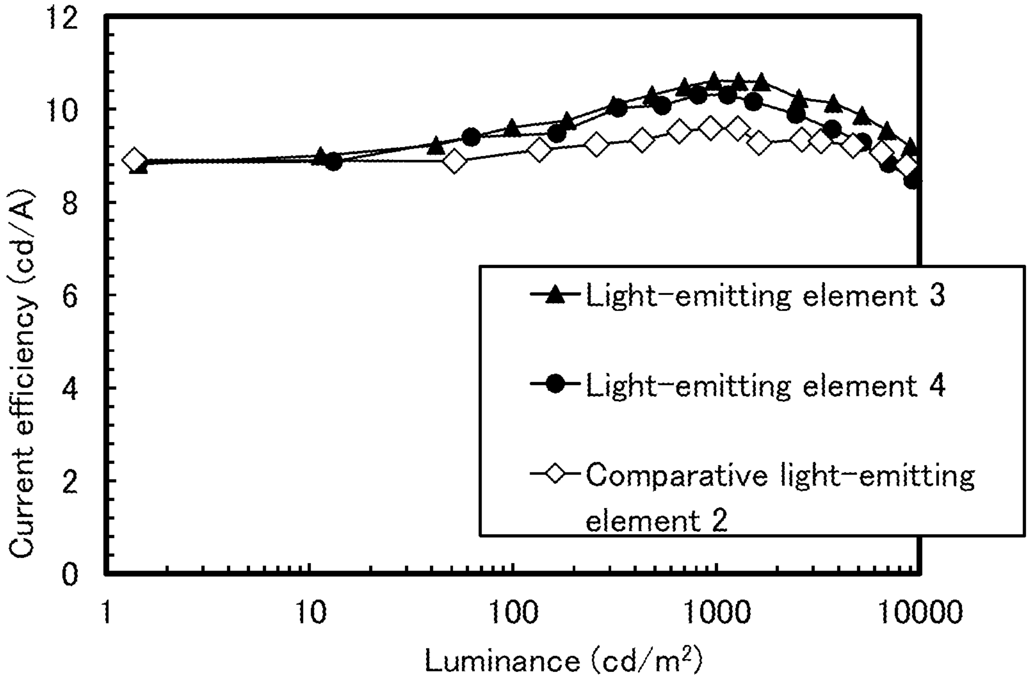
FIG. 31 Current efficiency-luminance characteristics of the light-emitting element 3, the light-emitting element 4, and the comparative light-emitting element 2.
Figure 32:
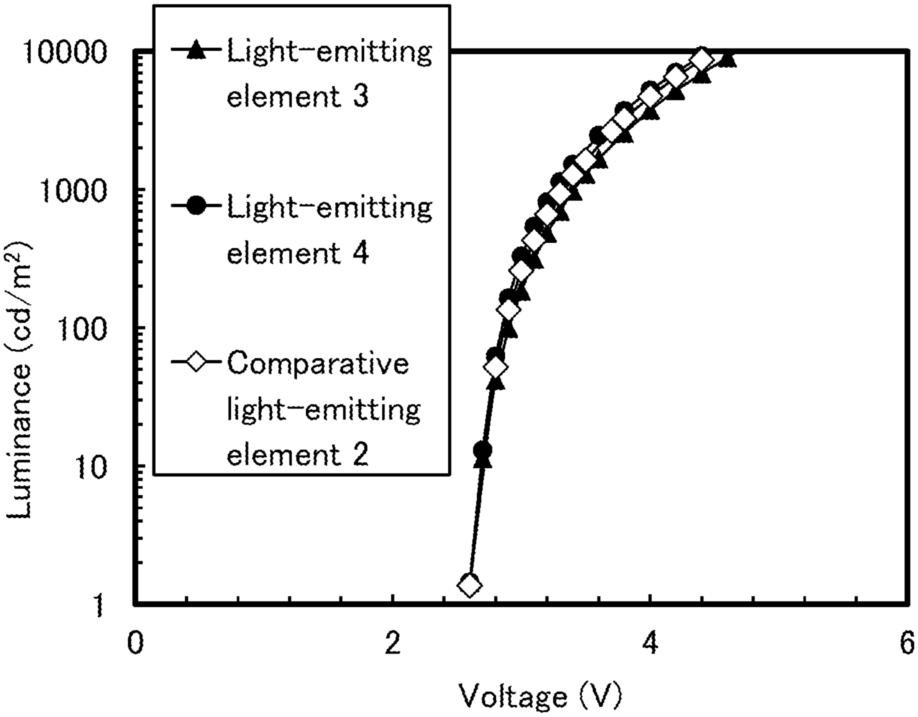
FIG. 32 Luminance-voltage characteristics of the light-emitting element 3, the light-emitting element 4, and the comparative light-emitting element 2.
Figure 33:
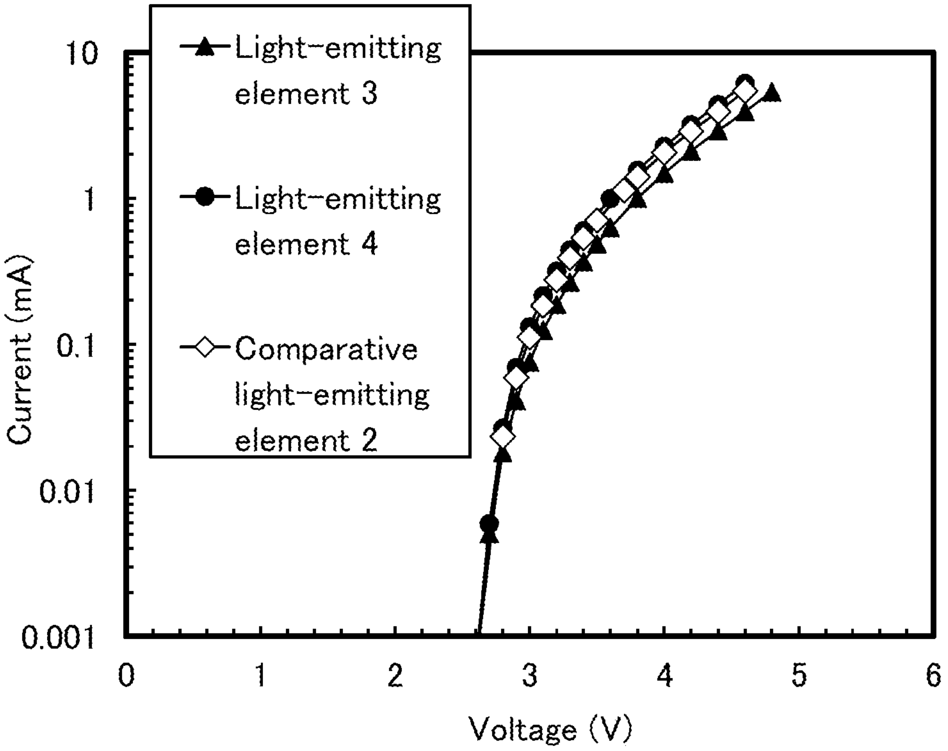
FIG. 33 Current-voltage characteristics of the light-emitting element 3, the light-emitting element 4, and the comparative light-emitting element 2.
Figure 34:
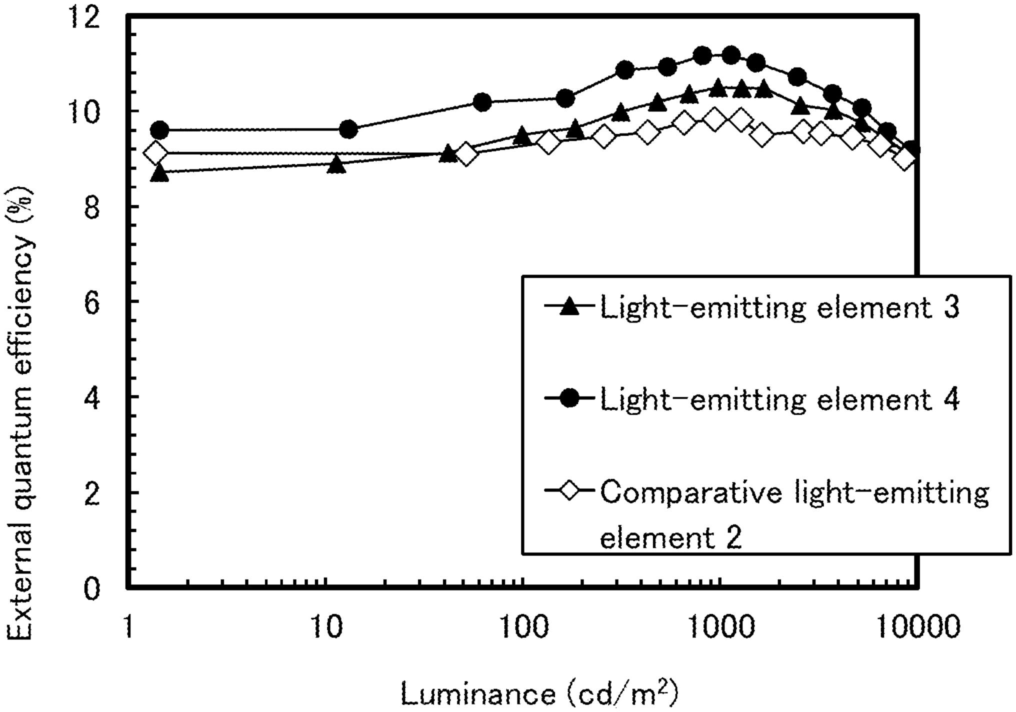
FIG. 34 External quantum efficiency-luminance characteristics of the light-emitting element 3, the light-emitting element 4, and the comparative light-emitting element 2.
Figure 35:
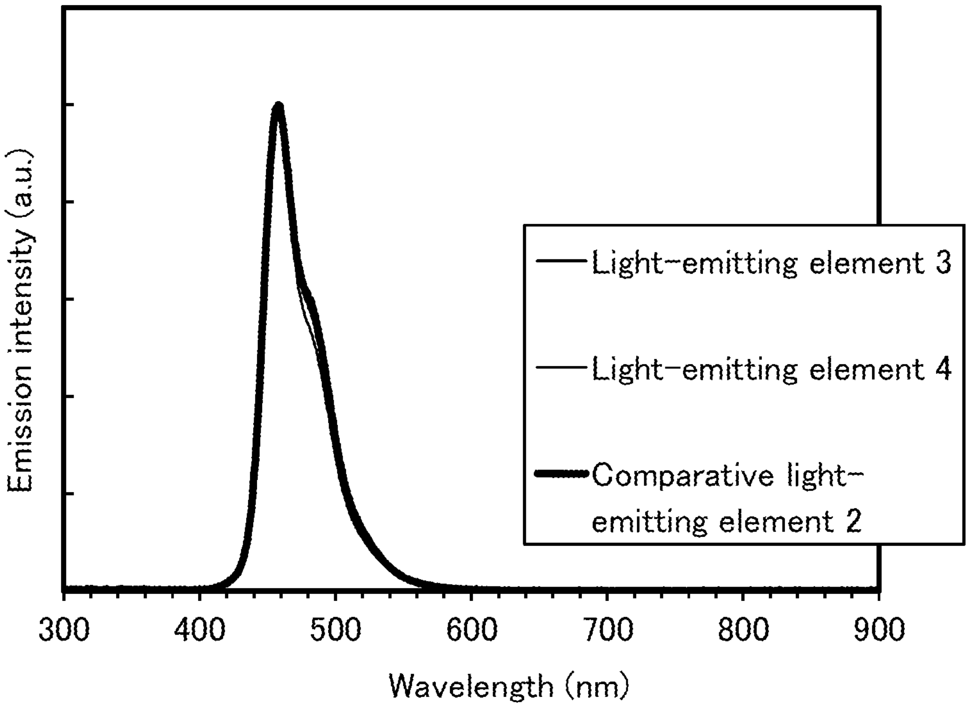
FIG. 35 Emission spectra of the light-emitting element 3, the light-emitting element 4, and the comparative light-emitting element 2.

FIG. 30 shows the luminance-current density characteristics of the light-emitting element 3, the light-emitting element 4, and the comparative light-emitting element 2; FIG. 31 shows the current efficiency-luminance characteristics thereof; FIG. 32 shows the luminance-voltage characteristics thereof; FIG. 33 shows the current-voltage characteristics thereof, FIG. 34 shows the external quantum efficiency-luminance characteristics thereof, and FIG. 35 shows the emission spectra thereof. In addition, Table 4 shows the main characteristics of each of the light-emitting elements at around 1000 cd/$m^2$.

TABLE 4

| | Voltage (V) | Current (mA) | Current density (mA/$cm^2$) | Chromaticity x | Chromaticity y | Current efficiency (cd/A) | External quantum efficiency (%) |
|---|---|---|---|---|---|---|---|
| Light-emitting element 3 | 3.4 | 0.37 | 9.2 | 0.14 | 0.13 | 10.6 | 10.5 |
| Light-emitting element 4 | 3.3 | 0.44 | 11.0 | 0.14 | 0.11 | 10.3 | 11.2 |
| Comparative light-emitting element 2 | 3.3 | 0.39 | 9.8 | 0.14 | 0.12 | 9.6 | 9.8 |

It was found from FIG. 30 to FIG. 35 and Table 4 that the light-emitting element 3 and the light-emitting element 4 of one embodiment of the present invention were blue light-emitting elements with favorable characteristics such as driving voltage and emission efficiency. When the organic compound in which not only the benzonaphthofuranyl group but also a carbazolyl group is bonded to the amine skeleton as a substituent is used as a hole-transport material, the carrier balance is improved and a highly efficient element can be fabricated.

Example 6

In this example, a light-emitting element 5 of one embodiment of the present invention and a comparative light-emitting element 3 will be described. The structural formulae of organic compounds used in the light-emitting element 5 and the comparative light-emitting element 3 are shown below.

[Chemical Formula 80]
(xi)
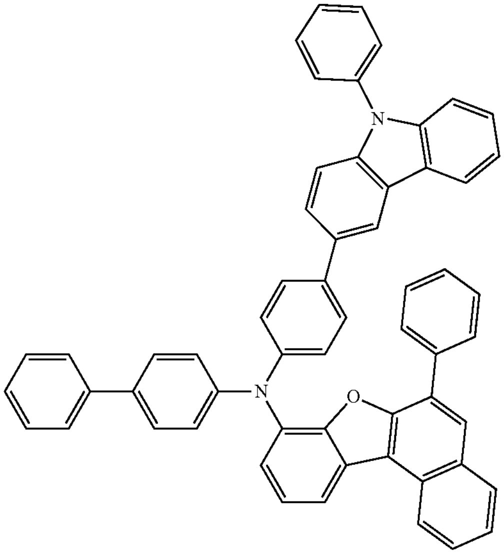
PCBBiBnf
(xii)
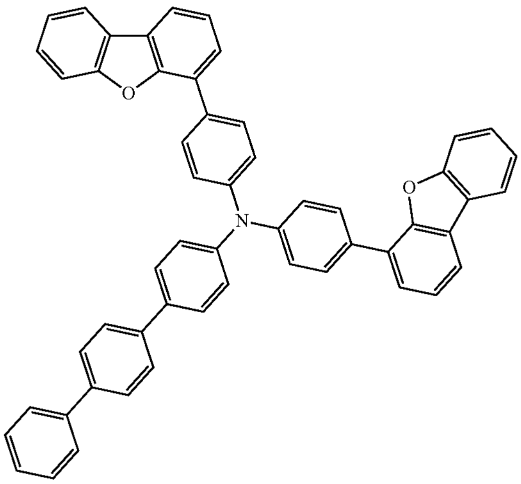
DBfBB1TP
-continued
(iv)
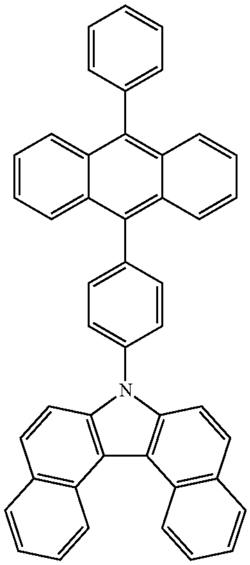
cgDBCzPA
(v)
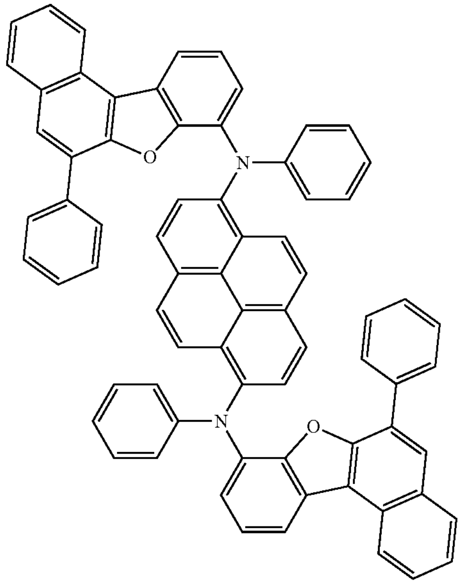
1,6BnfAPrn-03

-continued (xiv)

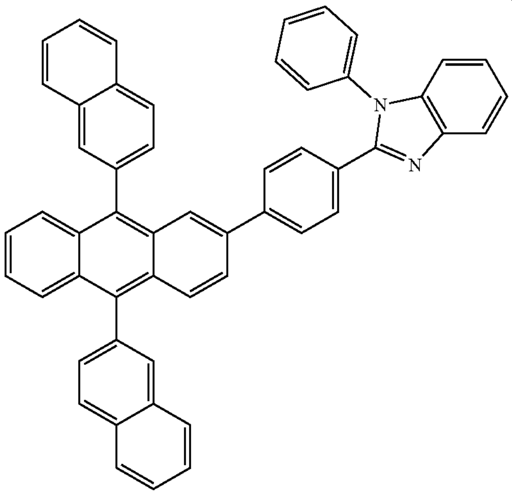

ZADN (xv)

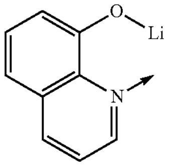

Liq (xiii)

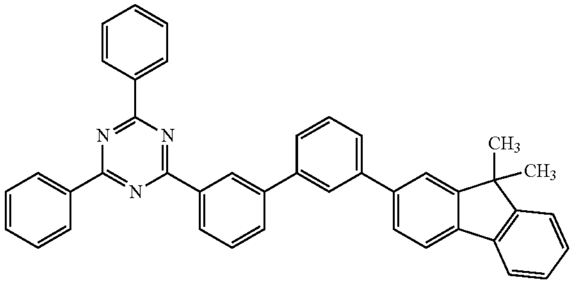

mFBPTzn

-continued (xvi)

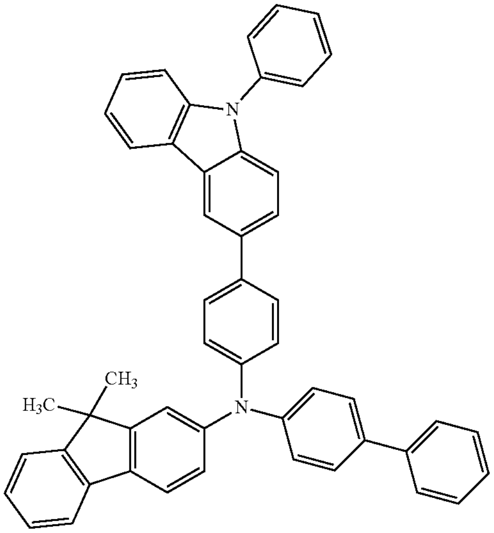

PCBBiF (Fabrication Method of Light-Emitting Element 5)

First, a film of indium tin oxide containing silicon oxide (ITSO) was formed over a glass substrate by a sputtering method, so that the first electrode 101 was formed. Note that the thickness was 70 nm and the area of the electrode was 2 mm×2 mm.

Next, in pretreatment for forming the light-emitting element over the substrate, the surface of the substrate was washed with water and baked at 200° C. for 1 hour, and then UV ozone treatment was performed for 370 seconds.

After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Then, the substrate over which the first electrode 101 was formed was fixed to a substrate holder provided in the vacuum evaporation apparatus so that the surface over which the first electrode 101 was formed faced downward; and over the first electrode 101, N-(1,1'-biphenyl-4-yl)-6-phenyl-N-[4-(9-phenylcarbazol-3-yl)phenyl]benzo[b]naptho[d]furan-8-amine (abbreviation: PCBBiBnf) represented by Structural Formula (xi) above and NDP-9 (produced by Analysis Atelier Corporation, material serial No. 1S20170124) were co-evaporated to 10 nm at a weight ratio of 1:0.1 (=PCBBiBnf: NDP-9) by an evaporation method using resistance heating, so that the hole-injection layer 111 was formed.

Next, over the hole-injection layer 111, PCBBiBnf was deposited to 20 nm by evaporation as the first hole-transport layer 112-1, and then N,N-bis[4-(dibenzofuran-4-yl)phenyl]-4-amino-p-terphenyl (abbreviation: DBfBB1TP) represented by Structural Formula (xii) above was evaporated to 10 nm as the second hole-transport layer 112-2, whereby the hole-transport layer 112 was formed.

Subsequently, 7-[4-(10-phenyl-9-anthryl)phenyl]-7H-dibenzo[c,g]carbazole (abbreviation: cgDBCzPA) represented by Structural Formula (iv) above and N,N-(pyrene- 1,6-diyl)bis[(6,N-diphenylbenzo[b]naphtho[1,2-d]furan)-8-amine] (abbreviation: 1,6BnfAPrn-03) represented by Structural Formula (v) above were co-evaporated to 25 nm at a weight ratio of 1:0.03 (=cgDBCzPA:1,6BnfAPrn-03), whereby the light-emitting layer 113 was formed.

After that, over the light-emitting layer 113, 2-[3'-(9,9-dimethyl-9H-fluoren-2-yl)-1,1'-biphenyl-3-yl]-4,6-diphenyl-1,3,5-triazine (abbreviation: mFBPTzn) represented by Structural Formula (xiii) above was deposited by evaporation to a thickness of 10 nm, and then 2-{4-[9,10-di(naphthalen-2-yl)-2-anthryl]phenyl}-1-phenyl-1H-benzoimidazole (abbreviation: ZADN) represented by Structural Formula (xiv) above and 8-hydroxyquinolinolato-lithium (abbreviation: Liq) represented by Structural Formula (xv) above were co-evaporated to 15 nm at a weight ratio of 1:1 (=ZADN:Liq), whereby the electron-transport layer 114 was formed.

After the formation of the electron-transport layer 114, Liq was deposited by evaporation to a thickness of 1 nm to form the electron-injection layer 115, and then aluminum was deposited by evaporation to a thickness of 200 nm to form the second electrode 102, whereby the light-emitting element 3 of this example was fabricated.

(Fabrication Method of Comparative Light-Emitting Element 3)

The comparative light-emitting element 3 was fabricated in a manner similar to that of the light-emitting element 5 except that N-(1,1'-biphenyl-4-yl)-9,9-dimethyl-N-[4-(9-phenyl-9H-carbazol-3-yl)phenyl]-9H-fluoren-2-amine (abbreviation: PCBBiF) represented by Structural Formula (xvi) above was used instead of PCBBiBnf in the light-emitting element 5.

The element structures of the light-emitting element 5 and the comparative light-emitting element 3 are listed in the following table.

TABLE 5

| | Hole-injection layer | Hole-transport layer 1 | Hole-transport layer 2 | Light-emitting layer | Electron-transport layer | | Electron-injection layer |
|---|---|---|---|---|---|---|---|
| | 10 nm | 20 nm | 10 nm | 25 nm | 10 nm | 15 nm | 1 nm |
| Light-emitting element 5 | PCBBiBnf: NDP-9 (1:0.1) | PCBBiBnf | DBfBB1TP | cgDBCzPA: 1,6BnfAPrn-03 (1:0.03) | mFBPTzn | ZADN: Liq (1:1) | Liq |
| Comparative light-emitting element 3 | PCBBiF: NDP-9 (1:0.1) | PCBBiF | | | | | |

The light-emitting element 5 and the comparative light-emitting element 3 were subjected to sealing with a glass substrate (a sealant was applied to surround the element, followed by UV treatment and one-hour heat treatment at 80° C. at the time of sealing) in a glove box containing a nitrogen atmosphere so that the light-emitting elements are not exposed to the air, and then the initial characteristics and reliabilities of these light-emitting elements were measured. Note that the measurement was performed at room temperature.

Figure 36:
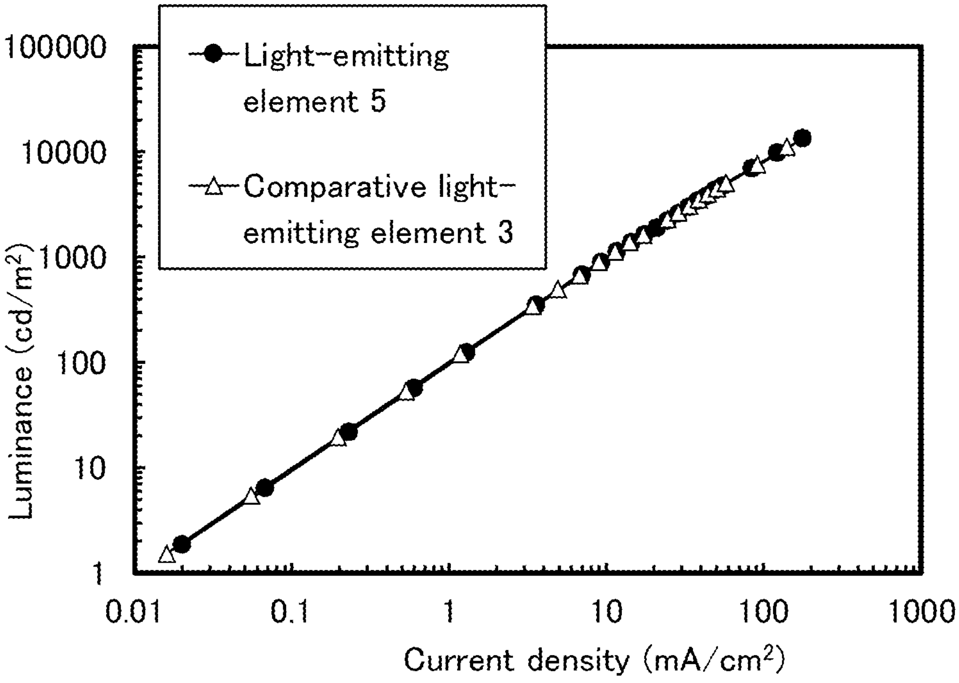
FIG. 36 Luminance-current density characteristics of a light-emitting element 5 and a comparative light-emitting element 3.
Figure 37:
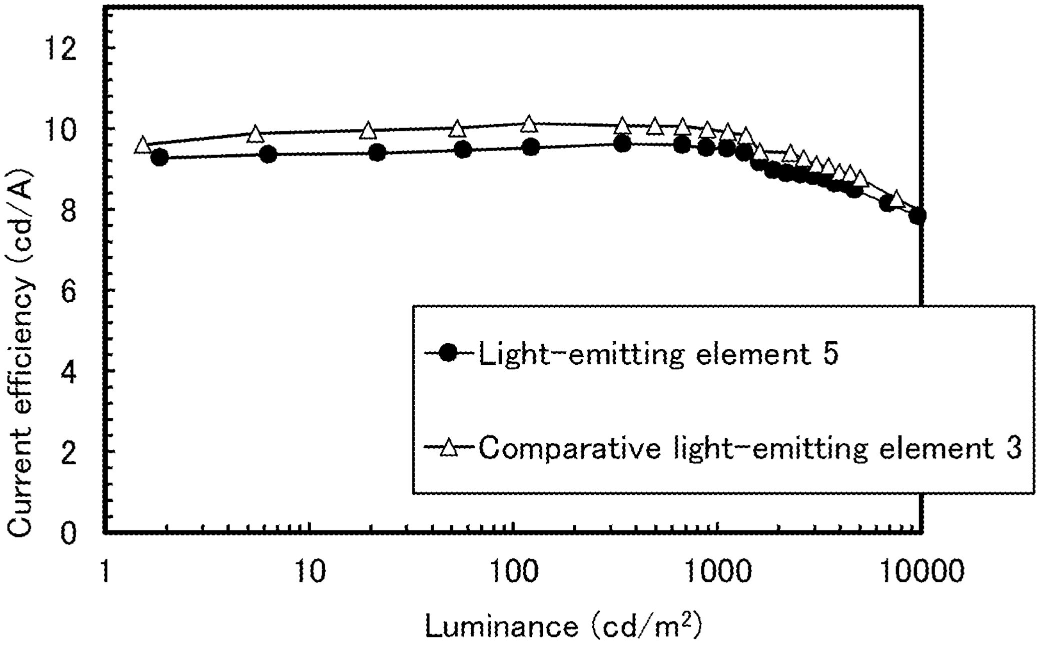
FIG. 37 Current efficiency-luminance characteristics of the light-emitting element 5 and the comparative light-emitting element 3.
Figure 38:
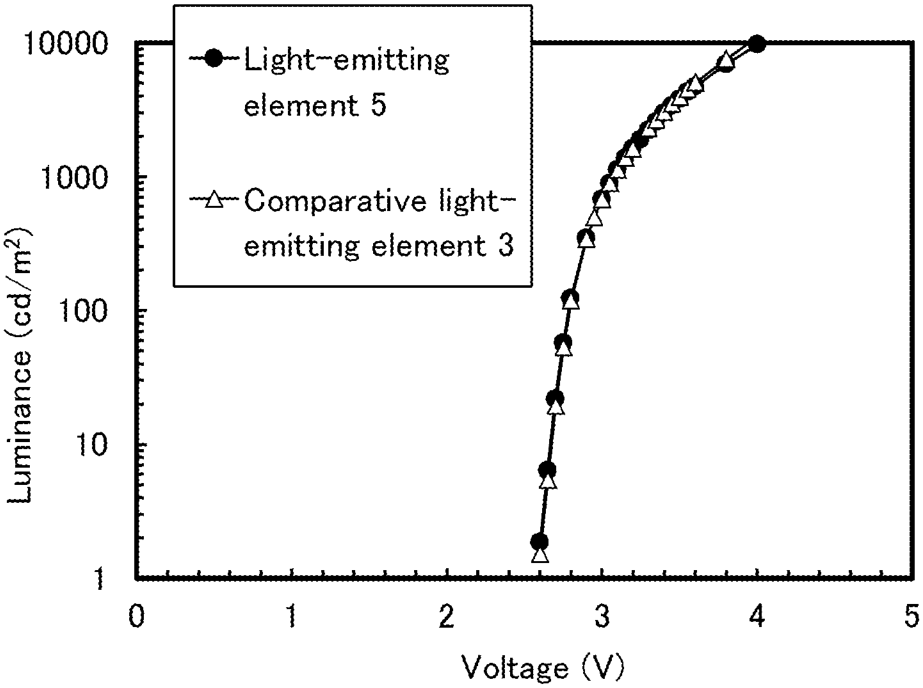
FIG. 38 Luminance-voltage characteristics of the light-emitting element 5 and the comparative light-emitting element 3.
Figure 39:
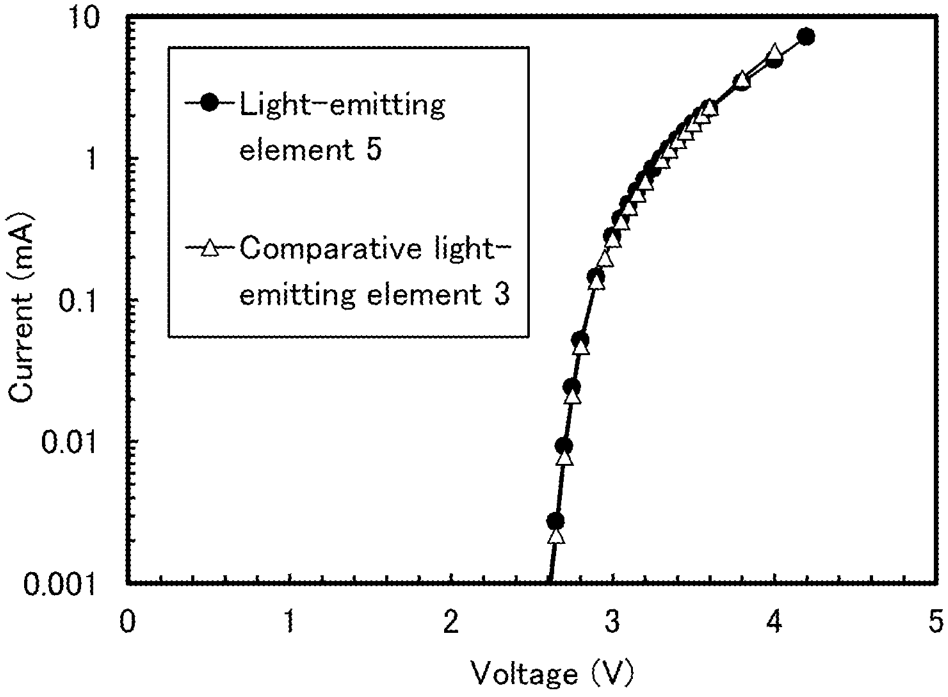
FIG. 39 Current-voltage characteristics of the light-emitting element 5 and the comparative light-emitting element 3.
Figure 40:
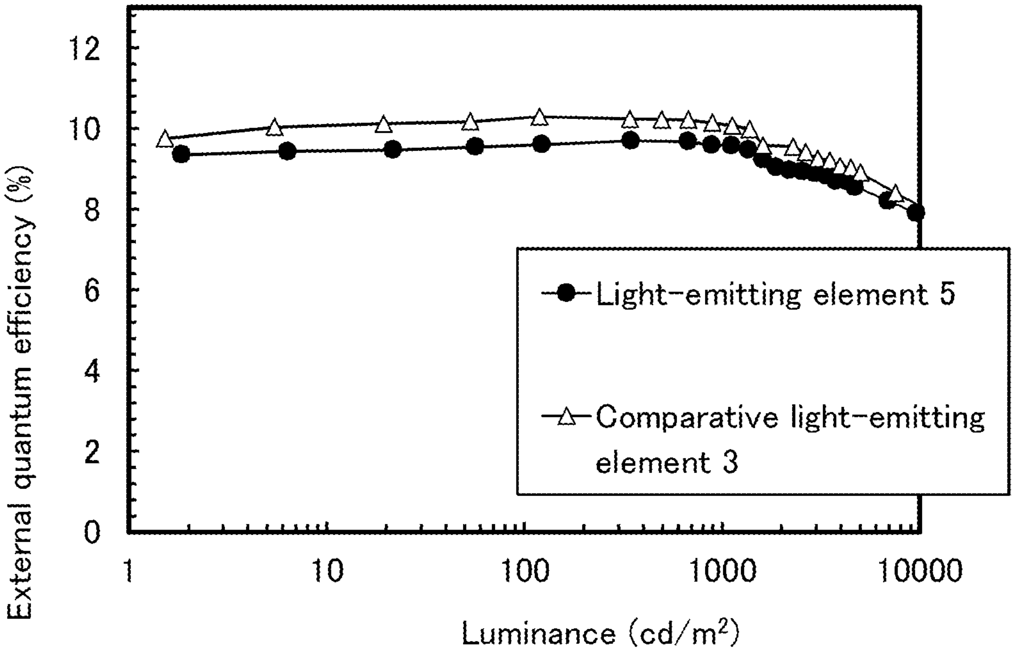
FIG. 40 External quantum efficiency-luminance characteristics of the light-emitting element 5 and the comparative light-emitting element 3.
Figure 41:
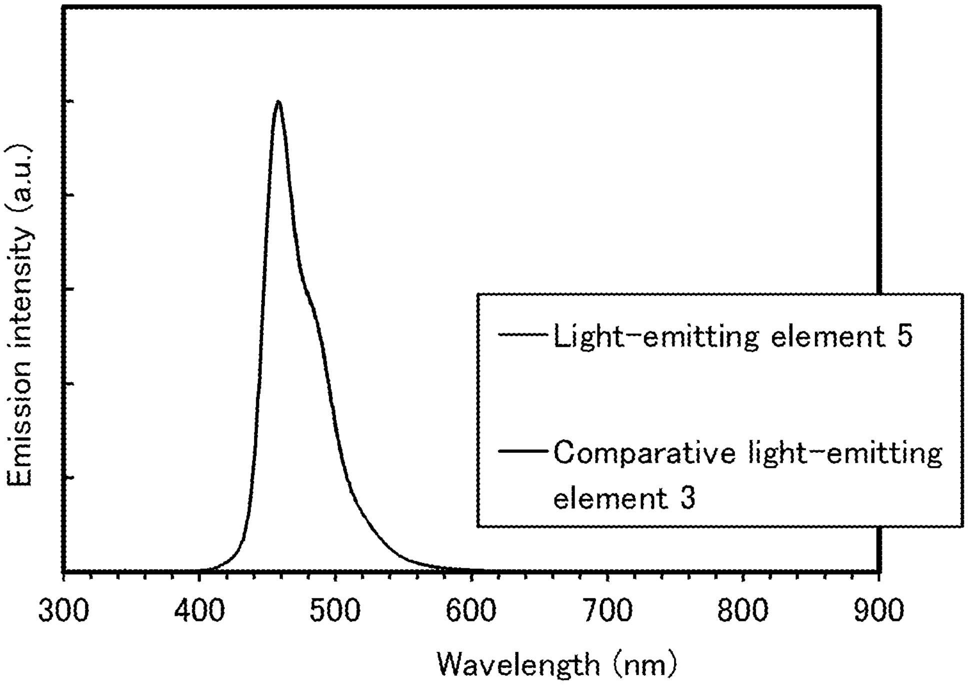
FIG. 41 Emission spectra of the light-emitting element 5 and the comparative light-emitting element 3.

FIG. 36 shows the luminance-current density characteristics of the light-emitting element 5 and the comparative light-emitting element 3; FIG. 37 shows the current efficiency-luminance characteristics thereof; FIG. 38 shows the luminance-voltage characteristics thereof; FIG. 39 shows the current-voltage characteristics thereof; FIG. 40 shows the external quantum efficiency-luminance characteristics thereof; and FIG. 41 shows the emission spectra thereof. In addition, Table 6 shows the main characteristics of each of the light-emitting elements at around 1000 cd/m$^2$.

TABLE 6

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting element 5 | 3.1 | 0.37 | 9.3 | 0.14 | 0.12 | 9.5 | 9.6 |
| Comparative light-emitting element 3 | 3.1 | 0.36 | 8.9 | 0.14 | 0.12 | 10.0 | 10.1 |

It was found from FIG. 36 to FIG. 41 and Table 6 that the light-emitting element 5 of one embodiment of the present invention was a favorable blue light-emitting element with characteristics comparable to those of the comparative light-emitting element 3.

Figure 42:
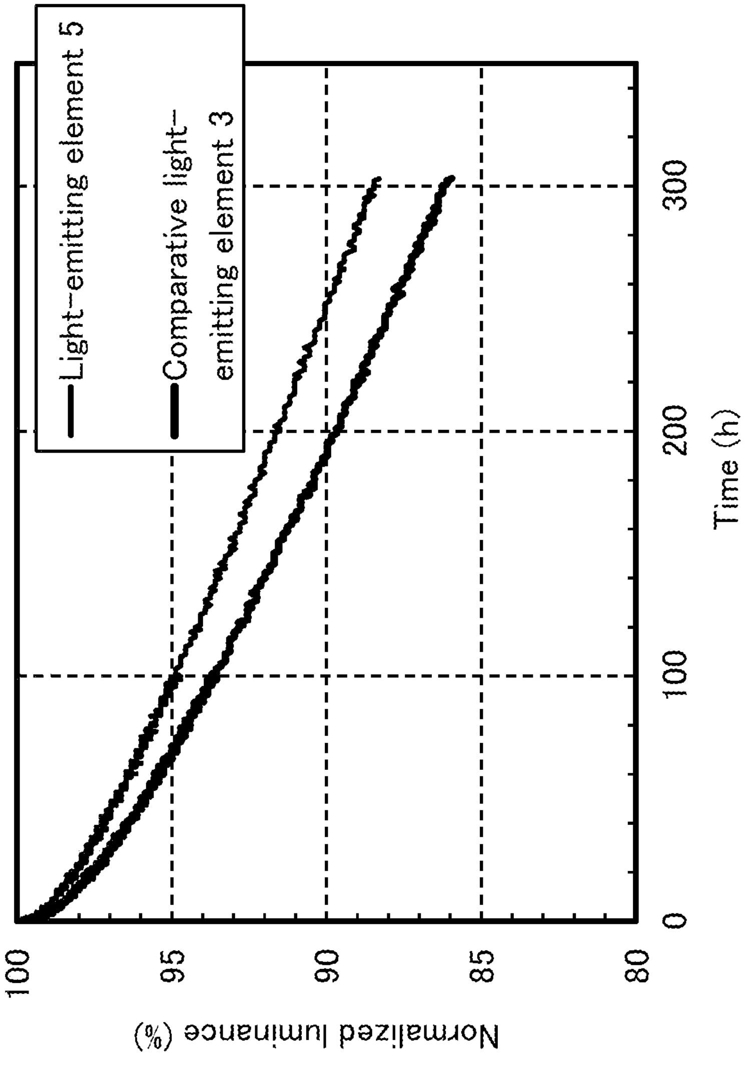
FIG. 42 A graph showing a change in luminance over driving time at a current density of 50 $mA/cm^2$ of the light-emitting element 5 and the comparative light-emitting element 3.

A graph showing a change in luminance over driving time at a current density of 50 $mA/cm^2$ is shown in FIG. 42. As shown in FIG. 42, the light-emitting element 5, which is a light-emitting element of one embodiment of the present invention, was found to be a light-emitting element with a favorable lifetime with a smaller decrease in luminance over driving time than the comparative light-emitting element 3.

Example 7

In this example, a light-emitting element 6 of one embodiment of the present invention and a comparative light-emitting element 4 will be described. The structural formulae of organic compounds used in the light-emitting element 6 and the comparative light-emitting element 4 are shown below.

[Chemical Formula 81]

(xi)

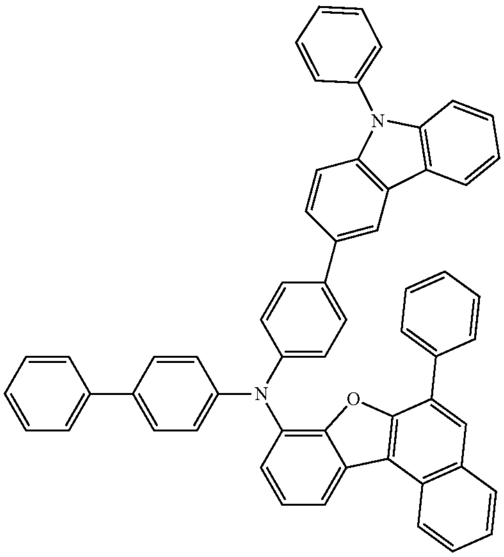

PCBBiBnf

-continued (xii)

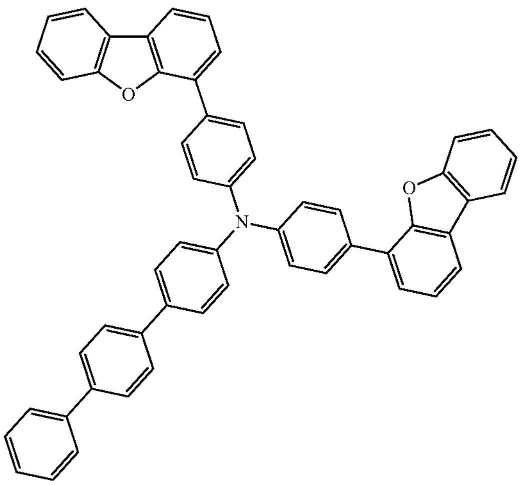

DBfBBlTP (iv)

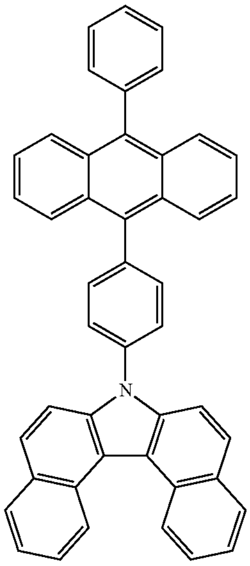

cgDBCzPA

-continued (v)

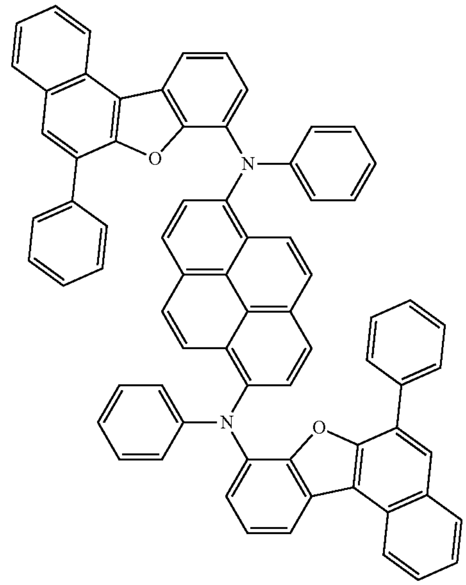

1,6BnfAPrn-03

(xiv)

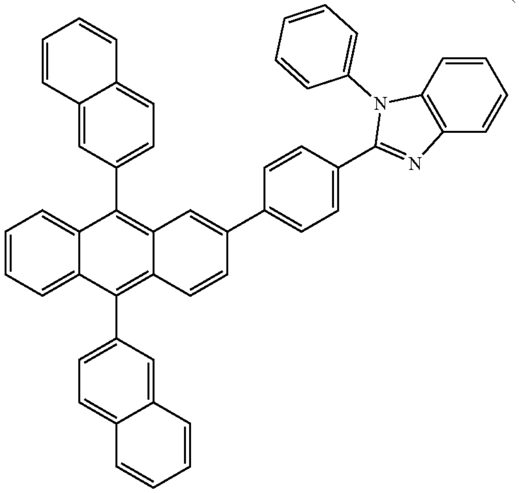

ZADN (xv)

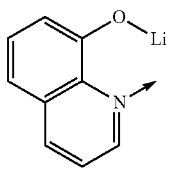

Liq

-continued (xiii)

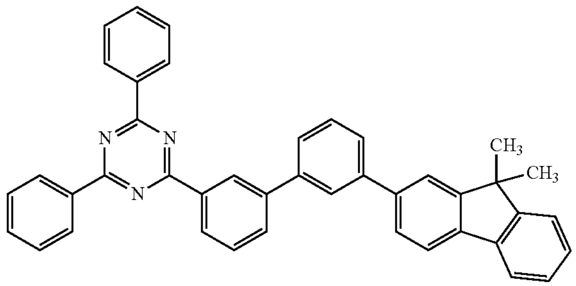

mFBPTzn (x)

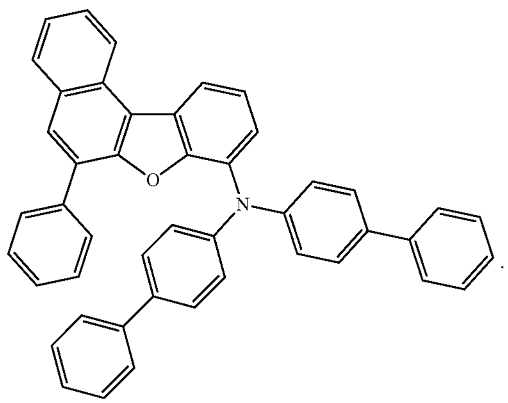

BBABnf (Fabrication Method of Light-Emitting Element 6

First, a film of indium tin oxide containing silicon oxide (ITSO) was formed over a glass substrate by a sputtering method, so that the first electrode 101 was formed. Note that the thickness was 70 nm and the area of the electrode was 2 mm×2 mm.

Next, in pretreatment for forming the light-emitting element over the substrate, the surface of the substrate was washed with water and baked at 200° C. for 1 hour, and then UV ozone treatment was performed for 370 seconds.

After that, the substrate was transferred into a vacuum evaporation apparatus in which the pressure was reduced to approximately 104 Pa, vacuum baking at 170° C. for 30 minutes was performed in a heating chamber in the vacuum evaporation apparatus, and then the substrate was cooled down for approximately 30 minutes.

Then, the substrate over which the first electrode 101 was formed was fixed to a substrate holder provided in the vacuum evaporation apparatus so that the surface over which the first electrode 101 was formed faced downward; and over the first electrode 101, N-(1,1'-biphenyl-4-yl)-6-phenyl-N-[4-(9-phenylcarbazol-3-yl)phenyl]benzo[b]naptho[d]furan-8-amine (abbreviation: PCBBiBnf) represented by Structural Formula (xi) above and NDP-9 (produced by Analysis Atelier Corporation, material serial No. 1S20170124) were co-evaporated to 10 nm at a weight ratio of 1:0.1 (=PCBBiBnf:NDP-9) by an evaporation method using resistance heating, so that the hole-injection layer 111 was formed.

Next, over the hole-injection layer 111, PCBBiBnf was deposited to 20 nm by evaporation as the first hole-transport layer 112-1, and then N,N-bis[4-(dibenzofuran-4-yl)phenyl]-4-amino-p-terphenyl (abbreviation: DBfBB1TP) represented by Structural Formula (xii) above was evaporated to 10 nm as the second hole-transport layer 112-2, whereby the hole-transport layer 112 was formed.

Subsequently, 7-[4-(10-phenyl-9-anthryl)phenyl]-7H-dibenzo[c,g]carbazole (abbreviation: cgDBCzPA) represented by Structural Formula (iv) above and N,N'-(pyrene-1,6-diyl)bis[(6,N-diphenylbenzo[b]naphtho[1,2-d]furan)-8-amine] (abbreviation: 1,6BnfAPrn-03) represented by Structural Formula (v) above were co-evaporated to 25 nm at a weight ratio of 1:0.03 (=cgDBCzPA:1,6BnfAPrn-03), whereby the light-emitting layer 113 was formed.

After that, over the light-emitting layer 113, 2-[3'-(9,9-dimethyl-9H-fluoren-2-yl)-1,1'-biphenyl-3-yl]-4,6-diphenyl-1,3,5-triazine (abbreviation: mFBPTzn) represented by Structural Formula (xiii) above was deposited by evaporation to a thickness of 10 nm, and then 2-{4-[9,10-di(naphthalen-2-yl)-2-anthryl]phenyl}-1-phenyl-1H-benzoimidazole (abbreviation: ZADN) represented by Structural Formula (xiv) above and 8-hydroxyquinolinolato-lithium (abbreviation: Liq) represented by Structural Formula (xv) above were co-evaporated to 15 nm at a weight ratio of 1:1 (=ZADN:Liq), whereby the electron-transport layer 114 was formed.

After the formation of the electron-transport layer 114, Liq was deposited by evaporation to a thickness of 1 nm to form the electron-injection layer 115, and then aluminum was deposited by evaporation to a thickness of 200 nm to form the second electrode 102, whereby the light-emitting element 3 of this example was fabricated.

(Fabrication Method of Comparative Light-Emitting Element 4)

The comparative light-emitting element 4 was fabricated in a manner similar to that of the light-emitting element 6 except that N,N-bis(4-biphenyl)-6-phenylbenzo[b]naphtho[1,2-d]furan-8-amine (abbreviation: BBABnf) represented by Structural Formula (x) above was used instead of PCBBiBnf in the light-emitting element 5.

The element structures of the light-emitting element 5 and the comparative light-emitting element 3 are listed in the following table.

TABLE 7

| | Hole-injection layer | Hole-transport layer 1 | Hole-transport layer 2 | Light-emitting layer | Electron-transport layer | | Electron-injection layer |
|---|---|---|---|---|---|---|---|
| | 10 nm | 20 nm | 10 nm | 25 nm | 10 nm | 15 nm | 1 nm |
| Light-emitting element 6 | PCBBiBnf: NDP-9 (1:0.1) | PCBBiBnf | DBfBB1TP | cgDBCzPA: 1,6BnfAPrn-03 (1:0.03) | mFBPTzn | ZADN: Liq (1:1) | Liq |
| Comparative light-emitting element 4 | BBABnf: NDP-9 (1:0.1) | BBABnf | | | | | |

The light-emitting element 6 and the comparative light-emitting element 4 were subjected to sealing with a glass substrate (a sealant was applied to surround the element, followed by UV treatment and one-hour heat treatment at 80° C. at the time of sealing) in a glove box containing a nitrogen atmosphere so that the light-emitting elements are not exposed to the air, and then the initial characteristics and reliabilities of these light-emitting elements were measured. Note that the measurement was performed at room temperature.

Figure 43:
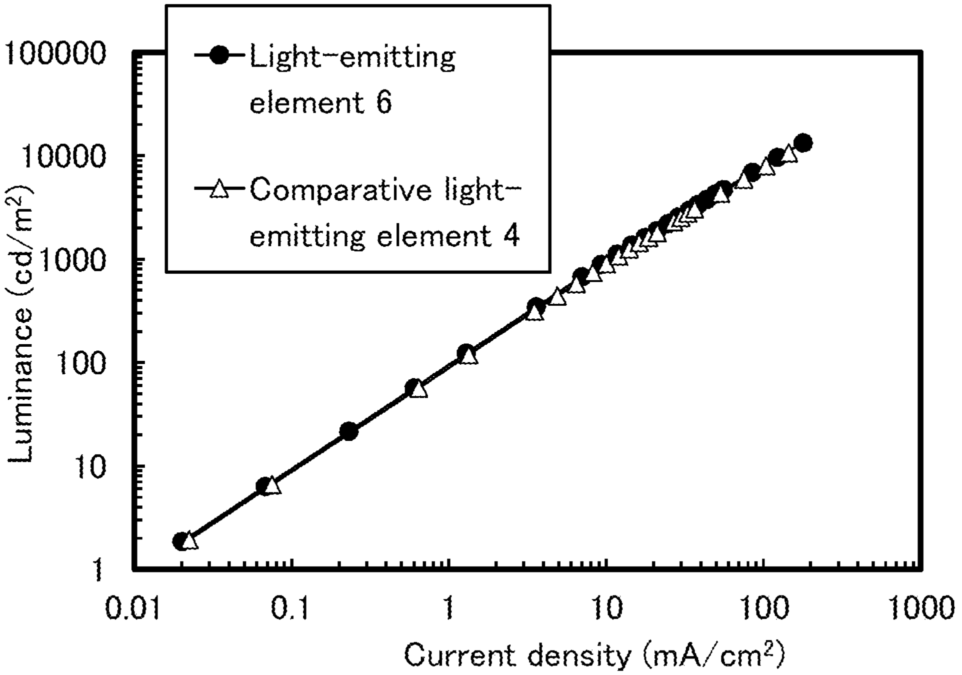
FIG. 43 Luminance-current density characteristics of a light-emitting element 6 and a comparative light-emitting element 4.
Figure 44:
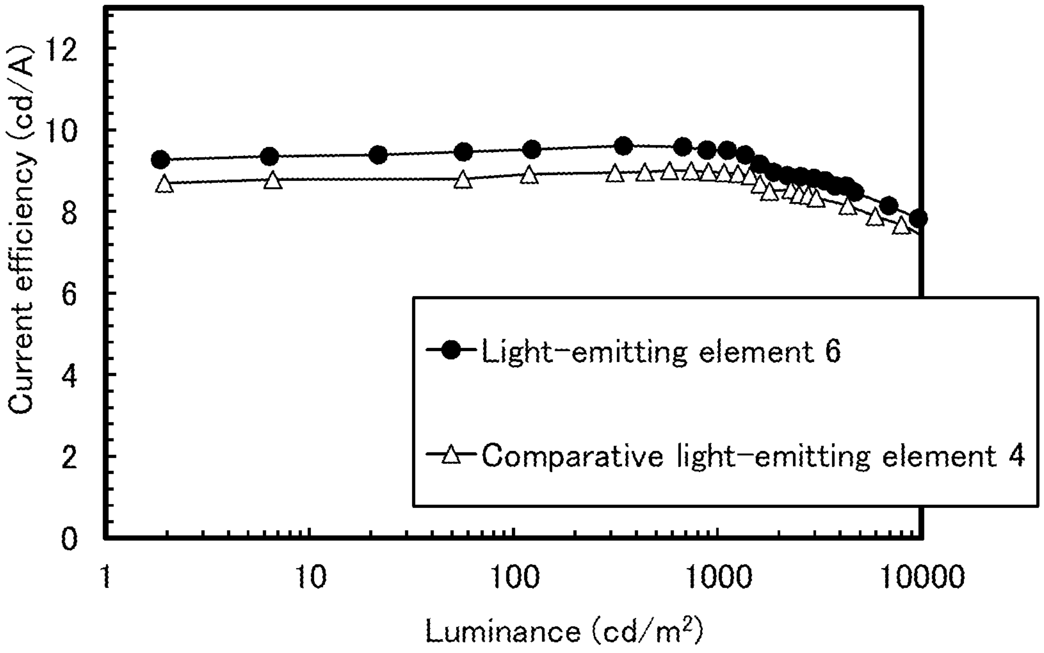
FIG. 44 Current efficiency-luminance characteristics of the light-emitting element 6 and the comparative light-emitting element 4.
Figure 45:
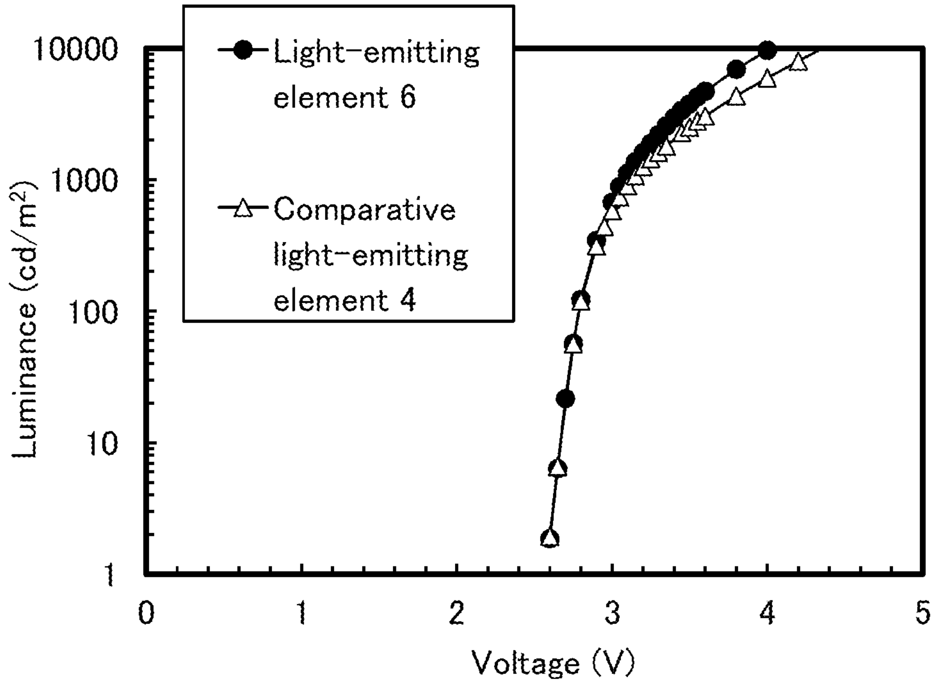
FIG. 45 Luminance-voltage characteristics of the light-emitting element 6 and the comparative light-emitting element 4.
Figure 46:
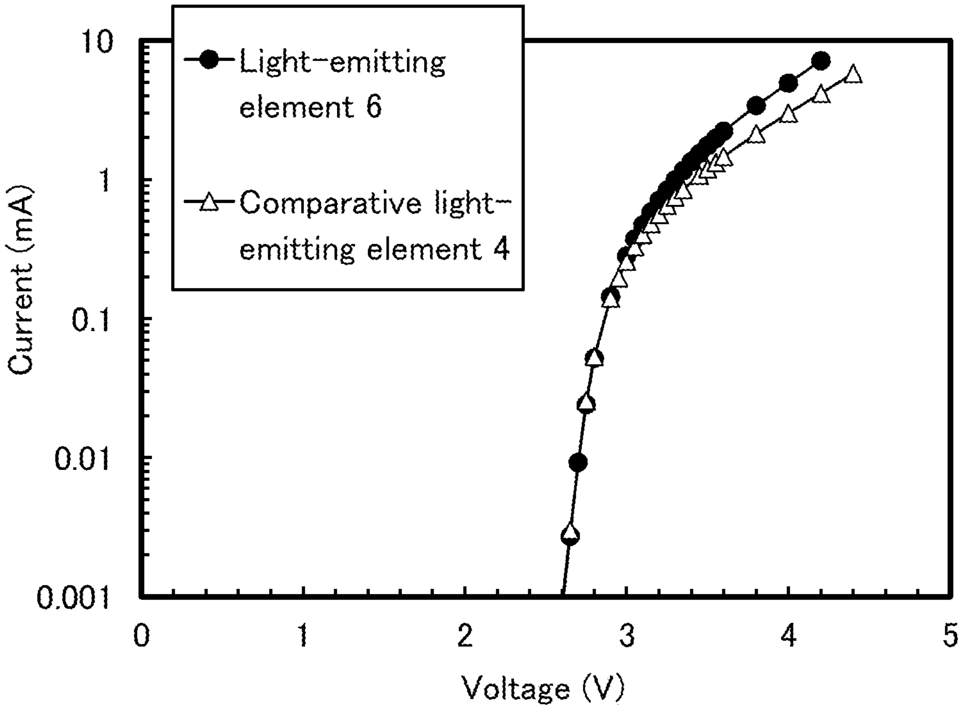
FIG. 46 Current-voltage characteristics of the light-emitting element 6 and the comparative light-emitting element 4.
Figure 47:
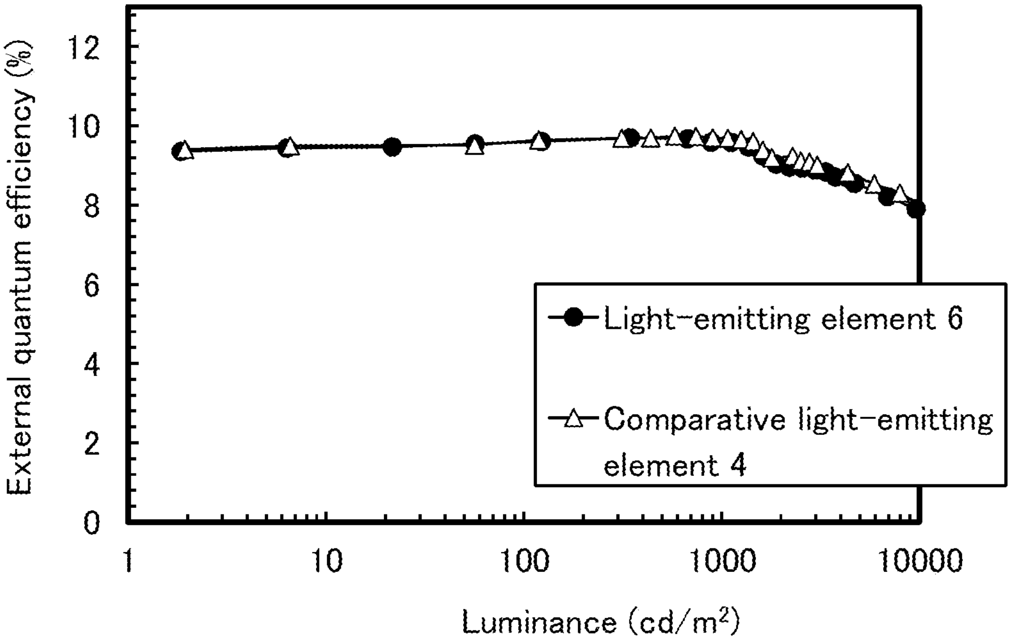
FIG. 47 External quantum efficiency-luminance characteristics of the light-emitting element 6 and the comparative light-emitting element 4.
Figure 48:
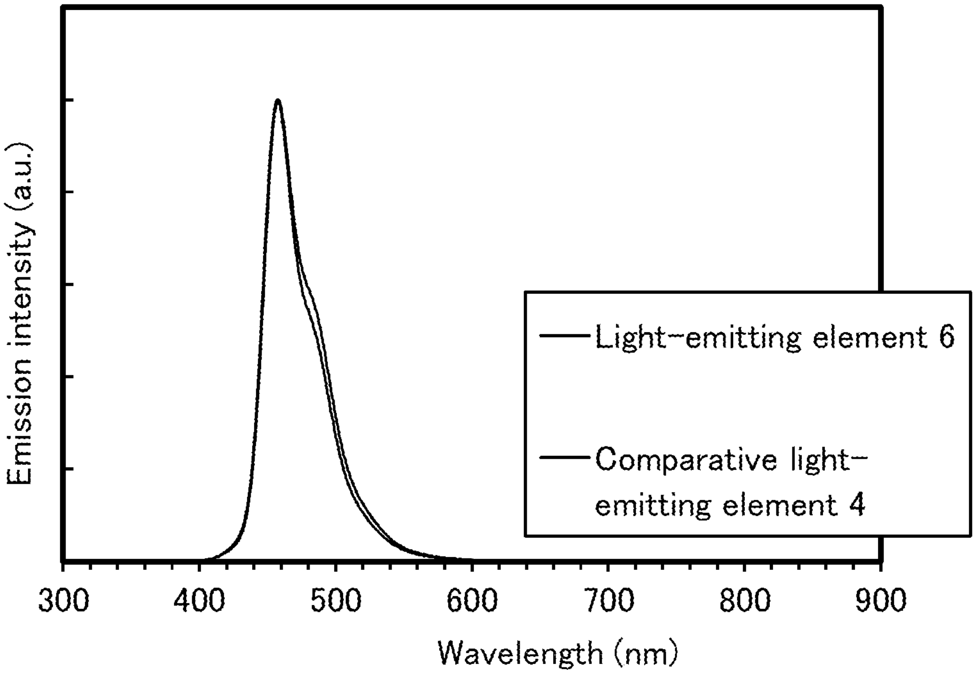
FIG. 48 Emission spectra of the light-emitting element 6 and the comparative light-emitting element 4.

FIG. 43 shows the luminance-current density characteristics of the light-emitting element 6 and the comparative light-emitting element 4; FIG. 44 shows the current efficiency-luminance characteristics thereof, FIG. 45 shows the luminance-voltage characteristics thereof, FIG. 46 shows the current-voltage characteristics thereof; FIG. 47 shows the external quantum efficiency-luminance characteristics thereof; and FIG. 48 shows the emission spectra thereof. In addition, Table 6 shows the main characteristics of each of the light-emitting elements at around 1000 cd/m$^2$.

TABLE 8

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting element 6 | 3.1 | 0.37 | 9.3 | 0.14 | 0.12 | 9.5 | 9.6 |
| Comparative light-emitting element 4 | 3.2 | 0.48 | 12.0 | 0.14 | 0.11 | 9.0 | 9.7 |

It was found from FIG. 43 to FIG. 48 and Table 8 that the light-emitting element 6 of one embodiment of the present invention had a lower driving voltage than the comparative light-emitting element 4 and was a blue light-emitting element with favorable emission efficiency.

Figure 49:
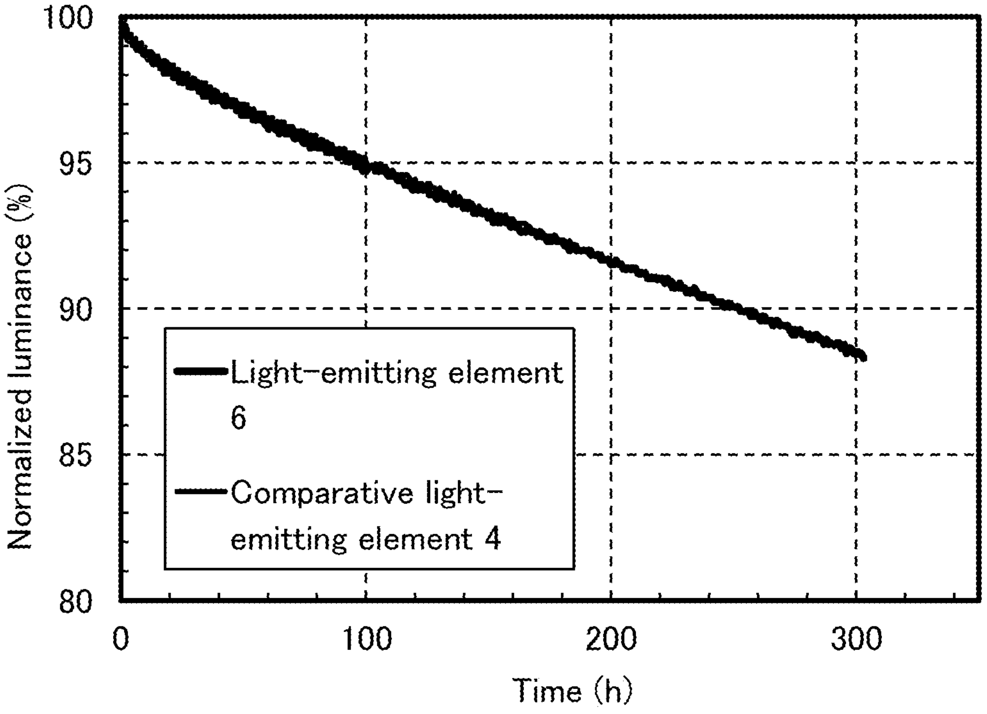
FIG. 49 A graph showing a change in luminance over driving time at a current density of 50 $mA/cm^2$ of the light-emitting element 6 and the comparative light-emitting element 4.
Figure 50:
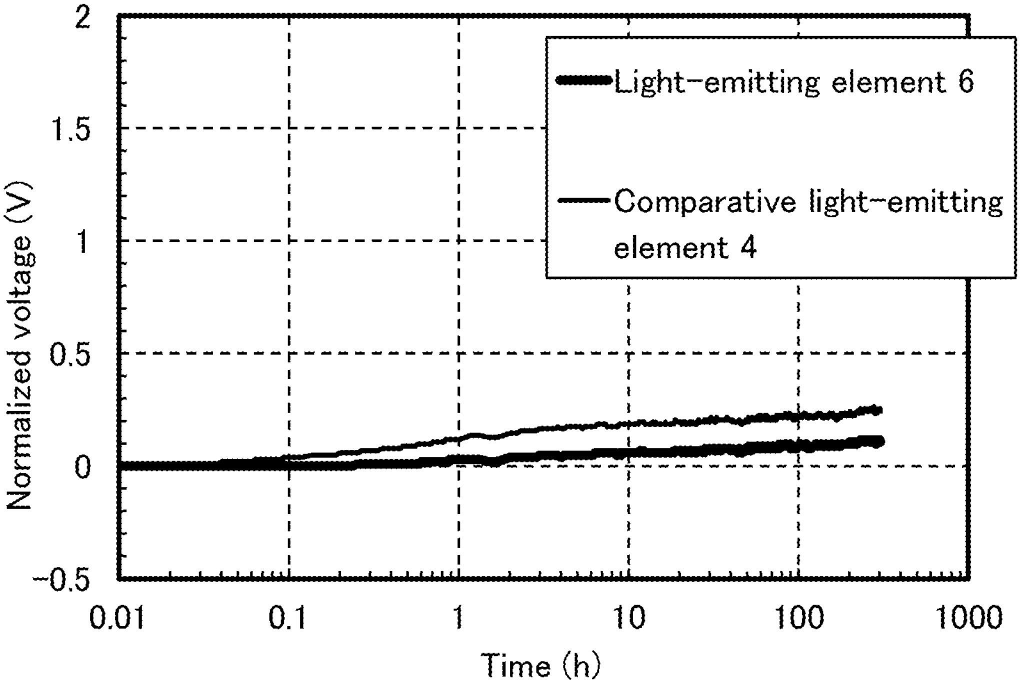
FIG. 50 A graph showing a change in driving voltage over driving time at a current density of 50 $mA/cm^2$ of the light-emitting element 6 and the comparative light-emitting element 4.

A graph showing a change in luminance over driving time at a current density of 50 mA/cm$^2$ is shown in FIG. 49, and a graph showing a change in voltage is shown in FIG. 50. As shown in FIG. 49, a change in luminance of the light-emitting element of one embodiment of the present invention was similar between the light-emitting element 6 and the comparative light-emitting element 4; however, a change in voltage of the light-emitting element 6 was smaller as shown in FIG. 50, showing that the light-emitting element 6 was a light-emitting element with favorable reliability.

REFERENCE NUMERALS

101: first electrode, 102: second electrode, 103: EL layer, 111: hole-injection layer, 112: hole-transport layer, 112-1: first hole-transport layer, 112-2: second hole-transport layer, 112-3: third hole-transport layer, 113: light-emitting layer, 114: electron-transport layer, 115: electron-injection layer, 116: charge-generation layer, 117: P-type layer, 118: electron-relay layer, 119: electron-injection buffer layer, 400: substrate, 401: first electrode, 403: EL layer, 404: second electrode, 405: sealant, 406: sealant, 407: sealing substrate, 412: pad, 420: IC chip, 501: first electrode, 502: second electrode, 511: first light-emitting unit, 512: second light-emitting unit, 513: charge-generation layer, 601: driver circuit portion (source line driver circuit), 602: pixel portion, 603: driver circuit portion (gate line driver circuit), 604: sealing substrate, 605: sealant, 607: space, 608: wiring, 609: FPC (flexible printed circuit), 610: element substrate, 611: switching FET, 612: current control FET, 613: first electrode, 614: insulator, 616: EL layer, 617: second electrode, 618: light-emitting element, 951: substrate, 952: electrode, 953: insulating layer, 954: partition layer, 955: EL layer, 956: electrode, 1001: substrate, 1002: base insulating film, 1003: gate insulating film, 1006: gate electrode, 1007: gate electrode, 1008: gate electrode, 1020: first interlayer insulating film, 1021: second interlayer insulating film, 1022: electrode, 1024W: first electrode, 1024R: first electrode, 1024G: first electrode, 1024B: first electrode, 1025: partition, 1028: EL layer, 1029: second electrode, 1031: sealing substrate, 1032: sealant, 1033: transparent base material, 1034R: red coloring layer, 1034G: green coloring layer, 1034B: blue coloring layer, 1035: black matrix, 1036: overcoat layer, 1037: third interlayer insulating film, 1040: pixel portion, 1041: driver circuit portion, 1042: peripheral portion, 2001: housing, 2002: light source, 2100: robot, 2110: arithmetic device, 2101: illuminance sensor, 2102: microphone, 2103: upper camera, 2104: speaker, 2105: display, 2106: lower camera, 2107: obstacle sensor, 2108: moving mechanism, 3001: lighting device, 5000: housing, 5001: display portion, 5002: second display portion, 5003: speaker, 5004: LED lamp, 5005: operation key, 5006: connection terminal, 5007: sensor, 5008: microphone, 5012: support, 5013: earphone, 5100: cleaning robot, 5101: display, 5102: camera, 5103: brush, 5104: operation button, 5150: portable information terminal, 5151: housing, 5152: display region, 5153: bend portion, 5120: dust, 5200: display region, 5201: display region, 5202: display region, 5203: display region, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7210: second display portion, 7401: housing, 7402: display portion, 7403: operation button, 7404: external connection port, 7405: speaker, 7406: microphone, 7400: mobile phone, 9310: portable information terminal, 9311: display panel, 9313: hinge, 9315: housing This application is based on Japanese Patent Application Serial No. 2018-144189 filed with Japan Patent Office on Jul. 31, 2018, the entire contents of which are hereby incorporated herein by reference.

The invention claimed is:

1. An organic compound represented by Formula (G1),

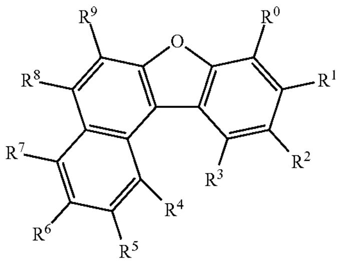

(G1)

wherein one of $R^0$ and $R^9$ is a group represented by Formula (g1), wherein each of $R^1$ to $R^8$ and the other of $R^0$ and $R^9$ independently represents any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms,

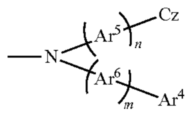

(g1)

wherein Cz represents a substituted or unsubstituted carbazolyl group, wherein $Ar^4$ represents any one of a substituted or unsubstituted aromatic hydrocarbon group having 6 to 60 carbon atoms and a substituted or unsubstituted carbazolyl group, wherein $Ar^5$ represents a 1,4-phenylene group, wherein $Ar^6$ represents a phenylene group, wherein m represents any one integer of 0, 1, 2 and 3, and wherein n represents any one integer of 1, 2 and 3.

2. The organic compound according to claim 1, wherein Cz is a group represented by Formula (g2),

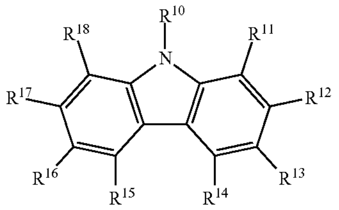

(g2)

wherein one of $R^{10}$ to $R^{18}$ represents a dangling bond bonded to $Ar^5$, and wherein each of the others of $R^{10}$ to $R^{18}$ independently represents any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms.

3. The organic compound according to claim 2, wherein $R^{10}$ represents the dangling bond bonded to $Ar^5$.

4. The organic compound according to claim 1, wherein $Ar^4$ is a group represented by Formula (g3), (g3)

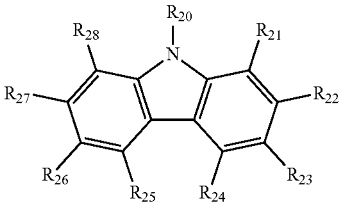

wherein one of $R^{20}$ to $R^{28}$ represents a dangling bond bonded to $Ar^6$, and wherein each of the others of $R^{20}$ to $R^{28}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 60 carbon atoms.

5. The organic compound according to claim 1, wherein $Ar^4$ represents any one of a phenyl group, a naphthyl group, a fluorenyl group and a phenanthryl group.

6. The organic compound according to claim 5, wherein the organic compound is represented by Formula (312):

(312)

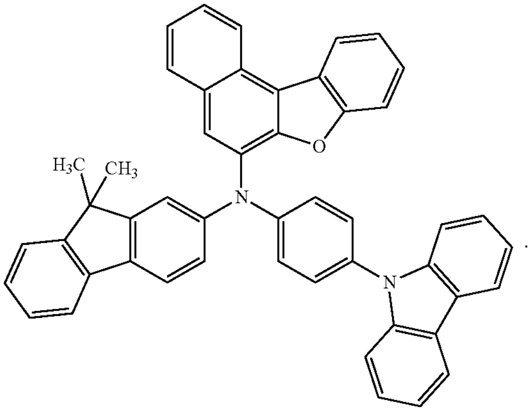

7. The organic compound according to claim 1, wherein the one of $R^0$ and $R^9$ is $R^0$.

8. The organic compound according to claim 1, wherein the $Ar^6$ represents a 1,4-phenylene group.

9. The organic compound according to claim 1, wherein the organic compound is represented by one of the following formulae:

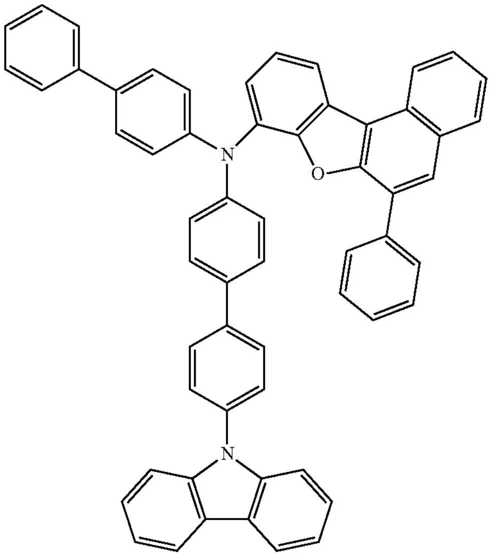

YGBBiBnf

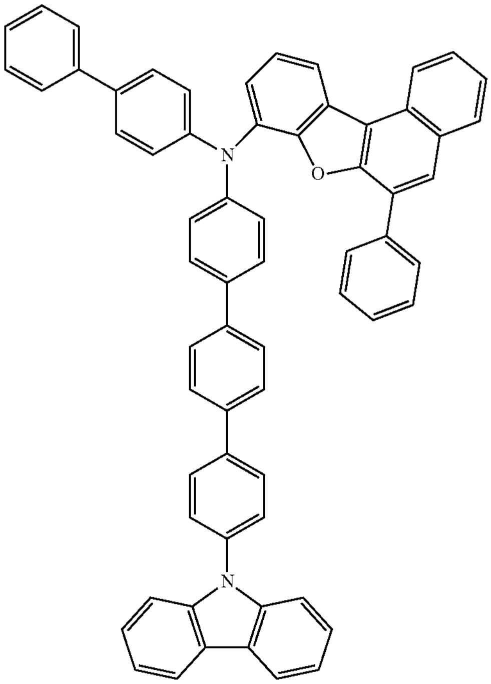

YGTBiBnf

-continued

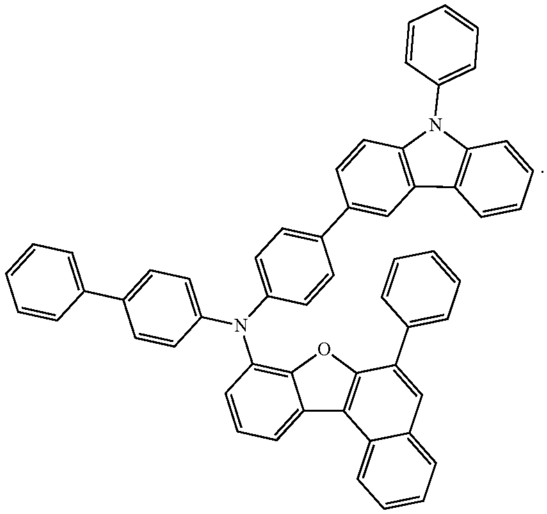

PCBBiBnf

10. A light-emitting device comprising:

a first electrode;

a layer comprising the organic compound according to claim 1 over the first electrode; and a second layer over the layer comprising the organic compound.

11. The light-emitting device according to claim 10, wherein the layer comprising the organic compound is a hole-transport layer adjacent to a light-emitting layer.

12. The light-emitting device according to claim 10, wherein the layer comprising the organic compound further comprises a phosphorescent material.

13. An electronic device comprising:

the light-emitting device according to claim 12; and at least one of a sensor, an operation button, a speaker and a microphone.

14. A lighting device comprising:

the light-emitting device according to claim 12; and a housing.

* * * * *